(12) United States Patent
Schann et al.

(10) Patent No.: US 9,029,393 B2
(45) Date of Patent: May 12, 2015

(54) ADENOSINE RECEPTOR LIGANDS AND USES THEREOF

(75) Inventors: Stephan Schann, Graffenstaden (FR); Stanislas Mayer, Eschau (FR)

(73) Assignee: Kaldi Pharma, SAS, Illkirch Graffenstaden (FR)

( * ) Notice: Subject to any disclaimer, the term of this patent is extended or adjusted under 35 U.S.C. 154(b) by 147 days.

(21) Appl. No.: 13/146,327

(22) PCT Filed: Jan. 25, 2010

(86) PCT No.: PCT/IB2010/000416
§ 371 (c)(1),
(2), (4) Date: Jul. 26, 2011

(87) PCT Pub. No.: WO2010/084425
PCT Pub. Date: Jul. 29, 2010

(65) Prior Publication Data
US 2011/0288074 A1    Nov. 24, 2011

(30) Foreign Application Priority Data
Jan. 26, 2009 (EP) .................................... 09360007

(51) Int. Cl.
*A61K 31/47* (2006.01)
*A01N 43/42* (2006.01)
*C07D 215/00* (2006.01)
*C07D 471/04* (2006.01)
*C07D 487/04* (2006.01)
*C07D 519/00* (2006.01)

(52) U.S. Cl.
CPC ............ *C07D 487/04* (2013.01); *C07D 471/04* (2013.01); *C07D 519/00* (2013.01)

(58) Field of Classification Search
USPC ........... 546/121, 152, 153; 514/248, 311, 312
See application file for complete search history.

(56) References Cited

U.S. PATENT DOCUMENTS

| 7,754,717 B2 * | 7/2010 | Dimauro et al. ............... 514/248 |
| 8,178,532 B2 * | 5/2012 | Bannen et al. ............. 514/237.2 |
| 2006/0135526 A1 | 6/2006 | Clasby et al. |

FOREIGN PATENT DOCUMENTS

| WO | WO 2007-022380 | * | 3/2007 | ........... C07D 239/42 |
| WO | WO 2009/060197 A1 | | 5/2009 | |

OTHER PUBLICATIONS

International Search Report (PCT/ISA/210) issued on Apr. 7, 2010, by European Patent Office as the International Searching Authority for International Application No. PCT/IB2010/000416.
Neustadt et al., "Potent selective, and orally active adenosine $A_{2A}$ receptor antagonists: Arylpiperazine derivatives of pyrazolo[4,3-*e*]-1,2,4-triazolo[1,5-*c*]pyrimidines", Bioorganic & Medicinal Chemistry Letters, 2007, pp. 1376-1380, vol. 17, No. 5.

* cited by examiner

*Primary Examiner* — Paul V. Ward
(74) *Attorney, Agent, or Firm* — Buchanan, Ingersoll & Rooney PC

(57) ABSTRACT

The present invention provides new compounds with high affinity for adenosine $A_{2A}$ receptors. It also provides antagonists of adenosine $A_{2A}$ receptors and their use as medicaments for the treatment and/or prophylaxis of diseases and disorders where the partial or total inactivation of adenosine $A_{2A}$ receptors signalling pathways could be beneficial such as Alzheimer's disease, Parkinson's disease, attention deficit and hyperactivity disorders (ADHD), Huntington's disease, neuroprotection, schizophrenia, anxiety and pain. The present invention further relates to pharmaceutical compositions containing such new compounds with high affinity for adenosine $A_{2A}$ receptors and their use for the treatment and/or prophylaxis of diseases and disorders where the partial or total inactivation of adenosine $A_{2A}$ receptors could be beneficial.

22 Claims, 2 Drawing Sheets

Figure 1: Effect of the compound of Example 14 administered intraperitoneally in the Haloperidol-induced Catalepsy Test in the mouse.
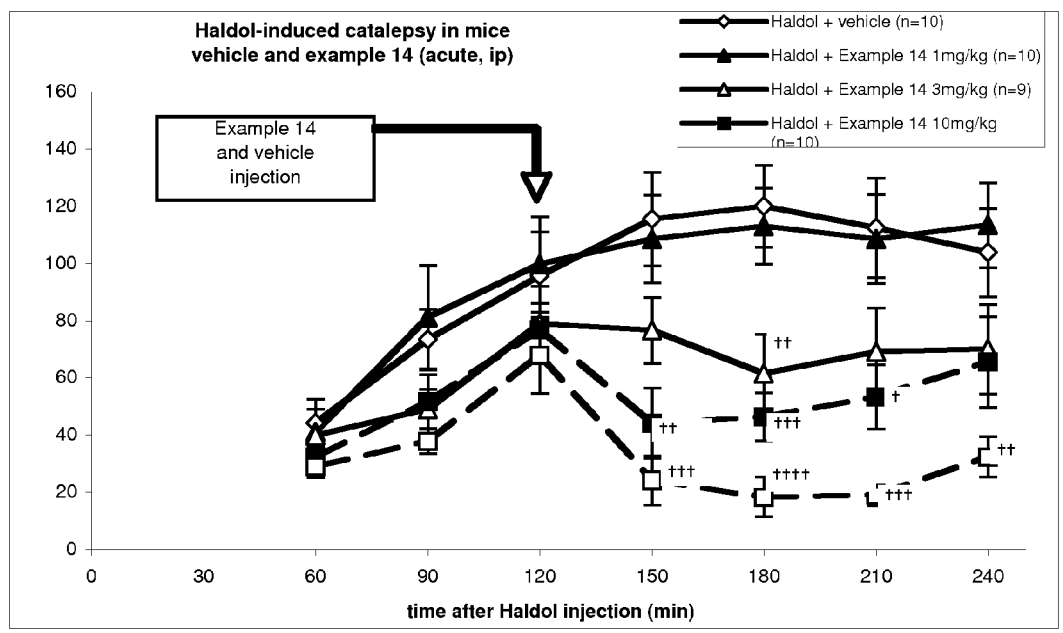

Figure 2: Effect of the compound of Example 14 administered orally in the Haloperidol-induced Catalepsy Test in the mouse.
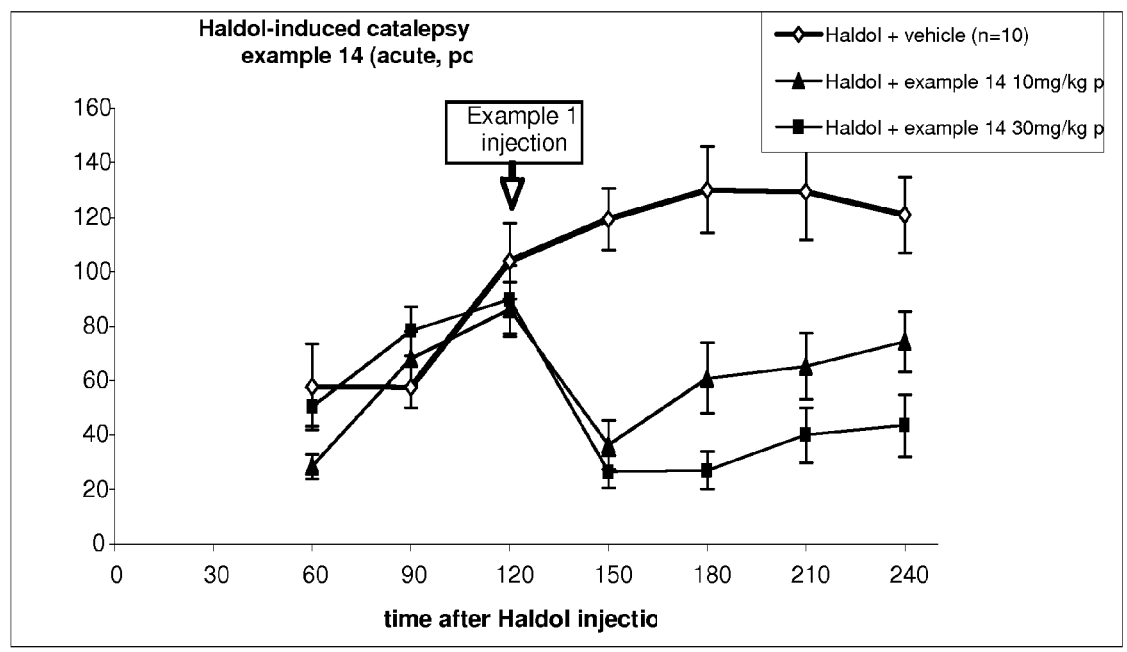

ADENOSINE RECEPTOR LIGANDS AND USES THEREOF

The present invention provides new compounds with high affinity for adenosine $A_{2A}$ receptors. It also provides antagonists of adenosine $A_{2A}$ receptors and their use as medicaments for the treatment and/or prophylaxis of diseases and disorders where the partial or total inactivation of adenosine $A_{2A}$ receptors signalling pathways could be beneficial such as Alzheimer's disease, Parkinson's disease, attention deficit and hyperactivity disorders (ADHD), Huntington's disease, neuroprotection, schizophrenia, anxiety and pain. The present invention further relates to pharmaceutical compositions containing such new compounds with high affinity for adenosine $A_{2A}$ receptors and their use for the treatment and/or prophylaxis of diseases and disorders where the partial or total inactivation of adenosine $A_{2A}$ receptors could be beneficial.

Adenosine is an ubiquitous modulator of numerous physiological activities, particularly within the cardiovascular and nervous systems. Via cell surface receptors, adenosine modulates diverse physiological functions including induction of sedation, vasodilatation, suppression of cardiac rate and contractility, inhibition of platelet aggregability, stimulation of gluconeogenesis and inhibition of lipolysis. Studies show that adenosine is able to activate adenylate cyclases, open potassium channels, reduce flux through calcium channels, and inhibit or stimulate phosphoinositide turnover through receptor-mediated mechanisms (Muller C. E. and Stein B., *Current Pharmaceutical Design*, 2:501, 1996, and Muller C. E., *Exp. Opin. Ther. Patents*, 7(5):419, 1997).

Adenosine receptors belong to the superfamily of G-protein-coupled receptors (GPCRs). Four major subtypes of adenosine receptors have been pharmacologically, structurally and functionally characterized (Fredholm et al., *Pharm. Rev.* (1994) 46:143-156) and referred to as $A_1$, $A_{2A}$, $A_{2B}$ and $A_3$. Though the same adenosine receptor can couple to different G-proteins, adenosine $A_1$ and $A_3$ receptors usually couple to inhibitory G-proteins referred to as $G_i$ and $G_o$ whereas the adenosine $A_{2A}$ and $A_{2B}$ receptors couple to stimulatory G-proteins referred to as $G_s$ (Linden J., *Annu Rev Pharmacol Toxicol.* (2001) 41:775-87). Accordingly, adenosine $A_{2A}$ receptors stimulate adenylate cyclase, whereras adenosine $A_1$ and $A_3$ receptors may lead to inhibition of this enzyme. These receptors are encoded by distinct genes and are classified according to their affinities for adenosine analogues and methylxanthine antagonists (Klinger et al., *Cell Signal.* 2002 February; 14(2):99-108).

Concerning the role of adenosine on the nervous system, the first observations were made on the effects of the most widely used of all psychoactive drugs being caffeine. Actually caffeine is a well-known adenosine receptor antagonist that is able to enhance the awareness and learning abilities of mammals. The adenosine $A_{2A}$ receptor pathway is responsible for these effects (Fredholm et al., *Pharmacol Rev.* 1999 March; 51(1):83-133; Huang et al., *Nat. Neurosci.* 2005 July; 8(7):858-9), and the effects of caffeine on the adenosine $A_{2A}$ receptor signalling pathway encouraged the research of highly specific and potent adenosine $A_{2A}$ antagonists.

In mammals, adenosine $A_{2A}$ receptors have a limited distribution in the brain and are found in the striatum, olfactory tubercle and nucleus acumbens (Dixon et al., *Br J Pharmacol.* 1996 July; 118(6):1461-8). High and intermediate levels of expression can be observed in immune cells, heart, lung and blood vessels. In the peripheral system, $G_s$ seems to be the major G-protein associated with adenosine $A_{2A}$ receptor but in the striatum, it has been shown that striatal adenosine $A_{2A}$ receptors mediate their effects through activation of a G-protein referred to as $G_{olf}$ (Kull et al., *Mol. Pharmacol.* 2000 October; 58(4):771-7), which is similar to $G_s$ and also couples to adenylate cyclase.

To date, studies on genetically modified mice and pharmacological analysis suggest that $A_{2A}$ receptor is a promising therapeutic target for the treatment of central nervous system (CNS) disorders and diseases such as Parkinson's disease, Huntington's disease, attention deficit hyperactivity disorders (ADHD), stroke (ischemic brain injury), and Alzheimer's disease (Fredholm et al., *Annu. Rev. Pharmacol. Toxicol.* 2005 45:385-412; Higgins et al.; *Behav. Brain Res.* 2007 185:32-42; Dall'Igna et al., *Exp Neurol.* 2007 Jan.; 203(1): 241-5; Arendash et al., *Neuroscience* 2006 Nov. 3; 142(4): 941-52) but also for various psychoses of organic origin (Weiss et al., *Neurology.* 2003 Dec. 9; 61(11 Suppl 6):S88-93).

The use of adenosine $A_{2A}$ receptor knockout mice has shown that adenosine $A_{2A}$ receptor inactivation protects against neuronal cell death induced by ischaemia (Chen et al., *J. Neurosci.* 1999 Nov. 1; 19(21):9192-200 and Monopoli et al., *Neuroreport.* 1998 Dec. 1; 9(17):3955-9) and the mitochondrial toxin 3-NP (Blum et al., *J. Neurosci.* 2003 Jun. 15; 23(12):5361-9). Those results provided a basis for treating ischaemia and Huntington's disease with adenosine $A_{2A}$ antagonists. The blockade of adenosine $A_{2A}$ receptors has also an antidepressant effect (El Yacoubi et al., *Neuropharmacology.* 2001 March; 40(3):424-32). Finally, this blockade prevents memory dysfunction (Cunha et al., *Exp. Neurol.* 2008 April; 210(2):776-81; Takahashi et al., *Front. Biosci.* 2008 Jan. 1; 13:2614-32) and this could be a promising therapeutic route for the treatment and/or prevention of Alzheimer's disease. To date, several adenosine $A_{2A}$ receptor antagonists have shown promising potential for treatment of Parkinson's disease. As an example, KW-6002 (istradefylline) completed a phase III clinical trial in the USA after studies demonstrated its efficacy in alleviation of symptoms of the disease (Bara-Himenez et al., *Neurology.* 2003 Aug. 12; 61(3):293-6 and Hauser et al., *Neurology.* 2003 Aug. 12; 61(3):297-303). SCH420814 (Privadenant), which is now in phase II clinical trial in the USA and produces an improvement in motor function in animal models of Parkinson's disease (Neustadt et al., *Bioorg Med Chem. Lett.* 2007 Mar. 1; 17(5):1376-80) and also in human patients (Hunter J. C., poster Boston 2006-http://www.a2apd.org/Speaker_abstracts/Hunter.pdf).

As described above, several antagonists of the $A_{2A}$ receptor were discovered and are currently undergoing preclinical or clinical trials. In this context, the inventors surprisingly discovered compounds with high affinity for the adenosine $A_{2A}$ receptors and acting as an antagonist of the adenosine $A_{2A}$ receptors.

The present invention provides compounds of general formula (I):

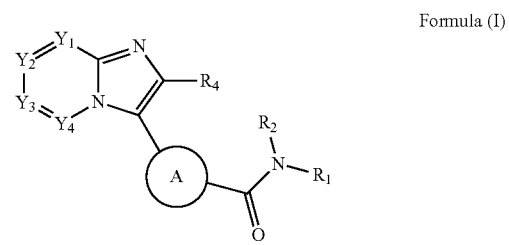

Formula (I)

and pharmaceutically acceptable salts thereof.

In Formula (I), the variables are defined as follows: $R_1$ and $R_2$ are independently selected from alkyl, alkenyl, alkynyl, aryl, cycloalkyl, heteroaryl or heterocycloalkyl, or $R_1$ and $R_2$, together with the nitrogen atom they are attached to, form a heterocycloalkyl ring or a heteroaryl ring.

In a preferred embodiment, $R_1$ and $R_2$ are independently selected from $C_{1-10}$-alkyl, $C_{6-10}$-aryl, $C_{3-10}$-cycloalkyl, heteroaryl having 5-11 ring atoms of which one or two are heteroatoms or heterocycloalkyl having 4-10 ring atoms of which one or two are heteroatoms, or $R_1$ and $R_2$, together with the nitrogen atom they are attached to, form a heterocycloalkyl ring having 5 to 10 ring atoms of which one, two or three are heteroatoms.

In a more preferred embodiment, $R_1$ and $R_2$ are independently selected from $C_{1-6}$-alkyl, $C_6$-aryl, $C_{3-7}$-cycloalkyl or heteroaryl having 5-8 ring atoms of which one or two are heteroatoms or $R_1$ and $R_2$, together with the nitrogen atom they are attached to, form a heterocycloalkyl ring having 5 to 10 ring atoms of which one or two are heteroatoms.

In a particularly preferred embodiment, $R_1$ and $R_2$ are independently selected from $C_{1-6}$-alkyl or $C_{5-7}$-cycloalkyl or $R_1$ and $R_2$, together with the nitrogen atom they are attached to, form a heterocycloalkyl ring having 5 to 10 ring atoms of which one is a heteroatom.

In an even more preferred embodiment, $R_1$ and $R_2$, together with the nitrogen atom they are attached to, form a heterocycloalkyl ring having 5 to 10 ring atoms.

Preferred heteroatoms which may be present in the heteroaryl or heterocycloalkyl groups which may be represented by $R_1$ and/or $R_2$ are N—, O— and S—, particularly N— and O—, more particularly N-atoms.

If $R_1$ and/or $R_2$ represents an alkyl group, the alkyl group may be unsubstituted or substituted by one or more substituents which may be selected from COOH, COO(lower alkyl), CONH(lower alkyl), CON(lower alkyl) (lower alkyl), CO(heterocycloalkyl), heterocycloalkyl, $CF_3$, OH, O-(lower alkyl), S-(lower alkyl), $NH_2$, NH-(lower alkyl), N-(lower alkyl)(lower alkyl), cycloalkyl, aryl, heteroaryl or halogen. Preferably, the alkyl group is unsubstituted or substituted by one substituent selected from heterocycloalkyl, $CF_3$, O-(lower alkyl), $NH_2$, NH-(lower alkyl), N-(lower alkyl)(lower alkyl), cycloalkyl, aryl, heteroaryl or halogen. More preferably, the alkyl group is unsubstituted or substituted with one substituent selected from $CF_3$, O-(lower alkyl), $NH_2$, NH-(lower alkyl), N-(lower alkyl)(lower alkyl), cycloalkyl, aryl, heteroaryl or halogen. Particularly preferred are unsubstituted alkyl groups.

The aryl group which may be represented by $R_1$ and/or $R_2$ can be unsubstituted or substituted with one or more substituents which may be selected from halogen, CN, $CF_3$, $OCF_3$, lower alkyl, COOH, COO(lower alkyl), CONH(lower alkyl), CON(lower alkyl)(lower alkyl), CO(heterocycloalkyl), OH, O-(lower alkyl), S-(lower alkyl), $NH_2$, NH-(lower alkyl) N-(lower alkyl)(lower alkyl) or heterocycloalkyl. Preferably, the aryl group is unsubstituted or substituted with one, two or three substituents selected from halogen, $CF_3$, $OCF_3$, lower alkyl, O-(lower alkyl), S-(lower alkyl), $NH_2$, NH-(lower alkyl) or N-(lower alkyl)(lower alkyl). More preferably, the aryl group is unsubstituted or substituted with one, two or three substituents independently selected from halogen, $CF_3$, $OCF_3$, lower alkyl, O-(lower alkyl), $NH_2$, NH-(lower alkyl) or N-(lower alkyl)(lower alkyl).

The cycloalkyl group which may be represented by $R_1$ and/or $R_2$ can be unsubstituted or substituted with one or more substituents which may be selected from lower alkyl, halogen, $CF_3$, O-(lower alkyl) or OH. Preferably the cycloalkyl group is unsubstituted or substituted with an OH group or a halogen. More preferably, the cycloalkyl group is unsubstituted.

The heterocycloalkyl group which may be represented by $R_1$ and/or $R_2$ can be unsubstituted or substituted with one or more groups independently selected from lower alkyl, O-(lower alkyl), (lower alkyl)-O-(lower alkyl) or halogen. Moreover, an aryl ring may be fused to the heterocycloalkyl group. Preferably the heterocycloalkyl group is unsubstituted or substituted with one or more lower alkyl groups. More preferably the heterocycloalkyl group is unsubstituted.

The heteroaryl group which may be represented by $R_1$ and/or $R_2$ can be unsubstituted or may be substituted with one or more groups independently selected from lower alkyl, O-(lower alkyl), (lower alkyl)-O-(lower alkyl) or halogen. Preferably the heteroaryl group is unsubstituted.

$Y_1, Y_2, Y_3$ and $Y_4$ are independently selected from CH, $CR_3$ or N. It is preferred that not more than two of $Y_1, Y_2, Y_3$ and $Y_4$ are N, and the others are independently selected from CH or $CR_3$. It is more preferred that not more than one of $Y_1, Y_2, Y_3$ and $Y_4$ is N, and the others are independently selected from CH or $CR_3$.

It is particularly preferred that all of $Y_1, Y_2, Y_3$ and $Y_4$ are independently selected from CH or $CR_3$. For example, $Y_1$ and $Y_3$ may represent $CR_3$ and $Y_2$ and $Y_4$ represent CH, or $Y_2$ may represent $CR_3$ and $Y_1, Y_3$ and $Y_4$ represent CH, or $Y_3$ may represent $CR_3$ and $Y_1, Y_2$ and $Y_4$ represent CH. In the most preferred embodiment, $Y_3$ represents $CR_3$ and $Y_1, Y_2$ and $Y_4$ represent CH.

$R_3$ is selected from lower alkyl, cycloalkyl, O-(lower alkyl), S-(lower alkyl), $NH_2$, NH-(lower alkyl), N-(lower alkyl)(lower alkyl), halogen, $CF_3$ or CN.

Preferably, $R_3$ is selected from lower alkyl, cycloalkyl, N-(lower alkyl)(lower alkyl), halogen, $CF_3$ or CN. More preferably, $R_3$ is selected from fluorine or CN.

$R_4$ is selected from hydrogen, lower alkyl, cycloalkyl, O-(lower alkyl), S-(lower alkyl), $NH_2$, NH-(lower alkyl), N-(lower alkyl)(lower alkyl), halogen, $CF_3$ or CN. Preferably, $R_4$ is selected from hydrogen or lower alkyl. Most preferably, $R_4$ is hydrogen.

A represents a heterocyclic group selected from:

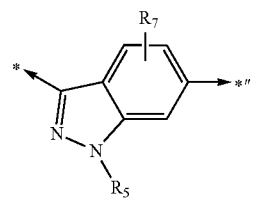

A1

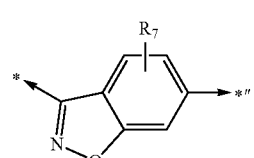

A2

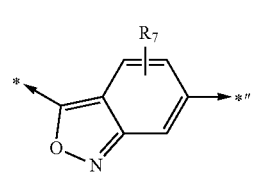

A3

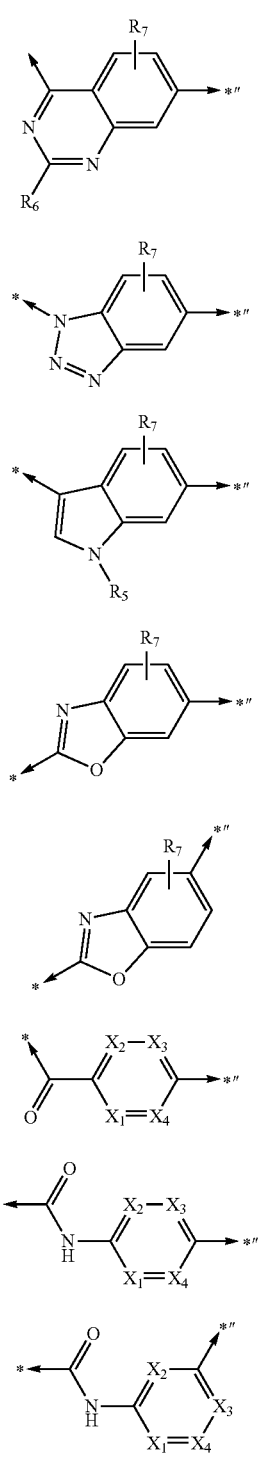

with

* being the position linked to the heterocyclic moiety comprising $Y_1, Y_2, Y_3$ and $Y_4$ in Formula (I) and *" being the position linked to the carbonyl group in Formula (I).

$R_5$ being selected from hydrogen, alkyl, cycloalkyl, aryl, heteroaryl, $(CH_2)_2$—O—$(CH_2)_2$—O—$CH_3$, CO-alkyl, CO-aryl, CO-heterocycloalkyl, CO-cycloalkyl, CO-heteroaryl, $SO_2$-alkyl, $SO_2$-aryl, $SO_2$-heterocycloalkyl, $SO_2$-cycloalkyl or $SO_2$-heteroaryl; preferably, $R_5$ is selected from hydrogen, $(CH_2)_2$—O—$(CH_2)_2$—O—$CH_3$ or alkyl; more preferably, $R_5$ is hydrogen or methyl.

If $R_5$ or part of $R_5$ (e.g. CO-alkyl) represents an alkyl group, the alkyl group may be unsubstituted or substituted by one or more substituents which may be selected from COOH, COO(lower alkyl), CONH(lower alkyl), CON(lower alkyl) (lower alkyl), CO(heterocycloalkyl), heterocycloalkyl, $CF_3$, OH, O-(lower alkyl), S-(lower alkyl), $NH_2$, NH-(lower alkyl), N-(lower alkyl)(lower alkyl), cycloalkyl, aryl, heteroaryl or halogen. Preferably, the alkyl group is unsubstituted or substituted by one substituent selected from heterocycloalkyl, $CF_3$, O-(lower alkyl), $NH_2$, NH-(lower alkyl), N-(lower alkyl)(lower alkyl), cycloalkyl, aryl, heteroaryl or halogen. More preferably, the alkyl group is unsubstituted or substituted with one substituent selected from $CF_3$, O-(lower alkyl), $NH_2$, NH-(lower alkyl), N-(lower alkyl)(lower alkyl), cycloalkyl, aryl, heteroaryl or halogen. Particularly preferred are unsubstituted alkyl groups.

The aryl group which may be represented by $R_5$ or part of $R_5$ (e.g. CO-aryl) can be unsubstituted or substituted with one or more substituents which may be selected from halogen, CN, $CF_3$, $OCF_3$, lower alkyl, COOH, COO(lower alkyl), CONH(lower alkyl), CON(lower alkyl)(lower alkyl), CO(heterocycloalkyl), OH, O-(lower alkyl), S-(lower alkyl), $NH_2$, NH-(lower alkyl) N-(lower alkyl)(lower alkyl) or heterocycloalkyl. Preferably, the aryl group is unsubstituted or substituted with one, two or three substituents selected from halogen, $CF_3$, $OCF_3$, lower alkyl, O-(lower alkyl), S-(lower alkyl), $NH_2$, NH-(lower alkyl) or N-(lower alkyl)(lower alkyl). More preferably, the aryl group is unsubstituted or substituted with one, two or three substituents independently selected from halogen, $CF_3$, $OCF_3$, lower alkyl, O-(lower alkyl), $NH_2$, NH-(lower alkyl) or N-(lower alkyl)(lower alkyl).

The cycloalkyl group which may be represented by $R_5$ or part of $R_5$ (e.g. CO-cycloalkyl) can be unsubstituted or substituted with one or more substituents which may be selected from lower alkyl, halogen, $CF_3$ or OH. Preferably the cycloalkyl group is unsubstituted or substituted with an OH group or a halogen. More preferably, the cycloalkyl group is unsubstituted.

The heterocycloalkyl group which may be represented by $R_5$ or part of $R_5$ (e.g. CO-heterocycloalkyl) can be unsubstituted or substituted with one or more groups independently selected from lower alkyl, O-(lower alkyl), (lower alkyl)-O-(lower alkyl) or halogen. Moreover, an aryl ring may be fused to the heterocycloalkyl group. Preferably the heterocycloalkyl group is unsubstituted or substituted with one or more lower alkyl groups. More preferably the heterocycloalkyl group is unsubstituted.

The heteroaryl group which may be represented by $R_5$ or part of $R_5$ (e.g. CO-heteroaryl) can be unsubstituted or may be substituted with one or more groups independently selected from lower alkyl, O-(lower alkyl), (lower alkyl)-O-(lower alkyl) or halogen. Preferably the heteroaryl group is unsubstituted.

$R_6$ being selected from hydrogen, lower alkyl, halogen, OH, O-(lower alkyl), $NH_2$, NH-(lower alkyl), N(lower alkyl) (lower alkyl) or heterocycloalkyl. Preferably, $R_6$ is selected from hydrogen, lower alkyl, OH, O-(lower alkyl), $NH_2$, NH-(lower alkyl), N(lower alkyl) (lower alkyl) or heterocycloalkyl. More preferably, $R_6$ is selected from hydrogen or lower alkyl.

The heterocycloalkyl group which may be represented by $R_6$ can be unsubstituted or substituted with one or more groups independently selected from lower alkyl, O-(lower alkyl) or (lower alkyl)-O-(lower alkyl). Moreover, an aryl ring may be fused to the heterocycloalkyl group. Preferably the heterocycloalkyl group is unsubstituted or substituted with one or more lower alkyl groups. More preferably the heterocycloalkyl group is unsubstituted.

$X_1$, $X_2$, $X_3$ and $X_4$ each representing CH, $CR_7$ or N. It is preferred that not more than two of $X_1$, $X_2$, $X_3$ and $X_4$ are N, and the others are independently selected from CH or $CR_7$. It is more preferred that not more than one of $X_1$, $X_2$, $X_3$ and $X_4$ is N, and the others are independently selected from CH or $CR_7$.

It is particularly preferred that all of $X_1$, $X_2$, $X_3$ and $X_4$ are independently selected from CH or $CR_7$. In the most preferred embodiment, $X_1$, $X_2$, $X_3$ and $X_4$ all represent CH.

The above formulae wherein $R_7$ is drawn with a line crossing a bond of a ring system indicates that the substituent $R_7$ may replace a hydrogen atom on any CH group of the respective ring. Generally, the substituent $R_7$ is present only once in the group of formula A.

$R_7$ being selected from lower alkyl, O-(lower alkyl), NH-(lower alkyl), N-(lower alkyl)-(lower alkyl), halogen, $NO_2$, $NH_2$, NH—OH, OH, CN. Preferably, $R_7$ is selected from OH, lower alkyl or halogen.

Preferably, A is selected from heterocyclic groups A1 to A8; more preferably, A is selected from heterocyclic groups A1 to A4; even more preferably, A is selected from heterocyclic groups A1 to A2; most preferably, A is the A2 heterocyclic group

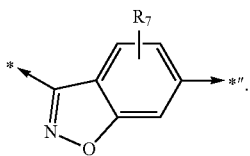

A2

In certain embodiments of the compound of Formula (I), the variables are defined as detailed above provided that when $R_1$ is an ethyl group, $R_2$ is a cyclohexyl group, A is an heterocyclic group A9 with $X_1$, $X_2$, $X_3$ and $X_4$ being CH, then:
if $Y_1$, $Y_2$, $Y_3$ and $Y_4$ correspond to CH, then $R_4$ is not isopropyl or hydrogen;
if $Y_1$, $Y_3$ and $Y_4$ correspond to CH and $Y_2$ is N, then $R_4$ is not hydrogen;
if $Y_1$ and $Y_3$ correspond to CH, $Y_2$ is C-phenyl and $Y_4$ is N, then $R_4$ is not hydrogen.

The present invention further provides pharmaceutical compositions comprising the compounds of Formula (I) as defined above as active ingredients. The compounds of Formula (I) are effective antagonists of adenosine $A_{2A}$ receptors that may be used for the treatment and/or prophylaxis of diseases and disorders related to partial or total inactivation of adenosine $A_{2A}$ receptors signalling pathways such as movement disorders, acute and chronic pain, affective disorders, central and peripheric nervous system degeneration disorders, schizophrenia and related psychoses, cognitive disorders, attention disorders, central nervous system injury, cerebral ischaemia, myocardial ischaemia, muscle ischaemia, sleep disorders, eye disorders, cardiovascular disorders, hepatic fibrosis, cirrhosis, fatty liver, and substance abuse (alcohol, amphetamine, cannabinoids, cocaine, nicotine, and opiods).

Unless indicated otherwise, the term "alkyl" as used herein preferably refers to straight or branched chain saturated hydrocarbon residues with 1-10 carbon atoms, such as methyl, ethyl, n-propyl, isopropyl, n-butyl, isobutyl, sec-butyl and t-butyl. More preferably, "alkyl" is $C_{1-6}$-alkyl; even more preferably, "alkyl" is methyl, ethyl, propyl or isopropyl.

Unless indicated otherwise, the term "lower alkyl" as used herein preferably refers to straight or branched chain saturated hydrocarbon residues with 1-4 carbon atoms, such as methyl, ethyl, n-propyl, isopropyl, n-butyl, isobutyl, sec-butyl or t-butyl.

Unless indicated otherwise, the term "alkenyl" as used herein preferably refers to straight or branched chain unsaturated hydrocarbon residues with 2-10 carbon atoms, preferably 2-4 carbon atoms (including vinyl and allyl), comprising at least one carbon-to-carbon double bond.

Unless indicated otherwise, the term "alkynyl" as used herein preferably refers to straight or branched chain unsaturated hydrocarbon residues with 2-10 carbon atoms, preferably 2-4 carbon atoms (including ethynyl and propynyl), comprising at least one carbon-to-carbon triple bond.

Unless indicated otherwise, the term "cycloalkyl" as used herein preferably refers to a 3-10 carbon atom ring or fused rings such as cyclopropyl, cyclobutyl, cyclopentyl, cyclohexyl, cycloheptyl, adamantyl, bicycloheptyl or bicyclooctyl. These cycloalkyls can contain unsaturated bonds. Preferably, "cycloalkyl" is $C_{3-7}$-cycloalkyl; more preferably, "cycloalkyl" is cyclopropyl, cyclohexyl, adamantyl, bicycloheptyl or bicyclooctyl; most preferably, "cycloalkyl" is cyclopropyl or cyclohexyl.

Unless indicated otherwise, the term "aryl" as used herein preferably refers to a 6-10 atom aromatic hydrocarbon ring or a fused aromatic hydrocarbon ring system containing at least one unsaturated aromatic ring. Preferred examples of the term "aryl" are phenyl, naphthyl and 1,2,3,4-tetrahydronaphthyl, most preferably, "aryl" is phenyl.

Unless indicated otherwise, the term "heteroaryl" as used herein preferably refers to a 5-11 atom aromatic ring or fused aromatic rings containing one or more O, S, or N atoms. Preferred examples of heteroaryls include pyridinyl, quinolinyl, isoquinolinyl, pyridazinyl, pyrimidinyl, pyrazinyl, furyl, benzofuryl, thienyl, benzothienyl, pyrrolyl, 2,5-dimethylpyrrolyl, indolyl, pyrazolyl, indazolyl, oxazolyl, benzoxazolyl, thiazolyl, benzothiazolyl, imidazolyl, benzimidazolyl, and tetrazolyl. Most preferably, "heteroaryl" is pyridinyl.

Unless indicated otherwise, the term "heterocycloalkyl" as used herein preferably refers to a 4-10 atom ring system containing one to four rings and one or more O, S, or N atoms. Preferred examples of heterocycloalkyls include azetidinyl, pyrrolidinyl, tetrahydrofuranyl, imidazolinyl, pyrrolidin-2-one, 8-azabicyclo[3.2.1]octanyl, morpholinyl, thiomorpholinyl, piperidinyl, piperidin-2-one, piperazinyl, azepanyl, azonanyl, and azocanyl.

The term "halogen" refers to bromine, chlorine, fluorine, or iodine.

The term "pharmaceutically acceptable salt" refers to salts with inorganic or organic acids, e.g. hydrochloric, hydrobromic, nitric, carbonic, formic, monohydrogencarbonic, phosphoric, monohydrogenphosphoric, dihydrogenphosphoric, perchloric, sulfuric, monohydrogensulfuric, hydroiodic, phosphorous, acetic, lactic, propionic, butyric, isobutyric, palmoic, maleic, glutamic, hydroxymaleic, malonic, benzoic, succinic, glycolic, suberic, fumaric, mandelic, phthalic, salicylic, benzenesulfonic, p-tolylsulfonic, citric, tartaric, methanesulfonic and hydroxynaphthoic acids. The term "pharmaceutically acceptable salt" can also refer to salts with inorganic bases, e.g. alkali metal bases, especially sodium or potassium bases or alkaline-earth metal bases, especially calcium or magnesium bases, or with pharmaceutically acceptable organic bases.

The term "$A_{2A}$ receptor antagonist" refers to a compound that blocks totally or partially, in a competitive or non competitive way, agonist activation of adenosine $A_{2A}$ receptor(s).

$A_{2A}$ receptor antagonists encompass compounds that inhibit the $A_{2A}$ agonist-induced cytosolic calcium ($Ca^{2+}$) increase, in cells stably expressing (i) the human $A_{2A}$ receptor and (ii) a G protein that activates protein phospholipase C, e.g. protein phospholipase C-β (PLC-β), preferably at least one of the PLC-β isoforms 1, 2, 3, or 4. $A_{2A}$ receptor antagonists encompass compounds that inhibit the $A_{2A}$ agonist-induced cytosolic calcium ($Ca^{2+}$) increase, in cells expressing (i) the human $A_{2A}$ receptor and (ii) a G protein of the Gq family, including the G protein Gα15. Cells expressing the said G protein includes cells that have been transfected by a nucleic acid comprising an expression cassette encoding the said G protein, e.g. the Gα15 protein. Thus, $A_{2A}$ receptor antagonists encompass compounds that inhibit the cytosolic calcium increase induced by the $A_{2A}$ receptor antagonist CGS21680, in cells stably expressing the human $A_{2A}$ receptor and that have been tranfected by a plasmid encoding Gα15, e.g. cells of the HEK-293 cell line (ATCC Ref CRL-1573) that have been transfected both (i) by a plasmid encoding the human $A_{2A}$ receptor fused at its amino terminal domain to GFP and (ii) by a plasmid encoding Gα15. Inhibition of a cytosolic calcium increase by a $A_{2A}$ receptor antagonist may be expressed as the $IC_{50}$ value, using the assay disclosed in Example 142 herein. More precisely, $A_{2A}$ receptor antagonists encompass those compounds exhibiting, at least in this assay system, an $IC_{50}$ value of less than 2000 nM, which includes $IC_{50}$ values of less than 1500, 1000, 900, 800, 700, 600, 500, 400, 300, 200, 100, 50, 40, 30 or 20 nM.

The terms "treatment and/or prophylaxis" as used herein relates to the amelioration or prevention of the condition being treated or of one or more of the biological symptoms of the condition being treated or alleviated.

The term "patient" refers to a human or other animal, preferably human.

The present invention provides the compounds of Formula (I) as modulators of the $A_{2A}$ receptor that may be useful for the treatment and/or prophylaxis of diseases and disorders in which the partial or total inactivation of $A_{2A}$ receptor may be beneficial.

If a compound of the invention is an $A_{2A}$ antagonist, the compounds of the invention may be used for the treatment and/or prophylaxis of diseases and disorders that may include:

movement disorders such as Parkinson's disease (PD), drug-induced Parkinsonism, post-encephalic Parkinsonism, toxin-induced Parkinsonism (e.g. MPTP, manganese, carbon monoxide) and post-traumatic Parkinson's disease (also called punch-drunk syndrome), progressive supranuclear palsy, Huntington's disease, multiple system atrophy, corticobasal degeneration, Wilson's disease, Hallerrorden-Spatz disease, progressive pallidal atrophy, Dopa responsive dystonia Parkinsonism, spasticity or other disorders of the basal ganglia which result in abnormal movement or posture; the compounds of the invention may also be effective in treating Parkinson's with on-off phenomena, Parkinson's with freezing (end of dose deterioration) and Parkinson's with prominent dyskinesias.

acute and chronic pain, for example neuropathic pain, cancer pain, trigeminal neuralgia, migraine and other conditions associated with cephalic pain, primary and secondary hyperalgesia, inflammatory pain, nociceptive pain, tabes dorsalis, phantom limb pain, spinal cord injury pain, central pain, post-herpetic pain and HIV pain;

affective disorders including mood disorders such as bipolar disorder, seasonal affective disorder, depression, manic depression, atypical depression and monodepressive disease;

central and peripheral nervous system degenerative disorders including corticobasal degeneration, demyelinating disease (multiple sclerosis, disseminated sclerosis), Freidrich's ataxia, motoneurone disease (amyotrophic lateral sclerosis, progressive bulbar atrophy), multiple system atrophy, myelopathy, radiculopathy, peripheral neuropathy (diabetic neuropathy, tabes dorsalis, drug-induced neuropathy, vitamin deficiency), systemic lupus erythamatosis, granulomatous disease, olivo-ponto-cerebellar atrophy, progressive pallidal atrophy, progressive supranuclear palsy, spasticity;

schizophrenia and related psychoses;

cognitive disorders including dementia, Alzheimer's Disease, Frontotemporal dementia, multi-infarct dementia, AIDS dementia, dementia associated with Huntington's Disease, Lewy body dementia, senile dementia, age-related memory impairment, cognitive impairment associated with dementia, Korsakoff syndrome, dementia pugilans;

attention disorders such as attention-deficit hyperactivity disorder (ADHD), attention deficit disorder, minimal brain dysfunction, brain-injured child syndrome, hyperkinetic reaction childhood, and hyperactive child syndrome;

central nervous system injury including traumatic brain injury, neurosurgery (surgical trauma), neuroprotection for head injury, raised intracranial pressure, cerebral oedema, hydrocephalus, spinal cord injury;

cerebral ischaemia including transient ischaemic attack, stroke (thrombotic stroke, ischaemic stroke, embolic stroke, haemorrhagic stroke, lacunar stroke) subarachnoid haemorrhage, cerebral vasospasm, neuroprotection for stroke, perinatal asphyxia, drowning, cardiac arrest, subdural haematoma;

myocardial ischaemia;

muscle ischaemia;

sleep disorders such as hypersomnia and narcolepsy;

eye disorders such as retinal ischaemia-reperfusion injury and diabetic neuropathy;

cardiovascular disorders such as claudication and hypotension;

hepatic fibrosis, cirrhosis, fatty liver, and their complications; and substance abuse (alcohol, amphetamine, cannabinoids, cocaine, nicotine, and opiods).

Another object of this invention consists of the use of a compound of formula (I) as defined in the present specification and pharmaceutically acceptable salts thereof, for use as a medicament.

This invention also relates to a compound of formula (I) as described herein and pharmaceutically acceptable salts thereof for the treatment of a disease or a disorder selected from the group of diseases and disorders specified above.

This invention also pertains to the use of a compound of formula (I) as described herein for manufacturing a pharmaceutical composition for the treatment and/or prophylaxis of a disease or disorder selected from the group consisting of movement disorders, acute and chronic pain, affective disorders, central and peripheral nervous system degeneration disorders, schizophrenia and related psychosis, cognitive disorders, attention disorders, central nervous system injury, cerebral ischaemia, myocardial ischaemia, muscle ischaemia, sleep disorders, eye disorders, cardiovascular disorders, hepatic fibrosis, cirrhosis, fatty liver, and substance abuse.

In some embodiments, the disease or disorder is selected from the group consisting of Parkinson's disease, Alzheimer's disease or attention-deficit hyperactivity disorder.

According to a further aspect of the invention there is provided a method of treating and/or preventing a disorder or a disease in which the partial or total inactivation of $A_{2A}$ receptors might be beneficial, such method comprising administration of a safe and effective amount of at least one compound selected form the compounds of general formula (I) or a pharmaceutically acceptable salt thereof, or a pharmaceutical composition containing at least one compound selected from the compounds of formula (I), to a patient/subject in need thereof.

A safe and effective amount of a compound of the invention will vary with the particular compound chosen; the route of administration chosen; the condition being treated; the severity of the condition being treated; the age, size, weight, and physical condition of the patient being treated; the duration of the treatment and like factors. It can be routinely determined by the skilled practitioner. Typical daily dosages may vary depending upon the particular route of administration chosen and range from about 0.01 mg to about 1000 mg per day of a compound of general formula (I) or of the corresponding amount of a pharmaceutically acceptable salt thereof.

The compounds of the invention may be administered by any suitable route of administration, including systemic administration and topical administration. Systemic administration includes oral, parenteral, transdermal, or rectal administration; or inhalation. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, optic, intravaginal, and intranasal administration. In view of the beneficial bioavailability of the compounds according to the invention via the oral route, oral administration is preferred. This includes the administration via the mouth or the nose.

The compounds of the invention may be administered once or in doses at varying intervals of time for a given period of time. For example, doses may be administered one, two, three, or four times per day. Suitable dosage regimens for a compound of the invention can be routinely determined by the skilled practitioner.

According to a further aspect of the invention, there is provided a pharmaceutical composition comprising a therapeutically effective amount of a compound of the present invention in combination with a pharmaceutically acceptable carrier and/or excipient and a method of making such a composition comprising combining a therapeutically effective amount of a compound of the present invention with a pharmaceutically acceptable carrier and/or excipient.

The pharmaceutical compositions employed in the present invention comprise a compound of the present invention, or pharmaceutically acceptable salts thereof, and may also contain a pharmaceutically acceptable carrier and optionally other therapeutic ingredients known to those skilled in the art.

The pharmaceutical compositions of the invention may be prepared and packaged in bulk form or in unit dosage forms. When provided in unit dosage form, the pharmaceutical compositions of the invention typically contain from about 0.01 mg to about 1000 mg of a compound of general formula (I) or of the corresponding amount of a pharmaceutically acceptable salt thereof.

The pharmaceutical composition of the invention can be used for the treatment and/or prophylaxis of a disease or disorder selected from movement disorders, acute and chronic pain, affective disorders, central and peripheric nervous system degeneration disorders, schizophrenia and related psychosis, cognitive disorders, attention disorders, central nervous system injury, cerebral ischaemia, myocardial ischaemia, muscle ischaemia, sleep disorders, eye disorders, cardiovascular disorders, hepatic fibrosis, cirrhosis, fatty liver, and substance abuse.

The compound of the invention and the pharmaceutically acceptable excipient or excipients will typically be formulated into a dosage form adapted for administration to the patient by the desired route of administration. Dosage forms adapted for oral administration include tablets, capsules, pills, troches, powders, syrups, elixirs, suspensions, solutions, emulsions, and sachets.

Suitable pharmaceutically acceptable excipients will vary depending upon the particular dosage form chosen. They include binders, lubricants, glidants, disintegrants, granulating agents, coating agents, wetting agents, solvents, co-solvents, suspending agents, flavoring agents, flavor masking agents, anticaking agents, humectants, chelating agents, plasticizers, viscosity regulating agents, antioxidants, preservatives, stabilizers, surfactants, emulsifiers, and buffering agents. The pharmaceutical compositions of the invention are prepared using techniques and methods known to those skilled in the art, e.g. as described in Remington's Pharmaceutical Sciences (Mack Publishing Company).

The compounds of the invention may be used per se or in combination with one or more additional medicaments useful in the treatment of the targeted disease(s) or disorder(s). In such case, the medicaments are in a same formulation or in separate formulations for a simultaneous or a sequential administration.

The invention is illustrated by the following examples wherein the term "compound" refers to a synthesis intermediate that may already be known and the term "example" refers to a compound of general formula (I) according to the invention.

The compounds of general formula (I) and their pharmaceutically acceptable salts can be synthesized according to methods described in the following schemes:

Scheme 1:

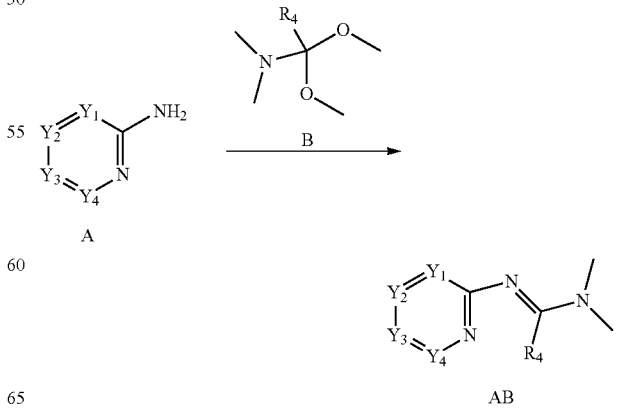

Scheme 2:
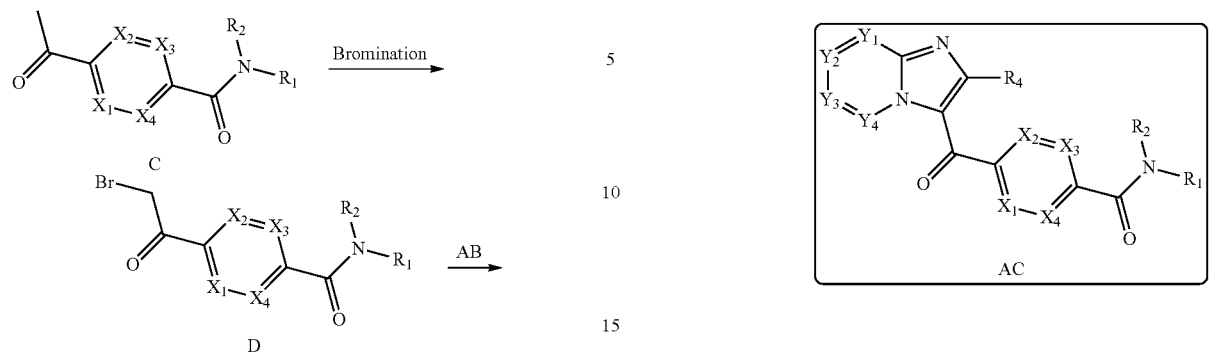
Scheme 3:
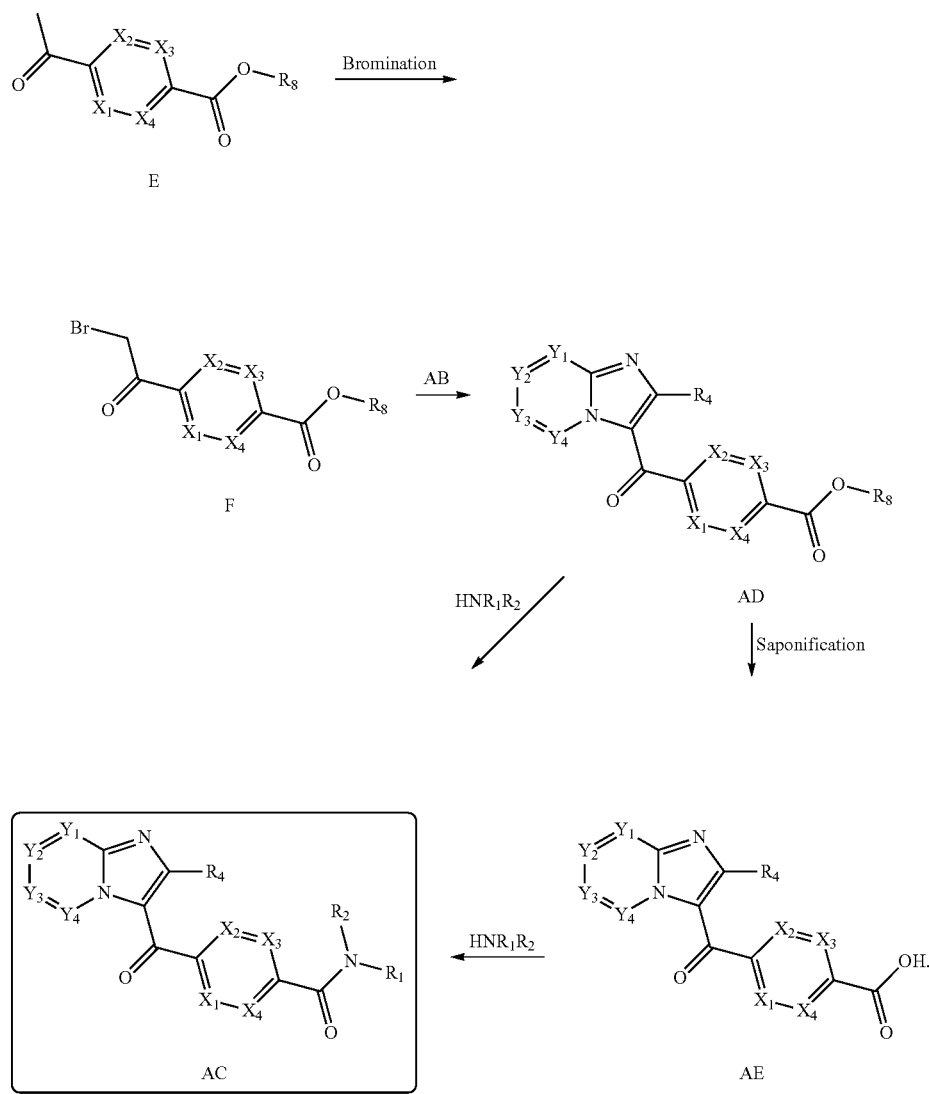
with R$_8$ being lower alkyl or aryl

Scheme 4: Preparations of compounds C and E
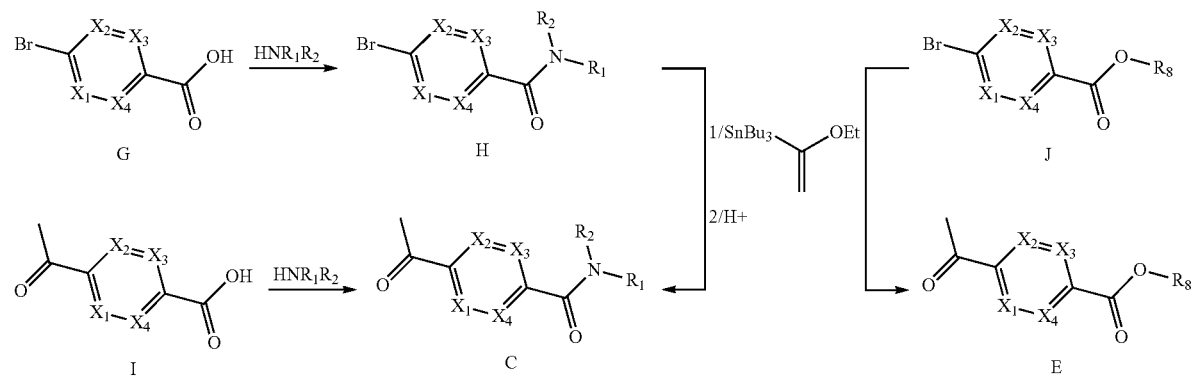

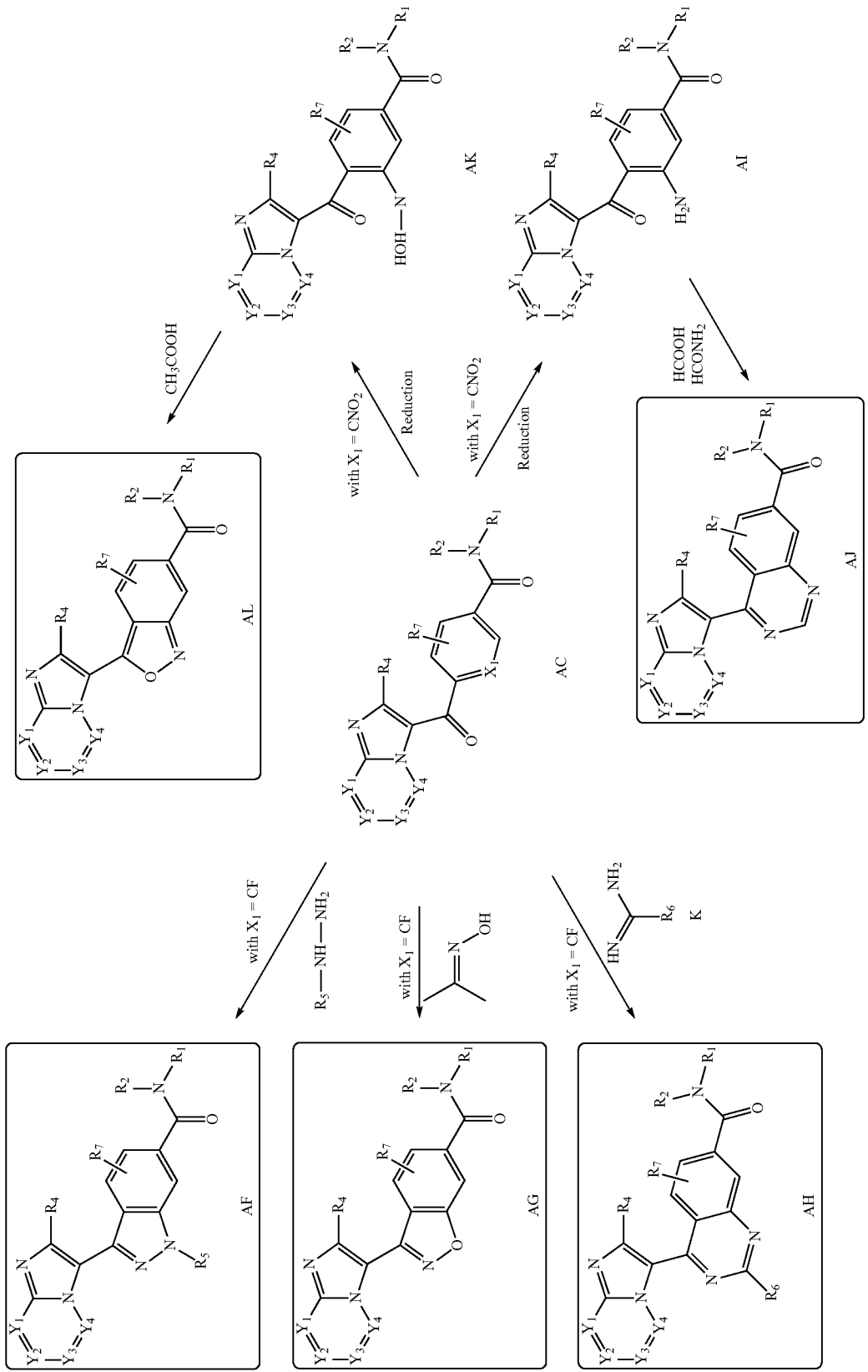

Scheme 6: Alternative route to generate AF
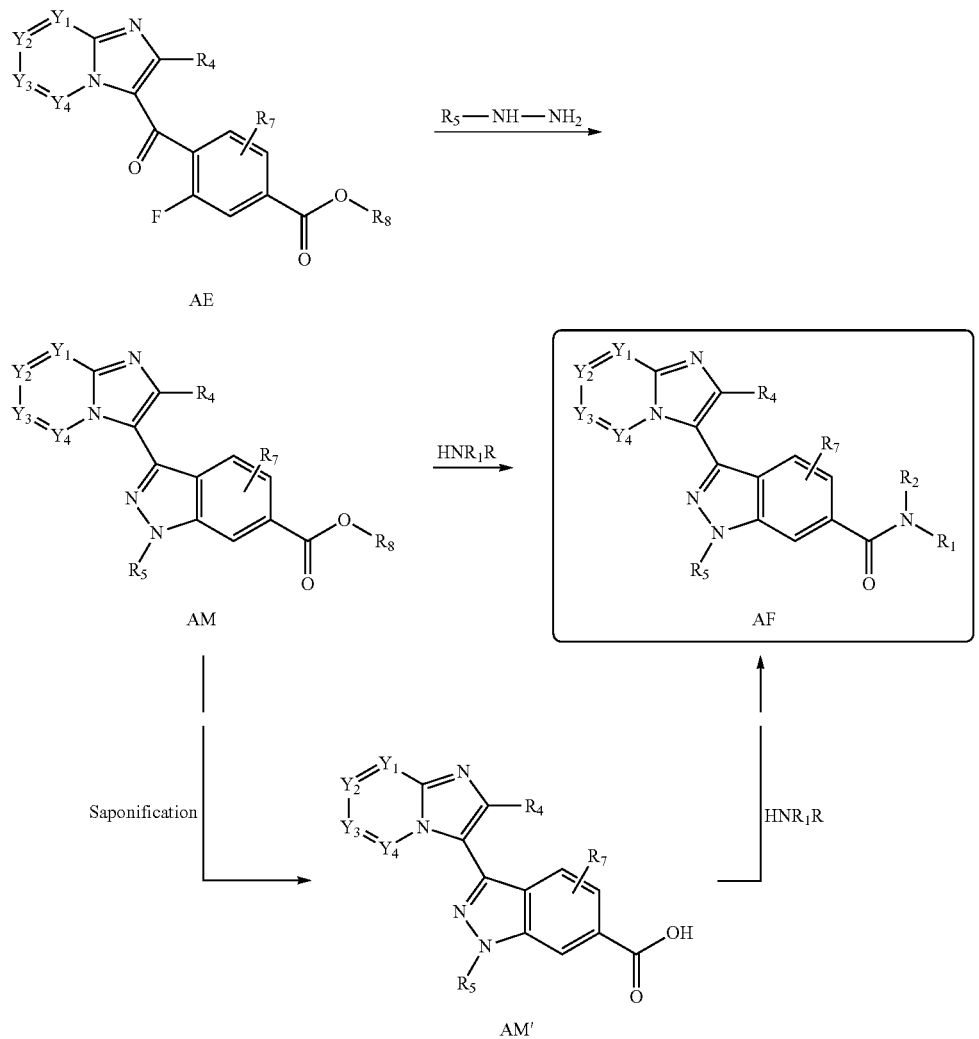
Scheme 7:
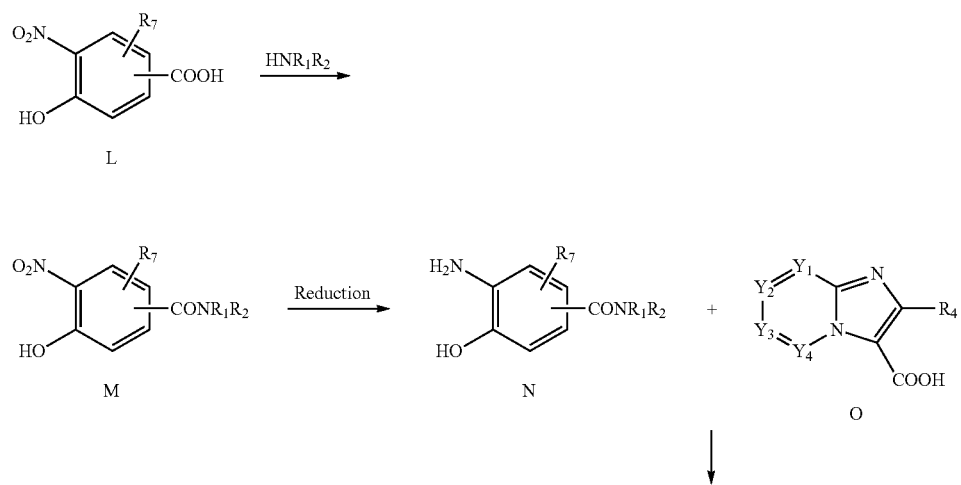

-continued
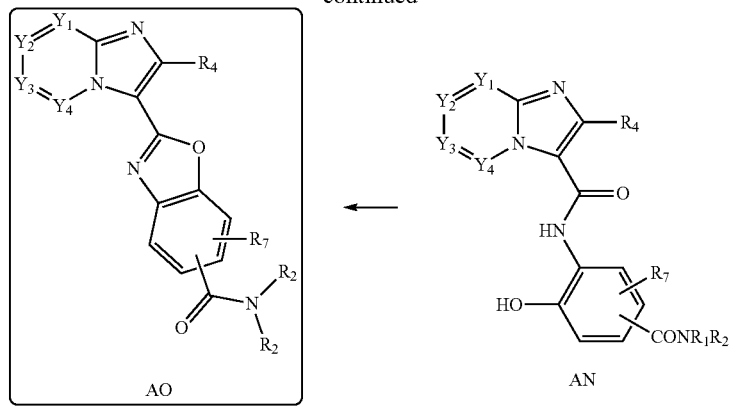

Scheme 8:
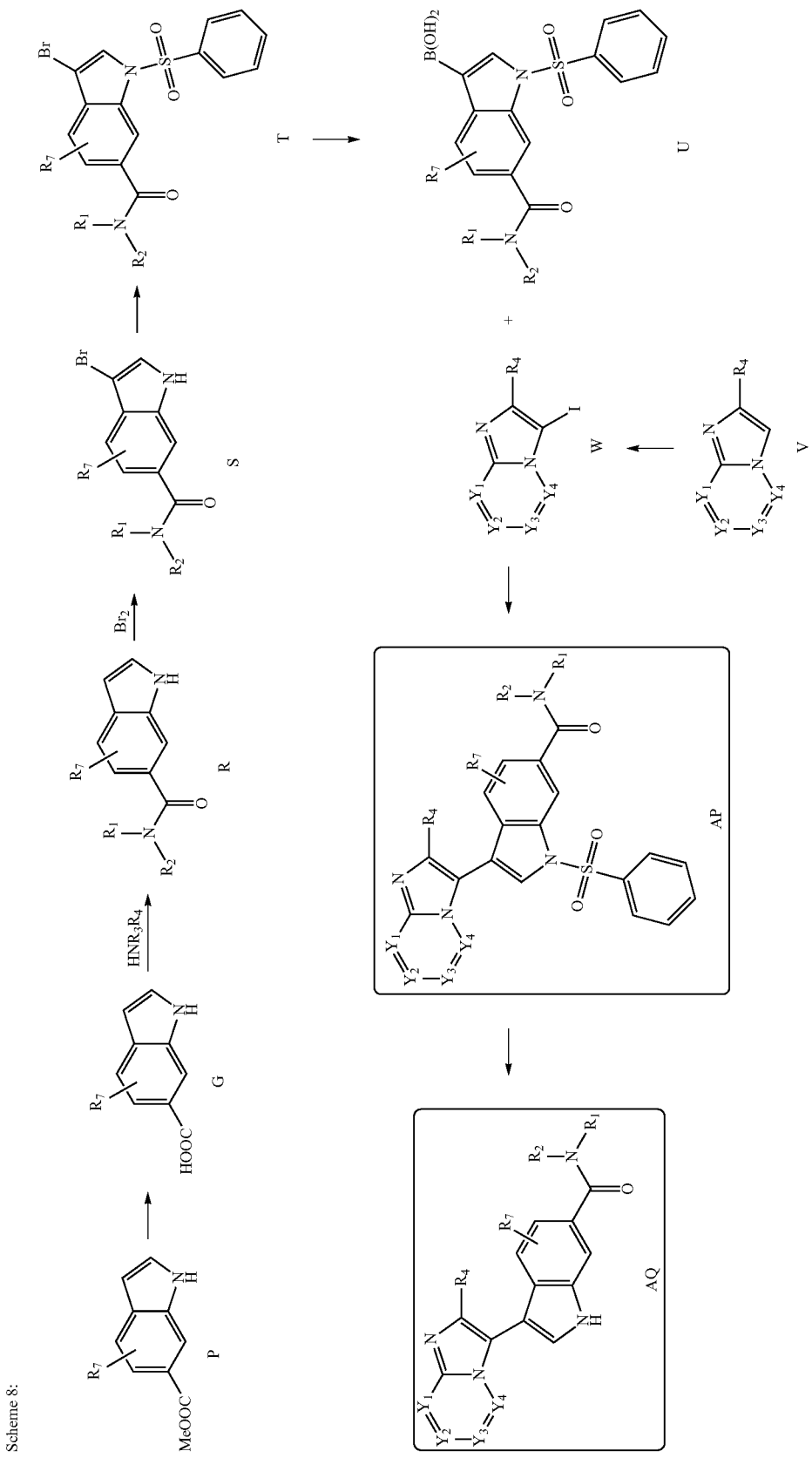

Scheme 9:

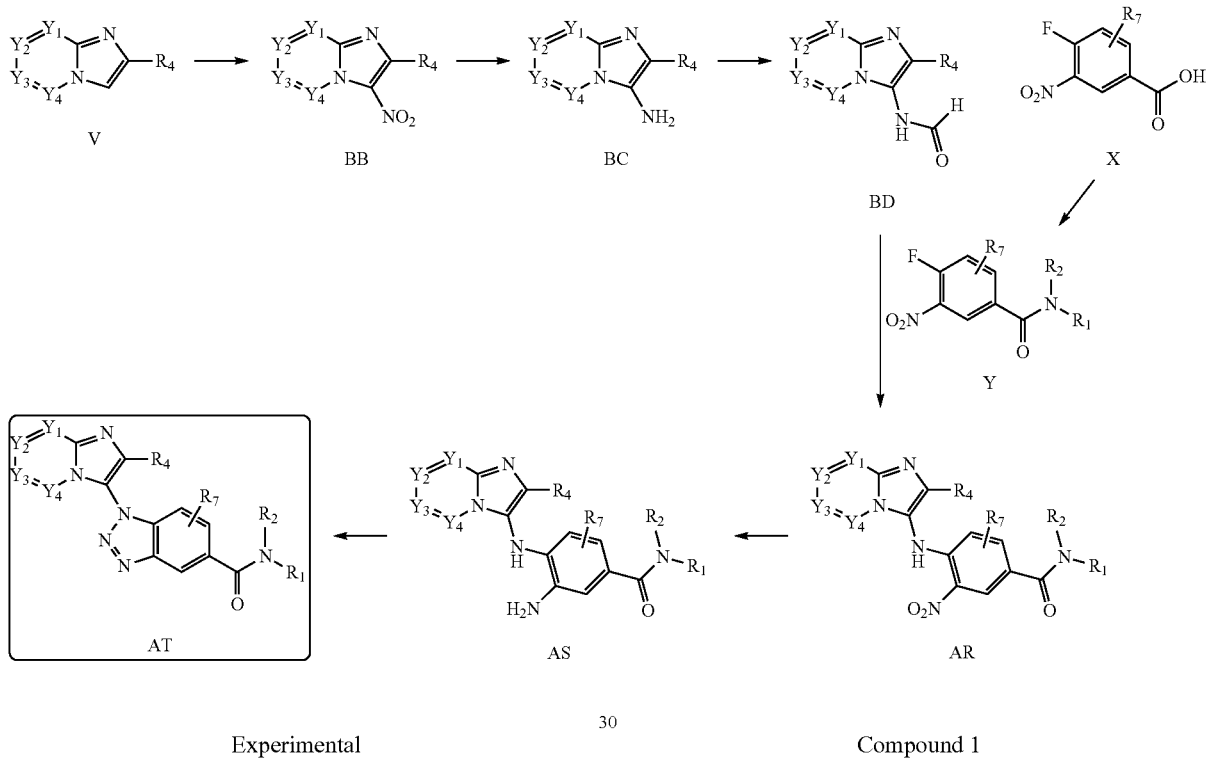

Experimental

General Conditions

All reagents were commercial grade and used without further purification. Commercially available anhydrous solvents were used for reactions conducted under inert atmosphere. Silica gel used for column chromatography was SDS silica gel (60AAC 40-63 μM). Thin layer chromatography was carried out using pre-coated silica gel F-254plate.

$^1$H NMR spectra were recorded on a Bruker® 400 MHz spectrometer. Proton chemical shifts are listed relative to residual CDCl$_3$ (7.27 ppm) or DMSO (2.50 ppm). Splitting patterns are designated as s (singlet), d (doublet), dd (double-doublet), t (triplet), q (quartet), m (multiplet), br (broad).

Electrospray MS spectra were obtained on a Waters® micromass platform LCMS spectrometer.

All mass spectra were full-scan experiments (mass range 100-1500 amu). Mass spectra were obtained using an electro spray ionization. The HPLC system was a Waters® platform with a 2767 sample manager, a 2525 pump, a photodiode array detector (190-400 nm). The column used was an Xterra C$_{18}$ 3.5 μM (4.6×50 mm) in analytical mode and an Atlantis d$_{C18}$ 5 μM (19×50 mm) in preparative mode. The mobile phase in both cases consisted in an appropriate gradient of A and B. A was water with 0.05% of TFA and B was acetonitrile with 0.05% of TFA. Flow rate was 1 mL per min. in analytical mode and 16.5 mL min in preparative mode. All LCMS were performed at room temperature.

General Procedure I: Formation of Compounds AB from Derivatives A in Presence Amide-Dimethylacetal B (Scheme 1).

A mixture of the selected amino-heterocycles A (1.0 equiv.) and dimethylformamide-dimethylacetal was heated through microwave irradiation for 7 min at 150° C. The reaction mixture was concentrated under reduced pressure to afford the product without further purification.

Compound 1

N,N-Dimethyl-N'-pyridin-2-yl-formamidine

Compound 1 was obtained according to general procedure I starting from 2-aminopyridine, as an orange oil in a quantitative yield.
M/Z (M+H)$^+$=150.

Compound 2

N'-(3-Bromo-pyridin-2-yl)-N,N-dimethyl-formamidine

Compound 2 was obtained according to general procedure I starting from 3-bromo-2-aminopyridine, as an orange oil in a quantitative yield.
M/Z (M[$^{79}$Br]+H)$^+$=228.

Compound 3

N'-(4-Methyl-pyridin-2-yl)-N,N-dimethyl-formamidine

Compound 3 was obtained according to general procedure starting from 2-amino-4-picoline, as a cream solid in a quantitative yield.
M/Z (M+H−27)$^+$=137.

Compound 4

N'-(4-Ethyl-pyridin-2-yl)-N,N-dimethyl-formamidine

Compound 4 was obtained according to general procedure I starting from 2-amino-4-ethylpyridine, as a cream solid in a quantitative yield.
M/Z (M+H)$^+$=178.

Compound 5

N'-(4-Cyano-pyridin-2-yl)-N,N-dimethyl-formamidine

Compound 5 was obtained according to general procedure I starting from 2-amino-4-cyanopyridine, as a cream solid in a quantitative yield.
M/Z (M+H)$^+$=175.

Compound 6

N'-(4-Chloro-pyridin-2-yl)-N,N-dimethyl-formamidine

Compound 6 was obtained according to general procedure I starting from 2-amino-4-chloropyridine, as a cream solid in a quantitative yield.
M/Z (M[$^{35}$Cl]+H)$^+$=184.

Compound 7

N'-(5-Cyano-pyridin-2-yl)-N,N-dimethyl-formamidine

Compound 7 was obtained according to general procedure I starting from 2-amino-5-cyanopyridine, as a cream solid in a quantitative yield.
M/Z (M+H)$^+$=175.

Compound 8

N'-(5-Fluoro-pyridin-2-yl)-N,N-dimethyl-formamidine

Compound 8 was obtained according to general procedure I starting from 2-amino-5-fluoropyridine, as a cream solid in a quantitative yield.
M/Z (M+H)$^+$=168.

Compound 9

N'-(5-Chloro-pyridin-2-yl)-N,N-dimethyl-formamidine

Compound 9 was obtained according to general procedure I starting from 2-amino-5-chloropyridine, as a cream solid in a quantitative yield.
M/Z (M[$^{35}$Cl]+H)$^+$=184.

Compound 10

N'-(5-Bromo-pyridin-2-yl)-N,N-dimethyl-formamidine

Compound 10 was obtained according to general procedure I starting from 2-amino-5-bromopyridine, as a cream solid in a quantitative yield.
M/Z (M[$^{79}$Br]+H)$^+$=228.

Compound 11

N,N-Dimethyl-N'-(5-methyl-pyridin-2-yl)-formamidine

Compound 11 was obtained according to general procedure I starting from 6-amino-3-picoline, as a cream solid in a quantitative yield.
M/Z (M+H)$^+$=164.

Compound 12

N'-(5-Methoxy-pyridin-2-yl)-N,N-dimethyl-formamidine

Compound 12 was obtained according to general procedure I starting from 2-amino-5-methoxy-pyridine, as dark brown oil in a quantitative yield.
M/Z (M+H)$^+$=180.

Compound 13

N,N-Dimethyl-N'-pyridin-2-yl-acetamidine

Compound 13 was obtained according to general procedure I with 2-aminopyridine in presence of dimethylacetamide-dimethylacetal instead of dimethylformamide-dimethyl-acetal, as an orange oil in a quantitative yield.
M/Z (M+H)$^+$=164.

Compound 14

N,N-Dimethyl-N'-(5-trifluoromethyl-pyridin-2-yl)-formamidine

Compound 14 was obtained according to general procedure I starting from 2-aminopyridine-5-(trifluoromethyl)-pyridine as a white solid in a quantitative yield.
M/Z (M+H)$^+$=218.

Compound 15

N'-(3,5-Dichloro-pyridin-2-yl)-N,N-dimethyl-formamidine

Compound 15 was obtained according to general procedure I starting from 2-aminopyridine-3,5-dichloropyridine as a pale brown solid in a quantitative yield.
M/Z (M[$^{35}$Cl$_2$]+H)$^+$=218.

Compound 16

N,N-Dimethyl-N'-(5-ethyl-pyridin-2-yl)-formamidine

Compound 16 was obtained according to general procedure I starting from 2-amino-5-ethyl-pyridine as a brown oil in a quantitative yield.
M/Z (M+H)$^+$=178.

Compound 17

N,N-Dimethyl-N'-(5-cyclopropyl-pyridin-2-yl)-formamidine

Compound 17 was obtained according to general procedure I starting from 2-amino-5-cyclopropyl-pyridine as a yellow oil. Compound 17, was contaminated (45%) by compound 1. The formation of this product is due to the presence of 2-amino-pyridine in the 2-amino-5-cyclopropyl-pyridine batch used in this reaction.
$^1$H-NMR (400 MHz, CDCl$_3$): 0.63-0.67 (m, 2H, CH$_2$); 0.92-0.96 (m, 2H, CH$_2$); 1.81-1.88 (m, 1H, CH); 3.08 (s, 3H, N—CH$_3$); 3.10 (s, 3H, N—CH$_3$); 6.86 (d, J 8.3 Hz, 1H, Ar); 7.21 (dd, J 2.6 Hz, J 8.3 Hz, 1H, Ar); 8.08 (d, J 2.6 Hz, 1H, Ar); 8.36 (s, 1H, N=CH—N).

Compound 18

N'-(5-Cyano-pyridin-2-yl)-N,N-dimethyl-acetamidine

Compound 18 was obtained according to general procedure I with 2-amino-5-cyanopyridine in presence of dimethyl-acetamidedimethylacetal instead of dimethylformamide-dimethylacetal, as a brown solid in a quantitative yield.
M/Z (M+H)$^+$=188.

General Procedure II: Formation of Compounds C or H from Benzoïc Acids I or G (scheme 4).

Method A: DIC or EDCI/HOBt coupling:

To a solution of the selected benzoïc acid I or G (1.0 equiv.) in a mixture of DMF and pyridine (9:1), DIC (1.5 equiv.) or EDCI (1.5 equiv.), HOBt (1.5 equiv.) and the selected amine (2.0-5.0 equiv.) were added. The resulting mixture was stirred at R.T. or heated at 60° C. for 0.5 to 15 days.

The reaction mixture was diluted with AcOEt, washed twice with HCl 1M, twice with water and once with brine. The organic layer was dried over MgSO$_4$, concentrated under reduced pressure and purified by flash-chromatography to afford the desired product.

Method B: POCl$_3$/Pyridine Coupling:

To a solution of the selected benzoïc acid I or G (1.2 equiv.) in pyridine under argon atmosphere and cooled at −20° C./0° C., the selected amine (5.0 equiv.) and phosphorus oxychloride (1.5 equiv) were successively added. After 30-40 min at 0° C., the reaction was hydrolyzed with HCl 1M and extracted with AcOEt. The organic layer was washed with brine, dried over MgSO$_4$ and concentrated under reduced pressure. Purification by flash-chromatography afforded the expected benzamide.

Method C: Via Acid Chloride Formation:

To a suspension of the selected benzoïc acid I or G (1.0 equiv.) in CH$_2$Cl$_2$ cooled at 0° C. under argon stream, DMF (5%) and oxalyl chloride (1.3 equiv.) were successively added dropwise. The reaction mixture was stirred at R.T. until a clear solution was obtained, then the selected amine (3.0 equiv.) was added. The reaction mixture was stirred at R.T. for 1 Hr, and then was hydrolyzed with HCl 1M. The layers were separated, the organic was washed with NaOH 1M, brine, dried over MgSO$_4$ and concentrated under reduced pressure. Purification by flash-chromatography afforded the product.

Compound 19

4-Acetyl-N-cyclohexyl-N-ethyl-benzamide

Compound 19 was obtained according to general procedure II, method A, starting from 4-acetylbenzoïc acid, cyclohexylethylamine (2.0 equiv.) and using DIC as coupling agent. The reaction was completed after 12 Hrs at R.T. Purification by flash-chromatography (AcOEt 25% to 50% in cyclohexane) afforded the product as an orange oil in 90% yield.
M/Z (M+H)$^+$=274.

Compound 20

1-[4-(Azepane-1-carbonyl)-phenyl]-ethanone

Compound 20 was obtained according to general procedure II, method A, starting from 4-acetylbenzoïc acid, hexamethyleneimine (2.0 equiv.) and using EDCI as coupling agent. The reaction was completed after 24 Hrs at R.T. followed by 12 Hrs at 60° C. Purification by flash-chormatography (AcOEt 50% in cyclohexane) afforded the product as an orange oil in 70% yield.
M/Z (M+H)$^+$=246.

Compound 21

4-Bromo-N-cyclohexyl-N-ethyl-3-methyl-benzamide

Compound 21 was obtained according to general procedure II, method A, starting from 4-bromo-3-methylbenzoïc acid, cyclohexylethylamine (5.0 equiv.) and using EDCI as coupling agent. The reaction was completed after 48 Hrs at R.T. Purification by flash chromatography (AcOEt 60% in cyclohexane) and trituration in pentane afforded the product in 24% yield.
M/Z (M[$^{79}$Br]+H)$^+$=324.

Compound 22

4-Bromo-N-cyclohexyl-N-ethyl-3-methoxy-benzamide

Compound 22 was obtained according to general procedure II, method A, starting from 4-bromo-3-methoxybenzoïc acid, cyclohexylethylamine (5.0 equiv.) and using EDCI as coupling agent. The reaction was completed after 48 Hrs at R.T. The product was isolated after trituration in pentane in 18% yield.
M/Z (M[$^{79}$Br]+H)$^+$=340.

Compound 23

4-Bromo-3-chloro-N-cyclohexyl-N-ethyl-benzamide

Compound 23 was obtained according to general procedure II, method A, starting from 4-bromo-3-chlorobenzoïc acid, cyclohexylethylamine (5.0 equiv.) and using EDCI as coupling agent. The reaction was completed after 48 Hrs at R.T. The product was isolated after trituration in pentane in 44% yield.
M/Z (M[$^{79}$Br$^{35}$Cl]+H)$^+$=344.

Compound 24

4-Bromo-N-cyclohexyl-N-ethyl-3-fluoro-benzamide

Compound 24 was obtained according to general procedure II, method A, starting from 4-bromo-3-fluorobenzoïc acid, cyclohexylethylamine (2.0 equiv.) and using EDCI as coupling agent. The reaction was completed after 48 Hrs at R.T. Purification by flash-chromatography (AcOEt 20% in cyclohexane) afforded the product as a pale yellow oil in 60% yield.
M/Z (M[$^{79}$Br]+H)$^+$=328.

Compound 25

4-Bromo-N-cyclohexyl-N-ethyl-3-nitro-benzamide

Compound 25 was obtained according to general procedure II, method B, starting from 4-bromo-3-nitrobenzoïc acid and cyclohexylethylamine. The reaction was cooled at −20° C. for 10 min, then allowed to reach 0° C. and hydrolysed after 30 min at 0° C. Purification by flash-chromatography (10% to 20% AcOEt in cyclohexane) afforded the product in 91% yield.

M/Z (M[$^{79}$Br]+H)$^+$=355.

Compound 26

6-Bromo-N-cyclohexyl-N-ethyl-nicotinamide

Compound 26 was obtained according to general procedure II, method A, starting from 6-bromonicotinic acid, cyclohexylethylamine (5.0 equiv.) and using EDCI (4.5 equiv.) as coupling agent. The reaction was stopped after 12 days at R.T. and 12 Hrs at 80° C. Purification by flash-chromatography (AcOEt 20% in cyclohexane) afforded the product in 14% yield.

M/Z (M[$^{79}$Br]+H)$^+$=311.

Compound 27

4-Bromo-2-chloro-N-cyclohexyl-N-ethyl-benzamide

Compound 27 was obtained according to general procedure II, method B, starting from 4-bromo-2-chlorobenzoïc acid and cyclohexylethylamine. The reaction was performed at 0° C. and was hydrolysed after 40 min. Purification by flash-chromatography (20% AcOEt in cyclohexane) afforded the product as a pale yellow solid in quantitative yield.

$^1$H-NMR (400 MHz, CDCl$_3$): mixture of 2 rotamers:

M/Z (M[$^{79}$Br$^{35}$Cl]+H)$^+$=344.

Compound 28

Azepan-1-yl-(4-bromo-3-fluoro-phenyl)-methanone

Compound 28 was obtained according to general procedure II, method C, starting from 4-bromo-3-fluorobenzoïc acid and hexamethyleneimine. Purification by flash-chromatography (10% to 30% AcOEt in cyclohexane) afforded the product in 88% yield.

M/Z (M[$^{79}$Br]+H)$^+$=300.

Compound 29

Azepan-1-yl-(4-bromo-3-nitro-phenyl)-methanone

Compound 29 was obtained according to general procedure II, method B, starting from 4-bromo-3-nitrobenzoïc acid and hexamethyleneimine. The reaction was cooled at −20° C. for 15 min then was allowed to reach R.T. and was hydrolyzed after 10 min. Purification by flash-chromatography (10% to 30% AcOEt in cyclohexane) afforded the product in 80% yield.

M/Z (M[$^{79}$Br]+H)$^+$=327.

Compound 30

N-Cyclohexyl-N-ethyl-3-hydroxy-4-nitro-benzamide

Compound 30 was obtained according to general procedure II, method A, starting from 3-hydroxy-4-nitrobenzoïc acid, cyclohexylethylamine (5.0 equiv.) and using EDCI as coupling agent. The reaction was completed after 12 Hrs at R.T. Purification by flash-chromatography (AcOEt 20% to 30% in cyclohexane) afforded the product as a yellow oil in 73% yield.

M/Z (M+H)$^+$=293.

Compound 31

N-Cyclohexyl-N-ethyl-4-hydroxy-3-nitro-benzamide

Compound 31 was obtained according to general procedure II, method A, starting from 4-hydroxy-3-nitrobenzoïc acid, cyclohexylethylamine (5.0 equiv.) and using EDCI as coupling agent. The reaction was completed after 48 Hrs at R.T. Purification by flash-chromatography (AcOEt 20% to 30% in cyclohexane) afforded the product as a yellow oil in 80% yield.

M/Z (M+H)$^+$=293.

Compound 32

Azepan-1-yl-(4-fluoro-3-nitro-phenyl)-methanone

Compound 32 was obtained according to general procedure II, method C, starting from 4-fluoro-3-nitrobenzoïc acid and hexamethyleneimine. Purification by flash-chromatography (0.5% to 1% MeOH in CH$_2$Cl$_2$) afforded the product in 76% yield.

M/Z (M+H)$^+$=267.

General Procedure III: Formation of Compounds C and E from Derivatives H and J (Scheme 4).

Method A:

To a solution of the selected bromo derivative H or J (1.0 equiv.) in trifluorotoluene and under argon atmosphere, (1-ethoxyvinyl)tributyltin (1.1 equiv.) and PdCl$_2$(PPh$_3$)$_2$ (0.05 equiv.) were added. The resulting mixture was heated through microwave irradiation at 150° C. for 15 min (maximum power limited to 70 Watt).

The catalyst was filtered off on celite and washed with AcOEt. The filtrate was washed with HCl 1M, brine, dried over MgSO$_4$ and concentrated under reduced pressure.

The residue was hydrolyzed with a mixture of THF/HCl 1M (1:1) over 2 Hrs at R.T.

The reaction mixture was diluted with AcOEt, washed with water, brine, dried over MgSO$_4$ and concentrated under reduced pressure. The residue was purified by flash-chromatography to afford the product.

Method B:

A mixture of the selected 4-bromo derivative H or J (1.0 equiv.), (1-ethoxyvinyl)tributyltin (1.1 equiv.), Pd(PPh$_3$)$_4$ (0.05 equiv.), copper (I) iodide (0.2 equiv.) and cesium fluoride (2.0 equiv.) was flushed with argon for 10 min, then DMF was added. The resulting mixture was heated at 80-100° C. overnight under argon stream.

The catalyst was filtered off on celite and washed with AcOEt. The filtrate was washed with HCl 1M, brine, dried over MgSO$_4$ and concentrated under reduced pressure.

The residue was hydrolyzed with a mixture of THF/HCl 1M (1:1) over 2 Hrs at R.T.

The reaction mixture was diluted with AcOEt, washed with HCl 1M, brine, dried over MgSO$_4$ and concentrated under reduced pressure. The residue was purified by flash-chromatography to afford the product.

Compound 33

4-Acetyl-N-cyclohexyl-N-ethyl-3-methyl-benzamide

Compound 33 was obtained according to general procedure III, method A, starting from compound 21. Purification by flash-chromatography (AcOEt 50% in cyclohexane) afforded the product in 75% yield.
M/Z (M+H)$^+$=288.

Compound 34

4-Acetyl-N-cyclohexyl-N-ethyl-3-methoxy-benzamide

Compound 34 was obtained according to general procedure III, method A, starting from compound 22. Purification by flash-chromatography (AcOEt 50% in cyclohexane) afforded the product in 52% yield.
M/Z (M+H)$^+$=304.

Compound 35

4-Acetyl-3-chloro-N-cyclohexyl-N-ethyl-benzamide

Compound 35 was obtained according to general procedure III, method A, starting from compound 23. Purification by flash-chromatography (AcOEt 50% in cyclohexane) afforded the product in 79% yield.
M/Z (M[$^{35}$Cl]+H)$^+$=308.

Compound 36

4-Acetyl-3-fluoro-N-cyclohexyl-N-ethyl-benzamide

Compound 36 was obtained according to general procedure III, method A, starting from compound 24. Purification by flash-chromatography (AcOEt 10% to 35% in cyclohexane) afforded the product as a yellow oil in 57% yield.
M/Z (M+H)$^+$=292.

Compound 37

4-Acetyl-N-cyclohexyl-N-ethyl-3-nitro-benzamide

Compound 37 was obtained according to general procedure III, method A, starting from compound 25. Purification by flash-chromatography (AcOEt 50% in cyclohexane) afforded the product in 62% yield.
M/Z (M+H)$^+$=319.

Compound 38

6-Acetyl-N-cyclohexyl-N-ethyl-nicotinamide

Compound 38 was obtained according to general procedure III, method A, starting from compound 26. Purification by flash-chromatography (AcOEt 20% to 50% in cyclohexane) afforded the product in 41% yield.
M/Z (M+H)$^+$=275.

Compound 39

6-Acetyl-N-cyclohexyl-N-ethyl-nicotinamide

Compound 39 was obtained according to general procedure III, method A, starting from compound 27 and adding LiCl (1.7 equiv.) to the reaction mixture. Purification by flash-chromatography (AcOEt 35% in cyclohexane) afforded the product as a pale yellow oil in 63% yield.
M/Z (M[$^{35}$Cl]+H)$^+$=308.

Compound 40

1-[4-(Azepane-1-carbonyl)-2-fluoro-phenyl]-ethanone

Compound 40 was obtained according to general procedure III, method B, starting from compound 28. Purification by flash-chromatography (AcOEt 10% to 50% in cyclohexane) afforded the product in 70% yield.
M/Z (M+H)$^+$=264.

Compound 41

1-[4-(Azepane-1-carbonyl)-2-nitro-phenyl]-ethanone

Compound 41 was obtained according to general procedure III, method B, starting from compound 29. Purification by flash-chromatography (AcOEt 10% to 50% in cyclohexane) afforded the product in 65% yield.
M/Z (M+H)$^+$=291.

Compound 42

Ethyl 4-bromo-3-fluorobenzoate

To a suspension of 4-bromo-3-fluorobenzoïc acid (15.0 g) in EtOH (230 mL), concentrated sulphuric acid (8.0 mL) was added. Reaction mixture was warmed at 60° C. for 66 Hrs. After cooling to room temperature, solvent was removed under reduced pressure. The residue was treated with NaOH 1N solution (70 mL), then extracted with EtOAc (500 mL). Organic layer was washed with water (250 mL), brine (250 mL), dried over MgSO$_4$ and then concentrated under reduced pressure. Product was obtained as a light yellow solid (17.0 g) in quantitative yield.
M/Z (M[$^{79}$Br]+H)$^+$=247.

Compound 43

Ethyl 4-acetyl-3-fluorobenzoate

Compound 43 was obtained according to general procedure III, method B, starting from compound 42. Purification by flash-chromatography (AcOEt 10% in cyclohexane) afforded the product in 86% yield.
M/Z (M+H)$^+$=211.

General Procedure IV: Formation of Compounds D and F from Derivatives C and E (Schemes 2 and 3).
Method A: using CuBr$_2$ To a refluxing suspension of copper (II) bromide (2.0 equiv.) in CHCl$_3$, under nitrogen stream, a solution of 4-acetyl derivative C or E (1.0 equiv.) in AcOEt (final ratio CHCl$_3$:AcOEt 1.2:1) was added dropwise. The reaction mixture was heated at reflux overnight.

After cooling at R.T., the inorganic materials were removed by filtration on celite and washed with AcOEt. The filtrate was concentrated under reduced pressure and purified by flash-chromatography to afford the desired product.
Method B: using Br$_2$ To a solution of 4-acetyl derivative C or E (1.0 equiv.) in chloroform under nitrogen atmosphere and cooled at 0° C., a solution of bromine (1.1 equiv.) in chloroform was added dropwise. The mixture was stirred at 0° C. for 30 min, then was allowed to warm to R.T. and stirred for 1H30.

The reaction mixture was treated with a saturated aqueous solution of NaHCO$_3$ and was extracted with CH$_2$Cl$_2$. The organic layer was washed with brine, dried over MgSO$_4$ and concentrated under reduced pressure. The resulting oil was purified by flash-chromatography to afford the desired product.

Compound 44

4-(2-Bromo-acetyl)-N-cyclohexyl-N-ethyl-benzamide

Compound 44 was obtained according to general procedure IV, method A, starting from compound 19. Purification by flash-chromatography (AcOEt 25% in cyclohexane) afforded the product as a cream waxy solid in 60% yield.
M/Z (M[$^{79}$Br]+H)$^+$=352.

Compound 45

1-[4-(Azepane-1-carbonyl)-phenyl]-2-bromo-ethanone

Compound 45 was obtained according to general procedure IV, method A, starting from compound 20. Purification by flash-chromatography (AcOEt 25% to 50% in cyclohexane) afforded the product as a cream waxy solid in 59% yield.
M/Z (M[$^{79}$Br]+H)$^+$=324.

Compound 46

4-(2-Bromo-acetyl)-N-cyclohexyl-N-ethyl-3-methyl-benzamide

Compound 46 was obtained according to general procedure IV, method A, starting from compound 33. Purification by flash-chromatography (AcOEt 10% to 50% in cyclohexane) afforded the product as a yellow oil in 52% yield.
M/Z (M[$^{79}$Br]+H)$^+$=364.

Compound 47

4-(2-Bromo-acetyl)-N-cyclohexyl-N-ethyl-3-methoxy-benzamide

Compound 47 was obtained according to general procedure IV, method A, starting from compound 34. Purification by flash-chromatography (AcOEt 50% in cyclohexane) afforded the product as a yellow oil in 33% yield.
M/Z (M[$^{79}$Br]+H)$^+$=382.

Compound 48

4-(2-Bromo-acetyl)-N-cyclohexyl-N-ethyl-3-chloro-benzamide

Compound 48 was obtained according to general procedure IV, method A, starting from compound 35. Purification by flash-chromatography (AcOEt 50% in cyclohexane) afforded the product in 66% yield.
M/Z (M[$^{79}$Br$^{35}$Cl]+H)$^+$=386.

Compound 49

4-(2-Bromo-acetyl)-N-cyclohexyl-N-ethyl-3-fluoro-benzamide

Compound 49 was obtained according to general procedure IV, method A, starting from compound 36. Purification by flash-chromatography (AcOEt 10% to 20% in cyclohexane) afforded the product as a yellow oil in 52% yield.
M/Z (M[$^{79}$Br]+H)$^+$=370.

Compound 50

4-(2-Bromo-acetyl)-N-cyclohexyl-N-ethyl-3-nitro-benzamide

Compound 50 was obtained according to general procedure IV, method A, starting from compound 37. Purification by flash-chromatography (AcOEt 50% in cyclohexane) afforded the product in 80% yield.
M/Z (M[$^{79}$Br]+H)$^+$=397.

Compound 51

6-(2-Bromo-acetyl)-N-cyclohexyl-N-ethyl-nicotinamide

Compound 51 was obtained according to general procedure IV, method A, starting from compound 38. Purification by flash-chromatography (AcOEt 50% in cyclohexane) afforded the product in 30% yield.
M/Z (M[$^{79}$Br]+H)$^+$=353.

Compound 52

4-(2-Bromo-acetyl)-2-chloro-N-cyclohexyl-N-ethyl-benzamide

Compound 52 was obtained according to general procedure IV, method A, starting from compound 39. Purification by flash-chromatography (AcOEt 30% in cyclohexane) afforded the product as a pale yellow oil in 76% yield.
M/Z (M[$^{79}$Br$^{35}$Cl]+H)$^+$=385.

Compound 53

1-[4-(Azepane-1-carbonyl)-2-fluoro-phenyl]-2-bromo-ethanone

Compound 53 was obtained according to general procedure IV, method A, starting from compound 40. Purification by flash-chromatography (AcOEt 10% to 50% in cyclohexane) afforded the product in 70% yield.
M/Z (M[$^{79}$Br]+H)$^+$=342.

Compound 54

1-[4-(Azepane-1-carbonyl)-2-nitro-phenyl]-2-bromo-ethanone

Compound 54 was obtained according to general procedure IV, method A, starting from compound 41. Purification by flash-chromatography (AcOEt 10% to 50% in cyclohexane) afforded the product in 60% yield.
M/Z (M[$^{79}$Br]+H)$^+$=369.

Compound 55

Ethyl 4-(2-bromo-acetyl)-3-fluorobenzoate

Compound 55 was obtained according to general procedure IV, method A, starting from compound 43. Purification by flash-chromatography (AcOEt 5% in cyclohexane) then trituration in pentane afforded the product as a white solid in 50% yield.

M/Z (M[$^{79}$Br]+H)$^+$=289

Compound 56

4-(2-Bromo-acetyl)-benzoïc acid methyl ester

Compound 56 was obtained according to general procedure IV, method B, starting from methyl 4-acetylbenzoate. Purification by flash-chromatography (EtOAc 10% in cyclohexane) afforded the product in 75% yield.

M/Z (M[$^{79}$Br]+H)$^+$=257.

General Procedure V: Formation of Examples AC and Compounds AD by Condensation of Derivatives D and F with Compounds AB (Schemes 2 and 3).

A mixture of the selected compounds AB (1.0 equiv.) and D or F (1.0 equiv.) in an appropriate solvent was heated either through microwave irradiation for 5-10 min at 130-200° C. or under conventional heating.

The reaction mixture was diluted with AcOEt and washed with aqueous HCl 1N, water, brine, dried over MgSO$_4$ and concentrated under reduced pressure. The residue was purified by flash-chromatography to afford the desired product.

Compound 57

4-(Imidazo[1,2-a]pyridine-3-carbonyl)-benzoïc acid methyl ester

Compound 57 was obtained according to general procedure V starting from compounds 1 and 56 in trifluorotoluene, through microwave irradiation for 5 min at 200° C. The product was isolated by reprecipitation from methanol as a white solid in 60% yield.

M/Z (M+H)$^+$=281.

Compound 58

4-(6-Fluoro-imidazo[1,2-a]pyridine-3-carbonyl)-benzoïc acid methyl ester

Compound 58 was obtained according to general procedure V starting from compounds 8 and 56 in toluene, through heating at 80° C. overnight.

Purification by flash-chromatography (EtOAc 50% in cyclohexane) afforded the product as a solid in 19% yield.

M/Z (M+H)$^+$=299.

Compound 59

Ethyl 4-[(6-cyanoimidazo[1,2-a]pyridin-3-yl)carbonyl]-3-fluorobenzoate

Compound 59 was obtained according to general procedure V starting from compounds 7 and 55 in DMF, through heating at 80° C. for 60 min.

Crystallization was induced by triturating crude with Et$_2$O to afford the product in 72% yield as a brown solid.

M/Z (M+H)$^+$=338.

Compound 60

Ethyl 4-[(6-fluoroimidazo[1,2-a]pyridin-3-yl)carbonyl]-3-fluorobenzoate

Compound 60 was obtained according to general procedure V starting from compounds 8 and 55 in DMF, through heating at 80° C. for 60 min.

Purification by flash-chromatography (EtOAc 90 to 50% in cyclohexane) followed by trituration in Et$_2$O afforded the product in 38% yield as a beige solid.

M/Z (M+H)$^+$=331.

Example 1

4-(8-Bromo-imidazo[1,2-a]pyridine-3-carbonyl)-N-cyclohexyl-N-ethyl-benzamide

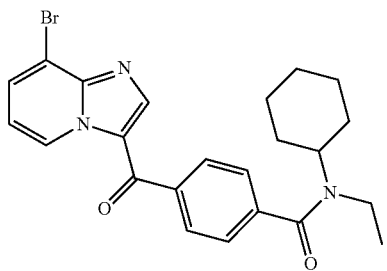 [SMILES: CCN(C(=O)c1ccc(C(=O)c2cnc3c(Br)cccn23)cc1)C1CCCCC1]

Example 1 was obtained according to general procedure V starting from compounds 2 and 44 in acetonitrile through microwave irradiation for 10 min at 150° C.

Purification by flash-chromatography (MeOH 2% in CH$_2$Cl$_2$) followed by preparative HPLC afforded the product as a pale green solid in 17% yield.

$^1$H-NMR (400 MHz, DMSO): 1.14-1.78 (m, 13H, 5*CH$_2$+CH$_3$); 3.36 (q, J 7.0 Hz, 2H, N—CH$_2$); 3.65 (bs, 1H, N—CH); 7.25 (t, J 7.1 Hz, 1H, Ar); 7.52 (m, 2H, Ar); 7.95 (m, 2H, Ar); 8.01 (m, 1H, Ar); 8.30 (s, 1H, Ar); 9.63 (m, 1H, Ar). M/Z (M[$^{79}$Br]+H)$^+$=454.

Example 2

N-Cyclohexyl-N-ethyl-4-(7-methyl-imidazo[1,2-a]pyridine-3-carbonyl)-benzamide

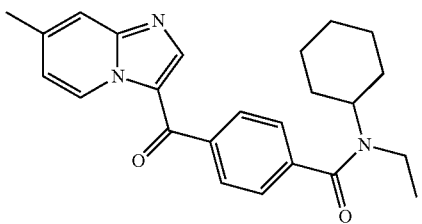 [SMILES: CCN(C(=O)c1ccc(C(=O)c2cnc3cc(C)ccn23)cc1)C1CCCCC1]

Example 2 was obtained according to general procedure V starting from compounds 3 and 44 in acetonitrile through microwave irradiation for 5 min at 130° C.

Purification by flash-chromatography (MeOH 2% in CH$_2$Cl$_2$) afforded the product as a pale yellow solid in 39% yield.

$^1$H-NMR (400 MHz, DMSO): 1.13-1.77 (m, 13H, 5*CH$_2$+CH$_3$); 3.36 (q, J 6.9 Hz, 2H, N—CH$_2$); 3.66 (bs, 1H, N—CH); 7.19 (dd, J 1.8 Hz, J 7.0 Hz, 1H, Ar); 7.50 (m, 2H, Ar); 7.66

(m, 1H, Ar); 7.92 (m, 2H, Ar); 8.19 (s, 1H, Ar); 9.53 (m, 1H, Ar). CH$_3$ signal under DMSO peak. M/Z (M+H)$^+$=390.

Example 3

N-Cyclohexyl-N-ethyl-4-(7-ethyl-imidazo[1,2-a]pyridine-3-carbonyl)-benzamide

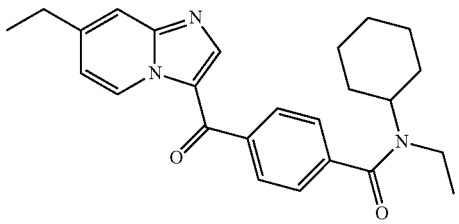 [SMILES: CCc1ccn2c(C(=O)c3ccc(C(=O)N(CC)C4CCCCC4)cc3)cnc2c1]

Example 3 was obtained according to general procedure V starting from compounds 4 and 44 in acetonitrile through microwave irradiation for 5 min at 130° C.

Purification by flash-chromatography (MeOH 1 to 2% in CH$_2$Cl$_2$) followed by preparative HPLC afforded the product as a white solid in 38% yield.

$^1$H-NMR (400 MHz, DMSO): 1.15 (m, 6H, 3*CH$_2$); 1.32 (t, J 7.5 Hz, 3H, CH$_3$); 1.57-1.77 (m, 7H, 2*CH$_2$+CH$_3$); 2.83 (q, J 7.6 Hz, 2H, CH$_2$); 3.66 (bs, 1H, N—CH); 7.26 (dd, J 1.7 Hz, J 7.1 Hz, 1H, Ar); 7.50 (m, 2H, Ar); 7.67 (m, 1H, Ar); 7.92 (m, 2H, Ar); 8.24 (s, 1H, Ar); 9.55 (d, J 7.1 Hz, 1H, Ar). N—CH$_2$ signal under water peak. M/Z (M+H)$^+$=404.

Example 4

4-(7-Cyano-imidazo[1,2-a]pyridine-3-carbonyl)-N-cyclohexyl-N-ethyl-benzamide

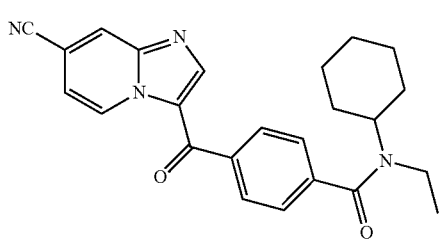 [SMILES: CCN(C(=O)c1ccc(C(=O)c2cnc3cc(C#N)ccn23)cc1)C1CCCCC1]

Example 4 was obtained according to general procedure V starting from compounds 5 and 44 in acetonitrile through microwave irradiation for 5 min at 150° C.

Purification by flash-chromatography (MeOH 1 to 2% in CH$_2$Cl$_2$) followed by preparative HPLC afforded the product as a white solid in 27% yield.

$^1$H-NMR (400 MHz, DMSO): 1.14-1.77 (m, 13H, 5*CH$_2$+CH$_3$); 3.36 (q, J 6.9 Hz, 2H, N—CH$_2$); 3.66 (bs, 1H, N—CH); 7.53 (m, 2H, Ar); 7.57 (dd, J 1.7 Hz, J 7.2 Hz, 1H, Ar); 7.97 (m, 2H, Ar); 8.44 (s, 1H, Ar); 8.53 (m, 1H, Ar); 9.68 (dd, J 1.0 Hz, J 7.1 Hz, 1H, Ar). M/Z (M+H)$^+$=401.

Example 5

4-(7-Chloro-imidazo[1,2-a]pyridine-3-carbonyl)-N-cyclohexyl-N-ethyl-benzamide

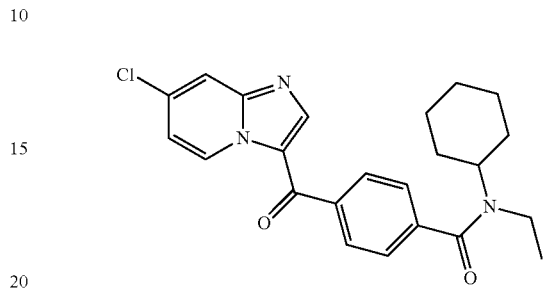

Example 5 was obtained according to general procedure V starting from compounds 6 and 44 in acetonitrile through microwave irradiation for 5 min at 130° C.

Purification by flash-chromatography (MeOH 1 to 2% in CH$_2$Cl$_2$) followed by preparative HPLC afforded the product as a white solid in 43% yield.

$^1$H-NMR (400 MHz, DMSO): 1.13-1.77 (m, 13H, 5*CH$_2$+CH$_3$); 3.36 (q, J 7.0 Hz, 2H, N—CH$_2$); 3.66 (bs, 1H, N—CH); 7.39 (dd, J 2.2 Hz, J 7.3 Hz, 1H, Ar); 7.51 (m, 2H, Ar); 7.94 (m, 2H, Ar); 8.01 (dd, J 0.7 Hz, J 2.3 Hz, 1H, Ar); 8.28 (s, 1H, Ar); 9.61 (dd, J 0.7 Hz, J 7.3 Hz, 1H, Ar). M/Z (M[$^{35}$Cl]+H)$^+$=410. Mp: 133-135° C.

Example 6

4-(7-Fluoro-imidazo[1,2-a]pyridine-3-carbonyl)-N-cyclohexyl-N-ethyl-benzamide

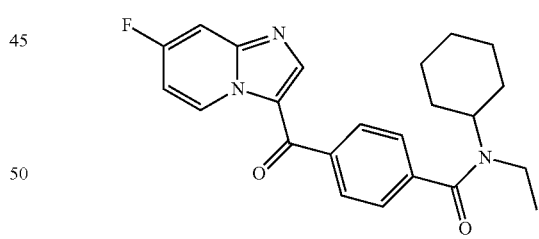

To a solution of example 5 (50 mg, 1.0 equiv.) in DMA (1 mL), spraydry potassium fluoride (71 mg, 10 equiv.) and kryptofix (138 mg, 3.0 equiv.) were added. The resulting mixture was heated through microwave irradiation for 5 min at 180° C. twice. After cooling at R.T., the reaction mixture was diluted with AcOEt (10 mL) and washed with water (3*10 mL), brine (10 mL), dried over MgSO$_4$ and concentrated under reduced pressure. Purification by flash-chromatography (MeOH 2% in CH$_2$Cl$_2$) followed by preparative HPLC afforded the product as an off-white solid (26 mg, 50%).

$^1$H-NMR (400 MHz, DMSO): 1.13-1.77 (m, 13H, 5*CH$_2$+CH$_3$); 3.36 (q, J 6.9 Hz, 2H, N—CH$_2$); 3.66 (bs, 1H, N—CH);

7.34 (m, 1H, Ar); 7.51 (m, 2H, Ar); 7.70 (m, 1H, Ar); 7.93 (m, 2H, Ar); 8.26 (s, 1H, Ar); 9.67 (m, 1H, Ar). M/Z (M+H)$^+$=394.

Example 7

4-(6-Cyano-imidazo[1,2-a]pyridine-3-carbonyl)-N-cyclohexyl-N-ethyl-benzamide

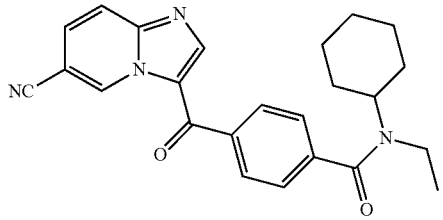 [SMILES: CCN(C(=O)c1ccc(C(=O)c2cnc3ccc(C#N)cn23)cc1)C1CCCCC1]

Example 7 was obtained according to general procedure V starting from compounds 7 and 44 in acetonitrile through microwave irradiation for 5 min at 130° C.

Purification by flash-chromatography (MeOH 1 to 2% in CH$_2$Cl$_2$) followed by preparative HPLC afforded the product as a white solid in 25% yield.

$^1$H-NMR (400 MHz, DMSO): 1.14-1.77 (m, 13H, 5*CH$_2$+CH$_3$); 3.36 (q, J 7.0 Hz, 2H, N—CH$_2$); 3.66 (bs, 1H, N—CH); 7.53 (m, 2H, Ar); 7.91 (dd, J 1.7 Hz, J 9.2 Hz, 1H, Ar); 7.96-8.03 (m, 3H, Ar); 8.43 (s, 1H, Ar); 10.05 (m, 1H, Ar). M/Z (M+H)$^+$=401.

Example 8

4-(6-Fluoro-imidazo[1,2-a]pyridine-3-carbonyl)-N-cyclohexyl-N-ethyl-benzamide

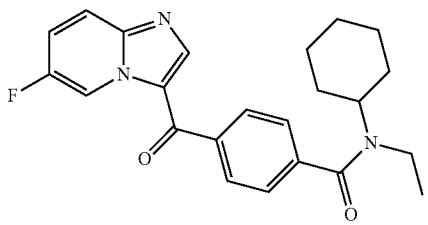 [SMILES: CCN(C(=O)c1ccc(C(=O)c2cnc3ccc(F)cn23)cc1)C1CCCCC1]

Example 8 was obtained according to general procedure V starting from compounds 8 (1.6 equiv.) and 44 in trifluorotoluene through microwave irradiation for 10 min at 150° C. and 5 min at 200° C.

Purification by flash-chromatography (MeOH 1 to 2% in CH$_2$Cl$_2$) followed by preparative HPLC afforded the product as a white solid in 16% yield.

$^1$H-NMR (400 MHz, DMSO): 0.99-1.67 (m, 13H, 5*CH$_2$+CH$_3$); 3.32-3.40 (m, 3H, N—CH$_2$+N—CH); 7.52 (m, 2H, Ar); 7.85 (m, 1H, Ar); 7.95 (m, 2H, Ar); 8.01 (m, 1H, Ar); 8.39 (s, 1H, Ar); 9.67 (m, 1H, Ar). M/Z (M+H)$^+$=394.

Example 9

4-(6-Chloro-imidazo[1,2-a]pyridine-3-carbonyl)-N-cyclohexyl-N-ethyl-benzamide

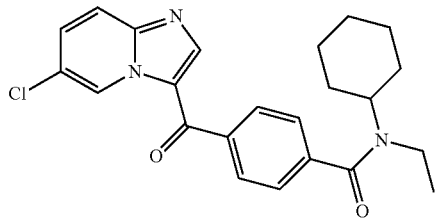 [SMILES: CCN(C(=O)c1ccc(C(=O)c2cnc3ccc(Cl)cn23)cc1)C1CCCCC1]

Example 9 was obtained according to general procedure V starting from compounds 9 and 44 in trifluorotoluene through microwave irradiation for 5 min at 130° C.

Purification by preparative HPLC afforded the product as a yellow solid in 37% yield.

$^1$H-NMR (400 MHz, DMSO): 1.13-1.78 (m, 13H, 5*CH$_2$+CH$_3$); 3.36 (q, J 7.0 Hz, 2H, N—CH$_2$); 3.66 (bs, 1H, N—CH); 7.52 (m, 2H, Ar); 7.75 (m, 1H, Ar); 7.90-7.96 (m, 3H, Ar); 8.31 (s, 1H, Ar); 9.70 (m, 1H, Ar). M/Z (M[$^{35}$Cl]+H)$^+$=410

Example 10

4-(6-Bromo-imidazo[1,2-a]pyridine-3-carbonyl)-N-cyclohexyl-N-ethyl-benzamide

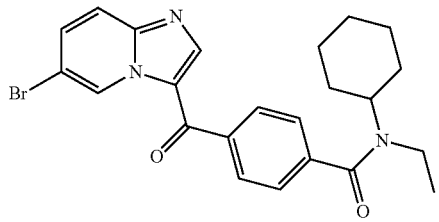 [SMILES: CCN(C(=O)c1ccc(C(=O)c2cnc3ccc(Br)cn23)cc1)C1CCCCC1]

Example 10 was obtained according to general procedure V starting from compounds 10 and 44 in trifluorotoluene through microwave irradiation for 5 min at 130° C.

Purification by flash-chromatography (MeOH 2% in CH$_2$Cl$_2$) followed by preparative HPLC afforded the product as a cream solid in 15% yield.

$^1$H-NMR (400 MHz, DMSO): 0.99-1.69 (m, 13H, 5*CH$_2$+CH$_3$); 3.19-3.40 (m, 3H, N—CH$_2$+N—CH); 7.52 (m, 2H, Ar); 7.86-7.95 (m, 4H, Ar); 8.36 (s, 1H, Ar); 9.78 (m, 1H, Ar). M/Z (M[$^{79}$Br]+H)$^+$=454. Mp: 96-101° C.

Example 11

N-Cyclohexyl-N-ethyl-4-(6-methyl-imidazo[1,2-a]pyridine-3-carbonyl)-benzamide

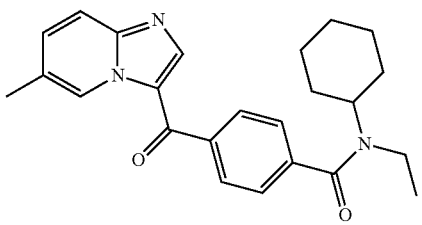 [SMILES: CCN(C(=O)c1ccc(C(=O)c2cnc3ccc(C)cn23)cc1)C1CCCCC1]

Example 11 was obtained according to general procedure V starting from compounds 11 and 44 in acetonitrile through microwave irradiation for 5 min at 150° C.

Purification by flash-chromatography (MeOH 2% in CH$_2$Cl$_2$) afforded the product as a pale yellow solid in 42% yield.

$^1$H-NMR (400 MHz, DMSO): 1.10-1.77 (m, 13H, 5*CH$_2$+CH$_3$); 2.46 (d, J 0.99 Hz, 3H, CH$_3$); 3.36 (m, 2H, N—CH$_2$); 3.66 (bs, 1H, N—CH); 7.50 (m, 2H, Ar); 7.57 (dd, J 1.8 Hz, J 9.0 Hz, 1H, Ar); 7.78 (d, J 9.1 Hz, 1H, Ar); 7.92 (m, 2H, Ar); 8.19 (s, 1H, Ar); 9.50 (m, 1H, Ar). M/Z (M+H)$^+$=390.

Example 12

N-Cyclohexyl-N-ethyl-4-(6-methoxy-imidazo[1,2-a]pyridine-3-carbonyl)-benzamide

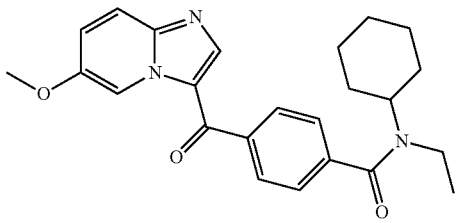 [SMILES: CCN(C(=O)c1ccc(C(=O)c2cnc3ccc(OC)cn23)cc1)C1CCCCC1]

Example 12 was obtained according to general procedure V starting from compounds 12 and 44 in acetonitrile through microwave irradiation for 10 min at 150° C.

Purification by flash-chromatography (MeOH 2% in CH$_2$Cl$_2$) followed by preparative HPLC afforded the product as a pale yellow solid in 11% yield.

$^1$H-NMR (400 MHz, DMSO): 1.13-1.77 (m, 13H, 5*CH$_2$+CH$_3$); 3.36 (m, 2H, N—CH$_2$); 3.66 (bs, 1H, N—CH); 3.94 (s, 3H, O—CH$_3$); 7.52 (m, 3H, Ar); 7.81 (d, J 9.6 Hz, 1H, Ar); 7.92 (m, 2H, Ar); 8.21 (s, 1H, Ar); 9.36 (m, 1H, Ar). M/Z (M+H)$^+$=406.

Example 13

N-Cyclohexyl-N-ethyl-4-(2-methyl-imidazo[1,2-a]pyridine-3-carbonyl)-benzamide

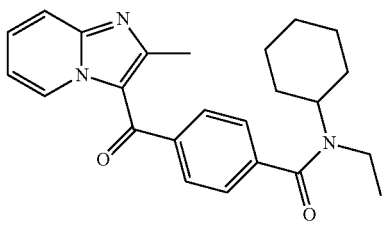 [SMILES: CCN(C(=O)c1ccc(C(=O)c2c(C)nc3ccccn23)cc1)C1CCCCC1]

Example 13 was obtained according to general procedure V starting from compounds 13 and 44 in acetonitrile through microwave irradiation for 5 min at 150° C.

Purification by flash-chromatography (MeOH 2% in CH$_2$Cl$_2$) followed by preparative HPLC afforded the product as a cream solid in 59% yield.

$^1$H-NMR (400 MHz, DMSO): 1.10-1.79 (m, 13H, 5*CH$_2$+CH$_3$); 2.10 (s, 3H, CH$_3$); 3.36 (q, J 7.2 Hz, 2H, N—CH$_2$); 3.60 (bs, 1H, N—CH); 7.27 (m, 1H, Ar); 7.49 (m, 2H, Ar); 7.65-7.76 (m, 4H, Ar); 9.40 (m, 1H, Ar). M/Z (M+H)$^+$=390.

Example 14

[4-(Azepane-1-carbonyl)-phenyl]-(6-fluoro-imidazo[1,2-a]pyridin-3-yl)-methanone

Example 14 was obtained according to general procedure V starting from compounds 8 and 45 in DMF and heating at 80° C. for 60 min.

Purification by flash-chromatography (MeOH 0 to 5% in CH$_2$Cl$_2$) afforded the product as a yellow solid in 32% yield.

$^1$H-NMR (400 MHz, DMSO): 1.15-1.76 (m, 8H, 4*CH$_2$); 3.34 (m, 2H, N—CH$_2$); 3.60 (t, J 5.9 Hz, 2H, N—CH$_2$); 7.55 (m, 2H, Ar); 7.84 (m, 1H, Ar); 7.94 (m, 2H, Ar); 8.01 (m, 1H, Ar); 8.38 (s, 1H, Ar); 9.67 (m, 1H, Ar). M/Z (M+H)$^+$=366. Mp: 165-169° C.

Example 15

3-[4-(Azepane-1-carbonyl)-benzoyl]-imidazo[1,2-a]pyridine-6-carbonitrile

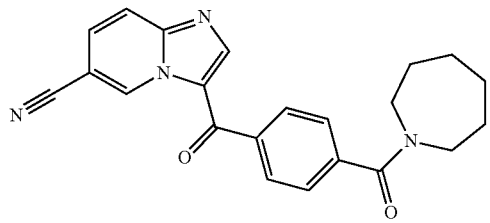 [SMILES: N#Cc1ccc2ncc(C(=O)c3ccc(C(=O)N4CCCCCC4)cc3)n2c1]

Example 15 was obtained according to general procedure V starting from compounds 7 and 45 in acetonitrile through microwave irradiation for 5 min at 130° C.

Purification by flash-chromatography (MeOH 2% to 4% in CH$_2$Cl$_2$) afforded the product as a cream solid in 20% yield.

$^1$H-NMR (400 MHz, DMSO): 1.62-1.70 (m, 8H, 4*CH$_2$); 3.51 (bs, 4H, 2*N—CH$_2$); 7.57 (m, 2H, Ar); 7.97 (m, 4H, Ar); 8.43 (s, 1H, Ar); 10.05 (s, 1H, Ar). M/Z (M+H)$^+$=373.

Example 16

N-Cyclohexyl-N-ethyl-4-(imidazo[1,2-a]pyridine-3-carbonyl)-3-methyl-benzamide

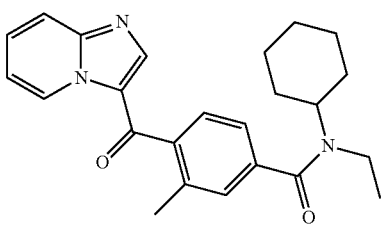 [SMILES: CCN(C(=O)c1ccc(C(=O)c2cnc3ccccn23)c(C)c1)C1CCCCC1]

Example 16 was obtained according to general procedure V starting from compounds 1 and 46 in trifluorotoluene through microwave irradiation for 5 min at 200° C.

Purification by preparative HPLC afforded the product as an orange oil in 46% yield.

$^1$H-NMR (400 MHz, DMSO): 1.13-1.71 (m, 13H, 5*CH$_2$+CH$_3$); 2.37 (s, 3H, CH$_3$); 3.36 (q, J 6.3 Hz, 2H, N—CH$_2$); 3.69 (bs, 1H, N—CH); 7.24-7.32 (m, 2H, Ar); 7.37 (t, J 6.8 Hz, 1H, Ar); 7.56 (d, J 6.9 Hz, 1H, Ar); 7.73 (t, J 7.9 Hz, 1H, Ar); 7.87 (m, 2H, Ar); 9.69 (dd, J 0.9 Hz, J 6.9 Hz, 1H, Ar). M/Z (M+H)$^+$=390.

Example 17

N-Cyclohexyl-N-ethyl-4-(6-fluoro-imidazo[1,2-a]pyridine-3-carbonyl)-3-methyl-benzamide

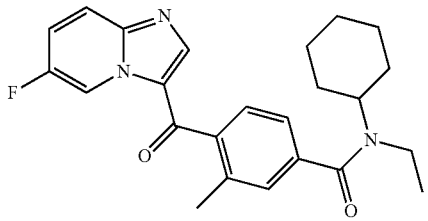

Example 17 was obtained according to general procedure V starting from compounds 8 and 46 in trifluorotoluene through microwave irradiation for 5 min at 200° C.

Purification by preparative HPLC afforded the product as an orange oil in 37% yield.

$^1$H-NMR (400 MHz, DMSO): 1.13-1.76 (m, 13H, 5*CH$_2$+CH$_3$); 2.37 (s, 3H, CH$_3$); 3.35 (bm, 2H, N—CH$_2$); 3.69 (bs, 1H, N—CH); 7.19-7.33 (m, 2H, Ar); 7.57 (m, 1H, Ar); 7.78 (m, 1H, Ar); 7.93 (m, 2H, Ar); 9.68 (m, 1H, Ar). M/Z (M+H)$^+$=408.

Example 18

N-Cyclohexyl-N-ethyl-4-(imidazo[1,2-a]pyridine-3-carbonyl)-3-methoxy-benzamide

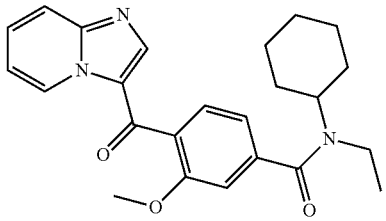 [SMILES: CCN(C(=O)c1ccc(C(=O)c2cnc3ccccn23)c(OC)c1)C1CCCCC1]

Example 18 was obtained according to general procedure V starting from compounds 1 and 47 in trifluorotoluene through microwave irradiation for 5 min at 200° C.

Purification by preparative HPLC afforded the product as an orange oil in 20% yield.

$^1$H-NMR (400 MHz, CDCl$_3$): 0.99-1.32 (m, 13H, 5*CH$_2$+CH$_3$); 3.23 (bs, 1H, N—CH); 3.39 (bs, 2H, N—CH$_2$); 3.78 (s, 3H, O—CH$_3$); 7.01 (dd, J 1.2 Hz, J 7.5 Hz, 1H, Ar); 7.11 (d, J 1.2 Hz, 1H, Ar); 7.42 (m, 1H, Ar); 7.49 (d, J 7.5 Hz, 1H, Ar); 7.78 (m, 1H, Ar); 7.92 (d, J 9.0 Hz, 1H, Ar); 8.05 (s, 1H, Ar); 9.68 (d, J 6.8 Hz, 1H, Ar). M/Z (M+H)$^+$=406.

Example 19

N-Cyclohexyl-N-ethyl-4-(imidazo[1,2-a]pyridine-3-carbonyl)-3-chloro-benzamide

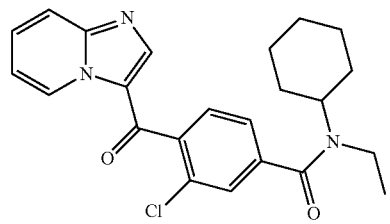 [SMILES: CCN(C(=O)c1ccc(C(=O)c2cnc3ccccn23)c(Cl)c1)C1CCCCC1]

Example 19 was obtained according to general procedure V starting from compounds 1 and 48 in trifluorotoluene through microwave irradiation for 5 min at 200° C.

Purification by preparative HPLC afforded the product as a green solid in 33% yield.

$^1$H-NMR (400 MHz, DMSO): 1.13-1.82 (m, 13H, 5*CH$_2$+CH$_3$); 3.36 (q, J 7.0 Hz, 2H, N—CH$_2$); 3.66 (bs, 1H, N—CH); 7.40 (m, 1H, Ar); 7.44 (dd, J 1.6 Hz, J 7.7 Hz, 1H, Ar); 7.53 (dd, J 0.3 Hz, J 1.6 Hz, 1H, Ar); 7.69 (dd, J 0.3 Hz, J 7.7 Hz, 1H, Ar); 7.76 (m, 1H, Ar); 7.89 (m, 1H, Ar); 7.94 (s, 1H, Ar); 9.66 (m, 1H, Ar). M/Z (M[$^{35}$Cl]+H)$^+$=410.

Example 20

3-Chloro-N-cyclohexyl-N-ethyl-4-(6-fluoro-imidazo[1,2-a]pyridine-3-carbonyl)-benzamide

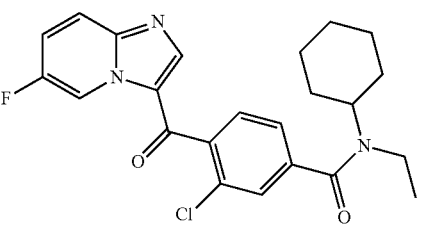

Example 20 was obtained according to general procedure V starting from compounds 8 and 48 in trifluorotoluene through microwave irradiation for 5 min at 200° C.

Purification by preparative HPLC afforded the product as a cream solid (yield<5%).

$^1$H-NMR (400 MHz, DMSO): 1.11-1.83 (m, 13H, 5*CH$_2$+CH$_3$); 3.36 (q, J 7.0 Hz, 2H, N—CH$_2$); 3.66 (bs, 1H, N—CH); 7.45 (dd, J 1.5 Hz, J 7.7 Hz, 1H, Ar); 7.54 (dd, J 0.4 Hz, J 1.5

Hz, 1H, Ar); 7.69 (dd, J 0.4 Hz, J 7.7 Hz, 1H, Ar); 7.82 (m, 1H, Ar); 7.95-8.00 (m, 2H, Ar); 9.64 (m, 1H, Ar). M/Z (M[$^{35}$Cl]+H)$^+$=428.

Example 21

N-Cyclohexyl-N-ethyl-3-fluoro-4-(6-fluoro-imidazo[1,2-a]pyridine-3-carbonyl)-benzamide

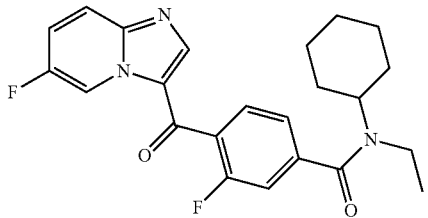 [SMILES: CCN(C(=O)c1ccc(C(=O)c2cnc3ccc(F)cn23)c(F)c1)C1CCCCC1]

Example 21 was obtained according to general procedure V starting from compounds 8 and 49 in acetonitrile through microwave irradiation for 5 min at 130° C.

Purification by flash-chromatography (MeOH 2% in CH$_2$Cl$_2$) followed by preparative HPLC afforded the product as a green solid in 22% yield.

$^1$H-NMR (400 MHz, DMSO): 1.14-1.79 (m, 13H, 5*CH$_2$+CH$_3$); 3.37 (q, J 7.0 Hz, 2H, N—CH$_2$); 3.66 (bs, 1H, N—CH); 7.33 (m, 2H, Ar); 7.73-7.83 (m, 2H, Ar); 7.96 (m, 1H, Ar); 8.16 (bs, 1H, Ar). M/Z (M+H)$^+$=412.

Example 22

N-Cyclohexyl-N-ethyl-4-(6-fluoro-imidazo[1,2-a]pyridine-3-carbonyl)-3-nitro-benzamide

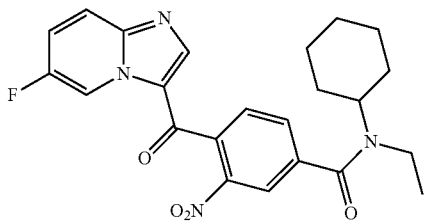

Example 22 was obtained according to general procedure V starting from compounds 8 and 50 in trifluorotoluene through microwave irradiation for 5 min at 200° C.

Purification by flash-chromatography (MeOH 1% in CH$_2$Cl$_2$) afforded the product in 41% yield.

$^1$H-NMR (400 MHz, DMSO): 1.13-1.83 (m, 13H, 5*CH$_2$+CH$_3$); 3.39 (q, J 7.0 Hz, 2H, N—CH$_2$); 3.67 (bs, 1H, N—CH); 7.82 (m, 1H, Ar); 7.87 (d, J 1.0 Hz, 2H, Ar); 7.97 (m, 1H, Ar); 8.09 (s, 1H, Ar); 8.13 (t, J 1.0 Hz, 1H, Ar); 9.58 (m, 1H, Ar). M/Z (M+H)$^+$=439.

Example 23

N-Cyclohexyl-N-ethyl-6-(imidazo[1,2-a]pyridine-3-carbonyl)-nicotinamide

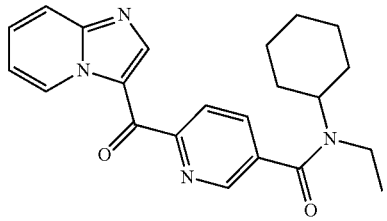 [SMILES: CCN(C(=O)c1ccc(C(=O)c2cnc3ccccn23)nc1)C1CCCCC1]

Example 23 was obtained according to general procedure V starting from compounds 1 and 51 in trifluorotoluene through microwave irradiation for 5 min at 200° C.

Purification by preparative HPLC afforded the product as a black solid in 8% yield.

$^1$H-NMR (400 MHz, DMSO): 1.12-1.83 (m, 13H, 5*CH$_2$+CH$_3$); 3.39 (q, J 7.0 Hz, 2H, N—CH$_2$); 3.65 (bs, 1H, N—CH); 7.37 (m, 1H, Ar); 7.73 (m, 1H, Ar); 7.90 (m, 1H, Ar); 8.02 (dd, J 2.1 Hz, J 8.0 Hz, 1H, Ar); 8.17 (dd, J 0.8 Hz, J 8.0 Hz, 1H, Ar); 8.76 (dd, J 0.8 Hz, J 2.1 Hz, 1H, Ar); 9.12 (s, 1H, Ar); 9.81 (m, 1H, Ar). M/Z (M+H)$^+$=377.

Example 24

2-Chloro-N-cyclohexyl-N-ethyl-4-(6-fluoro-imidazo[1,2-a]pyridine-3-carbonyl)-benzamide

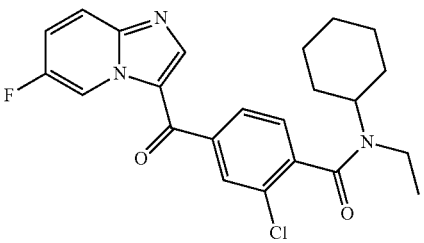 [SMILES: CCN(C(=O)c1ccc(C(=O)c2cnc3ccc(F)cn23)cc1Cl)C1CCCCC1]

Example 24 was obtained according to general procedure V starting from compounds 8 and 52 in DMF through microwave irradiation for 5 min at 200° C.

Purification by flash-chromatography (AcOEt 100%) followed by trituration in Et$_2$O afforded the product as a cream solid in 14% yield.

$^1$H-NMR (400 MHz, DMSO): 0.89-1.85 (m, 13H, 5*CH$_2$+CH$_3$); 3.09 (m, 1H, N—CH); 3.51 (m, 1H, N—CH); 7.56 (m, 1H, Ar); 7.82-7.95 (m, 3H, Ar); 8.01 (m, 1H, Ar); 8.41 (s, 1H,

Ar); 9.63 (m, 1H, Ar). N—CH signal under water peak. M/Z (M[$^{35}$Cl]+H)$^+$=428. Mp: 163-168° C.

Example 25

[4-(Azepane-1-carbonyl)-phenyl]-(6-trifluoromethyl-imidazo[1,2-a]pyridin-3-yl)-methanone

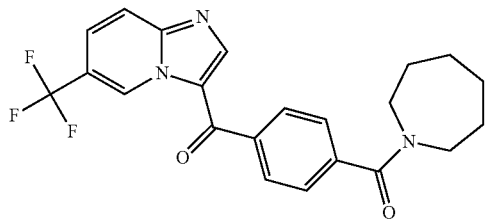 [SMILES: O=C(c1ccc(C(=O)N2CCCCCC2)cc1)c1cnc2ccc(C(F)(F)F)cn12]

Example 25 was obtained according to general procedure V starting from compounds 14 and 45 in DMA through microwave irradiation for 5 min at 130° C.

Purification by flash-chromatography (MeOH 2% in CH$_2$Cl$_2$) followed by trituration in Et$_2$O afforded the product as a pale yellow solid in 20% yield.

$^1$H-NMR (400 MHz, DMSO): 1.50-1.64 (bm, 6H, 3*CH$_2$); 1.72-1.79 (bm, 2H, CH$_2$); 3.35 (m, 2H, N—CH$_2$); 3.60 (t, J 5.8 Hz, 2H, N—CH$_2$); 7.57 (m, 2H, Ar); 7.95-7.99 (m, 3H, Ar); 8.12 (m, 1H, Ar); 8.49 (s, 1H, Ar); 9.99 (m, 1H, Ar). M/Z (M+H)$^+$=416.

Example 26

[4-(Azepane-1-carbonyl)-phenyl]-(6,8-dichloro-imidazo[1,2-a]pyridin-3-yl)-methanone

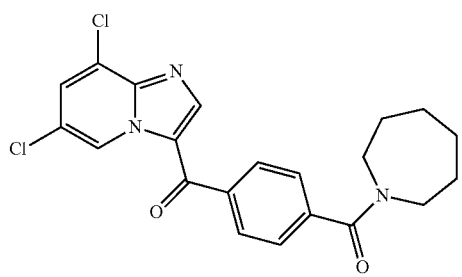 [SMILES: O=C(c1ccc(C(=O)N2CCCCCC2)cc1)c1cnc2c(Cl)cc(Cl)cn12]

Example 26 was obtained according to general procedure V starting from compounds 15 and 45 in trifluorotoluene through microwave irradiation for 15 min at 180° C.

Purification by flash-chromatography (AcOEt 20% to 80% in cyclohexane) afforded the product as a white solid in 12% yield.

$^1$H-NMR (400 MHz, DMSO): 1.56-1.60 (bm, 6H, 3*CH$_2$); 1.73-1.78 (bm, 2H, CH$_2$); 3.60 (m, 2H, N—CH$_2$); 7.57 (m, 2H, Ar); 7.94 (m, 2H, Ar); 8.18 (d, J 1.8 Hz, 1H, Ar); 8.41 (s, 1H, Ar); 9.63 (d, J 1.8 Hz, 1H, Ar). N—CH$_2$ signal under water peak. M/Z (M[$^{35}$Cl$_2$]+H)$^+$=416.

Example 27

[4-(Azepane-1-carbonyl)-2-fluoro-phenyl]-(6-fluoro-imidazo[1,2-a]pyridin-3-yl)-methanone

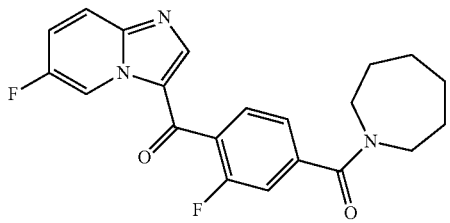 [SMILES: O=C(c1ccc(C(=O)N2CCCCCC2)cc1F)c1cnc2ccc(F)cn12]

Example 27 was obtained according to general procedure V starting from compounds 8 and 53 in DMF and with standard heating at 40° C. for 12 Hrs.

Purification by flash-chromatography (MeOH 2% in CH$_2$Cl$_2$) followed by trituration in Et$_2$O afforded the product as a green solid in 31% yield.

$^1$H-NMR (400 MHz, CDCl$_3$): 1.61-1.72 (m, 6H, 3*CH$_2$); 1.86-1.92 (m, 2H, CH$_2$); 3.42 (t, J 5.7 Hz, 2H, N—CH$_2$); 3.72 (t, J 5.7 Hz, 2H, N—CH$_2$); 7.27 (m, 1H, Ar); 7.33 (m, 1H, Ar); 7.53 (m, 1H, Ar); 7.67 (m, 1H, Ar); 7.82 (m, 1H, Ar); 8.14 (d, J 2.1 Hz, 1H, Ar); 9.78 (m, 1H, Ar). M/Z (M+H)$^+$=384.

Example 28

[4-(Azepane-1-carbonyl)-2-nitro-phenyl]-(6-fluoro-imidazo[1,2-a]pyridin-3-yl)-methanone

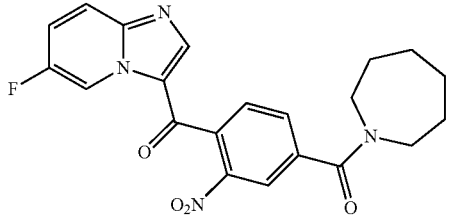

Example 28 was obtained according to general procedure V starting from compounds 8 and 54 in DMF through microwave irradiation for 5 min at 110° C.

Purification by flash-chromatography (MeOH 1% in CH$_2$Cl$_2$) afforded the product in 50% yield.

$^1$H-NMR (400 MHz, CDCl$_3$): 1.58-1.75 (m, 6H, 3*CH$_2$); 1.87-1.94 (m, 2H, CH$_2$); 3.44 (t, J 5.8 Hz, 2H, N—CH$_2$); 3.75 (t, J 5.9 Hz, 2H, N—CH$_2$); 7.55 (m, 1H, Ar); 7.67 (m, 1H, Ar); 7.82-7.88 (m, 3H, Ar); 8.00 (s, 1H, Ar); 8.25 (d, J 1.4 Hz, 1H, Ar). M/Z (M+H)$^+$=411.

Example 29

[4-(Azepane-1-carbonyl)-2-hydroxyamino-phenyl]-(6-fluoro-imidazo[1,2-a]pyridin-3-yl)-methanone

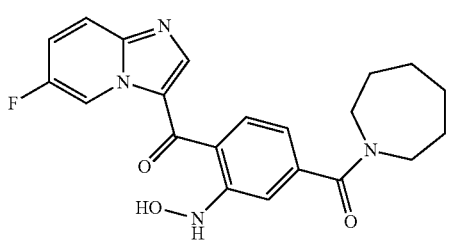 [SMILES: O=C(c1ccc(C(=O)N2CCCCCC2)cc1NO)c1cnc2ccc(F)cn12]

To a solution of example 28 (150 mg, 1.0 equiv.) in DMF (1.5 mL), Pd/C 10% weight (15 mg) was added. The reaction mixture was purged with hydrogen and stirred at R.T. under hydrogen atmosphere overnight.

The catalyst was filtered off on celite and washed with AcOEt (3 mL); the filtrate was washed with water (3*3 mL), brine (3 mL), dried over MgSO$_4$ and concentrated under reduced pressure. Purification by flash-chromatography (MeOH 1% to 5% in CH$_2$Cl$_2$) afforded the product as a cream solid in 70% yield.

$^1$H-NMR (400 MHz, DMSO): 1.51-1.63 (m, 6H, 3*CH$_2$); 1.70-1.76 (m, 2H, CH$_2$); 3.57 (t, J 5.9 Hz, 2H, N—CH$_2$); 6.83 (dd, J 1.6 Hz, J 7.9 Hz, 1H, Ar); 7.17 (d, J 1.6 Hz, 1H, Ar); 7.67 (d, J 7.8 Hz, 1H, Ar); 7.81 (m, 1H, Ar); 7.97 (m, 1H, Ar); 8.17 (s, 1H, Ar), 8.95 (d, J 1.4 Hz, 1H, NH); 9.55 (m, 1H, Ar). N—CH$_2$ signal under water peak. M/Z (M+H)$^+$=397.

Example 30

[2-Amino-4-(azepane-1-carbonyl)-phenyl]-(6-fluoro-imidazo[1,2-a]pyridin-3-yl)-methanone

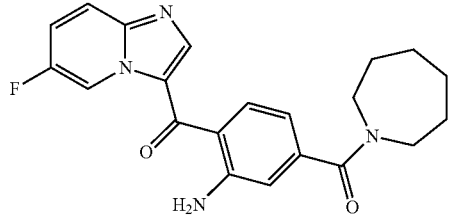

To a solution of example 28 (320 mg, 1.0 equiv.) in EtOH (4 mL), tin (II) chloride (740 mg, 5.0 equiv.) was added. The reaction mixture was heated through microwave irradiation at 130° C. for 5 min.

The reaction mixture was diluted in AcOEt (10 mL) and washed with NaOH 30% (10 mL), brine (10 mL), dried over MgSO$_4$ and concentrated under reduced pressure. Purification by flash-chromatography (MeOH 1% to 5% in CH$_2$Cl$_2$) afforded the product in 40% yield.

$^1$H-NMR (400 MHz, DMSO): 1.51-1.64 (m, 6H, 3*CH$_2$); 1.68-1.76 (m, 2H, CH$_2$); 3.35 (t, J 5.7 Hz, 2H, N—CH$_2$); 3.55 (t, J 5.8 Hz, 2H, N—CH$_2$); 6.55 (dd, J 1.6 Hz, J 8.0 Hz, 1H, Ar); 6.64 (bs, 2H, NH$_2$); 6.78 (d, J 1.5 Hz, 1H, Ar); 7.70 (d, J 8.1 Hz, 1H, Ar); 7.78 (m, 1H, Ar); 7.95 (m, 1H, Ar); 8.20 (s, 1H, Ar); 9.51 (m, 1H, Ar). M/Z (M+H)$^+$=381. Mp: 141-152° C.

Example 31

3-Amino-N-cyclohexyl-N-ethyl-4-(6-fluoro-imidazo[1,2-a]pyridine-3-carbonyl)-benzamide

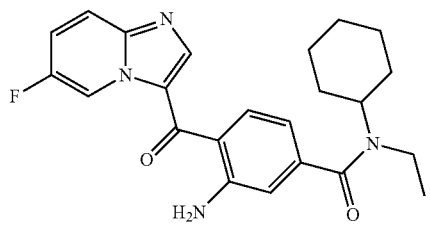 [SMILES: CCN(C(=O)c1ccc(C(=O)c2cnc3ccc(F)cn23)c(N)c1)C1CCCCC1]

To a solution of example 22 (440 mg, 1.0 equiv.) in DMF (4 mL), PtO$_2$ (165 mg, 0.7 equiv.) was added. The mixture was purged with hydrogen and stirred under hydrogen atmosphere at R.T. overnight. The catalyst was filtered off on celite and washed with DMF.

Purification by preparative HPLC afforded the product as a solid (48 mg, 12%).

$^1$H-NMR (400 MHz, DMSO): 1.10-1.80 (m, 13H, 5*CH$_2$+CH$_3$); 3.34 (q, J 7.0 Hz, 2H, N—CH$_2$); 3.69 (bs, 1H, N—CH); 6.56 (dd, J 1.5 Hz, J 8.1 Hz, 1H, Ar); 6.80 (d, J 1.5 Hz, 1H, Ar); 7.70 (m, 2H, Ar); 7.89 (dd, J 5.1 Hz, J 9.5 Hz, 1H, Ar); 8.15 (s, 1H, Ar); 9.51 (dd, J 2.6 Hz, J 5.1 Hz, 1H, Ar). M/Z (M+H)$^+$=409.

Example 32

[4-(azepan-1-ylcarbonyl)-2-fluorophenyl](6-chloroimidazo[1,2-a]pyridin-3-yl)methanone

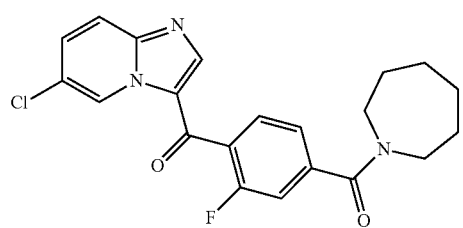 [SMILES: O=C(c1ccc(C(=O)N2CCCCCC2)cc1F)c1cnc2ccc(Cl)cn12]

Example 32 was obtained according to general procedure V starting from compounds 9 and 53 in DMF through microwave irradiation for 10 min at 130° C.

Purification by flash-chromatography (EtOAc) afforded the product as a green residue in 44% yield.

$^1$H-NMR (400 MHz, CDCl$_3$): 1.57-1.70 (m, 6H, 3*CH$_2$); 1.88 (m, 2H, CH$_2$); 3.43 (m, 2H, N—CH$_2$); 3.75 (m, 2H, N—CH$_2$); 7.27 (m, 1H, Ar); 7.33 (dd, J 1.4 Hz, J 7.8 Hz, 1H, Ar); 7.59 (dd, J 2.0 Hz, J 9.5 Hz, 1H, Ar); 7.66 (m, 1H, Ar); 7.80 (d, J 9.3 Hz, 1H, Ar); 8.13 (s, 1H, Ar); 9.98 (d, J 1.8 Hz, 1H, Ar). M/Z (M[$^{35}$Cl]+H)$^+$=400.

Example 33

[4-(azepan-1-ylcarbonyl)-2-fluorophenyl](6-bromoimidazo[1,2-a]pyridin-3-yl)methanone

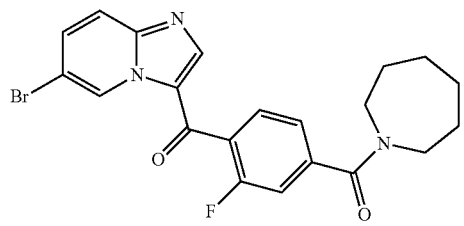

Example 33 was obtained according to general procedure V starting from compounds 10 and 53 in DMF through microwave irradiation for 10 min at 100° C.

Purification by flash-chromatography (EtOAc) afforded the product as a green gum in 56% yield.

$^1$H-NMR (400 MHz, CDCl$_3$): 1.62-1.73 (m, 6H, 3*CH$_2$); 1.96-191 (m, 2H, CH$_2$); 3.43 (m, 2H, N—CH$_2$); 3.73 (m, 2H, N—CH$_2$); 7.27 (d, J 1.3 Hz, J 9.6 Hz, 1H, Ar); 7.33 (d, J 1.5 Hz, J 7.8 Hz, 1H, Ar); 7.65 (m, 1H, Ar); 7.69 (m, 1H, Ar); 7.74

(d, J 0.7 Hz, J 9.4 Hz, 1H, Ar); 8.10 (d, J 2.1 Hz, 1H, Ar); 9.97 (m, 1H, Ar). M/Z (M[$^{79}$Br]+H)$^+$=444.

Example 34

[4-(azepan-1-ylcarbonyl)-2-fluorophenyl](6-methylimidazo[1,2-a]pyridin-3-yl)methanone

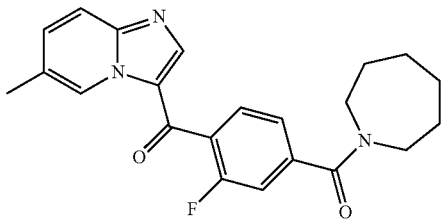 [SMILES: Cc1ccc2ncc(C(=O)c3ccc(C(=O)N4CCCCCC4)cc3F)n2c1]

Example 34 was obtained according to general procedure V starting from compounds 11 and 53 in DMF through microwave irradiation for 10 min at 120° C.

Purification by flash-chromatography (EtOAc) afforded the product as a brown residue in 39% yield.

$^1$H-NMR (400 MHz, CDCl$_3$): 1.60-1.70 (m, 6H, 3*CH$_2$); 1.87 (m, 2H, CH$_2$); 2.50 (s, 3H, CH$_3$); 3.43 (m, 2H, N—CH$_2$); 3.72 (t, J 5.9 Hz, 1H, N—CH$_2$); 7.26 (dd, J 1.3 Hz, J 9.6 Hz, 1H, Ar); 7.31 (dd, J 1.3 Hz, J 7.7 Hz, 1H, Ar); 7.47 (dd, J 1.6 Hz, J 9.1 Hz, 1H, Ar); 7.65 (t, J 7.3 Hz, 1H, Ar); 7.76 (d, J 9.0 Hz, 1H, Ar); 8.06 (s, 1H, Ar); 9.61 (s, 1H). M/Z (M+H)$^+$=380.

Example 35

[4-(azepan-1-ylcarbonyl)-2-fluorophenyl][6-(trifluoromethyl)imidazo[1,2-a]pyridin-3-yl]methanone

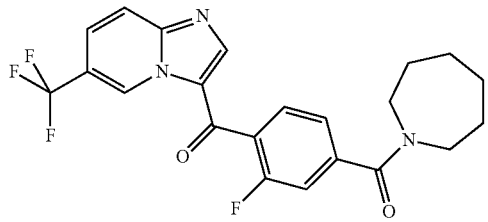 [SMILES: O=C(c1ccc(C(=O)N2CCCCCC2)cc1F)c1cnc2ccc(C(F)(F)F)cn12]

Example 35 was obtained according to general procedure V starting from compounds 14 and 53 in DMF through microwave irradiation for 10 min at 120° C.

Purification by flash-chromatography (EtOAc) afforded the product as a brown residue in 60% yield.

$^1$H-NMR (400 MHz, CDCl$_3$): 1.60-1.70 (m, 6H, 3*CH$_2$); 1.90 (m, 2H, CH$_2$); 3.44 (m, 2H, N—CH$_2$); 3.73 (m, 2H, N—CH$_2$); 7.27 (m, 1H, Ar); 7.35 (dd, J 1.4 Hz, J 7.8 Hz, 1H, Ar); 7.66 (m, 1H, Ar); 7.76 (dd, J 1.9 Hz, J 9.5 Hz, 1H, Ar); 7.96 (d, J 9.4 Hz, 1H, Ar); 8.23 (d, J 2.0 Hz, 1H, Ar); 10.17 (m, 1H, Ar). M/Z (M+H)$^+$=434.

Example 36

[4-(azepan-1-ylcarbonyl)-2-fluorophenyl](6-ethylimidazo[1,2-a]pyridin-3-yl)methanone

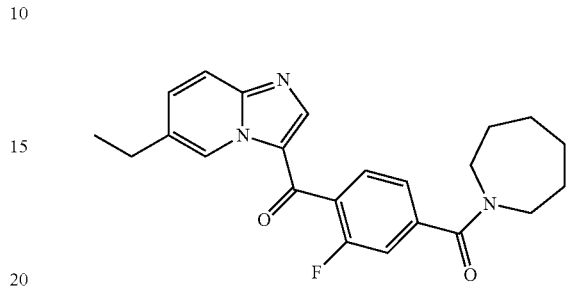

Example 36 was obtained according to general procedure V starting from compounds 16 and 53 in DMF through microwave irradiation for 10 min at 120° C.

Purification by flash-chromatography (EtOAc) afforded the product as a brown residue in 60% yield.

$^1$H-NMR (400 MHz, CDCl$_3$): 1.36 (t, J 7.6 Hz, 3H, CH$_2$—CH$_3$); 1.61-1.71 (m, 6H, 3*CH$_2$); 1.84 (m, 2H, CH$_2$); 2.81 (q, J 7.6 Hz, 2H, CH$_2$—CH$_3$); 3.42 (m, 2H, N—CH$_2$); 3.71 (t, J 5.9 Hz, 1H, N—CH$_2$); 7.25 (dd, J 1.4 Hz, J 9.6 Hz, 1H, Ar); 7.30 (dd, J 1.4 Hz, J 7.7 Hz, 1H, Ar); 7.50 (dd, J 1.9 Hz, J 9.1 Hz, 1H, Ar); 7.65 (t, J 7.2 Hz, 1H, Ar); 7.76 (d, J 9.1 Hz, 1H, Ar); 8.05 (d, J 1.4 Hz, 1H, Ar); 9.61 (s, 1H). M/Z (M+H)$^+$=394.

Example 37

[4-(azepan-1-ylcarbonyl)-2-fluorophenyl](6-cyclopropylimidazo[1,2-a]pyridin-3-yl)methanone

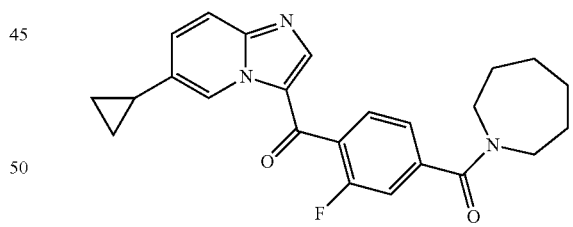

Example 37 was obtained according to general procedure V starting from compounds 17 and 53 in DMF through microwave irradiation for 10 min at 120° C.

Purification by flash-chromatography (EtOAc) afforded the product as a brown residue in 44% yield. Example 37 was isolated with a purity of 67% (based on LCMS). Side product was example 38. This example is obtained due to the presence of amidine 1 in amidine 17.

$^1$H-NMR (400 MHz, CDCl$_3$): 0.83 (m, 2H, CH$_2$); 1.10 (m, 2H, CH$_2$); 1.63-1.72 (m, 6H, 3*CH$_2$); 1.86-1.92 (m, 2H, CH$_2$); 2.04-2.10 (m, 1H, CH); 3.43 (m, 2H, CH$_2$); 3.72 (m, 2H, N—CH$_2$); 7.26 (dd, J 1.4 Hz, J 9.6 Hz, 1H, Ar); 7.31 (dd, J 1.4 Hz, J 7.7 Hz, 1H, Ar); 7.35 (dd, J 1.9 Hz, J 9.2 Hz, 1H,

Ar); 7.65 (t, J 7.32 Hz, 1H, Ar); 7.73 (d, J 9.2 Hz, 1H, Ar); 8.05 (d, J 1.8 Hz, 1H, Ar); 9.61 (s, 1H). M/Z (M+H)$^+$=406 (major product).

Example 38

[4-(azepan-1-ylcarbonyl)-2-fluorophenyl](imidazo[1,2-a]pyridin-3-yl)methanone

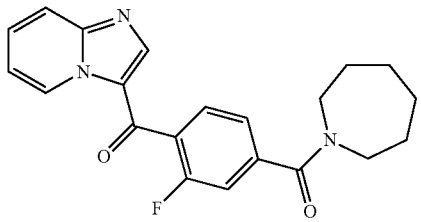 [SMILES: O=C(c1ccc(C(=O)N2CCCCCC2)cc1F)c1cnc2ccccn12]

Example 38 was obtained as a side product in example 37.
$^1$H-NMR (400 MHz, CDCl$_3$): 1.63-1.72 (m, 6H, 3*CH$_2$); 1.86-1.92 (m, 2H, CH$_2$); 3.43 (m, 2H, CH$_2$); 3.72 (m, 2H, N—CH$_2$); 7.22 (dd, J 1.1 Hz, J 6.9 Hz, 1H, Ar); 7.25 (dd, J 1.4 Hz, J 6.1 Hz, 1H, Ar); 7.32 (dd, J 1.4 Hz, J 7.7 Hz, 1H, Ar); 7.46-7.50 (m, 1H, Ar); 7.60-7.70 (m, 2H, Ar); 7.86 (d, J 9.0 Hz, 1H, Ar); 8.12 (d, J 1.9 Hz, 1H, Ar); 9.79 (d, J 6.8 Hz, 1H, Ar). M/Z (M+H)$^+$=366 (minor product).

General Procedure VI: Formation of Compounds AE by Soponification of Compounds AD (Scheme 3).

To a mixture of compounds AE (1.0 equiv.) in an appropriate solvent, aqueous LiOH (1N, 1.5 equiv.) was added. Reaction mixture was stirred 2 Hrs at R.T. or at refluxed, then was treated with aqueous acidic solution (Saturated NH$_4$Cl or 2N HCl). The expected acid precipitated. Solid was collected, washed with water and dried under reduced pressure at 80° C.

Compound 61

4-(Imidazo[1,2-a]pyridine-3-carbonyl)-benzoic acid

Compound 61 was obtained according to general procedure VI starting from compound 57. Saponification was performed in MeOH at reflux, and product was obtained as a white solid in 93% yield.
M/Z (M+H)$^+$=267.

Compound 62

4-(6-Fluoro-imidazo[1,2-a]pyridine-3-carbonyl)-benzoic acid

Compound 62 was obtained according to general procedure VI starting from compound 58. Saponification was performed in MeOH at reflux, and product was obtained as a pale pink solid in 80% yield.
M/Z (M+H)$^+$=285.

Compound 63

3-Fluoro-4-(6-fluoro-imidazo[1,2-a]pyridine-3-carbonyl)-benzoic acid

Compound 63 was obtained according to general procedure VI starting from compound 60. Saponification was performed in THF at room temperature, and product was obtained as a white solid in 90% yield.
M/Z (M+H)$^+$=303.

Compound 64

3-Fluoro-4-(6-cyano-imidazo[1,2-a]pyridine-3-carbonyl)-benzoic acid

Compound 64 was obtained according to general procedure VI starting from compound 59. Saponification was performed in THF at room temperature for 3 days. Reaction mixture was treated with HCl 1N and was extracted with EtOAc. Organic layer was washed with brine, dried over MgSO$_4$ and concentrated. Residue was taken in Et$_2$O and the resulting solid was filtered off, washed with Et$_2$O and dried under reduced pressure. Compound 64 was obtained as a brown solid in 40% yield.
M/Z (M+H)$^+$=310.

General Procedure VII: Formation of Examples AC and AF from Compounds AE, AM', AD or AM (Schemes 3 and 6).
Method A: HATU Coupling To a suspension of compound AE or AM' (1.0 equiv.) in a mixture of DMF:pyridine (9:1), HATU (1.1-2.0 equiv.) and the selected amine (1.1-2.0 equiv.) were added. The mixture was stirred at R.T. overnight or heated through microwave irradiation.

The reaction mixture was diluted with AcOEt and washed 3 times with water, brine, dried over MgSO$_4$ and concentrated under reduced pressure. Purification by flash-chromatography afforded the product.
Method B: Carbodiimide/HOBt Coupling To a suspension of compound AE or AM' (1.0 equiv.) in DMF, DIC (1.5 equiv.) or EDCI (1.5 equiv.), HOBt (1.5 equiv.) and the selected amine (1.5-5.0 equiv.) were added. The mixture was stirred at R.T. for 12-72 Hrs or heated through microwave irradiation for 5 min at 150° C.

The crude reaction mixture was purified by preparative HPLC to afford the product.
Method C: POCl$_3$/Pyridine Coupling:

To a solution of compound AE or AM' (1.0 equiv.) in pyridine under argon atmosphere and cooled at −20° C./0° C., the selected amine (5.0 equiv.) and phosphorus oxychloride (1.5 equiv) were successively added. After 30-40 min at 0° C., the reaction was treated with HCl 1M and extracted with AcOEt. The organic layer was washed with brine, dried over MgSO$_4$ and concentrated under reduced pressure. Purification by flash-chromatography afforded the product.
Method D: Via Acid Chloride Formation by Oxalyl Chloride:

To a suspension of compound AE or AM' (1.0 equiv.) in CH$_2$Cl$_2$ cooled at 0° C. under argon stream, DMF (5%) and oxalyl chloride (1.5 to 2.5 equiv.) were successively added dropwise. The reaction mixture was stirred at R.T. until a clear solution was obtained, then the selected amine (3.0 to 7.0 equiv.) was added. The reaction mixture was stirred at R.T. for 1 Hr, and then was treated with HCl 1M. The layers were separated, the organic was washed with NaOH 1M, brine, dried over MgSO$_4$ and concentrated under reduced pressure.
Method E: Via Acid Chloride Formation by Thionyl Chloride:

A suspension of compound AE or AM' in SOCl$_2$ was warmed at 100° C. 3 Hrs (until a clear solution was obtained). After cooling, solution was concentrated, and co-evaporation with toluene was performed twice.

The residue (assumed acid chloride formation quantitative, 1 equiv.) was dissolved in CH$_2$Cl$_2$ and amine (5 equiv.) was added. Reaction mixture was stirred overnight at R.T., treated with HCl 1N and was extracted with CH$_2$Cl$_2$. Organic layer was washed with brine, dried over MgSO$_4$ and concentrated under reduced pressure. Purification by flash-chromatography afforded the product.

Method F: from Ester in Presence of Me$_3$Al:

To a solution of amine (4.0 equiv.) in CH$_2$Cl$_2$ cooled at 0° C. under argon stream, AlMe$_3$ in solution in toluene (2N, 4.2 equiv.) was added carefully. Mixture was stirred 30 min., then compound AD or AM in solution in CH$_2$Cl$_2$ was added. Reaction mixture was heated through microwave irradiation for 10 to 30 min at 120° C. to 130° C., then hydrolyzed with aqueous HCl 1N solution. Amide AC or AF were extracted with CH$_2$Cl$_2$. Organic layer was washed with brine, dried over MgSO$_4$ and concentrated under reduced pressure. Specific purification afforded the product or HCl salt was generated. Salt formation: To the crude material dissolved in CH$_2$Cl$_2$ and filtered through a pad of celite, HCl in Et$_2$O was added. Targeted example was filtrated, washed with CH$_2$Cl$_2$ and dried under reduced pressure.

Example 39

N-Cyclohexyl-4-(imidazo[1,2-a]pyridine-3-carbonyl)-N-methyl-benzamide

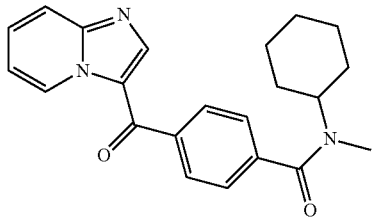 [SMILES: CN(C(=O)c1ccc(C(=O)c2cnc3ccccn23)cc1)C1CCCCC1]

Example 39 was obtained according to general procedure VII, method B, using compound 61 and N-methylcyclohexylamine (1.7 equiv.) in presence of EDCI. The reaction was completed after 72 Hrs at R.T. The product was obtained as a solid in 8% yield.

$^1$H-NMR (400 MHz, DMSO): 1.02-1.80 (m, 10H, 5*CH$_2$); 2.89 (s, 3H, N—CH$_3$); 7.40 (m, 1H, Ar); 7.54 (bm, 2H, Ar); 7.76 (m, 1H, Ar); 7.93 (m, 3H, Ar); 8.37 (s, 1H, Ar); 9.67 (m, 1H, Ar). N—CH signal under water peak. M/Z (M+H)$^+$=362.

Example 40

N-Cyclohexyl-4-(imidazo[1,2-a]pyridine-3-carbonyl)-N-propyl-benzamide

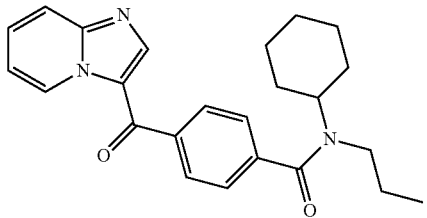 [SMILES: CCCN(C(=O)c1ccc(C(=O)c2cnc3ccccn23)cc1)C1CCCCC1]

Example 40 was obtained according to general procedure VII, method B, using compound 61 and cyclohexylpropylamine hydrochloride in presence of DIC and was heated through microwave irradiation for 5 min at 150° C., as a cream solid in 35% yield.

$^1$H-NMR (400 MHz, DMSO): 0.85 (t, J 7.5 Hz, 3H, CH$_3$); 1.14 (m, 3H, CH$_2$+CH); 1.54-1.81 (m, 9H, 4*CH$_2$+CH); 3.25 (m, 2H, N—CH$_2$); 3.65 (bs, 1H, N—CH); 7.34 (m, 1H, Ar); 7.50 (m, 2H, Ar); 7.72 (m, 1H, Ar); 7.88 (m, 1H, Ar); 7.94 (m, 2H, Ar); 8.26 (s, 1H, Ar); 9.66 (m, 1H, Ar). M/Z (M+H)$^+$=390.

Example 41

N-Cyclohexyl-4-(imidazo[1,2-a]pyridine-3-carbonyl)-N-isopropyl-benzamide

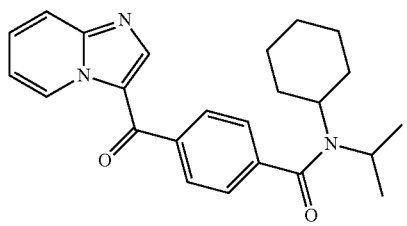 [SMILES: CC(C)N(C(=O)c1ccc(C(=O)c2cnc3ccccn23)cc1)C1CCCCC1]

Example 41 was obtained according to general procedure VII, method B, using compound 61 and N-isopropylcyclohexylamine in presence of DIC and was heated through microwave irradiation for 5 min at 150° C., as a cream solid in 10% yield.

$^1$H-NMR (400 MHz, DMSO): 1.11-1.80 (m, 14H, 4*CH$_2$+2*CH$_3$); 2.04 (bs, 2H, CH$_2$); 3.23 (m, 1H, N—CH); 3.73 (m, 1H, N—CH); 7.35 (m, 1H, Ar); 7.46 (m, 2H, Ar); 7.72 (m, 1H, Ar); 7.88 (m, 1H, Ar); 7.93 (m, 2H, Ar); 8.27 (s, 1H, Ar); 9.66 (m, 1H, Ar). M/Z (M+H)$^+$=390.

Example 42

N-Cyclohexyl-4-(imidazo[1,2-a]pyridine-3-carbonyl)-N-prop-2-ynyl-benzamide

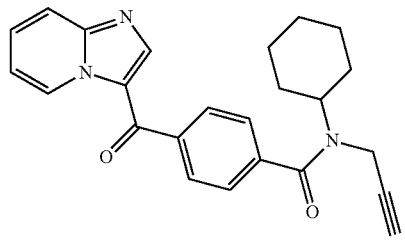 [SMILES: C#CCN(C(=O)c1ccc(C(=O)c2cnc3ccccn23)cc1)C1CCCCC1]

Example 42 was obtained according to general procedure VII, method B, using compound 61 and N-cyclohexyl-N-prop-2-ynylamine hydrochloride in presence of DIC and was heated through microwave irradiation for 5 min at 150° C., as a green oil in 20% yield.

$^1$H-NMR (400 MHz, DMSO): 1.11-1.84 (m, 10H, 5*CH$_2$); 3.82 (bs, 1H, CH); 4.11 (d, J 2.2 Hz, 2H, N—CH$_2$); 7.36 (m, 1H, Ar); 7.57 (d, J 7.8 Hz, 2H, Ar); 7.72 (m, 1H, Ar); 7.87 (d, J 8.8 Hz, 1H, Ar); 7.94 (d, J 7.8 Hz, 2H, Ar); 8.25 (s, 1H, Ar); 9.65 (m, 1H, Ar). CH signal under water peak. M/Z (M+H)$^+$=386.

Example 43

N-Cyclohexyl-N-cyclopropylmethyl-4-(imidazo[1,2-a]pyridine-3-carbonyl)-benzamide

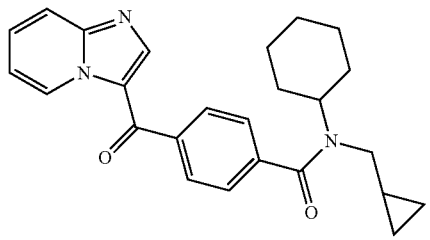 [SMILES: O=C(c1ccc(C(=O)N(CC2CC2)C2CCCCC2)cc1)c1cnc2ccccn12]

Example 43 was obtained according to general procedure VII, method B, using compound 61 and cyclohexylcyclopropyl-methylamine hydrochloride in presence of DIC and was heated through microwave irradiation for 5 min at 150° C., as a brown solid in 33% yield.

$^1$H-NMR (400 MHz, DMSO): 0.21 (m, 2H, CH$_2$); 0.49 (m, 2H, CH$_2$); 1.02-1.29 (m, 4H, 2*CH$_2$); 1.53-1.83 (m, 7H, 3*CH$_2$+CH); 3.25 (d, J 6.3 Hz, 2H, N—CH$_2$); 3.67 (bt, 1H, N—CH); 7.35 (m, 1H, Ar); 7.52 (m, 2H, Ar); 7.72 (m, 1H, Ar); 7.88 (m, 1H, Ar); 7.94 (m, 2H, Ar); 8.27 (s, 1H, Ar); 9.66 (m, 1H, Ar). M/Z (M+H)$^+$=402.

Example 44

N-Allyl-N-cyclohexyl-4-(imidazo[1,2-a]pyridine-3-carbonyl)-benzamide

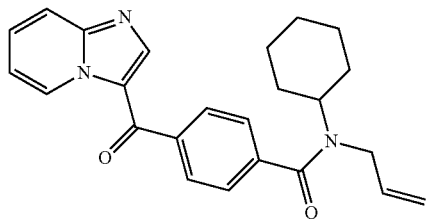 [SMILES: C=CCN(C(=O)c1ccc(C(=O)c2cnc3ccccn23)cc1)C1CCCCC1]

Example 44 was obtained according to general procedure VII, method B, using compound 61 and allylcyclohexylamine in presence of DIC and was heated through microwave irradiation for 5 min at 150° C., as a cream solid in 64% yield.

$^1$H-NMR (400 MHz, DMSO): 1.00-1.75 (bm, 10H, 5*CH$_2$); 3.40 (bs, 1H, N—CH); 4.03 (bs, 2H, N—CH$_2$); 5.10-5.46 (bm, 2H, C=CH$_2$); 5.91 (bs, 1H, HC=C); 7.42 (m, 1H, Ar); 7.55 (bm, 2H, Ar); 7.78 (m, 1H, Ar); 7.95 (bm, 3H, Ar); 8.39 (bs, 1H, Ar); 9.66 (d, J 6.9 Hz, 1H, Ar). M/Z (M+H)$^+$=388.

Example 45

N-Cyclohexyl-4-(imidazo[1,2-a]pyridine-3-carbonyl)-N-(2,2,2-trifluoro-ethyl)-benzamide

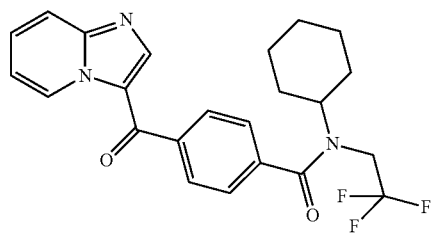 [SMILES: O=C(c1ccc(C(=O)N(CC(F)(F)F)C2CCCCC2)cc1)c1cnc2ccccn12]

Example 45 was obtained according to general procedure VII, method B, using compound 61 and cyclohexyl-(2,2,2-trifluoro-ethyl)-amine in presence of DIC and was heated through microwave irradiation for 5 min at 150° C., as a brown solid in 5% yield.

$^1$H-NMR (400 MHz, DMSO): 1.10-1.80 (bm, 10H, 5*CH$_2$); 4.26 (q, J 6.7 Hz, 2H, N—CH$_2$); 7.35 (m, 1H, Ar); 7.57 (m, 2H, Ar); 7.72 (m, 1H, Ar); 7.88 (m, 1H, Ar); 7.97 (m, 2H, Ar); 8.27 (s, 1H, Ar); 9.66 (m, 1H, Ar). N—CH signal under water peak. M/Z (M+H)$^+$=430.

Example 46

N-Cyclohexyl-N-(2-dimethylamino-ethyl)-4-(imidazo[1,2-a]pyridine-3-carbonyl)-benzamide

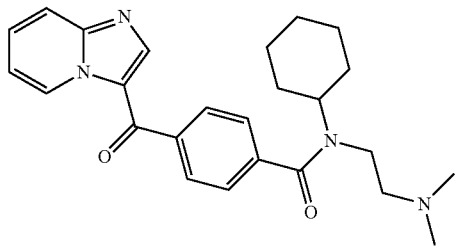 [SMILES: CN(C)CCN(C(=O)c1ccc(C(=O)c2cnc3ccccn23)cc1)C1CCCCC1]

Example 46 was obtained according to general procedure VII, method B, using compound 61 and N' cyclohexyl-N,N-dimethylethane-1,2-diamine in presence of DIC and was heated through microwave irradiation for 5 min at 150° C., as a green oil in 38% yield.

$^1$H-NMR (400 MHz, DMSO): 1.00-1.27 (bm, 4H, 2*CH$_2$); 1.56-1.76 (bm, 6H, 3*CH$_2$); 2.95 (s, 6H, 2*N—CH$_3$); 3.32 (t, J 7.0 Hz, 2H, N—CH$_2$); 3.52 (bt, 1H, N—CH); 3.72 (t, J 7.4 Hz, 2H, N—CH$_2$); 7.36 (m, 1H, Ar); 7.59 (m, 2H, Ar); 7.72 (m, 1H, Ar); 7.88 (m, 1H, Ar); 7.96 (m, 2H, Ar); 8.27 (s, 1H, Ar); 9.68 (m, 1H, Ar). M/Z (M+H)$^+$=419.

Example 47

N-Butyl-N-cyclohexyl-4-(imidazo[1,2-a]pyridine-3-carbonyl)-benzamide

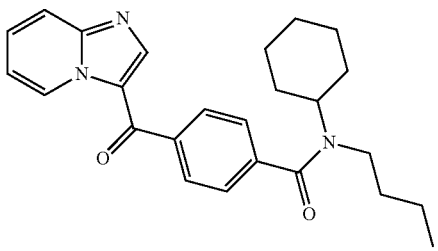 [SMILES: CCCCN(C(=O)c1ccc(C(=O)c2cnc3ccccn23)cc1)C1CCCCC1]

Example 47 was obtained according to general procedure VII, method B, using compound 61 and butyl-cyclohexyl-amine (1.6 equiv.) in presence of DIC and was heated through microwave irradiation for 5 min at 150° C., as a brown solid in 4% yield. M/Z (M+H)$^+$=404.

Example 48

N,N-Dicyclohexyl-4-(imidazo[1,2-a]pyridine-3-carbonyl)-benzamide

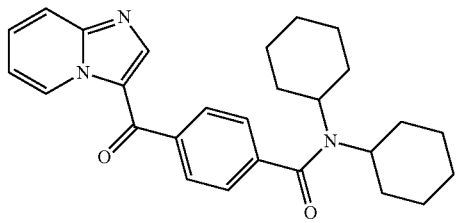 [SMILES: O=C(c1ccc(C(=O)N(C2CCCCC2)C2CCCCC2)cc1)c1cnc2ccccn12]

Example 48 was obtained according to general procedure VII, method B, using compound 61 and dicyclohexylamine in presence of DIC and was heated through microwave irradiation for 5 min at 150° C., as a solid in 12% yield.

$^1$H-NMR (400 MHz, DMSO): 1.08-1.69 (m, 20H, 10*CH$_2$); 3.16 (bs, 2H, 2*N—CH); 7.39-7.47 (m, 3H, Ar); 7.78 (m, 1H, Ar); 7.92-7.95 (m, 3H, Ar); 8.39 (s, 1H, Ar); 9.66 (m, 1H, Ar). M/Z (M+H)$^+$=430.

Example 49

4-(Imidazo[1,2-a]pyridine-3-carbonyl)-N-methyl-N-phenyl-benzamide

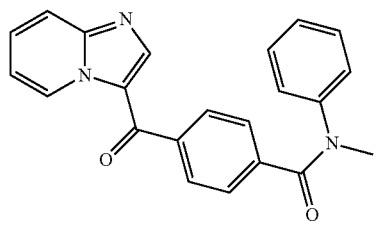 [SMILES: CN(C(=O)c1ccc(C(=O)c2cnc3ccccn23)cc1)c1ccccc1]

Example 49 was obtained according to general procedure VII, method B, using compound 61 and N-methylaniline in presence of DIC and was heated through microwave irradiation for 5 min at 150° C., as a cream solid in 22% yield.

$^1$H-NMR (400 MHz, DMSO): 3.42 (s, 3H, N—CH$_3$); 7.17-7.45 (m, 8H, Ar); 7.70-7.78 (m, 3H, Ar); 7.92 (m, 1H, Ar); 8.19 (s, 1H, Ar); 9.60 (m, 1H, Ar). M/Z (M+H)$^+$=356.

Example 50

4-(6-Fluoro-imidazo[1,2-a]pyridine-3-carbonyl)-N-methyl-N-phenyl-benzamide

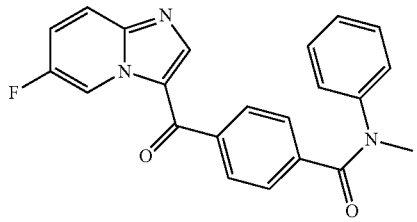 [SMILES: CN(C(=O)c1ccc(C(=O)c2cnc3ccc(F)cn23)cc1)c1ccccc1]

Example 50 was obtained according to general procedure VII, method B, using compound 62 and N-methylaniline in presence of DIC and was heated through microwave irradiation for 5 min at 150° C., as a cream solid in 45% yield.

$^1$H-NMR (400 MHz, DMSO): 3.43 (s, 3H, N—CH$_3$); 7.18-7.32 (m, 5H, Ar); 7.47 (m, 2H, Ar); 7.71-7.78 (m, 3H, Ar); 7.92 (m, 1H, Ar); 8.13 (s, 1H, Ar); 9.59 (m, 1H, Ar). M/Z (M+H)$^+$=374. Mp: 131-135° C.

Example 51

4-(6-Fluoro-imidazo[1,2-a]pyridine-3-carbonyl)-N-(4-methoxy-phenyl)-N-methyl-benzamide

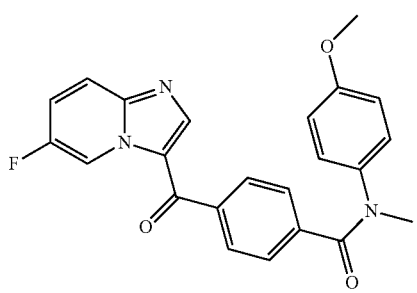 [SMILES: COc1ccc(N(C)C(=O)c2ccc(C(=O)c3cnc4ccc(F)cn34)cc2)cc1]

Example 51 was obtained according to general procedure VII, method B, using compound 62 and 4-methoxy-N-methylaniline in presence of DIC and was heated through microwave irradiation for 5 min at 150° C., as a cream solid in 40% yield.

$^1$H-NMR (400 MHz, DMSO): 3.38 (s, 3H, N—CH$_3$); 3.72 (s, 3H, O—CH$_3$); 6.84 (m, 2H, Ar); 7.15 (m, 2H, Ar); 7.46 (m, 2H, Ar); 7.71-7.78 (m, 3H, Ar); 7.92 (m, 1H, Ar); 8.14 (s, 1H, Ar); 9.59 (m, 1H, Ar). M/Z (M+H)$^+$=404.

Example 52

4-(6-Fluoro-imidazo[1,2-a]pyridine-3-carbonyl)-N-methyl-N-p-tolyl-benzamide

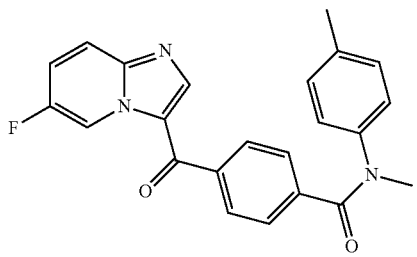 [SMILES: Cc1ccc(N(C)C(=O)c2ccc(C(=O)c3cnc4ccc(F)cn34)cc2)cc1]

Example 52 was obtained according to general procedure VII, method B, using compound 62 and N-methyl-p-toluidine in presence of DIC and was heated through microwave irradiation for 5 min at 150° C., as a white solid in 40% yield.

$^1$H-NMR (400 MHz, DMSO): 3.31 (s, 3H, CH$_3$); 3.38 (s, 3H, N—CH$_3$); 7.10 (m, 4H, Ar); 7.44 (d, J 8.0 Hz, 2H, Ar); 7.72 (d, J 8.0 Hz, 2H, Ar); 7.82 (m, 1H, Ar); 7.98 (m, 1H, Ar); 8.20 (s, 1H, Ar); 9.60 (m, 1H, Ar). M/Z (M+H)$^+$=388.

Example 53

N-(4-Chloro-phenyl)-4-(6-fluoro-imidazo[1,2-a]pyridine-3-carbonyl)-N-methyl-benzamide

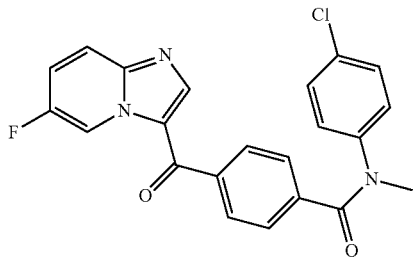 [SMILES: CN(C(=O)c1ccc(C(=O)c2cnc3ccc(F)cn23)cc1)c1ccc(Cl)cc1]

Example 53 was obtained according to general procedure VII, method B, using compound 62 and 4-chloro-N-methylaniline in presence of DIC and was heated through microwave irradiation for 5 min at 150° C., as a white solid in 13% yield.

$^1$H-NMR (400 MHz, DMSO): 3.40 (s, 3H, N—CH$_3$); 7.27 (m, 2H, Ar); 7.36 (m, 2H, Ar); 7.47 (m, 2H, Ar); 7.76 (m, 2H, Ar); 7.83 (m, 1H, Ar); 7.99 (m, 1H, Ar); 8.22 (s, 1H, Ar); 9.61 (m, 1H, Ar). M/Z (M+H)$^+$=408.

Example 54

4-(6-Fluoro-imidazo[1,2-a]pyridine-3-carbonyl)-N-methyl-N-pyridin-2-yl-benzamide

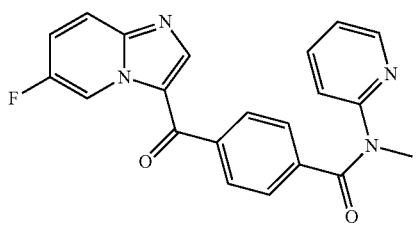

Example 54 was obtained according to general procedure VII, method B, using compound 62 and 2-(methylamino)pyridine in presence of DIC and was heated through microwave irradiation for 5 min at 150° C., as a cream solid in 30% yield.

$^1$H-NMR (400 MHz, DMSO): 3.48 (s, 3H, N—CH$_3$); 7.19-7.24 (m, 2H, Ar); 7.45 (m, 2H, Ar); 7.72 (m, 1H, Ar); 7.77 (m, 2H, Ar); 7.84 (m, 1H, Ar); 7.99 (m, 1H, Ar); 8.24 (s, 1H, Ar); 8.37 (m, 1H, Ar); 9.62 (m, 1H, Ar). M/Z (M+H)$^+$=375.

Example 55

4-(6-Fluoro-imidazo[1,2-a]pyridine-3-carbonyl)-N-methyl-N-pyridin-4-yl-benzamide

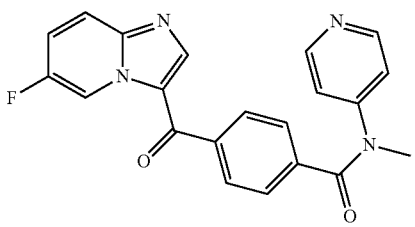

Example 55 was obtained according to the general procedure VII, method B, using compound 62 and 4-(methylamino)pyridine in presence of DIC and was heated through microwave irradiation for 5 min at 150° C., as a white solid in 38% yield.

$^1$H-NMR (400 MHz, DMSO): 3.51 (s, 3H, N—CH$_3$); 7.60 (bs, 2H, Ar); 7.66 (m, 2H, Ar); 7.83-7.89 (m, 3H, Ar); 8.01 (m, 1H, Ar); 8.31 (bs, 1H, Ar); 8.66 (bs, 2H, Ar); 9.65 (m, 1H, Ar). M/Z (M+H)$^+$=375.

Example 56

N-Ethyl-4-(imidazo[1,2-a]pyridine-3-carbonyl)-N-phenyl-benzamide

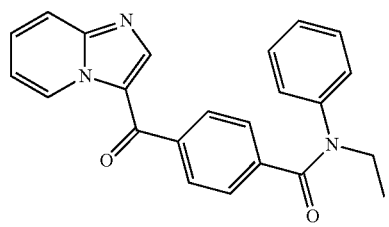 [SMILES: CCN(C(=O)c1ccc(C(=O)c2cnc3ccccn23)cc1)c1ccccc1]

Example 56 was obtained according to the general procedure VII, method A, using compound 61 and N-ethylaniline (2.0 equiv.) in presence of HATU (2.0 equiv.). The reaction mixture was heated through microwave irradiation for 10 min at 130° C. Purification by flash-chromatography (MeOH 3% in CH$_2$Cl$_2$) followed by preparative HPLC afforded the product as a pale orange solid in 49% yield.

$^1$H-NMR (400 MHz, DMSO): 1.13 (t, J 7.0 Hz, 3H, CH$_3$); 3.90 (q, J 6.8 Hz, J 14.7 Hz, 2H, N—CH$_2$); 7.21 (m, 3H, Ar); 7.30 (m, 2H, Ar); 7.38 (m, 1H, Ar); 7.44 (m, 2H, Ar); 7.70 (m, 2H, Ar); 7.75 (m, 1H, Ar); 7.91 (m, 1H, Ar); 8.17 (s, 1H, Ar); 9.60 (m, 1H, Ar). M/Z (M+H)$^+$=370. Mp: 141-145° C.

Example 57

N-Ethyl-4-(imidazo[1,2-a]pyridine-3-carbonyl)-N-pyridin-3-yl-benzamide

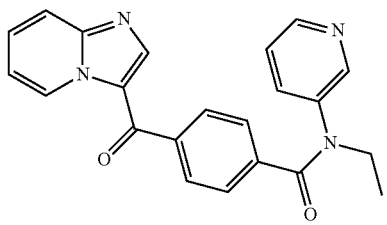 [SMILES: CCN(C(=O)c1ccc(C(=O)c2cnc3ccccn23)cc1)c1cccnc1]

Example 57 was obtained according to general procedure VII, method B, using compound 61 and ethyl-pyridin-3-yl-amine in presence of DIC and was heated through microwave irradiation for 5 min at 150° C., as a cream solid in 3% yield.

$^1$H-NMR (400 MHz, DMSO): 1.14 (t, J 7.1 Hz, 3H, CH$_3$); 3.93 (q, J 7.1 Hz, 2H, N—CH$_2$); 7.38-7.51 (m, 4H, Ar); 7.74-7.81 (m, 3H, Ar); 7.85 (m, 1H, Ar); 7.93 (m, 2H, Ar); 8.23 (s, 1H, Ar); 8.45 (bs, 1H, Ar); 9.61 (m, 1H, Ar). M/Z (M+H)$^+$=371.

Example 58

N,N-Diethyl-4-(imidazo[1,2-a]pyridine-3-carbonyl)-benzamide

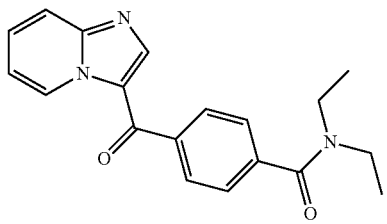 [SMILES: CCN(CC)C(=O)c1ccc(C(=O)c2cnc3ccccn23)cc1]

Example 58 was obtained according to general procedure VII, method B, using compound 61 and diethylamine in presence of DIC and was heated through microwave irradiation for 5 min at 150° C., as a cream solid in 61% yield.

$^1$H-NMR (400 MHz, DMSO): 1.13 (m, 6H, 2*CH$_3$); 3.22 (bd, J 6.3 Hz, 2H, N—CH$_2$); 3.47 (bd, J 6.3 Hz, 2H, N—CH$_2$); 7.42 (m, 1H, Ar); 7.54 (m, 2H, Ar); 7.79 (m, 1H, Ar); 7.92-7.96 (m, 3H, Ar); 8.40 (s, 1H, Ar); 9.67 (m, 1H, Ar). M/Z (M+H)$^+$=322.

Example 59

N-Ethyl-4-(imidazo[1,2-a]pyridine-3-carbonyl)-N-isopropyl-benzamide

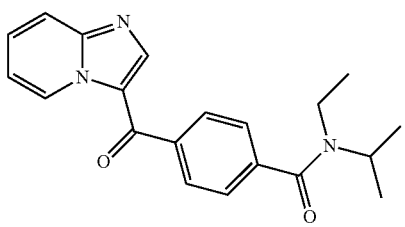 [SMILES: CCN(C(=O)c1ccc(C(=O)c2cnc3ccccn23)cc1)C(C)C]

Example 59 was obtained according to general procedure VII, method B, using compound 61 and N-ethylisopropylamine in presence of DIC and was heated through microwave irradiation for 5 min at 150° C., as an orange solid in 59% yield.

$^1$H-NMR (400 MHz, DMSO): 1.01-1.32 (m, 9H, 3*CH$_3$); 3.36 (bs, 2H, N—CH$_2$); 3.81 (bs, 1H, N—CH); 7.41 (m, 1H, Ar); 7.52 (m, 2H, Ar); 7.78 (m, 1H, Ar); 7.93-7.96 (m, 3H, Ar); 8.40 (s, 1H, Ar); 9.67 (m, 1H, Ar). M/Z (M+H)$^+$=336.

Example 60

4-(Imidazo[1,2-a]pyridine-3-carbonyl)-N,N-dimethyl-benzamide

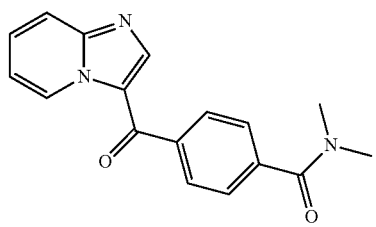 [SMILES: CN(C)C(=O)c1ccc(C(=O)c2cnc3ccccn23)cc1]

Example 60 was obtained according to general procedure VII, method A, using compound 61 and dimethylamine (2 M in THF-1.1 equiv.) in presence of HATU (1.1 equiv.). The reaction mixture was stirred overnight at room temperature.

Purification by flash-chromatography (MeOH 3% to 5% in CH$_2$Cl$_2$) afforded the product as a white solid in 22% yield.

$^1$H-NMR (400 MHz, DMSO): 2.90 (s, 3H, N—CH$_3$); 2.95 (s, 3H, N—CH$_3$); 7.37 (m, 1H, Ar); 7.59 (m, 2H, Ar); 7.73 (m, 1H, Ar); 7.92 (m, 3H, Ar); 8.32 (s, 1H, Ar); 9.66 (m, 1H, Ar). M/Z (M+H)$^+$=294.

Example 61

4-(Imidazo[1,2-a]pyridine-3-carbonyl)-N,N-dipropyl-benzamide

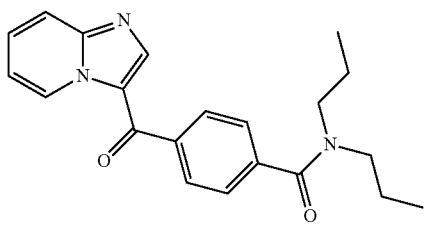 [SMILES: CCCN(CCC)C(=O)c1ccc(C(=O)c2cnc3ccccn23)cc1]

Example 61 was obtained according to general procedure VII, method B, using compound 61 and dipropylamine in presence of DIC and was heated through microwave irradiation for 5 min at 150° C., as a brown oil in 27% yield.

$^1$H-NMR (400 MHz, DMSO): 0.70 (t, J 7.1 Hz, 3H, CH$_3$); 0.93 (t, J 7.1 Hz, 3H, CH$_3$); 1.51 (m, 2H, CH$_2$); 1.63 (m, 2H, CH$_2$); 3.15 (bt, 2H, N—CH$_2$); 3.40 (bt, 2H, N—CH$_2$); 7.40 (m, 1H, Ar); 7.52 (m, 2H, Ar); 7.77 (m, 1H, Ar); 7.94 (m, 3H, Ar); 8.36 (s, 1H, Ar); 9.66 (m, 1H, Ar). M/Z (M+H)$^+$=350.

Example 62

Imidazo[1,2-a]pyridin-3-yl-[4-(pyrrolidine-1-carbonyl)-phenyl]-methanone

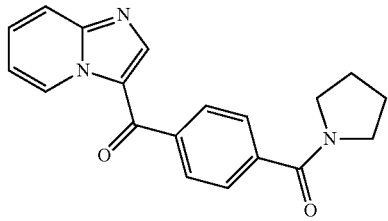 [SMILES: O=C(c1ccc(C(=O)N2CCCC2)cc1)c1cnc2ccccn12]

Example 62 was obtained according to general procedure VII, method B, using compound 61 and pyrrolidine in presence of DIC and was heated through microwave irradiation for 5 min at 150° C., as a white solid in 23% yield.

$^1$H-NMR (400 MHz, DMSO): 1.87 (m, 4H, 2*CH$_2$); 3.42 (t, J 6.3 Hz, 2H, N—CH$_2$); 3.51 (t, J 6.7 Hz, 2H, N—CH$_2$); 7.40 (m, 1H, Ar); 7.70 (m, 2H, Ar); 7.76 (m, 1H, Ar); 7.93 (m, 3H, Ar); 8.35 (s, 1H, Ar); 9.67 (m, 1H, Ar). M/Z (M+H)$^+$=320.

Example 63

Imidazo[1,2-a]pyridin-3-yl-[4-(piperidine-1-carbonyl)-phenyl]-methanone

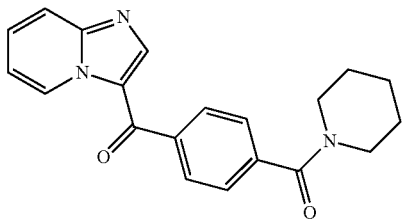 [SMILES: O=C(c1ccc(C(=O)N2CCCCC2)cc1)c1cnc2ccccn12]

Example 63 was obtained according to general procedure VII, method B, using compound 61 and piperidine in presence of DIC and was heated through microwave irradiation for 5 min at 150° C., as a white solid in 7% yield.

$^1$H-NMR (400 MHz, DMSO): 1.45-1.68 (m, 6H, 3*CH$_2$); 3.31 (bs, 2H, N—CH$_2$); 3.62 (bs, 2H, N—CH$_2$); 7.40 (m, 1H, Ar); 7.56 (m, 2H, Ar); 7.77 (m, 1H, Ar); 7.93 (m, 3H, Ar); 8.38 (s, 1H, Ar); 9.67 (d, J 7.0 Hz, 1H, Ar). M/Z (M+H)$^+$=334.

Example 64

[4-(Azepane-1-carbonyl)-phenyl]-imidazo[1,2-a]pyridin-3-yl-methanone

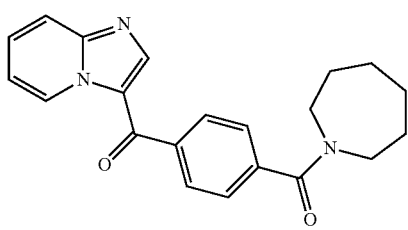 [SMILES: O=C(c1ccc(C(=O)N2CCCCCC2)cc1)c1cnc2ccccn12]

Example 64 was obtained according to general procedure VII, method B, using compound 61 and hexamethyleneimine in presence of DIC and was heated through microwave irradiation for 5 min at 150° C., as a cream solid in 76% yield.

$^1$H-NMR (400 MHz, DMSO): 1.51-1.63 (m, 6H, 3*CH$_2$); 1.70-1.78 (m, 2H, CH$_2$); 3.34 (t, J 5.7 Hz, 2H, N—CH$_2$); 3.60 (t, J 5.8 Hz, 2H, N—CH$_2$); 7.41 (m, 1H, Ar); 7.55 (m, 2H, Ar); 7.79 (m, 1H, Ar); 7.92-7.96 (m, 3H, Ar); 8.39 (s, 1H, Ar); 9.67 (m, 1H, Ar). M/Z (M+H)$^+$=348.

Example 65

[4-(Azocane-1-carbonyl)-phenyl]-imidazo[1,2-a]pyridin-3-yl-methanone

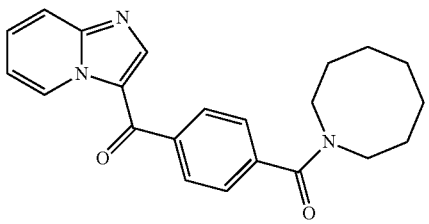 [SMILES: O=C(c1ccc(C(=O)N2CCCCCCC2)cc1)c1cnc2ccccn12]

Example 65 was obtained according to general procedure VII, method B, using compound 61 and heptamethyleneimine in presence of DIC and was heated through microwave irradiation for 5 min at 150° C., as a green oil in 28% yield.

$^1$H-NMR (400 MHz, DMSO): 1.56 (m, 8H, 4*CH$_2$); 1.77 (bs, 2H, N—CH$_2$); 3.30 (m, 2H, N—CH$_2$); 3.57 (t, J 5.9 Hz, 2H, N—CH$_2$); 7.43 (m, 1H, Ar); 7.54 (m, 2H, Ar); 7.80 (m, 1H, Ar); 7.95 (m, 3H, Ar); 8.40 (s, 1H, Ar); 9.67 (m, 1H, Ar). M/Z (M+H)$^+$=362.

Example 66

[4-(Azonane-1-carbonyl)-phenyl]-imidazo[1,2-a]pyridin-3-yl-methanone

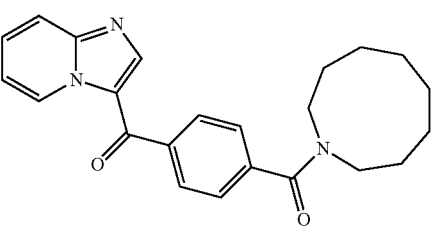 [SMILES: O=C(c1ccc(C(=O)N2CCCCCCCC2)cc1)c1cnc2ccccn12]

Example 66 was obtained according to general procedure VII, method B, using compound 61 and octamethyleneimine in presence of DIC and was heated through microwave irradiation for 5 min at 150° C., as a yellow oil in 25% yield.

$^1$H-NMR (400 MHz, DMSO): 1.55-1.82 (bm, 12H, 6*CH$_2$); 3.36 (bs, 2H, N—CH$_2$); 3.55 (bt, J 5.3 Hz, 2H, N—CH$_2$); 7.41 (m, 1H, Ar); 7.53 (m, 2H, Ar); 7.77 (m, 1H, Ar); 7.93-7.96 (m, 3H, Ar); 8.38 (s, 1H, Ar); 9.67 (m, 1H, Ar). M/Z (M+H)$^+$=376.

Example 67

Imidazo[1,2-a]pyridin-3-yl-[4-(morpholine-4-carbonyl)-phenyl]-methanone

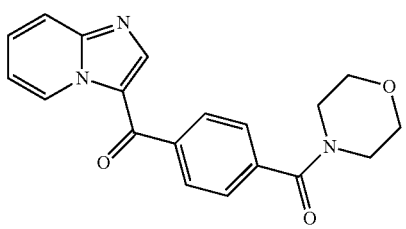 [SMILES: O=C(c1ccc(C(=O)N2CCOCC2)cc1)c1cnc2ccccn12]

Example 67 was obtained according to general procedure VII, method A, using compound 61 and morpholine (1.1 equiv.) in presence of HATU (1.1 equiv.). The reaction mixture was stirred 48 Hrs at R.T. Purification by flash-chromatography (MeOH 5% in CH$_2$Cl$_2$) afforded the product as a yellow solid in 43% yield.

$^1$H-NMR (400 MHz, DMSO): 3.39 (b, 2H, CH$_2$); 3.59-3.67 (b, 6H, 3*CH$_2$); 7.38 (m, 1H, Ar); 7.60 (d, J 6.2 Hz, 2H, Ar); 7.73 (m, 1H, Ar); 8.05 (m, 3H, Ar); 8.32 (s, 1H, Ar); 9.66 (d, J 8.4 Hz, 1H, Ar). M/Z (M+H)$^+$=336.

Example 68

Imidazo[1,2-a]pyridin-3-yl-[4-(4-methyl-piperazine-1-carbonyl)-phenyl]-methanone

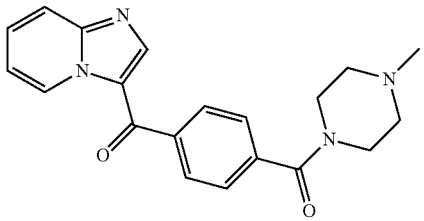 [SMILES: CN1CCN(C(=O)c2ccc(C(=O)c3cnc4ccccn34)cc2)CC1]

Example 68 was obtained according to general procedure VII, method A, using compound 61 and N-methylpiperazine (1.5 equiv.) in presence of HATU (1.5 equiv.). The reaction mixture was stirred 48 Hrs at R.T. Purification by flash-chromatography (MeOH 3% to 5% in CH$_2$Cl$_2$) afforded the product as a pale yellow solid in 23% yield.

$^1$H-NMR (400 MHz, DMSO): 2.27 (b, 2H, N—CH$_2$); 2.41 (b, 2H, N—CH$_2$); 3.38 (b, 2H, N—CH$_2$); 3.66 (b, 2H, N—CH$_2$); 7.37 (t, J 6.9 Hz, 1H, Ar); 7.58 (m, 2H, Ar); 7.73 (m, 1H, Ar); 7.92 (m, 3H, Ar); 8.32 (s, 1H, Ar); 9.66 (d, J 6.9 Hz, 1H, Ar). N—CH$_3$ signal under water peak. M/Z (M+H)$^+$=349.

Example 69

[4-(2,3-Dihydro-indole-1-carbonyl)-phenyl]-imidazo[1,2-a]pyridin-3-yl-methanone

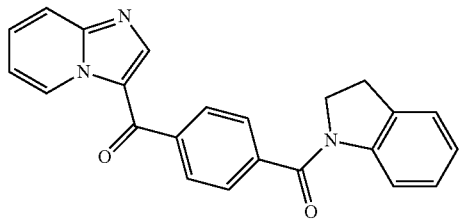 [SMILES: O=C(c1ccc(C(=O)N2CCc3ccccc32)cc1)c1cnc2ccccn12]

Example 69 was obtained according to general procedure VII, method B, using compound 61 and indoline in presence of DIC and was heated through microwave irradiation for 5 min at 150° C., as a cream solid in 16% yield.

$^1$H-NMR (400 MHz, DMSO): 3.12 (t, J 8.3 Hz, 2H, CH$_2$); 4.05 (t, J 8.3 Hz, 2H, N—CH$_2$); 7.02-7.21 (bm, 2H, Ar); 7.30 (d, J 7.4 Hz, 1H, Ar); 7.38 (m, 1H, Ar); 7.72-7.79 (m, 3H, Ar); 7.93-7.98 (m, 3H, Ar); 8.15 (bs, 1H, Ar); 8.33 (s, 1H, Ar); 9.68 (m, 1H, Ar). M/Z (M+H)$^+$=368.

Example 70

Imidazo[1,2-a]pyridin-3-yl-[4-(2-methyl-2,3-dihydro-indole-1-carbonyl)-phenyl]-methanone

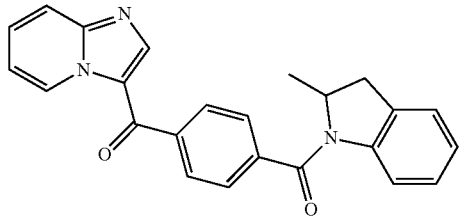 [SMILES: CC1Cc2ccccc2N1C(=O)c1ccc(C(=O)c2cnc3ccccn23)cc1]

Example 70 was obtained according to general procedure VII, method B, using compound 61 and 2-methylindoline in presence of DIC and was heated through microwave irradiation for 5 min at 150° C., as a red solid in 21% yield.

$^1$H-NMR (400 MHz, DMSO): 1.09 (bs, 3H, CH$_3$); 2.67 (d, J 15.7 Hz, 1H, CH); 3.47 (dd, J 9.0 Hz, J 15.7 Hz, 1H, CH); 4.64 (bs, 1H, N—CH); 7.04-7.20 (m, 2H, Ar); 7.32 (d, J 7.4 Hz, 1H, Ar); 7.41 (m, 1H, Ar); 7.77 (m, 3H, Ar); 7.93-8.00 (m, 3H, Ar); 8.37 (s, 1H, Ar); 9.68 (m, 1H, Ar). 1 aromatic proton is missing. By performing the $^1$H-NMR at 80° C., a new signal appeared around 7.40 (b, 1H, Ar). M/Z (M+H)$^+$=382.

Example 71

[4-(3,4-Dihydro-2H-quinoline-1-carbonyl)-phenyl]-imidazo[1,2-a]pyridin-3-yl-methanone

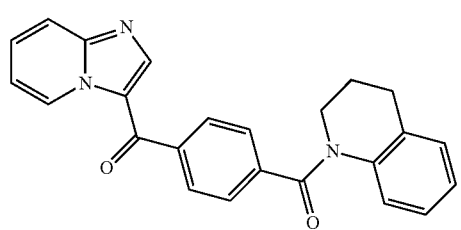 [SMILES: O=C(c1ccc(C(=O)N2CCCc3ccccc32)cc1)c1cnc2ccccn12]

Example 71 was obtained according to general procedure VII, method B, using compound 61 and 1,2,3,4-tetrahydroquinoline in presence of DIC and was heated through microwave irradiation for 5 min at 150° C., as an orange solid in 14% yield.

¹H-NMR (400 MHz, DMSO): 1.98 (m, 2H, CH₂); 2.84 (t, J 6.6 Hz, 2H, CH₂); 3.79 (t, J 6.4 Hz, 2H, N—CH₂); 6.88 (bs, 2H, Ar); 6.94 (t, J 7.6 Hz, 1H, Ar); 7.22 (d, J 7.4 Hz, 1H, Ar); 7.40 (m, 1H, Ar); 7.53 (d, J 8.0 Hz, 2H, Ar); 7.77 (m, 1H, Ar); 7.83 (d, J 8.0 Hz, 2H, Ar); 7.93 (m, 1H, Ar); 8.27 (s, 1H, Ar); 9.64 (m, 1H, Ar). M/Z (M+H)⁺=382. Mp: 169-175° C.

Example 72

Imidazo[1,2-a]pyridin-3-yl-[4-(octahydro-quinoline-1-carbonyl)-phenyl]-methanone

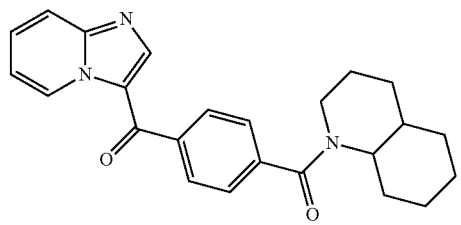 [SMILES: O=C(c1ccc(C(=O)N2CCCC3CCCCC32)cc1)c1cnc2ccccn12]

Example 72 was obtained according to general procedure VII, method B, using compound 61 and trans-decahydroquinoline in presence of DIC and was heated through microwave irradiation for 5 min at 150° C., as a colourless oil in 24% yield.

¹H-NMR (400 MHz, DMSO): 1.09-1.80 (m, 12H, 6*CH₂); 2.19 (m, 1H, CH); 3.32-3.45 (m, 3H, N—CH₂+N—CH); 7.35 (m, 1H, Ar); 7.54 (m, 2H, Ar); 7.72 (m, 1H, Ar); 7.87 (m, 1H, Ar); 7.92 (m, 2H, Ar); 8.27 (s, 1H, Ar); 9.66 (m, 1H, Ar). M/Z (M+H)⁺=388.

Example 73

3-[4-(Azepan-1-ylcarbonyl)-2-fluorobenzoyl]imidazo[1,2-a]pyridine-6-carbonitrile

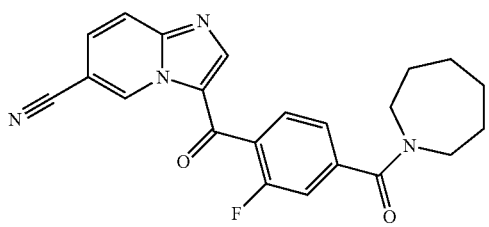 [SMILES: N#Cc1ccc2ncc(C(=O)c3ccc(C(=O)N4CCCCCC4)cc3F)n2c1]

Example 73 was obtained according to general procedure VII, method D, using compound 64 and hexamethyleneimine without purification as a beige solid in 77% yield.

¹H-NMR (400 MHz, DMSO): 1.54-1.63 (m, 6H, 3*CH₂); 1.73 (m, 2H, CH₂); 3.35 (m, 2H, N—CH₂); 3.59 (m, 2H, N—CH₂); 7.37 (dd, J 1.3 Hz, J 7.8 Hz, 1H, Ar); 7.45 (dd, J 1.0 Hz, J 10.2 Hz, 1H, Ar); 7.76 (t, J 7.4 Hz, 1H, Ar); 8.03 (dd, J 1.7 Hz, J 9.32 Hz, 1H, Ar); 8.09 (dd, J 0.8 Hz, J 9.3 Hz, 1H, Ar); 8.41 (d, J 1.5 Hz, 1H, Ar); 10.09 (s, 1H, Ar). M/Z (M+H)⁺=391. Mp: 128-130° C.

Example 74

4-[(6-Fluoroimidazo[1,2-a]pyridin-3-yl)carbonyl]-N,N-diisopropylbenzamide

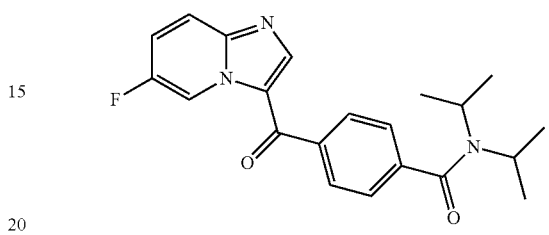

Example 74 was obtained according to general procedure VII, method E, using compound 62 and diisopropylamine. Purification by flash-chromatography (AcOEt 0% to 100% in cyclohexane) afforded the product as a beige solid in 47% yield.

¹H-NMR (400 MHz, DMSO): 1.20-1.45 (m, 12H, 4*CH₃); 3.67 (m, 2H, 2*CH); 7.48-7.50 (m, 2H, Ar); 7.83 (m, 1H, Ar); 7.93-8.03 (m, 3H, Ar); 8.38 (s, 1H, Ar); 9.67 (m, 1H, Ar). M/Z (M+H)⁺=368.

Example 75

N-Ethyl-3-fluoro-4-[(6-fluoroimidazo[1,2-a]pyridin-3-yl)carbonyl]-N-isopropylbenzamide

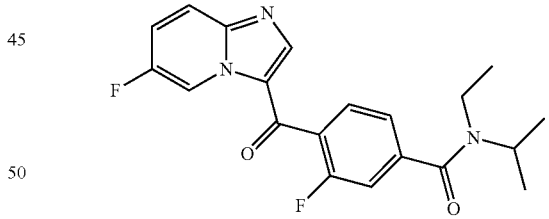

Example 75 was obtained according to general procedure VII, method C, using compound 63 and N-ethylisopropylamine. The reaction was cooled at −20° C. for 15 min then was allowed to reach R.T. and was hydrolyzed after 10 min. Purification by flash-chromatography (10% to 50% AcOEt in cyclohexane) afforded the product in 33% yield.

¹H-NMR (400 MHz, CDCl₃): 1.21-1.40 (m, 9H, 3*CH₃); 3.25-3.48 (m, 2H, CH₂); 3.94-3.97 (m, 1H, N—CH); 7.24 (dd, J 1.3 Hz, J 9.6 Hz, 1H, Ar); 7.30 (dd, J 1.2 Hz, J 7.7 Hz, 1H, Ar); 7.54 (ddd, J 2.4 Hz, J 7.3 Hz, J 9.7 Hz, 1H, Ar); 7.68 (dd, J 7.0 Hz, J 7.5 Hz, 1H, Ar); 7.84 (dd, J 4.9 Hz, J 9.7 Hz, 1H, Ar); 8.15 (d, J 2.0 Hz, 1H, Ar); 9.79 (dd, J 2.5 Hz, J 4.3 Hz, 1H, Ar). M/Z (M+H)⁺=372.

Example 76

(6-Fluoroimidazo[1,2-a]pyridin-3-yl)[2-fluoro-4-(piperidin-1-ylcarbonyl)phenyl]methanone

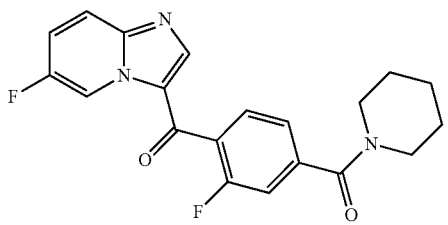 [SMILES: O=C(c1ccc(C(=O)N2CCCCC2)cc1F)c1cnc2ccc(F)cn12]

Example 76 was obtained according to general procedure VII, method C, using compound 63 and piperidine. The reaction was cooled at −20° C. for 15 min then was allowed to reach R.T. and was hydrolyzed after 10 min. Purification by flash-chromatography (50% to 100% AcOEt in cyclohexane) afforded the product in 85% yield.

$^1$H-NMR (400 MHz, DMSO): 1.49-1.64 (m, 6H, 3*CH$_2$); 3.32 (m, 2H, N—CH$_2$); 3.61 (m, 2H, N—CH$_2$); 7.36 (d, J 7.7 Hz, 1H, Ar); 7.43 (d, J 10.2 Hz, 1H, Ar); 7.85 (t, J 7.4 Hz, 1H, Ar); 7.85-7.91 (m, 1H, Ar); 8.02 (dd, J 5.2 Hz, J 9.8 Hz, 1H, Ar); 8.28 (s, 1H, Ar); 9.66 (m, 1H, Ar). M/Z (M+H)$^+$=370.

Compound 65

Ethyl 4-[(6-bromoimidazo[1,2-a]pyridin-3-yl)carbonyl]-3-fluorobenzoate

Compound 65 was obtained according to general procedure V starting from compounds 10 and 55 in DMF trough microwave irradiation 10 min at 120° C.

Purification by flash-chromatography (EtOAc 50% in cyclohexane) followed by trituration in Et$_2$O afforded the product in 22% yield as a grey solid.

M/Z (M[$^{79}$Br]+H)$^+$=391.

Example 77

(6-Bromoimidazo[1,2-a]pyridin-3-yl)[2-fluoro-4-(piperidin-1-ylcarbonyl)phenyl]methanone

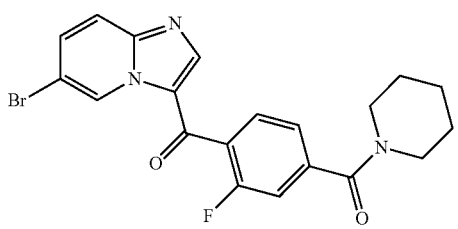 [SMILES: O=C(c1ccc(C(=O)N2CCCCC2)cc1F)c1cnc2ccc(Br)cn12]

Example 77 was obtained according to general procedure VII, method F, using compound 65 and piperidine. Purification by flash-chromatography (AcOEt), then trituration in Et$_2$O afforded the product as a beige solid in 24% yield.

$^1$H-NMR (400 MHz, CDCl$_3$): 1.75 (m, 6H, 3*CH$_2$); 3.40 (m, 2H, N—CH$_2$); 3.76 (m, 2H, N—CH$_2$); 7.29 (dd, J 1.4 Hz, J 8.2 Hz, 1H, Ar); 7.34 (dd, J 1.4 Hz, J 7.8 Hz, 1H, Ar); 7.65-7.70 (m, 2H, Ar); 7.74 (d, J 9.6 Hz, 1H, Ar); 8.10 (d, J 2.0 Hz, 1H, Ar); 9.97 (m, 1H, Ar). M/Z (M+H)$^+$=431.

General Procedure VIII: Formation of Indazoles AF and AM from Fluoroketones AC and AE (Schemes 5 and 6).

A mixture of fluoro ketone AC or AE (1.0 equiv.) and the selected hydrazine (10-75 equiv.) in the presence of a base (0 to 23 equiv.) in an appropriate solvent was heated through microwave irradiation for 5-45 min at 110-180° C. or under standard oil-bath heating.

After cooling at R.T., the reaction mixture was hydrolyzed with water. If precipitation occurred, solid was collected, washed with water and was dried under reduced pressure overnight. If not, reaction mixture was extracted with AcOEt. Organic layer was washed with brine, dried over MgSO$_4$ and concentrated.

Further purification could be performed by chromatography, trituration or by preparative HPLC followed by co-evaporation in HCl 1M to afford the product as a chlorhydrate salt.

Compound 66

Ethyl 3-(6-fluoroimidazo[1,2-a]pyridin-3-yl)-1-methyl-1H-indazole-6-carboxylate

Compound 66 was obtained according to general procedure VIII, using compound 60 and N-methyl-hydrazine (30 equiv.) in DMF and heating for 15 min at 110° C. Compound was isolated in 68% yield as a beige powder by triturating crude material in MeOH.

M/Z (M+H)$^+$=339.

Compound 67

Ethyl 3-(6-cyanoimidazo[1,2-a]pyridin-3-yl)-1-methyl-1H-indazole-6-carboxylate

Compound 67 was obtained according to general procedure VIII, using compound 59 and N-methyl-hydrazine (16 equiv.) in DMF and heating for 60 min at 90° C. Compound was isolated in 48% yield as a beige powder by triturating crude material in MeOH.

M/Z (M+H)$^+$=346.

Compound 68

3-(6-Fluoroimidazo[1,2-a]pyridin-3-yl)-1-methyl-1H-indazole-6-carboxylic acid

Compound 68 was obtained according to general procedure VI starting from compound 66 in THF and was stirred at room temperature overnight, to give a white solid in 90% yield.

M/Z (M+H)$^+$=303.

Compound 69

3-(6-Cyanoimidazo[1,2-a]pyridin-3-yl)-1-methyl-1H-indazole-6-carboxylic acid

Compound 69 was obtained according to general procedure VI starting from compound 67 in THF and was stirred at R.T. overnight, to give a white solid in 86% yield.

M/Z (M+H)$^+$=318.

Compound 70

Ethyl 4-[(6-cyano-2-methylimidazo[1,2-a]pyridin-3-yl)carbonyl]-3-fluorobenzoate Compound 70 was obtained according to general procedure V starting from compounds 18 and 55 in DMF through microwave irradiation 10 min at 120° C.

Compound 70 precipitated during hydrolysis with HCl 1M. Solid was filtered, washed with water and was dried under reduced pressure. Compound 70 was isolated as a brown solid in 73% yield.

M/Z (M+H)$^+$=352.

Compound 71

Ethyl 3-(6-cyano-2-methylimidazo[1,2-a]pyridin-3-yl)-1-methyl-1H-indazole-6-carboxylate Compound 71 was obtained according to general procedure VIII, using compound 70 and N-methyl-hydrazine (20 equiv.) in DMF and heating under microwave irradiation for 10 min at 120° C. During hydrolysis process, compound 71 precipitated. Triturating the dried solid in EtOAc afforded the product as a white solid.

M/Z (M+H)$^+$=360.

Example 78

Azepan-1-yl-[3-(6-fluoro-imidazo[1,2-a]pyridin-3-yl)-1H-indazol-6-yl]-methanone

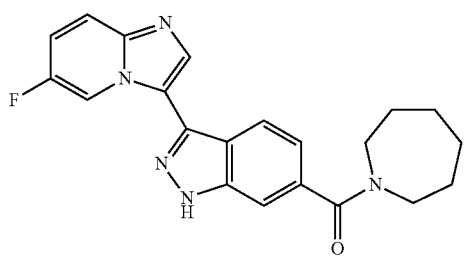 [SMILES: O=C(c1ccc2c(-c3cnc4ccc(F)cn34)n[nH]c2c1)N1CCCCCC1]

Example 78 was obtained according to general procedure VIII, using example 27 and hydrazine (26 equiv.) in DMA and heating through microwave irradiation for 15 min at 150° C.

Purification by flash-chromatography (MeoH 0 to 10% in CH$_2$Cl$_2$), then trituration in Et$_2$O afforded the product as a brown solid in 61% yield.

$^1$H-NMR (400 MHz, DMSO): 1.51-1.63 (bm, 6H, 3*CH$_2$); 1.72-1.79 (bm, 2H, CH$_2$); 3.34 (b, 2H, N—CH$_2$); 7.28 (dd, J 1.2 Hz, J 8.4 Hz, 1H, Ar); 7.67 (s, 1H, Ar); 7.99 (m, 1H, Ar); 8.08 (m, 1H, Ar); 8.26 (d, J 8.4 Hz, 1H, Ar); 8.93 (s, 1H, Ar); 9.78 (m, 1H, Ar); 13.96 (s, 1H, NH). N—CH$_2$ signal under water peak. M/Z (M+H)$^+$=378.

Example 79

Azepan-1-yl-[3-(6-fluoro-imidazo[1,2-a]pyridin-3-yl)-1-methyl-1H-indazol-6-yl]-methanone

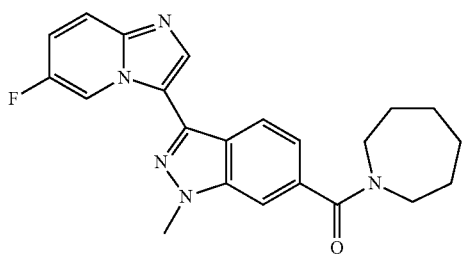 [SMILES: Cn1nc(-c2cnc3ccc(F)cn23)c2ccc(C(=O)N3CCCCCC3)cc21]

Example 79 was obtained according to general procedure VIII, using example 27 and methyl hydrazine (72 equiv.) in DMA and heating through microwave irradiation for 15 min at 150° C. Example 79 precipitated from the crude mixture after hydrolysis as a pale yellow solid in 50% yield.

$^1$H-NMR (400 MHz, DMSO): 1.51-1.65 (bm, 6H, 3*CH$_2$); 1.75-1.81 (bm, 2H, CH$_2$); 3.35 (b, 2H, N—CH$_2$); 3.63 (b, 2H, N—CH$_2$); 4.27 (s, 3H, N—CH$_3$); 7.29 (dd, J 1.2 Hz, J 8.4 Hz, 1H, Ar); 7.87 (s, 1H, Ar); 7.97 (m, 1H, Ar); 8.08 (m, 1H, Ar); 8.28 (dd, J 0.6 Hz, J 8.4 Hz, 1H, Ar); 8.95 (s, 1H, Ar); 9.81 (m, 1H, Ar). M/Z (M+H)$^+$=392.

Example 80

Azepan-1-yl-[3-(6-fluoro-imidazo[1,2-a]pyridin-3-yl)-1-(2-hydroxy-ethyl)-1H-indazol-6-yl]-methanone, HCl salt

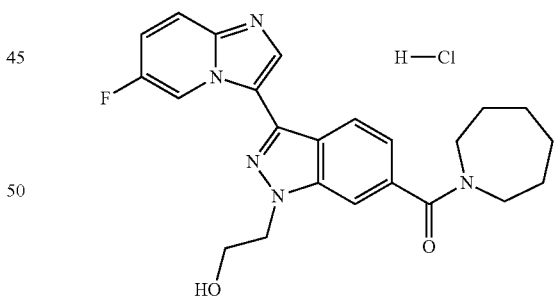

Example 80 was obtained according to general procedure VIII, using example 27 and 2-hydroxyethyl-hydrazine (55 equiv.) in presence of Cs$_2$CO$_3$ (1.2 equiv) in DMA and heating through microwave irradiation for 10 min at 150° C.

Purification by preparative HPLC followed by co-evaporation in HCl 1M afforded the product as a yellow solid in 23% yield.

$^1$H-NMR (400 MHz, DMSO): 1.50-1.65 (bm, 6H, 3*CH$_2$); 1.75-1.81 (bm, 2H, CH$_2$); 3.34 (b, 2H, N—CH$_2$); 3.62 (t, J 5.9 Hz, 2H, N—CH$_2$); 3.92 (t, J 5.2 Hz, 2H, N—CH$_2$); 4.69 (t, J 5.2 Hz, 2H, O—CH$_2$); 7.28 (dd, J 1.2 Hz, J 8.4 Hz, 1H, Ar);

7.87 (s, 1H, Ar); 7.98 (m, 1H, Ar); 8.09 (m, 1H, Ar); 8.26 (dd, J 0.7 Hz, J 8.4 Hz, 1H, Ar); 8.96 (s, 1H, Ar); 9.81 (m, 1H, Ar). M/Z (M+H)$^+$=422.

Example 81

[6-(Azepan-1-ylcarbonyl)]-1-ethyl-3[6-fluoro-imidazo[1,2-a]pyridin-3-yl]-1H-indazole, HCl salt

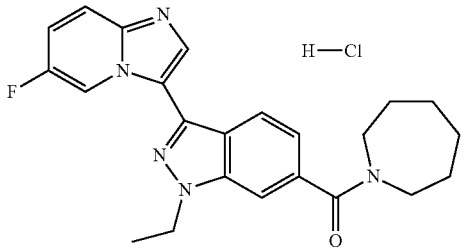 [SMILES: CCn1nc(-c2cnc3ccc(F)cn23)c2ccc(C(=O)N3CCCCCC3)cc21 ; Cl]

Example 81 was obtained according to general procedure VIII, using example 27 and ethylhydrazine oxalate (24 equiv.) in aqueous NaOH (2N, 46 equiv) and heating through microwave irradiation for 10 min at 180° C. twice. Purification by preparative HPLC followed by co-evaporation in HCl 1M afforded the product as a beige solid in 48% yield.

$^1$H-NMR (400 MHz, DMSO): 1.50 (t, J 7.1 Hz, 6H, CH$_2$CH$_3$); 1.52-1.60 (m, 6H, 3*CH$_2$); 1.73-1.77 (m, 2H, CH$_2$); 3.33 (m, 2H, N—CH$_2$); 3.60 (t, J 5.7 Hz, 2H, N—CH$_2$); 4.63 (q, J 7.1 Hz, 1H, CH$_2$CH$_3$); 7.26 (d, J 8.4 Hz, 1H, Ar); 7.82 (s, 1H, Ar); 7.94 (m, 1H, Ar); 8.03 (dd, J 4.5 Hz, J 9.7 Hz, 1H, Ar); 8.21 (d, J 8.4 Hz, 1H, Ar); 8.82 (s, 1H, Ar); 9.75 (s, 1H, Ar). M/Z (M+H)$^+$=406.

Example 82

[6-(Azepan-1-ylcarbonyl)]-1-isopropyl-3[6-fluoro-imidazo[1,2-a]pyridin-3-yl]-1H-indazole, HCl salt

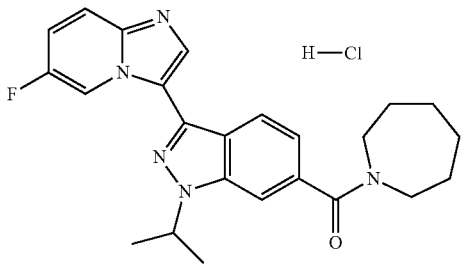 [SMILES: CC(C)n1nc(-c2cnc3ccc(F)cn23)c2ccc(C(=O)N3CCCCCC3)cc21 ; Cl]

Example 82 was obtained according to general procedure VIII, using example 27 and isopropylhydrazine hydrochloride (24 equiv.) in aqueous NaOH (2N, 23 equiv) and heating through microwave irradiation for 45 min at 160° C. Purification by preparative HPLC followed by co-evaporation in HCl 1M afforded the product as a beige solid in 10% yield.

$^1$H-NMR (400 MHz, DMSO): 1.57 (m, 6H, 3*CH$_2$); 1.62 (d, J 6.6 Hz, 6H, CH(CH$_3$)$_2$); 1.76-1.80 (m, 2H, CH$_2$); 3.63 (t, J 5.6 Hz, 2H, N—CH$_2$); 5.25 (sept, J 6.6 Hz, 1H, CH(CH$_3$)$_2$); 7.27 (d, J 8.3 Hz, 1H, Ar); 7.79 (m, 1H, Ar); 7.90 (s, H, Ar); 8.00 (dd, J 5.1 Hz, J 9.6 Hz, 1H, Ar); 8.28 (d, J 8.3 Hz, 1H, Ar); 8.78 (s, 1H, Ar); 9.68 (m, 1H, Ar). 1 signal is missing (CH$_2$) probably under HOD signal. M/Z (M+H)$^+$=420.

Example 83

[6-(Azepan-1-ylcarbonyl)]-1-isobutyl-3[6-fluoro-imidazo[1,2-a]pyridin-3-yl]-1H-indazole, HCl salt

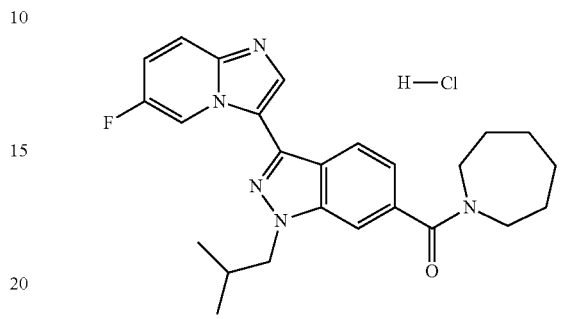

Example 83 was obtained according to general procedure VIII, using example 27 and 2-methylpropylhydrazine hydrochloride (24 equiv.) in aqueous NaOH (2N, 23 equiv) and heating through microwave irradiation for 30 min at 150° C. twice. Purification by preparative HPLC followed by co-evaporation in HCl 1M afforded the product as a beige solid in 31% yield.

$^1$H-NMR (400 MHz, DMSO): 0.94 (d, J 6.7 Hz, 6H, CH(CH$_3$)$_2$); 1.53-1.63 (m, 6H, 3*CH$_2$); 1.76-1.82 (m, 2H, CH$_2$); 2.35 (m, 1H, CH$_2$CH(CH$_3$)$_2$); 3.34 (m, 2H, N—CH$_2$); 3.63 (t, J 5.8 Hz, 2H, N—CH$_2$); 4.48 (d, J 7.2 Hz, 1H, CH$_2$CH(CH$_3$)$_2$); 7.28 (dd, J 1.0 Hz, J 8.3 Hz, 1H, Ar); 7.92 (m, 2H, Ar); 8.08 (dd, J 5.0 Hz, J 9.7 Hz, 1H, Ar); 8.30 (d, J 8.3 Hz, 1H, Ar); 8.94 (s, 1H, Ar); 9.76 (dd, J 2.2 Hz, J 4.3 Hz, 1H, Ar). M/Z (M+H)$^+$=434.

Example 84

3-[6-(Azepan-1-ylcarbonyl)-1-methyl-1H-indazol-3-yl]imidazo[1,2-a]pyridine-6-carbonitrile, HCl salt

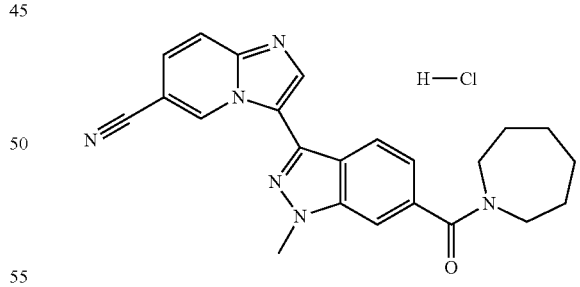

Example 84 was obtained according to general procedure VIII, using example 73 and N-methyl-hydrazine (15 equiv.) in DMF and heating through microwave irradiation for 10 min at 120° C. Trituration in MeOH afforded a beige solid which was dissolved in CH$_2$Cl$_2$. To the solution filtered through a pad of celite, HCl in Et$_2$O was added. Example 84 was filtrated, washed with CH$_2$Cl$_2$ and dried under reduced pressure.

$^1$H-NMR (400 MHz, DMSO): 1.55-1.62 (bm, 6H, 3*CH$_2$); 1.75-1.80 (bm, 2H, CH$_2$); 3.35 (m, 2H, N—CH$_2$); 3.63 (t, J 5.7 Hz, 2H, N—CH$_2$); 4.26 (s, 3H, N—CH$_3$); 7.27 (d, J 8.1

Hz, 1H, Ar); 7.85 (s, 1H, Ar); 7.86 (m, 1H, Ar); 8.02 (d, J 9.4 Hz, 1H, Ar); 8.28 (d, J 8.3 Hz, 1H, Ar); 8.80 (s, 1H, Ar); 10.16 (s, 1H, Ar). M/Z (M+H)⁺=399. Mp: >250° C.

Example 85

[6-(Azepan-1-ylcarbonyl)]-1-methyl-3[6-(trifluoromethyl)-imidazo[1,2-a]pyridin-3-yl]-1H-indazole, HCl salt

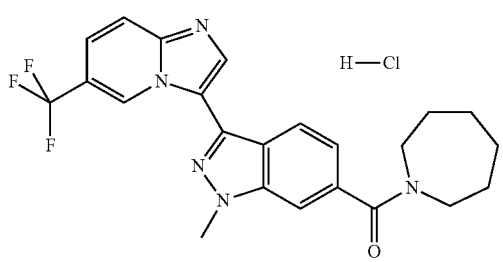 [SMILES: Cn1nc(-c2cnc3ccc(C(F)(F)F)cn23)c2ccc(C(=O)N3CCCCCC3)cc21 ; Cl]

Example 85 was obtained according to general procedure VIII, using example 35 and N-methyl-hydrazine (15 equiv.) in DMF and heating through microwave irradiation for 10 min at 120° C. twice. Purification by preparative HPLC followed by co-evaporation in HCl 1M afforded the product as a beige solid in 31% Yield.

¹H-NMR (400 MHz, DMSO): 1.57-1.61 (m, 6H, 3*CH₂); 1.78 (m, 2H, CH₂); 3.35 (m, 2H, CH₂); 3.62 (m, 2H, CH₂); 4.24 (s, 3H, CH₃); 7.28 (d, J 8.2 Hz, 1H, Ar); 7.85-7.89 (m, 2H, Ar); 8.08 (d, J 9.3 Hz, 1H, Ar); 8.30 (d, J 8.3 Hz, 1H, Ar); 8.83 (s, 1H, Ar); 10.09 (s, 1H, Ar). M/Z (M+H)⁺=442. Mp: 202-204° C.

Example 86

[6-(Azepan-1-ylcarbonyl)]-1-methyl-3[6-chloro-imidazo[1,2-a]pyridin-3-yl]-1H-indazole, HCl salt

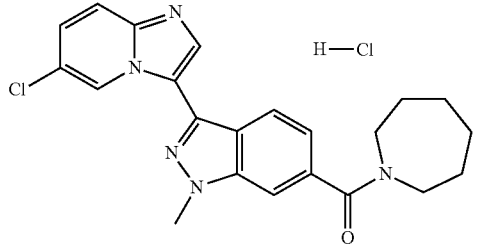 [SMILES: Cn1nc(-c2cnc3ccc(Cl)cn23)c2ccc(C(=O)N3CCCCCC3)cc21 ; Cl]

Example 86 was obtained according to general procedure VIII, using example 32 and N-methyl-hydrazine (60 equiv.) in DMF and heating through microwave irradiation for 5 min at 130° C. Purification by preparative HPLC followed by co-evaporation in HCl 1M afforded the product as a beige solid in 26% Yield.

¹H-NMR (400 MHz, DMSO): 1.50-1.61 (m, 6H, 3*CH₂); 1.74-1.91 (m, 2H, CH₂); 3.34 (m, 2H, CH₂); 3.70 (m, 2H, CH₂); 4.23 (s, 3H, CH₃); 7.28 (dd, J 0.8 Hz, J 8.4 Hz, 1H, Ar); 7.81-7.84 (m, 2H, Ar); 7.97 (d, J 9.5 Hz, 1H, Ar); 8.24 (d, J 8.5 Hz, 1H, Ar); 8.79 (s, 1H, Ar); 9.77 (s, 1H, Ar). M/Z (M[³⁵Cl]+H)⁺=408. Mp: 245-248° C.

Example 87

[6-(Azepan-1-ylcarbonyl)]-1-methyl-3[6-methyl-imidazo[1,2-a]pyridin-3-yl]-1H-indazole, HCl salt

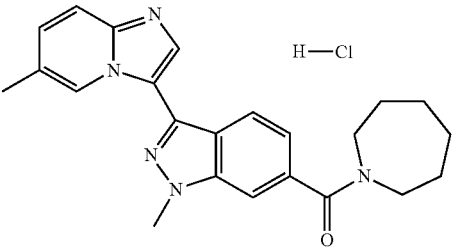 [SMILES: Cc1ccc2ncc(-c3nn(C)c4cc(C(=O)N5CCCCCC5)ccc34)n2c1 ; Cl]

Example 87 was obtained according to general procedure VIII, using example 34 and N-methyl-hydrazine (70 equiv.) in DMF and heating through microwave irradiation for 10 min at 120° C. Purification by preparative HPLC followed by co-evaporation in HCl 1M afforded the product as a white solid in 25% Yield.

¹H-NMR (400 MHz, DMSO): 1.53-1.59 (m, 6H, 3*CH₂); 1.73-1.79 (m, 2H, CH₂); 3.32 (m, 2H, CH₂); 3.61 (t, J 5.9 Hz, 2H, N—CH₂); 4.23 (s, 3H, CH₃); 7.28 (d, J 8.4 Hz, 1H, Ar); 7.81 (s, 1H, Ar); 7.85 (d, J 9.2 Hz, 1H, Ar); 7.94 (d, J 9.2 Hz, 1H, Ar); 8.18 (d, J 8.4 Hz, 1H, Ar); 8.81 (s, 1H, Ar); 9.51 (s, 1H, Ar). 1 signal is missing (CH₃) probably under DMSO signal. M/Z (M+H)⁺=388. Mp: >250° C.

Example 88

[6-(Azepan-1-ylcarbonyl)]-1-methyl-3[6-ethyl-imidazo[1,2-a]pyridin-3-yl]-1H-indazole, HCl salt

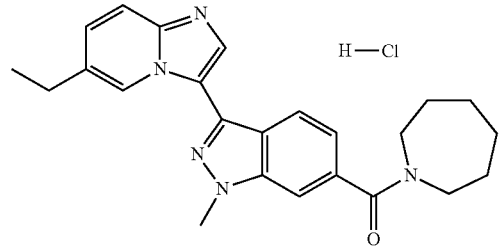 [SMILES: CCc1ccc2ncc(-c3nn(C)c4cc(C(=O)N5CCCCCC5)ccc34)n2c1 ; Cl]

Example 88 was obtained according to general procedure VIII, using example 36 and N-methyl-hydrazine (50 equiv.) in DMF and heating through microwave irradiation for 10 min at 120° C. Purification by preparative HPLC followed by co-evaporation in HCl 1M afforded the product as a beige solid in 26% Yield.

¹H-NMR (400 MHz, DMSO): 1.31 (t, J 7.5 Hz, 3H, CH₂—CH₃); 1.55-1.62 (m, 6H, 3*CH₂); 1.75-1.80 (m, 2H, CH₂); 2.85 (q, J 7.5 Hz, 2H, CH₂—CH₃); 3.37 (m, 2H, CH₂); 3.63 (t, J 5.8 Hz, 2H, N—CH₂); 4.27 (s, 3H, CH₃); 7.30 (dd, J 1.2 Hz, J 8.4 Hz, 1H, Ar); 7.88 (s, 1H, Ar); 7.94 (dd, J 1.6 Hz, J 9.2 Hz,

1H, Ar); 8.02 (d, J 9.2 Hz, 1H, Ar); 8.25 (d, J 8.4 Hz, 1H, Ar); 8.95 (s, 1H, Ar); 9.56 (s, 1H, Ar). M/Z (M+H)$^+$=402. Mp: >250° C.

Example 89

[6-(Azepan-1-ylcarbonyl)]-1-methyl-3[6-cyclopropyl-imidazo[1,2-a]pyridin-3-yl]-1H-indazole, HCl salt

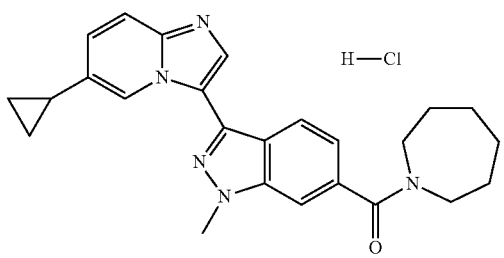 [SMILES: Cn1nc(-c2cnc3ccc(C4CC4)cn23)c2ccc(C(=O)N3CCCCCC3)cc21 ; Cl]

Example 89 was obtained according to general procedure VIII, using example 37 and N-methyl-hydrazine (60 equiv.) in DMF and heating through microwave irradiation for 5 min at 130° C. Purification by preparative HPLC followed by co-evaporation in HCl 1M afforded the product as an orange solid in 37% Yield.

$^1$H-NMR (400 MHz, DMSO): 0.83 (m, 2H, CH$_2$); 1.10 (m, 2H, CH$_2$); 1.52-1.59 (m, 6H, 3*CH$_2$); 1.74-1.76 (m, 2H, CH$_2$); 2.19-2.26 (m, 1H, CH); 3.24 (m, 2H, CH$_2$); 3.60 (m, 2H, N—CH$_2$); 4.23 (s, 3H, CH$_3$); 7.28 (d, J 8.7 Hz, 1H, Ar); 7.70 (d, J 9.2 Hz, 1H, Ar); 7.79 (s, 1H, Ar); 7.93 (m, 1H, Ar); 8.16 (m, 1H, Ar); 8.81 (s, 1H, Ar); 9.53 (s, 1H, Ar).

M/Z (M+H)$^+$=414. Mp: >250° C.

Example 90

[6-(Azepan-1-ylcarbonyl)]-1-methyl-3[6-imidazo[1,2-a]pyridin-3-yl]-1H-indazole, HCl salt

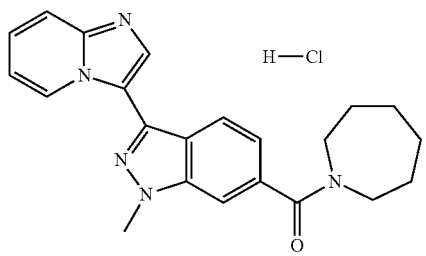 [SMILES: Cn1nc(-c2cnc3ccccn23)c2ccc(C(=O)N3CCCCCC3)cc21 ; Cl]

Example 90 was isolated as a side product of example 89 by preparative HPLC. Example 89's precursor was a side product of example 90's precursor. Co-evaporation with aqueous HCl 1N affords the product as an orange solid.

$^1$H-NMR (400 MHz, DMSO): 1.55-1.63 (m, 6H, 3*CH$_2$); 1.74-1.81 (m, 2H, CH$_2$); 3.36 (m, 2H, CH$_2$); 3.63 (t, J 5.8 Hz, 2H, N—CH$_2$); 4.26 (s, 3H, CH$_3$); 7.30 (dd, J 1.0 Hz, J 8.4 Hz, 1H, Ar); 7.59 (t, J 6.9 Hz, 1H, Ar); 7.88 (s, 1H, Ar); 7.95 (t, J 7.8 Hz, 1H, Ar); 8.05 (d, J 8.9 Hz, 1H, Ar); 8.27 (d, J 8.3 Hz, 1H, Ar); 8.96 (s, 1H, Ar); 9.77 (d, J 6.9 Hz, 1H, Ar). M/Z (M+H)$^+$=374. Mp: >250° C.

Example 91

[6-(Azepan-1-ylcarbonyl)]-1-methyl-3[6-bromoimidazo[1,2-a]pyridin-3-yl]-1H-indazole, HCl salt

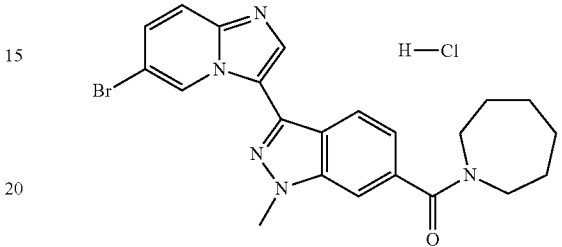

Example 91 was obtained according to general procedure VIII, using example 33 and N-methyl-hydrazine (60 equiv.) in DMF and heating through microwave irradiation for 10 min at 120° C. Purification by preparative HPLC followed by co-evaporation in HCl 1M afforded the product as a beige solid in 60% Yield. $^1$H-NMR (400 MHz, DMSO): 1.56-1.63 (m, 6H, 3*CH$_2$); 1.76-1.81 (m, 2H, CH$_2$); 3.36 (m, 2H, CH$_2$); 3.63 (t, J 5.8 Hz, 2H, N—CH$_2$); 4.27 (s, 3H, CH$_3$); 7.29 (dd, J 1.2 Hz, J 8.4 Hz, 1H, Ar); 7.87 (s, 1H, Ar); 7.98 (m, 2H, Ar); 8.28 (d, J 8.4 Hz, 1H, Ar); 8.91 (s, 1H, Ar); 9.99 (s, 1H, Ar). M/Z (M[$^{79}$Br]+H)$^+$=454.

Example 92

3-(6-Fluoroimidazo[1,2-a]pyridin-3-yl)-N,1-dimethyl-N-phenyl-1H-indazole-6-carboxamide, HCl salt

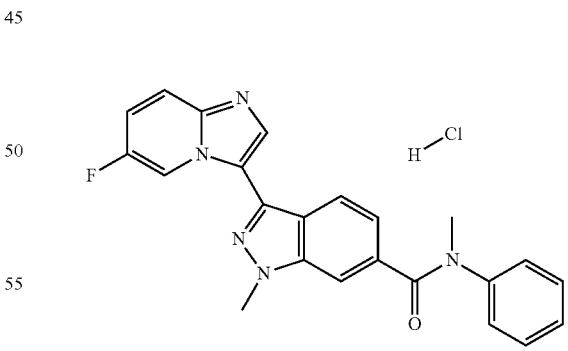

Example 92 was obtained according to general procedure VII, method B, using compound 68 and N-methylaniline (5.0 equiv.) in presence of DIC and was heated through microwave irradiation for 5 min at 150° C., as a beige solid in 9% yield.

$^1$H-NMR (400 MHz, DMSO): 3.43 (s, 3H, CH$_3$); 4.14 (s, 3H, CH$_3$); 7.12-7.15 (m, 2H, Ar); 7.24-7.26 (m, 4H, Ar); 7.80

(s, 1H, Ar); 7.89-7.94 (m, 1H, Ar); 7.99-8.04 (m, 2H, Ar); 8.81 (s, 1H, Ar); 9.74-9.76 (m, 1H, Ar). M/Z (M+H)$^+$=400. Mp: >250° C.

Example 93

N-Ethyl-3-(6-fluoroimidazo[1,2-a]pyridin-3-yl)-N-isopropyl-1-methyl-1H-indazole-6-carboxamide, HCl salt

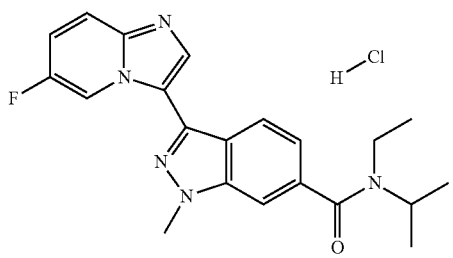 [SMILES: CCN(C(=O)c1ccc2c(-c3cnc4ccc(F)cn34)nn(C)c2c1)C(C)C ; Cl]

Example 93 was obtained according to general procedure VII, method B, using compound 68 and N-ethylisopropyl (5.0 equiv.) in presence of DIC and was heated through microwave irradiation for 5 min at 150° C., as a beige solid in 24% yield.

$^1$H-NMR (400 MHz, DMSO): 1.15-1.23 (bm, 9H, 3*CH$_3$); 4.26 (s, 3H, CH$_3$); 7.24-7.27 (m, 1H, Ar); 7.83 (s, 1H, Ar); 7.91-7.96 (m, 1H, Ar); 8.07 (dd, J 5.0 Hz, J 9.8 Hz, 1H, Ar); 8.29 (d, J 8.3 Hz, 1H, Ar); 8.93 (s, 1H, Ar); 9.80 (dd, J 2.3 Hz, J 4.4 Hz, 1H, Ar). 2 signal are missing (N—CH$_2$; N—CH) probably under H$_2$O signal. M/Z (M+H)$^+$=380. Mp: >250° C.

Example 94

[3-(6-Fluoroimidazo[1,2-a]pyridin-3-yl)-1-methyl-1H-indazol-6-yl]-(decahydroquinolin-1-yl)-methanone, HCl salt

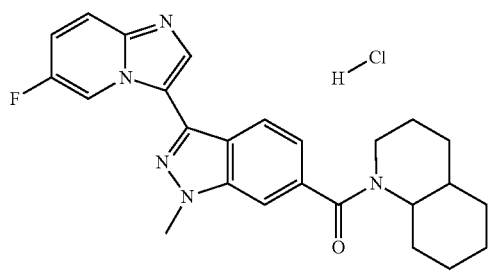 [SMILES: Cn1nc(-c2cnc3ccc(F)cn23)c2ccc(C(=O)N3CCCC4CCCCC43)cc21 ; Cl]

Example 94 was obtained according to general procedure VII, method B, using compound 68 and decahydroquinoline (5.0 equiv.) in presence of DIC and was heated through microwave irradiation for 5 min at 150° C., as a beige solid in 17% yield.

$^1$H-NMR (400 MHz, DMSO): 1.14-1.16 (m, 12H, 6*CH$_2$); 2.13-2.17 (m, 1H, CH); 3.23-3.28 (m, 1H, CH); 3.35-3.42 (m, 2H, CH$_2$); 4.24 (s, 3H, CH$_3$); 7.27 (dd, J 1.1 Hz, J 8.3 Hz, 1H, Ar); 7.80 (s, 1H, Ar); 7.89-7.94 (m, 1H, Ar); 8.03 (dd, J 5.0 Hz, J 9.9 Hz, 1H, Ar); 8.23 (d, J 8.3 Hz, 1H, Ar); 8.85 (s, 1H, Ar); 9.78 (dd, J 2.3 Hz, J 4.4 Hz, 1H, Ar). M/Z (M+H)$^+$=432. Mp: 248-249° C.

Example 95

3-(6-Fluoroimidazo[1,2-a]pyridin-3-yl)-1-methyl-1H-indazol-6-carboxylic acid cyclohexyl-cyclopropyl-methyl-amide, HCl salt

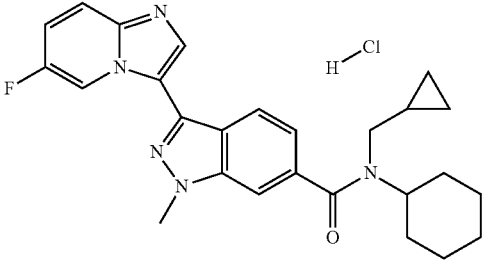 [SMILES: Cn1nc(-c2cnc3ccc(F)cn23)c2ccc(C(=O)N(CC3CC3)C3CCCCC3)cc21 ; Cl]

Example 95 was obtained according to general procedure VII, method B, using compound 68 and cyclohexylcyclopropyl-methylamine (5.0 equiv.) in presence of DIC and was heated through microwave irradiation for 5 min at 150° C., as a beige solid in 12% yield.

$^1$H-NMR (400 MHz, DMSO): 0.34-0.51 (m, 2H, 2*CH); 0.82-1.84 (m, 13H, 3*CH, 5*CH$_2$); 3.0-3.4 (m, 3H, CH, CH$_2$); 4.24 (s, 3H, CH$_3$); 7.25 (dd, J 1.0 Hz, J 8.3 Hz, 1H, Ar); 7.78 (s, 1H, Ar); 7.84-7.88 (m, 1H, Ar); 8.01 (dd, J 5.4 Hz, J 9.6 Hz, 1H, Ar); 8.25 (d, J 7.9 Hz, 1H, Ar); 8.83 (s, 1H, Ar); 9.78 (dd, J 2.2 Hz, J 4.6 Hz, 1H, Ar). M/Z (M+H)$^+$=446. Mp: 235-245° C.

Example 96

Azonan-1-yl-[3-(6-fluoro-imidazo[1,2-a]pyridin-3-yl)-1-methyl-1H-indazol-6-yl]-methanone, chlorhydrate salt

Example 96 was obtained according to general procedure VII, method B, using compound 68 and octamethyleneimine (5.0 equiv.) in presence of DIC and was heated through microwave irradiation for 5 min at 150° C., as a beige solid in 26% yield.

$^1$H-NMR (400 MHz, DMSO): 1.50-1.55 (m, 8H, 4*CH$_2$); 1.70 (m, 2H, CH$_2$); 1.84 (m, 2H, CH$_2$); 3.38 (m, 2H, CH$_2$); 3.56 (m, 2H, CH$_2$); 4.23 (s, 3H, CH$_3$); 7.27 (dd, J 1.0 Hz, J 8.4 Hz, 1H, Ar); 7.78 (s, 1H, Ar); 7.88-7.93 (m, 1H, Ar); 8.02 (dd,

J 5.0 Hz, J 9.9 Hz, 1H, Ar); 8.26 (d, J 8.4 Hz, 1H, Ar); 8.85 (s, 1H, Ar); 9.78 (dd, J 2.3 Hz, J 4.4 Hz, 1H, Ar). M/Z (M+H)⁺=420. Mp: 240-245° C.

Example 97

Azocan-1-yl-[3-(6-fluoro-imidazo[1,2-a]pyridin-3-yl)-1-methyl-1H-indazol-6-yl]-methanone, chlorhydrate salt

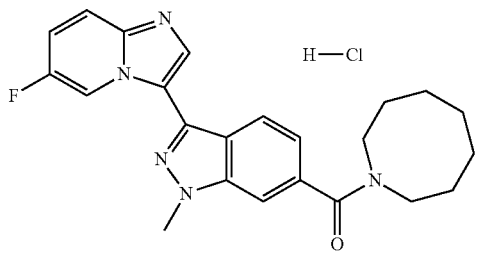

Example 97 was obtained according to general procedure VII, method B, using compound 68 and heptamethyleneimine (5.0 equiv.) in presence of DIC and was heated through microwave irradiation for 5 min at 150° C., as a beige solid in 36% yield.

¹H-NMR (400 MHz, DMSO): 1.54-1.60 (m, 8H, 4*CH₂); 1.80 (m, 2H, CH₂); 3.22 (m, 2H, CH₂); 3.60 (t, J 5.9 Hz, 2H, CH₂); 4.27 (s, 3H, CH₃); 7.27 (d, J 8.3 Hz, 1H, Ar); 7.84 (s, 1H, Ar); 7.90-7.95 (m, 1H, Ar); 8.05-8.09 (m, 1H, Ar); 8.30 (d, J 8.3 Hz, 1H, Ar); 8.92 (s, 1H, Ar); 9.80 (s, 1H, Ar). M/Z (M+H)⁺=406. Mp: 241-249° C.

Example 98

3-(6-Fluoroimidazo[1,2-a]pyridin-3-yl)-1-methyl-6-(piperidin-1-ylcarbonyl)-1H-indazole, chlorhydrate salt

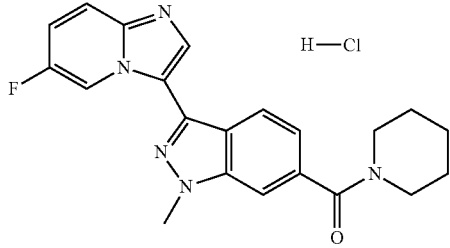 [SMILES: Cn1nc(-c2cnc3ccc(F)cn23)c2ccc(C(=O)N3CCCCC3)cc21 ; Cl]

Example 98 was obtained according to general procedure VII, method B, using compound 68 and piperidine (5.0 equiv.) in presence of DIC and was heated through microwave irradiation for 5 min at 150° C., as a beige solid in 28% yield.

¹H-NMR (400 MHz, DMSO): 1.47-1.62 (m, 6H, 3*CH₂); 3.29 (m, 2H, CH₂); 3.62 (m, 2H, CH₂); 4.23 (s, 3H, CH₃); 7.29 (d, J 8.4 Hz, 1H, Ar); 7.82 (s, 1H, Ar); 7.94-7.98 (m, 1H, Ar); 8.03-8.06 (m, 1H, Ar); 8.23 (d, J 8.4 Hz, 1H, Ar); 8.88 (s, 1H, Ar); 9.80 (s, 1H, Ar). M/Z (M+H)⁺=378. Mp: >250° C.

Example 99

3-[1-Methyl-6-(piperidin-1-ylcarbonyl)-1H-indazol-3-yl]imidazo[1,2-a]pyridine-6-carbonitrile, chlorhydrate salt

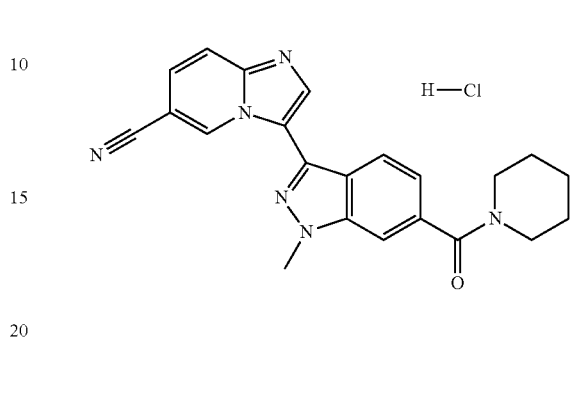

Example 99 was obtained according to general procedure VII, method F with HCl salt formation, using compound 67 and piperidine and heating through microwave irradiation 10 min at 120° C., as white off solid in 77% yield.

¹H-NMR (400 MHz, DMSO): 1.49-1.64 (m, 6H, 3*CH₂); 3.31 (m, 2H, CH₂); 3.64 (m, 2H, CH₂); 4.27 (s, 3H, CH₃); 7.28 (d, J 8.2 Hz, 1H, Ar); 7.83-7.85 (m, 2H, Ar); 8.02 (d, J 9.2 Hz, 1H, Ar); 8.28 (d, J 8.3 Hz, 1H, Ar); 8.79 (s, 1H, Ar); 10.16 (s, 1H, Ar). M/Z (M+H)⁺=385. Mp: >250° C.

Example 100

3-[1-Methyl-6-(pyrrolidin-1-ylcarbonyl)-1H-indazol-3-yl]imidazo[1,2-a]pyridine-6-carbonitrile, chlorhydrate salt

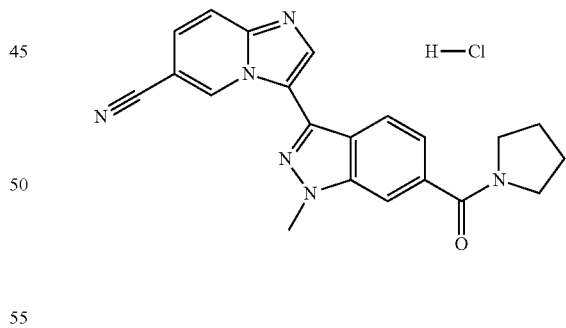

Example 100 was obtained according to general procedure VII, method F with HCl salt formation, using compound 67 and pyrrolidine and heating through microwave irradiation 10 min at 120° C., as beige solid in 17% yield.

¹H-NMR (400 MHz, DMSO): 1.83-1.92 (m, 4H, 2*CH₂); 3.39 (m, 2H, N—CH₂); 3.54 (m, 2H, N—CH₂); 4.27 (s, 3H, N—CH₃); 7.41 (dd, 1.0 Hz, J 8.4 Hz, 1H, Ar); 7.80 (dd, J 1.4 Hz, J 9.3 Hz, 1H, Ar); 7.97 (s, 1H, Ar); 8.00 (d, J 9.5 Hz, 1H, Ar); 8.27 (d, J 8.4 Hz, 1H, Ar); 8.76 (s, 1H, Ar); 10.15 (s, 1H, Ar). M/Z (M+H)⁺=371.

Example 101

3-(1-Methyl-6-{[(2R)-2-(methoxymethyl)pyrrolidin-1-yl]carbonyl}-1H-indazol-3-yl)imidazo[1,2-a]pyridine-6-carbonitrile, chlorhydrate salt

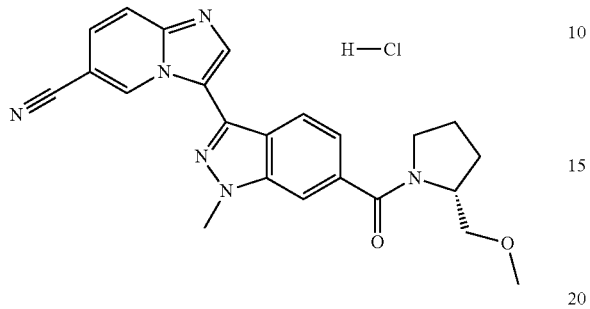

Example 101 was obtained according to general procedure VII, method F with HCl salt formation, using compound 67 and R-2-methoxymethylpyrilidine and heating through microwave irradiation 30 min at 120° C., as beige solid in 45% yield.

$^1$H-NMR (400 MHz, DMSO): 1.72-2.06 (m, 4H, 2*CH$_2$); 2.98 (m, 2H, O—CH$_2$); 3.34 (m, 3H, O—CH$_3$); 3.64 (m, 2H, CH$_2$); 4.20-4.35 (m, 1H, CH); 4.28 (s, 3H, N—CH$_3$); 7.37 (d, J 8.3 Hz, 1H, Ar); 7.81 (dd, J 0.9 Hz, J 9.5 Hz, 1H, Ar); 7.93 (s, 1H, Ar); 8.00 (d, J 9.3 Hz, 1H, Ar); 8.28 (d, J 8.4 Hz, 1H, Ar); 8.76 (s, 1H, Ar); 10.15 (s, 1H, Ar). M/Z (M+H)$^+$=415. Mp: 230-235° C.

Example 102

3-(1-Methyl-6-{[(2S)-2-(methoxymethyl)pyrrolidin-1-yl]carbonyl}-1H-indazol-3-yl)imidazo[1,2-a]pyridine-6-carbonitrile, chlorhydrate salt

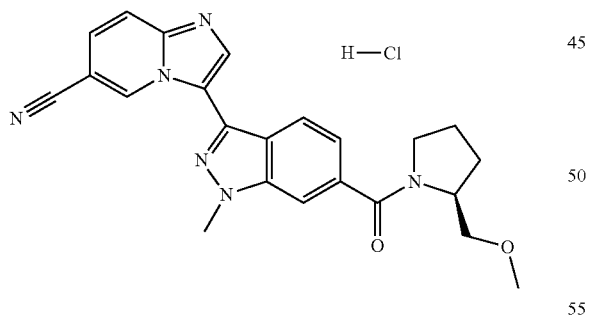

Example 102 was obtained according to general procedure VII, method F with HCl salt formation, using compound 67 and S-2-methoxymethylpyrilidine and heating through microwave irradiation 15 min at 130° C., then 20 min at 120° C. as beige solid in 9% yield.

$^1$H-NMR (400 MHz, DMSO): 1.72-2.06 (m, 4H, 2*CH$_2$); 2.98 (m, 2H, O—CH$_2$); 3.34 (m, 3H, O—CH$_3$); 3.64 (m, 2H, CH$_2$); 4.20-4.35 (m, 1H, CH); 4.28 (s, 3H, N—CH$_3$); 7.37 (d, J 8.3 Hz, 1H, Ar); 7.81 (dd, J 0.9 Hz, J 9.5 Hz, 1H, Ar); 7.93 (s, 1H, Ar); 8.00 (d, J 9.3 Hz, 1H, Ar); 8.28 (d, J 8.4 Hz, 1H, Ar); 8.76 (s, 1H, Ar); 10.15 (s, 1H, Ar). M/Z (M+H)$^+$=415.

Example 103

3-[6-(8-Aza-bicyclo[3.2.1]octane-8-carbonyl)-1-methyl-1H-indazol-3-yl]-imidazo[1,2-a]pyridine-6-carbonitrile, chlorhydrate salt

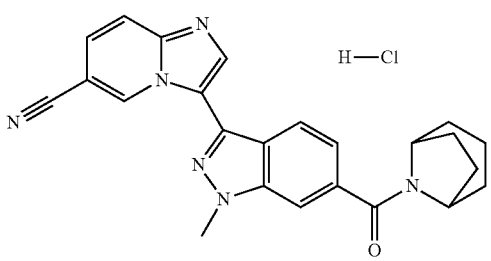 [SMILES: Cn1nc(-c2cnc3ccc(C#N)cn23)c2ccc(C(=O)N3C4CCCC3CC4)cc21 ; Cl]

Example 103 was obtained according to general procedure VII, method E, using compound 69, 8-azabicyclo[3.2.1]octane HCl salt (5 equiv.) and DBU (5 equiv.). Purification by preparative HPLC followed by co-evaporation in HCl 1M afforded the product as beige solid.

M/Z (M+H)$^+$=411.

Example 104

3-{1-Methyl-6-[(4-methylpiperazin-1-yl)carbonyl]}-1H-indazol-3-yl]imidazo[1,2-a]pyridine-6-carbonitrile, chlorhydrate salt

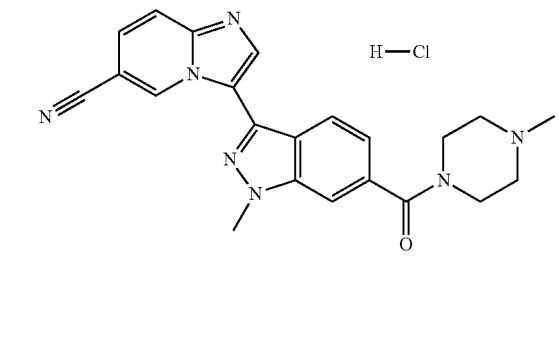 [SMILES: CN1CCN(C(=O)c2ccc3c(-c4cnc5ccc(C#N)cn45)nn(C)c3c2)CC1 ; Cl]

Example 104 was obtained according to general procedure VII, method F with HCl salt formation, using compound 67 and N-methylpiperazine and heating through microwave irradiation 10 min at 120° C., as beige solid in 33% yield.

$^1$H-NMR (400 MHz, DMSO): 2.80 (m, 3H, N—CH$_3$); 3.12 (m, 2H, CH$_2$); 4.20-4.35 (m, 1H, CH); 4.26 (s, 3H, N—CH$_3$); 7.37 (d, J 8.3 Hz, 1H, Ar); 7.77 (d, J 8.8 Hz, 1H, Ar); 7.93 (s, 1H, Ar); 7.98 (d, J 8.8 Hz, 1H, Ar); 8.34 (d, J 8.4 Hz, 1H, Ar); 8.76 (s, 1H, Ar); 10.13 (s, 1H, Ar); 11.14 (bs, exchange with D₂O, 1H, NH). Signals for 6 protons are missing (probably under HOD signal). M/Z (M+H)⁺=400.

Example 105

3-(6-Cyano-imidazo[1,2-a]pyridin-3-yl)-1-methyl-1H-indazole-6-carboxylic acid diisopropylamide, chlorhydrate salt

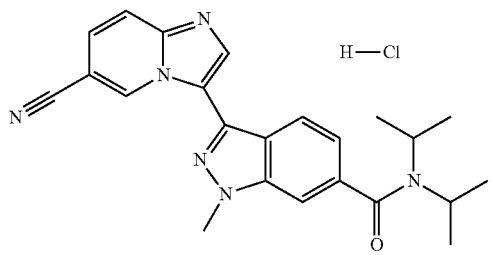 [SMILES: CC(C)N(C(=O)c1ccc2c(-c3cnc4ccc(C#N)cn34)nn(C)c2c1)C(C)C ; Cl]

Example 105 was obtained according to general procedure VII, method E, using compound 69 and diisopropylamine. Purification by preparative HPLC followed by co-evaporation in HCl 1M afforded the product as beige solid.
M/Z (M+H)⁺=401.

Example 106

2-Methyl-3-[1-Methyl-6-(azepan-1-ylcarbonyl)-1H-indazol-3-yl]-imidazo[1,2-a]pyridine-6-carbonitrile

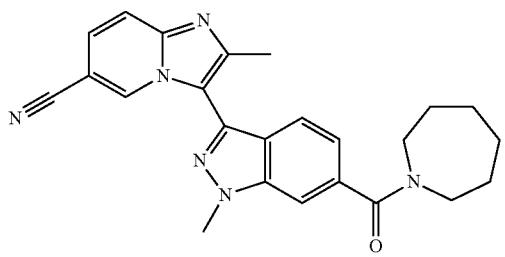 [SMILES: Cc1nc2ccc(C#N)cn2c1-c1nn(C)c2cc(C(=O)N3CCCCCC3)ccc12]

Example 106 was obtained according to general procedure VII, method F without HCl salt formation, using compound 71 and hexamethyleneimine and heating through microwave irradiation 10 min at 120° C. twice, as beige solid in 78% yield.
¹H-NMR (400 MHz, CDCl₃): 1.63-1.76 (m, 6H, 3*CH₂); 1.90-1.95 (m, 2H, CH₂); 2.79 (s, 3H, CH₃); 3.44 (m, 2H, CH₂); 3.77 (m, 2H, CH₂); 4.30 (s, 3H, N—CH₃); 7.33 (m, 1H, Ar); 7.64 (d, J 8.4 Hz, 1H, Ar); 7.66 (s, 1H, Ar); 7.70 (d, J 9.2 Hz, 1H, Ar); 8.22 (d, J 8.7 Hz, 1H, Ar); 9.23 (s, 1H, Ar). M/Z (M+H)⁺=413.

General procedure IX: Alkylations/Acylations of Indazoles.

Under anhydrous condition, to a solution of compounds AF (with R₆=H, 1.0 equiv.) in DMF cooled by an ice bath, NaH (2.0 equiv.) was added. Anion was stirred 15 minutes, then halide derivative (2.0 equiv.) was added. Reaction mixture was allowed to warm to R.T., then was stirred 16 Hrs. Reaction mixture was hydrolyzed with water, extracted with AcOEt. Organic layer was washed with brine (10 mL), dried over MgSO₄ and concentrated under reduced pressure.

Targeted examples were purified either by flash chromatography, precipitation or preparative HPLC.

Example 107

Azepan-1-yl-[1-benzyl-3-(6-fluoro-imidazo[1,2-a]pyridin-3-yl)-1H-indazol-6-yl]-methanone, HCl salt

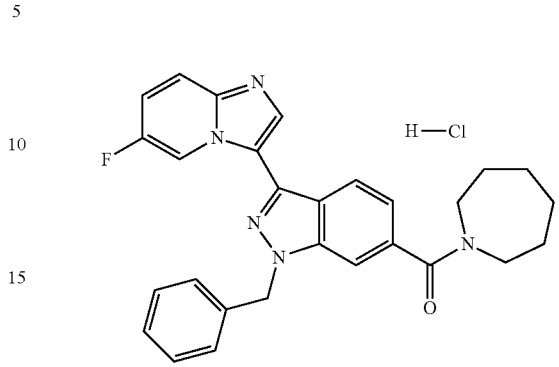

Example 107 was obtained according to general procedure IX, using example 78 and benzyl bromide and was purified by flash-chromatography (MeOH 0 to 1% in CH₂Cl₂). The residue was dissolved in HCl 1.25N in MeOH. The solution was concentrated to afford example 107 as a brown solid.
¹H-NMR (400 MHz, DMSO): 1.45-1.78 (bm, 8H, 4*CH₂); 3.26 (t, J 5.9 Hz, 2H, N—CH₂); 3.61 (t, J 5.9 Hz, 2H, N—CH₂); 5.93 (s, 2H, N—CH₂); 7.29-7.39 (m, 6H, Ar); 7.92 (s, 1H, Ar); 7.98 (m, 1H, Ar); 8.10 (dd, J 5.0 Hz, J 10.0 Hz, 1H Ar); 8.31 (d, J 8.3 Hz, 1H, Ar); 8.94 (s, 1H, Ar); 9.81 (dd, J 2.4 Hz, J 4.4 Hz, 1H, Ar). M/Z (M+H)⁺=468. Mp: 134-135° C.

Example 108

Azepan-1-yl-[3-(6-fluoro-imidazo[1,2-a]pyridin-3-yl)-1-phenethyl-1H-indazol-6-yl]-methanone, HCl salt

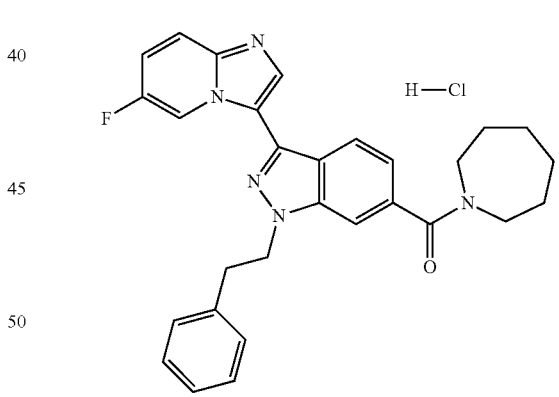

Example 108 was obtained according to general procedure IX, using example 78 and 2-bromoethylbenzene and was purified by flash-chromatography (MeOH 0 to 2% in CH₂Cl₂). The residue was dissolved in aqueous HCl 1N. The solution was concentrated to afford example 108 as a brown solid.
¹H-NMR (400 MHz, DMSO): 1.53-1.62 (bm, 6H, 3*CH₂); 1.74-1.78 (bm, 2H, CH₂); 3.26 (m, 2H, N—CH₂); 3.61 (m, 2H, N—CH₂); 4.92 (t, J 6.7 Hz, 2H, N—CH₂); 7.10-7.20 (m, 5H, Ar); 7.24 (dd, J 1.0 Hz, J 8.4 Hz, 1H, Ar); 7.78 (s, 1H, Ar); 7.99 (m, 1H, Ar); 8.09 (dd, J 4.9 Hz, J 9.9 Hz, 1H, Ar); 8.26 (d, J 8.4 Hz, 1H, Ar); 8.94 (s, 1H, Ar); 9.49 (m, 1H, Ar). 1 signal is missing (2H) probably under H₂O signal. M/Z (M+H)⁺=482. Mp: 139-140° C.

Example 109

Azepan-1-yl-[3-(6-fluoro-imidazo[1,2-a]pyridin-3-yl)-1-[2-(2-methoxyethoxy)ethyl]-1H-indazol-6-yl]-methanone, HCl salt

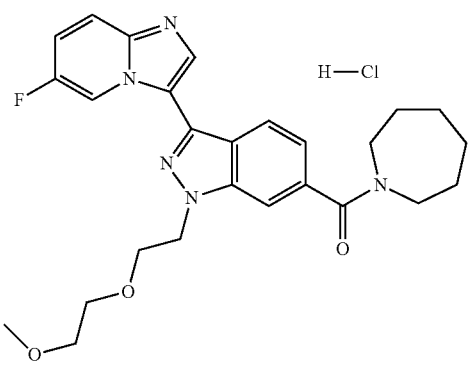

Example 109 was obtained according to general procedure IX, using example 78 and 1-bromo-2(2-methoxy-ethoxy) ethane] and was purified by flash-chromatography (MeOH 0 to 5% in $CH_2Cl_2$). The residue was dissolved in aqueous HCl 1N. The solution was concentrated to afford example 109 as a green solid.

$^1$H-NMR (400 MHz, DMSO): 1.55-1.62 (bm, 6H, 3*$CH_2$); 1.75-1.80 (bm, 2H, $CH_2$); 3.10 (s, 3H, O—$CH_3$); 3.31-3.38 (m, 6H, N—$CH_2$+2 O—$CH_2$); 3.63 (m, 2H, N—$CH_2$); 3.95 (t, J 5.1 Hz, 2H, O—$CH_2$); 4.82 (t, J 5.1 Hz, 2H, N—$CH_2$); 7.29 (dd, J 1.1 Hz, J 8.4 Hz, 1H, Ar); 7.90 (s, 1H, Ar); 8.00 (m, 1H, Ar); 8.10 (dd, J 5.1 Hz, J 9.8 Hz, 1H, Ar); 8.27 (d, J 8.4 Hz, 1H, Ar); 8.98 (s, 1H, Ar); 9.82 (dd, J 2.2 Hz, J 4.6 Hz, 1H, Ar). M/Z (M+H)$^+$=480. Mp: 159-165° C.

Example 110

Azepan-1-yl-[3-(6-fluoro-imidazo[1,2-a]pyridin-3-yl)-1-(2-morpholin-4-yl-ethyl)-1H-indazol-6-yl]-methanone, HCl salt

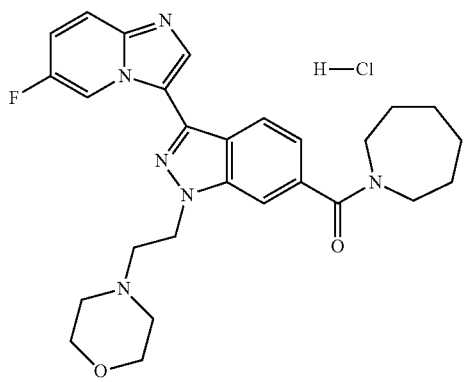

Example 110 was obtained according to general procedure IX, using example 78 and 4-(2-iodoethyl) morpholine and was purified by flash-chromatography (MeOH 0 to 5% in $CH_2Cl_2$). Purification by preparative HPLC followed by co-evaporation in HCl 1M afforded the product as a yellow solid in 31% Yield.

$^1$H-NMR (400 MHz, DMSO): 1.56-1.63 (bm, 6H, 3*$CH_2$); 1.76-1.81 (bm, 2H, $CH_2$); 3.25-3.35 (m, 6H, 3*$CH_2$); 3.63 (m, 2H, $CH_2$); 3.77 (m, 4H, $CH_2$); 3.99 (m, 2H, $CH_2$); 5.12 (m, 2H, $CH_2$); 7.29-7.32 (m, 1H, Ar); 7.72-7.83 (m, 1H, Ar); 7.97-8.00 (m, 2H, Ar); 8.32 (m, 1H, Ar); 8.78 (bs, 1H, Ar); 9.70 (bs, 1H, Ar); 11.0-11.8 (bs, 1H ($D_2O$ exchange), NH).

M/Z (M+H)$^+$=491. Mp: 230-245° C.

Example 111

Azepan-1-yl-[3-(6-fluoro-imidazo[1,2-a]pyridin-3-yl)-1-[(4-methylpiperazin-1-yl)carbonyl]-1H-indazol-6-yl]-methanone, HCl salt

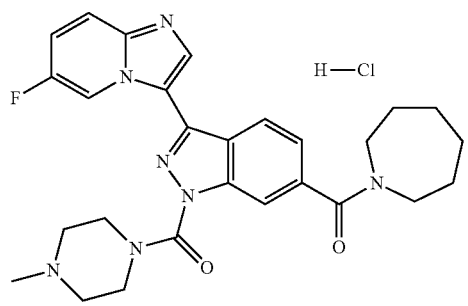

Example 111 was obtained according to general procedure IX, using example 78 and 4-methylpiperazinecarbonyl chloride (4.0 equiv.). Reaction was heated through microwave irradiation for min at 150° C. instead of R.T. Reaction mixture was hydrolyzed by $NaHCO_3$ saturated solution instead of water Purification by flash-chromatography (MeoH 0 to 3% in $CH_2Cl_2$), then by preparative HPLC followed by co-evaporation in HCl 1M afforded the product as a beige solid.

$^1$H-NMR (400 MHz, DMSO): 1.55-1.62 (bm, 6H, 3*$CH_2$); 1.75-1.80 (bm, 2H, $CH_2$); 2.46 (s, 3H, N—$CH_3$); 3.08-3.12 (m, 2H, N—$CH_2$); 3.22-3.26 (m, 2H, N—$CH_2$); 3.61-3.67 (m, 4H, (N—$CH_2$)$_2$); 4.72 (m, 2H, N—$CH_2$); 7.28 (dd, J 0.9 Hz, J 8.4 Hz, 1H, Ar); 7.90 (s, 1H, Ar); 7.96 (m, 1H, Ar); 8.08 (dd, J 4.9 Hz, J 9.9 Hz, Ar); 8.25 (d, J 8.5 Hz, 1H, Ar); 8.92 (s, 1H, Ar); 9.77 (m, 1H, Ar). 1 signal is missing (2H) probably under $H_2O$ signal. M/Z (M+H)$^+$=504. Mp: 193-199° C.

General Procedure X: Formation of Examples AG from Fluoroketones AC (in Scheme 5).

To a solution of fluoroketone AC (1.0 equiv.) in anhydrous THF, acetone oxime (1.1 equiv.) and sodium tert-butoxide (1.1 equiv.) were added. The resulting suspension was heated at 70° C. overnight.

The reaction mixture was allowed to cool to R.T. and diluted with AcOEt, washed with a saturated aqueous solution of $NH_4Cl$ and brine. The organic layer was dried over $MgSO_4$ and concentrated under reduced pressure. The residue in EtOH: aqueous HCl 1.5M (1:1) was heated through microwave irradiation for 5 min at 150° C.

After cooling to R.T., the reaction mixture was extracted with AcOEt. The organic layer was washed with 1N NaOH, brine, dried over $MgSO_4$ and concentrated under reduced pressure.

Targeted examples were purified either by flash chromatography, precipitation or preparative HPLC.

Example 112

3-(6-Fluoro-imidazo[1,2-a]pyridin-3-yl)-benzo[d]isoxazole-6-carboxylic acid cyclohexyl-ethyl-amide

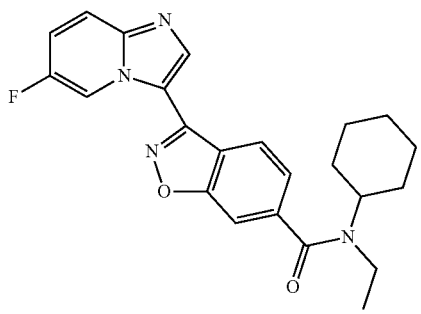 [SMILES: CCN(C(=O)c1ccc2c(-c3cnc4ccc(F)cn34)noc2c1)C1CCCCC1]

Example 112 was obtained according to general procedure X, using example 21. Trituration in DMSO afforded the product as as a white solid.
M/Z (M+H)$^+$=407.

Example 113

Azepan-1-yl-[3-(6-fluoro-imidazo[1,2-a]pyridin-3-yl)-benzo[d]isoxazol-6-yl]-methanone

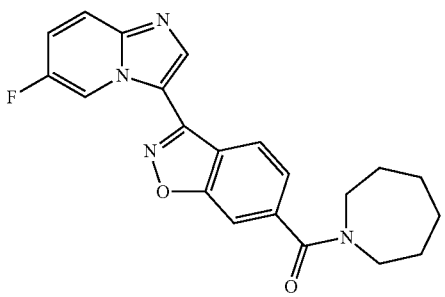 [SMILES: O=C(c1ccc2c(-c3cnc4ccc(F)cn34)noc2c1)N1CCCCCC1]

Example 113 was obtained according to general procedure X, using example 27. Trituration in Et$_2$O afforded the product as a yellow solid in 27% yield.
Mp: 218-219° C.
$^1$H-NMR (400 MHz, DMSO): 1.51-1.64 (bm, 6H, 3*CH$_2$); 1.73-1.80 (bm, 2H, CH$_2$); 3.62 (t, J 5.7 Hz, 2H, N—CH$_2$); 7.48 (d, J 7.9 Hz, 1H, Ar); 7.69 (m, 1H, Ar); 7.92 (s, 1H, Ar); 7.97 (m, 1H, Ar); 8.52 (d, J 8.2 Hz, 1H, Ar); 8.91 (s, 1H, Ar); 9.40 (m, 1H, Ar). N—CH$_2$ under water peak. M/Z (M+H)$^+$=379.

Example 114

[4-(Azepan-1-ylcarbonyl)-2-hydroxyphenyl](6-fluoroimidazo[1,2-a]pyridin-3-yl)methanone

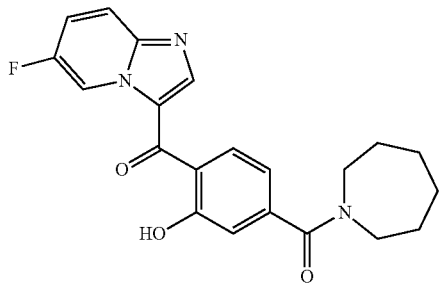 [SMILES: O=C(c1ccc(C(=O)N2CCCCCC2)cc1O)c1cnc2ccc(F)cn12]

Example 114 was isolated as a side product of example 113. Basic aqueous layer of example 113 was acidified to pH 1, then extracted with EtOAc. Organic layer was washed with brine, dried over MgSO$_4$ and concentrated under reduced pressure. Residue was triturated in Et$_2$O to afford example 114 as an orange solid in 10% yield.
$^1$H-NMR (400 MHz, DMSO): 1.56-1.62 (bm, 6H, 3*CH$_2$); 1.70-1.7 (bm, 2H, CH$_2$); 3.36 (m, 2H, N—CH$_2$); 3.67 (m, 2H, N—CH$_2$); 6.89-6.93 (m, 2H, Ar); 7.82 (ddd, J 2.6 Hz, J 7.6 Hz, J 10.1 Hz, 1H, Ar); 7.98 (dd, J 5.1 Hz, J 9.9 Hz, 1H, Ar); 8.15 (s, 1H, Ar); 9.65 (dd, J 2.4 Hz, J 4.4 Hz, 1H, Ar); 10.36 (s, exchange with D$_2$O, 1H, Ar). M/Z (M+H)$^+$=382.

Example 115

N-Ethyl-3-(6-fluoroimidazo[1,2-a]pyridin-3-yl)-N-isopropyl-1,2-benzisoxazole-6-carboxamide, HCl salt

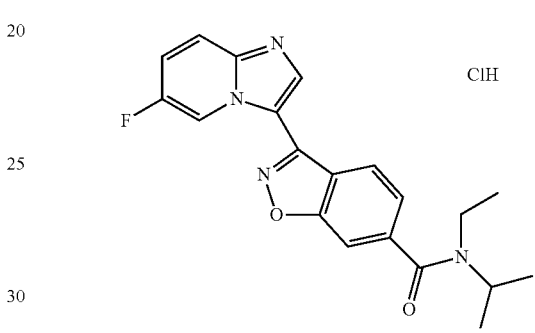

Example 115 was obtained according to general procedure X, using example 75. Purification by preparative HPLC followed by co-evaporation in HCl 1M afforded the product as an orange solid in 26% Yield.
$^1$H-NMR (400 MHz, DMSO): 0.98-1.33 (m, 9H, 3*CH$_3$); 3.39 (m, 2H, N—CH$_2$); 3.71 (m, H, N—CH); 7.48 (d, J 8.8 Hz, 1H, Ar); 7.83 (m, 1H, Ar); 7.94 (s, 1H, Ar); 8.05 (dd, J 5.2 Hz, J 10.0 Hz, 1H, Ar); 8.52 (d, J 8.2 Hz, 1H, Ar); 9.04 (s, 1H, Ar); 9.46 (m, 1H, Ar). M/Z (M+H)$^+$=367. Mp: 219-225° C.

Example 116

3-(6-Fluoroimidazo[1,2-a]pyridin-3-yl)-6-(piperidin-1-ylcarbonyl)-1,2-benzisoxazole, HCl salt

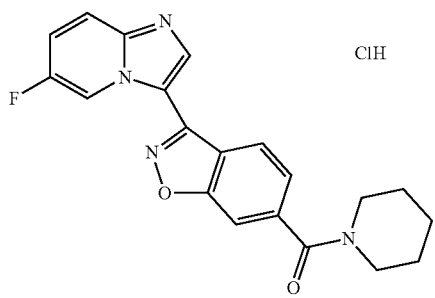 [SMILES: O=C(c1ccc2c(-c3cnc4ccc(F)cn34)noc2c1)N1CCCCC1 ; Cl]

Example 116 was obtained according to general procedure X, using example 76. To the crude material dissolved in CH$_2$Cl$_2$ and filtered through a pad of celite, HCl in Et$_2$O was added. Example 116 was filtrated, washed with CH$_2$Cl$_2$ and dried under reduced pressure.

¹H-NMR (400 MHz, DMSO): 1.49-1.69 (m, 6H, 3*CH₂); 3.27 (m, 2H, N—CH₂); 3.64 (m, 2H, N—CH₂); 7.52 (d, J 8.1 Hz, 1H, Ar); 7.83 (m, 1H, Ar); 7.94 (s, 1H, Ar); 8.05 (dd, J 5.2 Hz, J 9.8 Hz, 1H, Ar); 8.52 (d, J 8.1 Hz, 1H, Ar); 9.04 (s, 1H, Ar); 9.46 (m, 1H, Ar). M/Z (M+H)⁺=365. Mp: 203-205° C.

Example 117

3-(6-Bromoimidazo[1,2-a]pyridin-3-yl)-6-(piperidin-1-ylcarbonyl)-1,2-benzisoxazole

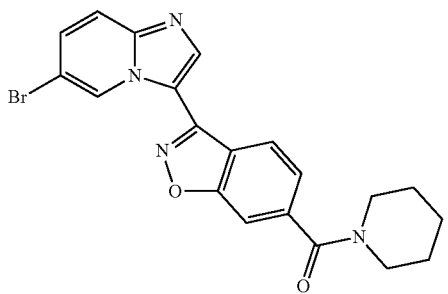 [SMILES: O=C(c1ccc2c(-c3cnc4ccc(Br)cn34)noc2c1)N1CCCCC1]

Example 117 was obtained according to general procedure X, using example 77. Trituration in Et₂O afforded the example as a beige solid in 60% yield.

¹H-NMR (400 MHz, CDCl₃): 1.51-1.80 (bm, 6H, 3*CH₂); 3.40 (bs, 2H, N—CH₂); 3.82 (bs, 2H, N—CH₂); 7.51 (dd, J 2.0 Hz, J 6.5 Hz, 1H, Ar); 7.53 (dd, J 1.6 Hz, J 7.3 Hz, 1H, Ar); 7.74 (m, 2H, Ar); 8.10 (d, J 8.2 Hz, 1H, Ar); 8.48 (s, 1H, Ar); 9.69 (s, 1H, Ar). M/Z (M[⁷⁹Br]+H)⁺=425.

Example 118

6-(Azepan-1-ylcarbonyl)-3-(6-bromoimidazo[1,2-a]pyridin-3-yl)-1,2-benzisoxazole

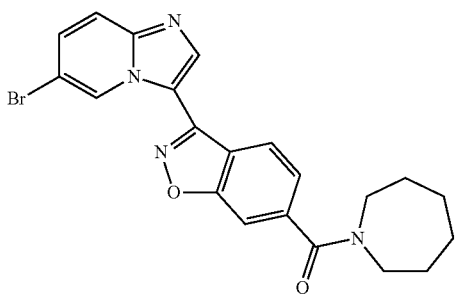 [SMILES: O=C(c1ccc2c(-c3cnc4ccc(Br)cn34)noc2c1)N1CCCCCC1]

Example 118 was obtained according to general procedure X, using example 33. Trituration in Et₂O afforded the example as a beige solid in 60% yield.

¹H-NMR (400 MHz, CDCl₃): 1.58-1.71 (m, 6H, 3*CH₂); 1.92 (m, 2H, CH₂); 3.42 (m, 2H, N—CH₂); 3.77 (m, 2H, N—CH₂); 7.51 (m, 2H, Ar); 7.73 (m, 2H, Ar); 8.10 (d, J 8.2 Hz, 1H, Ar); 8.47 (s, 1H, Ar); 9.69 (s, 1H, Ar). M/Z (M[⁷⁹Br]+H)⁺=439.

Compound 72

4-[(6-Bromoimidazo[1,2-a]pyridin-3-yl)carbonyl]-3-fluorobenzoic acid

Compound 72 was obtained according to general procedure VI starting from compound 65 in THF and was stirred 2 Hrs at R.T. as a light green solid in 84% yield.

M/Z (M[⁷⁹Br]+H)⁺=363.

Example 119

(6-Bromoimidazo[1,2-a]pyridin-3-yl)[2-fluoro-4-(morpholin-4-ylcarbonyl)phenyl]methanone

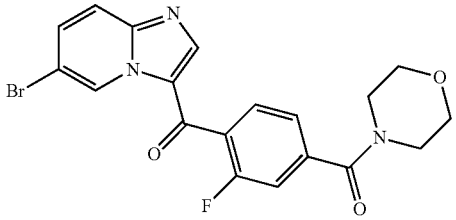 [SMILES: O=C(c1ccc(C(=O)N2CCOCC2)cc1F)c1cnc2ccc(Br)cn12]

Example 119 was obtained according to general procedure VII, method E, using compound 72 and morpholine without purification. Example 119 was isolated in 76% yield.

¹H-NMR (400 MHz, DMSO): 3.31-3.71 (m, 8H, 2*O—CH₂, 2*N—CH₂); 7.41 (dd, J 1.3 Hz, J 7.8 Hz, 1H, Ar); 7.49 (dd, J 0.9 Hz, J 10.2 Hz, 1H, Ar); 7.76 (d, J 7.4 Hz, 1H, Ar); 8.93 (m, 2H, Ar); 8.25 (d, J 1.4 Hz, 1H, Ar); 9.77 (m, 1H, Ar). M/Z (M[⁷⁹Br]+H)⁺=432.

Example 120

3-(6-Bromoimidazo[1,2-a]pyridin-3-yl)-6-(morpholin-4-ylcarbonyl)-1,2-benzisoxazole

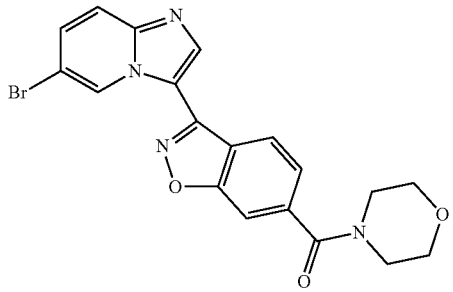 [SMILES: O=C(c1ccc2c(-c3cnc4ccc(Br)cn34)noc2c1)N1CCOCC1]

Example 120 was obtained according to general procedure X, using example 119. Precipitation after hydrolyses afforded the example as a brown solid in 33% yield.

¹H-NMR (400 MHz, CDCl₃): 3.31-3.71 (m, 8H, 2*O—CH₂, 2*N—CH₂); 7.43 (m, 2H, Ar); 7.65 (m, 2H, Ar); 8.01 (d, J 8.0 Hz, 1H, Ar); 8.37 (s, 1H, Ar); 9.51 (s, 1H, Ar). M/Z (M[⁷⁹Br]+H)⁺=427.

Example 121

[4-(8-Azabicyclo[3.2.1]oct-8-ylcarbonyl)-2-fluorophenyl](6-bromoimidazo[1,2-a]pyridin-3-yl)methanone

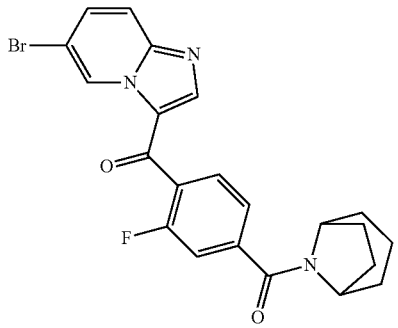 [SMILES: O=C(c1ccc(C(=O)N2C3CCCC2CC3)cc1F)c1cnc2ccc(Br)cn12]

Example 121 was obtained according to general procedure VII, method E, using compound 72, 8-azabicyclo[3.2.1]octane, HCl salt (5 equiv.) and DBU (5 equiv.) without purification. Example 121 was isolated in 41% yield.

¹H-NMR (400 MHz, DMSO): 1.51-2.00 (m, 10H, 5*CH₂); 3.98 (m, 1H, N—CH); 4.76 (m, 1H, N—CH); 7.28 (dd, J 0.6 Hz, J 9.8 Hz, 1H, Ar); 7.33 (dd, J 1.1 Hz, J 7.8 Hz, 1H, Ar); 7.56-7.61 (m, 2H, Ar); 7.65 (d, J 9.3 Hz, 1H, Ar); 8.01 (d, J 2.0 Hz, 1H, Ar); 9.88 (m, 1H, Ar). M/Z (M[⁷⁹Br]+H)⁺=456.

Example 122

6-(8-Azabicyclo[3.2.1]oct-8-ylcarbonyl)-3-(6-bromoimidazo[1,2-a]pyridin-3-yl)-1,2-benzisoxazole

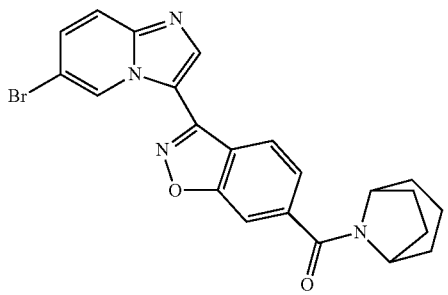 [SMILES: O=C(c1ccc2c(-c3cnc4ccc(Br)cn34)noc2c1)N1C2CCCC1CC2]

Example 122 was obtained according to general procedure X, using example 121. Trituration in Et₂O afforded the example as a beige solid in 73% yield.

¹H-NMR (400 MHz, CDCl₃): 1.39-1.97 (m, 10H, 5*CH₂); 3.96 (m, 1H, N—CH); 4.80 (m, 1H, N—CH); 7.43 (m, 1H, Ar); 7.51 (d, J 8.0 Hz, 1H, Ar); 7.64 (d, J 8.9 Hz, 1H, Ar); 7.73 (s, H, Ar); 8.01 (d, J 8.2 Hz, 1H, Ar); 8.38 (s, 1H, Ar); 9.60 (s, 1H, Ar). M/Z (M[⁷⁹Br]+H)⁺=451.

General Procedure XI: imidazo[1,2-a]pyridine cyanation

To a solution of bromo-imidazo[1,2-a]pyridine derivatives (1.0 equiv.) in DMF, Zinc cyanide (1.1 equiv.) and Pd(PPh₃)₄ (5%) were added under inert atmosphere. The resulting mixture was heated through microwave irradiation for 10 min at 130° C. (Power max tolerated was 70 W). The yellow cloudy reaction mixture was hydrolyzed with HCl 1N solution then extracted with Et₂O. Aqueous layer was cooled by an ice bath, and NaOH solid was added until a pH was greater than 10. The resulting aqueous basic layer was extracted with EtOAC. Organic layer was washed with brine, dried over MgSO₄ and concentrated under reduced pressure.

To the residue dissolved in CH₂Cl₂ and filtered through a pad of celite, HCl in Et₂O was added.

Targeted examples were filtrated, washed with CH₂Cl₂ and dried under reduced pressure.

Example 123

3-[6-(Piperidin-1-ylcarbonyl)-1,2-benzisoxazol-3-yl]imidazo[1,2-a]pyridine-6-carbonitrile, HCl salt

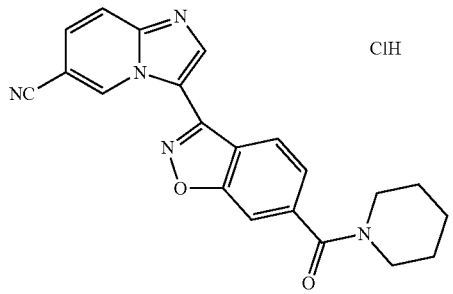 [SMILES: N#Cc1ccc2ncc(-c3noc4cc(C(=O)N5CCCCC5)ccc34)n2c1 ; Cl]

Example 123 was obtained according to general procedure XI, using example 116 as a beige solid in 35% yield.

¹H-NMR (400 MHz, DMSO): 1.48-1.62 (m, 6H, 3*CH₂); 3.26 (m, 2H, N—CH₂); 7.50 (m, 1H, Ar); 7.83-8.02 (m, 3H, Ar); 8.50 (m, 1H, Ar); 9.00 (m, 1H, Ar); 9.87 (s, 1H, Ar). N—CH₂ under water peak. M/Z (M+H)⁺=372.

Example 124

3-[6-(Azepan-1-ylcarbonyl)-1,2-benzisoxazol-3-yl]imidazo[1,2-a]pyridine-6-carbonitrile, HCl salt

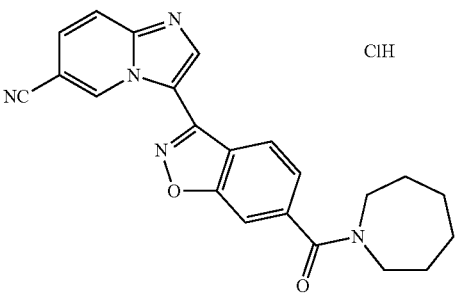 [SMILES: N#Cc1ccc2ncc(-c3noc4cc(C(=O)N5CCCCCC5)ccc34)n2c1 ; Cl]

Example 124 was obtained according to general procedure XI, using example 118 as a beige solid in 80% yield.

¹H-NMR (400 MHz, DMSO): 1.59-1.62 (m, 6H, 3*CH₂); 1.75-1.79 (m, 2H, CH₂); 3.31 (m, 2H, N—CH₂); 3.63 (m, 2H, N—CH₂); 7.51 (dd, J 0.9 Hz, J 8.2 Hz, 1H, Ar); 7.85 (dd, J 1.6 Hz, J 9.4 Hz, 1H, Ar); 7.96 (s, 1H, Ar); 8.05 (d, J 9.4 Hz, 1H,

Ar); 8.52 (d, J 8.2 Hz, 1H, Ar); 9.01 (s, 1H, Ar); 9.88 (s, 1H, Ar). M/Z (M+H)⁺=386. Mp: 234-235° C.

Example 125

3-[6-(Morpholin-4-ylcarbonyl)-1,2-benzisoxazol-3-yl]imidazo[1,2-a]pyridine-6-carbonitrile, HCl salt

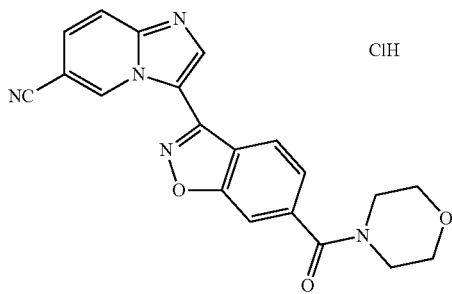 [SMILES: N#Cc1ccc2ncc(-c3noc4cc(C(=O)N5CCOCC5)ccc34)n2c1 ; Cl]

Example 125 was obtained according to general procedure XI, using example 119 as a beige solid in 37% yield.
M/Z (M+H)⁺=374.

Example 126

3-[6-(8-Azabicyclo[3.2.1]oct-8-ylcarbonyl)-1,2-benzisoxazol-3-yl]imidazo[1,2-a]pyridine-6-carbonitrile, HCl salt

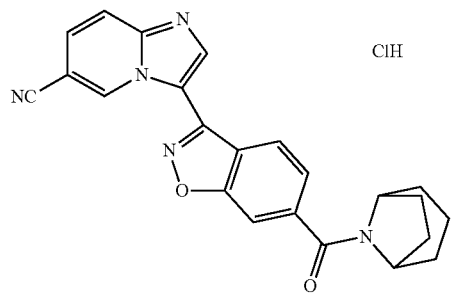 [SMILES: N#Cc1ccc2ncc(-c3noc4cc(C(=O)N5C6CCCC5CC6)ccc34)n2c1 ; Cl]

Example 126 was obtained according to general procedure XI, using example 121 as a beige solid in 14% yield.
¹H-NMR (400 MHz, DMSO): 1.39-2.03 (m, 10H, 5*CH₂); 3.91 (m, 1H, N—CH); 4.64 (m, 1H, N—CH); 7.59 (d, J 8.2 Hz, 1H, Ar); 7.85 (dd, J 1.5 Hz, J 9.3 Hz, 1H, Ar); 8.00 (s, 1H, Ar); 8.05 (d, J 9.2 Hz, 1H, Ar); 8.53 (d, J 8.2 Hz, 1H, Ar); 9.01 (s, 1H, Ar); 9.88 (s, 1H, Ar). M/Z (M+H)⁺=398.

Compound 73

4-Amino-N-cyclohexyl-N-ethyl-3-hydroxy-benzamide

To a solution of compound 30 (1.1 g) in ethanol (10 mL), Pd/C 10% weight (100 mg) was added. The reaction mixture was purged with hydrogen and stirred under hydrogen atmosphere for 48 Hrs at R.T. The catalyst was filtered off on celite and washed with EtOH. The filtrate was concentrated under reduced pressure to give the product as a purple foam (735 mg, 74%). M/Z (M+H)⁺=263.

Compound 74

3-Amino-N-cyclohexyl-N-ethyl-4-hydroxy-benzamide

Compound 74 was obtained according to the procedure described for compound 73, starting from compound 31, as a cream solid in 52% yield.
M/Z (M+H)⁺=263.

Example 127

Imidazo[1,2-a]pyridine-3-carboxylic acid [4-(cyclohexyl-ethyl-carbamoyl)-2-hydroxy-phenyl]-amide

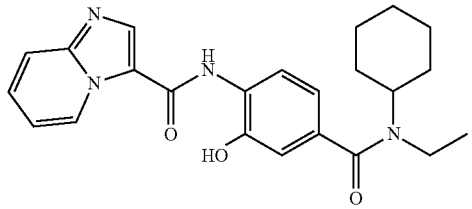 [SMILES: CCN(C(=O)c1ccc(NC(=O)c2cnc3ccccn23)c(O)c1)C1CCCCC1]

To a solution of imidazo[1,2-a]pyridine-3-carboxylic acid (250 mg) in DMF (7 mL), EDCI (443 mg, 1.5 equiv.), HOBt (312 mg, 1.5 equiv.), DIPEA (805 µL, 3.0 equiv.) and compound 73 (404 mg, 1.0 equiv.) were added. The resulting mixture was stirred at R.T. overnight.

The reaction mixture was diluted with AcOEt (15 mL), washed with HCl 1M (2*10 mL) and water (2*10 mL). Combined aqueous layers were saturated with NaHCO₃ and extracted with AcOEt (2*10 mL). The combined organic layers were washed with brine, dried over MgSO₄ and concentrated under reduced pressure. Purification by flash-chromatography (MeOH 2% to 5% in CH₂Cl₂) followed by preparative HPLC afforded the product as a white solid (9.3 mg, yield<5%).
¹H-NMR (400 MHz, DMSO): 1.11-1.79 (m, 13H, 5*CH₂+CH₃); 3.33 (q, J 7.0 Hz, 2H, N—CH₂); 6.81 (dd, J 1.9 Hz, J 8.1 Hz, 1H, Ar); 6.90 (d, J 2.0 Hz, 1H, Ar); 7.20 (m, 1H, Ar); 7.55 (m, 1H, Ar); 7.75-7.78 (m, 2H, Ar); 8.56 (s, 1H, Ar); 9.36 (bs, 1H, NH); 9.47 (m, 1H, Ar). N—CH signal under water peak.
M/Z (M+H)⁺=407.

Example 128

Imidazo[1,2-a]pyridine-3-carboxylic acid [5-(cyclohexyl-ethyl-carbamoyl)-2-hydroxy-phenyl]-amide

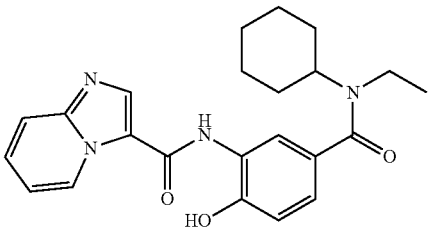 [SMILES: CCN(C(=O)c1ccc(O)c(NC(=O)c2cnc3ccccn23)c1)C1CCCCC1]

Example 128 was obtained according to the procedure described for example 127, using compound 74. The reaction was completed after 48 Hrs at R.T.

The reaction mixture was diluted with AcOEt, washed with a saturated aqueous solution of NaHCO₃, water, brine, dried over MgSO₄ and concentrated under reduced pressure.

Purification by flash-chromatography (MeOH 2% to 7% in CH$_2$Cl$_2$) followed by preparative HPLC afforded the product as a white solid (yield<5%).

$^1$H-NMR (400 MHz, DMSO): 1.11-1.79 (m, 13H, 5*CH$_2$+CH$_3$); 3.35 (q, J 7.0 Hz, 2H, N—CH$_2$); 3.78 (bm, 1H, N—CH); 6.97-7.05 (m, 2H, Ar); 7.20 (t, J 7.0 Hz, 1H, Ar); 7.55 (m, 1H, Ar); 7.72 (d, J 2.0 Hz, 1H, Ar); 7.77 (m, 1H, Ar); 8.56 (s, 1H, Ar); 9.37 (bs, 1H, NH); 9.46 (m, 1H, Ar). M/Z (M+H)$^+$=407.

Example 129

2-Imidazo[1,2-a]pyridin-3-yl-benzooxazole-6-carboxylic acid cyclohexyl-ethyl-amide

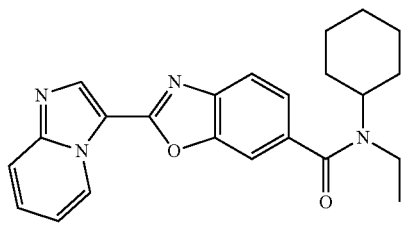 [SMILES: CCN(C(=O)c1ccc2nc(-c3cnc4ccccn34)oc2c1)C1CCCCC1]

To a solution of example 127 (55 mg) in anhydrous THF (1 mL), triphenylphosphine (93 mg, 2.7 equiv.) and DIAD (130 μL, 5.0 equiv.) were added. The reaction mixture was heated overnight at reflux.

The reaction mixture was allowed to cool to R.T. and was then diluted with AcOEt (5 mL), washed with water (2*5 mL), and extracted with HCl 1M (2*4 mL). The acidic aqueous layers were saturated with NaHCO$_3$ and extracted with AcOEt (2*5 mL). The combined organic layers were washed with brine (5 mL), dried over MgSO$_4$ and concentrated under reduced pressure.

Purification by flash-chromatography (MeOH 1% to 3% in CH$_2$Cl$_2$) followed by trituration in MeOH afforded the product as a white solid (11 mg, 21%).

$^1$H-NMR (400 MHz, DMSO): 1.07-1.81 (m, 13H, 5*CH$_2$+CH$_3$); 3.38 (q, J 7.0 Hz, 2H, N—CH$_2$); 3.69 (bs, 1H, N—CH); 7.33-7.39 (m, 2H, Ar); 7.61 (m, 1H, Ar); 7.72 (s, 1H, Ar); 7.85 (m, 2H, Ar); 8.53 (s, 1H, Ar); 9.60 (m, 1H, Ar). M/Z (M+H)$^+$=389. Mp: 203-206° C.

Example 130

2-Imidazo[1,2-a]pyridin-3-yl-benzooxazole-5-carboxylic acid cyclohexyl-ethyl-amide

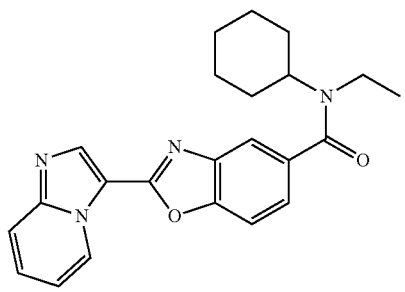 [SMILES: CCN(C(=O)c1ccc2oc(-c3cnc4ccccn34)nc2c1)C1CCCCC1]

Example 130 was obtained according to the procedure described for example 129, starting from example 128.

Purification by flash-chromatography (MeOH 2% in CH$_2$Cl$_2$) followed by trituration in AcOEt afforded the product as a white solid in 32% yield.

$^1$H-NMR (400 MHz, DMSO): 0.83-1.83 (m, 13H, 5*CH$_2$+CH$_3$); 4.12 (bs, 1H, N—CH); 7.34-7.40 (m, 2H, Ar); 7.63 (m, 1H, Ar); 7.75 (s, 1H, Ar); 7.84 (d, J 8.2 Hz, 1H, Ar); 7.90 (m, 1H, Ar); 8.57 (s, 1H, Ar); 9.59 (m, 1H, Ar). N—CH$_2$ under water peak. M/Z (M+H)$^+$=389.

Example 131

Azepan-1-yl-[3-(6-fluoro-imidazo[1,2-a]pyridin-3-yl)-benzo[c]isoxazol-6-yl]-methanone

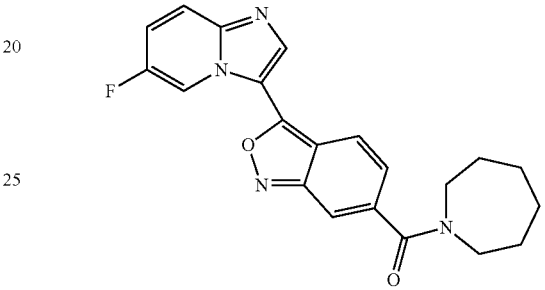

A solution of example 29 (80 mg) in acetic acid (800 μL) was stirred at R.T. overnight.

The reaction mixture was hydrolysed with HCl 1M (2 mL) and concentrated to a minimal volume. The residue was purified by preparative HPLC to afford the product as a yellow solid (8.1 mg, 11%).

$^1$H-NMR (400 MHz, DMSO): 1.51-1.63 (bm, 6H, 3*CH$_2$); 1.71-1.78 (bm, 2H, CH$_2$); 3.59 (t, J 5.7 Hz, 2H, N—CH$_2$); 7.08 (dd, J 0.9 Hz, J 8.9 Hz, 1H, Ar); 7.65 (s, 1H, Ar); 7.71 (m, 1H, Ar); 7.95 (m, 1H, Ar); 8.21 (m, 1H, Ar); 8.80 (s, 1H, Ar); 9.23 (m, 1H, Ar). N—CH$_2$ under water peak. M/Z (M+H)$^+$=379.

Compound 75

6-Fluoro-imidazo[1,2-a]pyridine

To a solution of 2-amino-5-fluoropyridine (10 g) in ethanol (200 mL), a solution of chloroacetaldehyde 50% in water (56 mL, 4.0 equiv.) was added. The reaction mixture was heated at reflux 2 Hrs, then was concentrated under reduced pressure to 100 mL. The residue was diluted in AcOEt (100 mL) and washed with a saturated aqueous solution of NaHCO$_3$ (2*150 mL). The combined aqueous were saturated with NaHCO$_3$ and extracted back with AcOEt (2*100 mL). The combined organic layers were washed with brine (100 mL), dried over Na$_2$SO$_4$ and concentrated under reduced pressure.

Purification by flash-chromatography (MeOH 2.5% in CH$_2$Cl$_2$) afforded the product as a cream solid (8.7 g, 72%).
M/Z (M+H)$^+$=137.

Compound 76

6-Fluoro-3-nitro-imidazo[1,2-a]pyridine

To a solution of compound 75 (2.0 g) in sulphuric acid 96% (7.5 mL, 10.0 equiv.) cooled at 0° C., nitric acid 93% (2.5 mL, 4.0 equiv.) was added dropwise. The reaction mixture was stirred at 0° C. for 10 min and was then poured onto a mixture of ice-water (30 mL).

The mixture was basified with NaOH 6M (60 mL). A solid was filtered off, washed with water (3*10 mL) and dried under vacuum to afford the product as a pale yellow solid (2.1 g, 81%).

M/Z (M+H)$^+$=182.

Compound 77

6-Fluoro-imidazo[1,2-a]pyridin-3-ylamine

To a solution of compound 76 (1.8 g) in ethanol (20 mL), tin (II) chloride (9.7 g, 5.0 equiv.) was added. The reaction mixture was heated at reflux for 1.5 Hr.

After cooling at R.T., the mixture was hydrolysed with NaOH 30% (30 mL). An insoluble was filtered off. The filtrate was extracted with AcOEt (3*20 mL), the combined organic layers were washed with brine (20 mL), dried over Na$_2$SO$_4$ and concentrated under reduced pressure.

Purification by flash-chromatography (MeOH 2.5% to 6% in CH$_2$Cl$_2$) afforded the product as a cream solid (820 mg, 53%). M/Z (M+H)$^+$=152.

Compound 78

N-(6-Fluoro-imidazo[1,2-a]pyridin-3-yl)-formamide

To a solution of compound 77 (450 mg) in formic acid (6 mL), acetic anhydride (2 mL, 7.0 equiv.) was added. The reaction mixture was stirred at R.T. for 2 Hrs, and was then hydrolysed with water (30 mL) and basified with K$_2$CO$_3$. A solid appeared and was filtered off to afford the product as a cream solid (357 mg, 66%).

M/Z (M+H)$^+$=180.

Compound 79

Azepan-1-yl-[4-(6-fluoro-imidazo[1,2-a]pyridin-3-ylamino)-3-nitro-phenyl]-methanone To a solution of compound 78 (475 mg) in anhydrous DMF (5 mL), sodium hydride 60% dispersion in oil (150 mg, 1.4 equiv.) was added. The mixture was stirred at R.T. for 15 min, then a solution of compound 32 (650 mg, 0.9 equiv.) in anhydrous DMF (1 mL) was added. The resulting dark mixture was heated at 100° C. for 45 min.

After cooling at R.T., the mixture was diluted with AcOEt (10 mL) and extracted with HCl 1M (2*10 mL). The combined aqueous layers were washed with AcOEt (10 mL), basified with NaOH pellets (900 mg) and extracted with AcOEt (3*10 mL). The combined organics were washed with brine (10 mL), dried over MgSO$_4$ and concentrated under reduced pressure.

Purification by flash-chromatography (MeOH 3% in CH$_2$Cl$_2$) afforded the product as an orange oil (850 mg, 85%).

M/Z (M+H)$^+$=398.

Compound 80

[3-Amino-4-(6-fluoro-imidazo[1,2-a]pyridin-3-ylamino)-phenyl]-azepan-1-yl-methanone To a solution of compound 79 (850 mg) in AcOEt (8.5 mL), Pd/C 10% weight (150 mg) was added. The mixture purged with hydrogen, and was stirred at R.T. for 20 Hrs under hydrogen atmosphere.

The catalyst was filtered off on celite and washed with AcOEt, and the filtrate was concentrated under reduced pressure.

Purification by flash-chromatography (MeOH 4% to 10% in CH$_2$Cl$_2$) afforded the product as an orange oil (400 mg, 51%).

M/Z (M+H)$^+$=368.

Example 132

5-(Azepan-1-ylcarbonyl)-1-(6-fluoroimidazo[1,2-a]pyridin-3-yl)-1H-1,2,3-benzotriazole

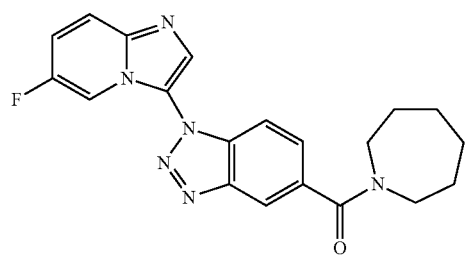 [SMILES: O=C(c1ccc2c(c1)nnn2-c1cnc2ccc(F)cn12)N1CCCCCC1]

To a solution of compound 80 (184 mg) in acetic acid (1.5 mL), sodium nitrite (38 mg, 1.1 equiv.) was added.

The reaction mixture was stirred at R.T. for 1 Hr, then was diluted with CH$_2$Cl$_2$ (15 mL) and washed with a saturated aqueous solution of NaHCO$_3$ (2*15 mL), dried over MgSO$_4$ and concentrated under reduced pressure.

Purification by flash-chromatography (MeOH 2% to 3% in CH$_2$Cl$_2$) followed by trituration in Et$_2$O afforded the product as a cream solid (84 mg, 44%).

$^1$H-NMR (400 MHz, DMSO): 1.51-1.64 (bm, 6H, 3*CH$_2$); 1.74-1.81 (bm, 2H, CH$_2$); 3.38 (b, 2H, N—CH$_2$); 3.62 (t, J 5.8 Hz, 2H, N—CH$_2$); 7.55-7.69 (m, 3H, Ar); 7.90 (m, 1H, Ar); 8.21 (s, 1H, Ar); 8.27 (m, 1H, Ar); 8.48 (m, 1H, Ar). M/Z (M+H)$^+$=379. Mp: 160-166° C.

Compound 81

1H-Indole-6-carboxylic acid

To a solution of methyl indole-6-carboxylate (3.0 g) in MeOH (34 mL), a 3M aqueous solution of LiOH (17 mL, 3.0 equiv.) was added. The reaction mixture was heated at reflux for 1 Hr, then cooled at 0° C., diluted with water (50 mL) and acidified with HCl 12M (5 mL). The mixture was extracted with AcOEt (3*30 mL). The combined organic layers were washed with brine (30 mL), dried over MgSO$_4$ and concentrated to give the product as a yellow solid (2.3 g, 85%).

M/Z (M+H)$^+$=162.

Compound 82

Azepan-1-yl-(1H-indol-6-yl)-methanone

Compound 82 was obtained according to general procedure II, method A, starting from compound 81 and hexamethyleneimine (3.0 equiv.), and using EDCI as coupling agent. The reaction was heated at 80° C. for 2 Hrs.

Purification by flash-chromatography (2% to 3% MeOH in CH$_2$Cl$_2$) followed by trituration in Et$_2$O afforded the product as a white solid in 27% yield.

M/Z (M+H)$^+$=243.

Compound 83

Azepan-1-yl-(3-bromo-1H-indol-6-yl)-methanone

To a solution of compound 82 (630 mg) in anhydrous DMF (6 mL) cooled at 0° C., bromine (148 µL, 1.1 equiv.) was added. The reaction mixture was allowed to warm to R.T. and stirred for min, then was diluted with AcOEt (10 mL) and hydrolysed with a saturated aqueous solution of NaHCO$_3$ (10 mL). The organic layer was washed with water (10 mL), brine (10 mL), dried over MgSO$_4$ and concentrated under reduced pressure.

Trituration in Et$_2$O afforded the product as a white solid in 96% yield.

M/Z (M[$^{79}$Br]+H)$^+$=321

Compound 84

Azepan-1-yl-(1-benzenesulfonyl-3-bromo-1H-indol-5-yl)-methanone

To a solution of compound 83 (150 mg) in anhydrous DMF (2 mL) cooled at 0° C. and under argon stream, sodium hydride 60% dispersion in oil (30 mg, 1.6 equiv.) was added. The reaction mixture was stirred at 0° C. for 15 min, then allowed to warm to R.T. and stirred for another 15 min. After cooling at 0° C., benzylsulfonyl chloride (90 µL, 1.5 equiv.) was added. The reaction mixture was stirred at 0° C. for 15 min, the allowed to warm to R.T. and stirred for another 15 min. reaction mixture then hydrolysed with HCl 1M (3 mL) and extracted with AcOEt (5 mL). The organic layer was washed with water (3 mL), brine (3 mL), dried over Na$_2$SO$_4$ and concentrated under reduced pressure.

Purification by flash-chromatography (AcOEt 20% to 80% in cyclohexane) afforded the product as a white solid in 54% yield.

M/Z (M[$^{79}$Br]+H)$^+$=461

Compound 85

Azepan-1-yl-(1-benzenesulfonyl-3-boronic-acid-indol-6-yl)-methanone

To a solution of bromoindole 84 (90 mg) in anhydrous THF (2 mL) cooled at −78° C. and under argon stream, n-BuLi 1.6 M in hexanes (136 µL, 1.1 equiv.) was added dropwise. The reaction mixture was stirred at −78° C. for 30 min, then triisopropyl borate (68 µL, 1.5 equiv.) was added dropwise. The reaction mixture was stirred at −78° C. for a further 30 min, then allowed to warm to R.T. and stirred for 40 min. Reaction mixture was hydrolysed with a saturated aqueous solution of NH$_4$Cl (1.5 mL) and extracted with AcOEt (1.5 mL). The organic layer was washed with a saturated aqueous solution of NH$_4$Cl (1.5 mL), brine (1.5 mL), dried over Na$_2$SO$_4$ and concentrated under reduced pressure.

Purification by flash-chromatography (MeOH 1% to 4% in CH$_2$Cl$_2$) afforded the product as a pale yellow oil in 13% yield.

M/Z (M+H)$^+$=427.

Compound 86

6-Fluoro-3-iodo-imidazo[1,2-a]pyridine

To a solution of compound 75 (1.0 g) in CCl$_4$ (10 mL), under argon stream, N-iodosuccinimide (1.9 g, 1.2 equiv.) and 1,1'-azabis(cyclohexanecarbonitrile) (72 mg, 0.04 equiv.) were added. The reaction mixture was irradiated with a 100 Watt lamp overnight.

After cooling at R.T., an insoluble was filtered off and washed with CCl$_4$. The filtrate was concentrated under reduced pressure and the resulting residue was purified by flash-chromatography (AcOEt 10% to 30% in cyclohexane) to afford the product as a pale yellow solid (430 mg, 22%).

M/Z (M+H)$^+$=263.

Example 133

Azepan-1-yl-[1-benzenesulfonyl-3-(6-fluoro-imidazo[1,2-a]pyridin-3-yl)-1H-indol-6-yl]-methanone

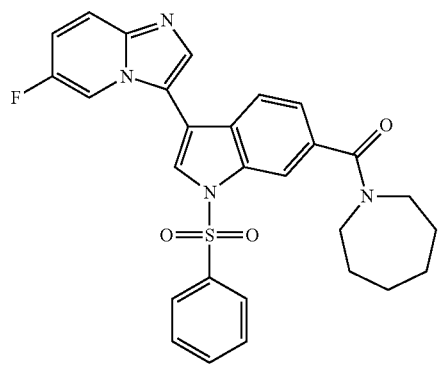 [SMILES: O=C(c1ccc2c(-c3cnc4ccc(F)cn34)cn(S(=O)(=O)c3ccccc3)c2c1)N1CCCCCC1]

To a solution of compounds 86 (1.0 equiv.) and 85 (1.0 equiv.) in dimethoxyethane, Pd(PPh$_3$)$_4$ (0.05 equiv.) and a 2M aqueous solution of Na$_2$CO$_3$ (2.0 equiv.) were added. The reaction mixture was heated through microwave irradiation for 10 min at 130° C. (P$_{max}$ 70 W).

After cooling at R.T., the reaction mixture was hydrolysed with a saturated aqueous solution of NH$_4$Cl and extracted with AcOEt. The organic layer was washed with water, brine, dried over Na$_2$SO$_4$ and concentrated under reduced pressure.

Purification by flash-chromatography (MeOH 1% to 3% in CH$_2$Cl$_2$) afforded the product as a blue solid in 32% yield.

$^1$H-NMR (400 MHz, DMSO): 1.48-1.55 (m, 6H, 3*CH$_2$); 1.68-1.70 (m, 2H, CH$_2$); 3.29 (m, 2H, N—CH$_2$); 3.52 (m, 2H, N—CH$_2$); 7.47 (dd, J 1.5 Hz, J 8.6 Hz, 1H, Ar); 7.60 (m, 1H, Ar); 7.68 (m, 2H, Ar); 7.78 (m, 1H, Ar); 7.90 (m, 1H, Ar); 8.03 (dd, J 4.6 Hz, J 9.5 Hz, 1H, Ar); 8.10 (d, J 8.5 Hz, 1H, Ar); 7.19 (m, 2H, Ar); 8.39 (bs, 1H, Ar); 8.54 (s, 1H, Ar); 8.90 (m, 1H, Ar). M/Z (M+H)$^+$=517.

Example 134

3-[6-(Azepan-1-ylcarbonyl)-1H-indol-3-yl]-6-fluoroimidazo[1,2-a]pyridine

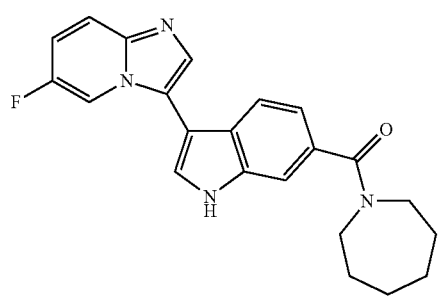 [SMILES: O=C(c1ccc2c(-c3cnc4ccc(F)cn34)c[nH]c2c1)N1CCCCCC1]

To a solution of example 133 (25 mg) in anhydrous THF (1 mL), a 1M solution of TBAF in THF (100 µL, 2.0 equiv.) was added. The reaction mixture was heated at reflux for 1 Hr, then was concentrated under reduced pressure.

Purification by preparative HPLC afforded the product as a pale yellow solid in 41% yield.

$^1$H-NMR (400 MHz, DMSO): 1.52-1.65 (bm, 6H, 3*CH$_2$); 1.70-1.82 (bm, 2H, CH$_2$); 7.13 (dd, J 1.4 Hz, J 8.1 Hz, 1H, Ar); 7.54 (m, 1H, Ar); 7.62 (d, J 8.2 Hz, 1H, Ar); 7.87 (m, 1H, Ar); 8.01 (m, 1H, Ar); 8.09 (d, J 2.7 Hz, 1H, Ar); 8.32 (bs, 1H, Ar); 8.81 (m, 1H, Ar); 11.99 (b, 1H, NH). 2*N—CH$_2$ signals under water peak. M/Z (M+H)$^+$=377. Mp: decomposition at 190° C.

Example 135

Azepan-1-yl-[4-(6-fluoro-imidazo[1,2-a]pyridin-3-yl)-quinazolin-7-yl]-methanone

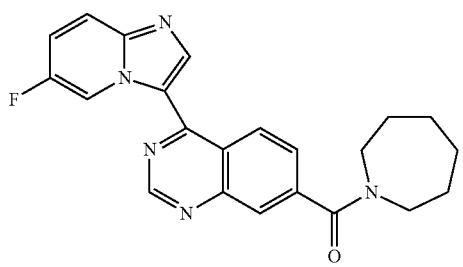 [SMILES: O=C(c1ccc2c(-c3cnc4ccc(F)cn34)ncnc2c1)N1CCCCCC1]

A solution of example 30 (50 mg) in a mixture of formic acid (160 µL, 32 equiv.) and formamide (640 µL, 122 equiv.), under argon atmosphere, was heated through microwave irradiation for 25 min at 170° C.

After cooling at R.T., a solid precipitated and was filtered off. Purification by preparative HPLC afforded the product as a yellow solid (6.5 mg, 13%)

$^1$H-NMR (400 MHz, DMSO): 1.52-1.66 (bm, 6H, 3*CH$_2$); 1.75-1.82 (bm, 2H, CH$_2$); 3.36 (m, 2H, N—CH$_2$); 3.65 (t, J 5.9 Hz, 2H, N—CH$_2$); 7.79 (dd, J 1.6 Hz, J 8.6 Hz, 1H, Ar); 7.93 (m, 1H, Ar); 8.04 (d, J 1.4 Hz, 1H, Ar); 8.08 (dd, J 5.2 Hz, J 9.9 Hz, 1H, Ar); 8.59 (d, J 8.6 Hz, 1H, Ar); 8.87 (s, 1H, Ar); 9.45 (s, 1H, Ar), 9.76 (m, 1H, Ar). M/Z (M+H)$^+$=390. Mp: decomposition at 200° C.

General Procedure XII: Formation of Examples AH from Fluoroketones AC (Scheme 5).

To a suspension of sodium hydride (10 equiv.) in DMA, amidine K (7.5 equiv.) was added gradually. The mixture was stirred 10 minutes at RT, then, the fluoroketone AC (1.0 equiv.) was introduced. Reaction was heated through microwave irradiation for 5 min at 180° C.

The crude reaction mixture was purified by preparative HPLC. Co-evaporation with aqueous HCl 1N affords the product.

Example 136

2-Amino-7-(azepan-1-ylcarbonyl)-4-(6-fluoroimidazo[1,2-a]pyridin-3-yl)quinazoline, HCl salt

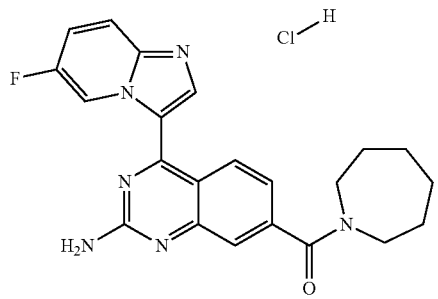 [SMILES: Nc1nc(-c2cnc3ccc(F)cn23)c2ccc(C(=O)N3CCCCCC3)cc2n1 ; Cl]

Example 136 was obtained according to general procedure XII, using guanidine hydrochloride and example 27, as a yellow solid in 31% yield.

$^1$H-NMR (400 MHz, DMSO): 1.57 (bm, 6H, 3*CH$_2$); 1.75 (bm, 2H, CH$_2$); 3.62 (m, 2H, N—CH$_2$); 7.49 (d, J 8.3 Hz, 1H, Ar); 7.67 (s, 1H, Ar); 7.87 (t, J 7.6 Hz, 1H, Ar); 8.04 (dd, J 5.2 Hz, J 9.2 Hz, 1H, Ar); 8.20-9.70 (bm, 2H, exchange with D$_2$O, NH$_2$); 8.55 (d, J 8.3 Hz, 1H, Ar); 8.91 (s, 1H, Ar); 9.97 (d, J 2.8 Hz, 1H, Ar). N—CH$_2$ under water peak. M/Z (M+H)$^+$=405.

Example 137

2-Methyl-7-(azepan-1-ylcarbonyl)-4-(6-fluoroimidazo[1,2-a]pyridin-3-yl)quinazoline, HCl salt

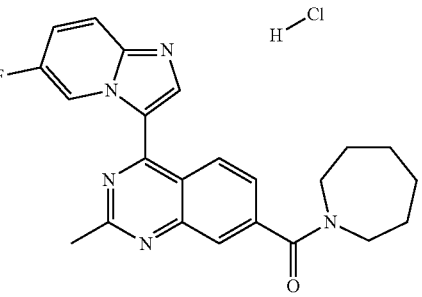

Example 137 was obtained according to general procedure XII, using acetamidine hydrochloride and example 27, as a yellow solid.

$^1$H-NMR (400 MHz, DMSO): 1.52-1.65 (bm, 6H, 3*CH$_2$); 1.75-1.81 (bm, 2H, CH$_2$); 2.87 (s, 3H, CH$_3$); 3.64 (t, J 5.7 Hz, 2H, N—CH$_2$); 7.67 (dd, J 1.3 Hz, J 8.6 Hz, 1H, Ar); 7.70-7.75 (m, 1H, Ar); 7.89 (d, J 1.1 Hz, 1H, Ar); 7.96 (dd, J 5.2 Hz, J 9.8 Hz, 1H, Ar); 8.55 (d, J 8.6 Hz, 1H, Ar); 8.65 (s, 1H, Ar); 9.73 (dd, J 2.3 Hz, J 5.1 Hz, 1H, Ar). N—CH$_2$ under water peak. M/Z (M+H)$^+$=404.

Compound 87

N,N-Dimethyl-N'-pyrimidin-2-ylimidoformamide

Compound 87 was obtained according to general procedure starting from 2-aminopyrimidine, as yellow solid in a quantitative yield.

M/Z (M+H)$^+$=151.

Example 138

N-Cyclohexyl-N-ethyl-4-(imidazo[1,2-a]pyrimidin-3-ylcarbonyl)-benzamide

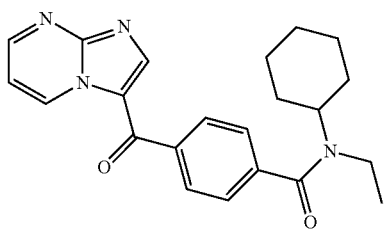 [SMILES: CCN(C(=O)c1ccc(C(=O)c2cnc3ncccn23)cc1)C1CCCCC1]

Example 138 was obtained according to general procedure V starting from compounds 87 and 44 in trifluorotoluene through microwave irradiation for 10 min at 200° C.

Trituration in DMSO afforded the product as a cream solid in 32% yield.

$^1$H-NMR (400 MHz, DMSO 80° C.): 1.14-1.78 (m, 13H, 5*$CH_2$+$CH_3$); 3.37 (q, J 7.0 Hz, 2H, N—$CH_2$); 3.66 (m, 1H, N—CH); 7.46 (dd, J 4.2 Hz, J 6.9 Hz, 1H, Ar); 7.53 (d, J 8.2 Hz, 2H, Ar); 7.97 (d, J 8.2 Hz, 2H, Ar); 8.44 (s, 1H, Ar); 8.89 (dd, J 2.0 Hz, J 4.2 Hz, 1H, Ar); 9.90 (dd, J 2.0 Hz, J 6.9 Hz, 1H, Ar). M/Z (M+H)$^+$=377.

Compound 88

N'-(6-Chloropyridazin-3-yl)-N,N-dimethylimidoformamide

Compound 88 was obtained according to general procedure I starting from 3-amino-6-chloropyridazine, as an orange solid in 94% yield.

M/Z (M[$^{35}$Cl]+H)$^+$=185.

Example 139

N-Cyclohexyl-N-ethyl-4-(6-chloroimidazo[1,2-b]pyridazin-3-ylcarbonyl)-benzamide

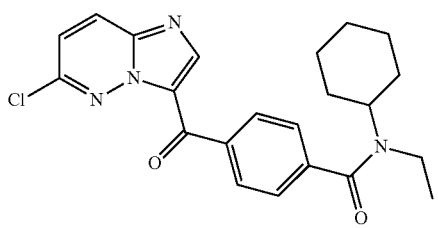

Example 139 was obtained according to general procedure V starting from compounds 88 and 44 in acetonitrile through microwave irradiation for 10 min at 150° C.

Purification by flash-chromatography (MeOH 2% in $CH_2Cl_2$) afforded the product as an orange solid in 56% yield.

$^1$H-NMR (400 MHz, DMSO 80° C.): 1.13-1.71 (m, 13H, 5*$CH_2$+$CH_3$); 3.36 (q, J 7.0 Hz, 2H, N—$CH_2$); 3.65 (m, 1H, N—CH); 7.50 (d, J 8.5 Hz, 2H, Ar); 7.61 (d, J 9.5 Hz, 1H, Ar); 7.93 (d, J 8.5 Hz, 2H, Ar); 8.29 (s, 1H, Ar); 8.36 (d, J 9.5 Hz, 1H, Ar). M/Z (M[$^{35}$Cl]+H)$^+$=411. Mp: 142-149° C.

Example 140

N-Cyclohexyl-N-ethyl-4-(imidazo[1,2-b]pyridazin-3-ylcarbonyl)-benzamide

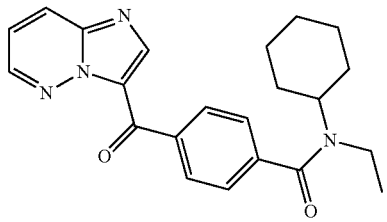 [SMILES: CCN(C(=O)c1ccc(C(=O)c2cnc3cccnn23)cc1)C1CCCCC1]

To a solution of example 139 (100 mg) in EtOH (1 mL) ammonium formate (35 mg, 2.3 equiv.) and 10% Pd on carbon (10 mg) were added. Reaction mixture was heated trough microwave irradiation 10 min at 130° C. After cooling to R.T., catalyst was filtered off and washed with EtoH. Filtrate was concentrated. Purification by preparative HPLC afforded the product as a white solid in 27% yield.

$^1$H-NMR (400 MHz, DMSO 80° C.): 1.10-1.77 (m, 13H, 5*$CH_2$+$CH_3$); 3.36 (q, J 7.0 Hz, 2H, N—$CH_2$); 3.65 (m, 1H, N—CH); 7.47-7.53 (m, 3H, Ar); 7.92 (d, J 8.5 Hz, 2H, Ar); 8.26 (s, 1H, Ar); 8.30 (dd, J 1.5 Hz, J 9.3 Hz, 1H, Ar); 8.72 (dd, J 1.5 Hz, J 4.4 Hz, 1H, Ar). M/Z (M+H)$^+$=377.

Example 141

Affinity Evaluations of Compounds of the Invention on an $A_{2A}$ FRET-Based Binding Assay Assay protocol: Compounds were evaluated on an in-vitro binding assay developed based on the technology described in the patent WO 98/55873. This assay was developed from h$A_{2A}$ receptor that was fused at its amino terminal domain to Green Fluorescent Protein (GFP) and stably expressed in HEK cells. The probe used is a dyed ligand derived from the non-selective CGS15943. For the FRET-binding experiment, HEK GFP-$A_{2A}$ stable cell line was seeded onto poly-D-lysine precoated black-walled 96-well plates in normal growth media (0.7 10$^5$ cells per well). After 24 hours of culture at 37° C., the cell media was removed and cells were washed. The tested compounds were applied on cells by the FLIPR$^{TETRA}$® (Molecular Devices®) and incubated for 10 minutes prior to addition of the dyed probe. When a drug interacts with the receptor, the FRET signal measured by the variation of GFP fluorescence at 510 nm is disrupted. The time curves of ligand binding were recorded during 1000 seconds. (excitation Light Emitting Diode 470-495 nm, emission 510+/−10 nm). The percentage of inhibition allows the evaluation of the inhibitory activity of compounds in comparison to the antagonist $A_{2A}$ reference CGS15943. The dose-inhibition curves were fitted with variable slope, using GraphPad® Prism software, in order to determine 1050 and Ki values. The dose-inhibition experiments were all performed in duplicate, three times independently. Examples 1 to 140 have Ki values inferior to 1 µM. Results of representative examples are shown in the following table:

| Compound | Ki (nM) | Compound | Ki (nM) |
|---|---|---|---|
| Example 7 | 171 ± 104 | Example 97 | 3 ± 0.4 |
| Example 10 | 108 ± 74 | Example 101 | 3 ± 0 |
| Example 14 | 12 ± 6 | Example 107 | 34 ± 5 |
| Example 23 | 264 ± 141 | Example 111 | 291 ± 30 |
| Example 24 | 34 ± 9 | Example 113 | 4 ± 1 |
| Example 30 | 103 ± 52 | Example 125 | 147 ± 54 |
| Example 48 | 138 ± 115 | Example 129 | 256 ± 83 |
| Example 56 | 188 ± 63 | Example 132 | 72 ± 10 |
| Example 71 | 171 ± 70 | Example 134 | 348 ± 95 |
| Example 79 | 4 ± 1 | Example 136 | 84 ± 11 |
| Example 85 | 177 ± 5 | Example 139 | 459 ± 270 |

Example 142

$A_{2A}$-antagonist property evaluations of compounds of the invention using a $Ca^{++}$ functional assay.

Assay protocol: HEK cells stably expressing the human $A_{2A}$ receptor fused at its amino terminal domain to GFP, and cultured in Modified Eagle's Medium supplemented with 10% FCS, were transiently transfected by electroporation with plasmid DNA encoding the promiscuous G protein Gα15 in order to deviate the natural coupling of the receptor from AMPc production to calcium ($Ca^{2+}$) release pathway (Brabet et al., Neuropharmacology 37:1043-1051, 1998). Receptor activity was detected by changes in intracellular $Ca^{2+}$, measured using the fluorescent $Ca^{2+}$ sensitive dye, Fluo4AM (Molecular Probes®).

Cells were plated after transfection onto polyornithine coated, clear bottom, black-walled, 96-well plates and cultured for 24 hours. The day of the test, cells were washed with freshly prepared buffer B (HBSS 1×, Hepes 20 mM, $MgSO_4.7H_2O$ 1 mM, $Na_2CO_3$ 3.3 mM, $CaCl_2-2H_2O$ 1.3 mM, 0.5% BSA, Probenecid 2.5 mM) and loaded at 37° C. in 5% $CO_2$ for 1.5 hours with buffer B containing 1 μM Fluo4AM and 0.1 mg/mL Pluronic Acid. Afterwards cells were washed twice with buffer B and 50 μL of this buffer were added to each well. The tested compounds were incubated minutes before addition of CGS21680 (used as reference agonist) at a concentration leading to 80% of its maximal activity ($EC_{80}$). Afterwards, the intracellular $Ca^{2+}$ measurements were performed on a 60s kinetic by detection of the fluorescence intensity (excitation 485 nm, emission 525 nm) using the fluorescence microplate reader FlexStation® (Molecular Devices®). All data reflect three independent experiments. Dose-response curves were fitted by using the sigmoidal dose-response (variable slope) analyze in GraphPad Prism® program (San Diego) and $IC_{50}$ of antagonist compound was calculated. Dose-response experiments were all performed in triplicate, three times independently. The results of representative examples are shown in the table below:

| Compound | $IC_{50}$ (nM) | Compound | $IC_{50}$ (nM) |
|---|---|---|---|
| Example 10 | 891 ± 571 | Example 79 | 15 ± 4 |
| Example 14 | 195 ± 100 | Example 97 | 21 ± 8 |
| Example 23 | 403 ± 163 | Example 101 | 12 ± 4 |
| Example 30 | 992 ± 11 | Example 113 | 46 ± 3 |
| Example 48 | 945 ± 419 | Example 132 | 326 ± 47 |
| Example 71 | 1832 ± 122 | | |

Example 143

In-Vivo Evaluations on a Haldoperidol-Induced Catalepsy Model in the Mouse

This method, which detects anti-cataleptic activity, follows those well-known by one skilled in the art and described in the literature (e.g. Pires et al., Braz J Med and Biol Res 38, 1867-1872, 2005; Shiozaki et al., Psychopharmacology 147, 90-95, 1999). The procedure applied to the compounds of the invention is as follows:

Catalepsy is assessed using the bar test in mice submitted to acute administration of haloperidol (1 mg/kg, intra-peritoneal or i.p.).

Mice (male Rj: NMRI mice, weighing 25-30 g at the beginning of the experiment) are placed (5 in each group) in Plexiglas cages, were injected with haloperidol (1 mg/kg i.p.). Within minutes after haloperidol administration, mice were calm and showed slow spontaneous activity. The catalepsy response of one mouse was measured when the animal maintained an imposed posture with both forelimbs placed on a horizontal 0.9 cm diameter wire bar suspended 4 cm above a platform. The end point of catalepsy was considered to occur when both forelimbs were removed from the bar, the mouse climbed onto the bar or if the animal moved its head in an exploratory manner. A cut-off time of 180 seconds was applied. The degree of catalepsy was scored 60 minutes after haloperidol administration and continued at 30 minutes intervals for a total of 240 minutes. Between determinations, the animals were returned to their home cages.

The compound of Example 14 was evaluated at 4 doses, administered i.p. 120 minutes after haloperidol, and compared with a vehicle control group.

Data Analysis

The FIGS. 1 and 2 show the mean time of latency spent on the bar in each group of animals.

At each time-point, the anti-cataleptic effect of the compound of Example 14 was compared to vehicle-treated group using ANOVA test followed by the Dunnett's test.

Results

In FIG. 1, the compound of Example 14 (1, 3, 30 and 100 mg/kg) administered i.p. 120 minutes after Haloperidol injection clearly showed a significant anti-cataleptic effect in a dose-dependent manner from 1 mg/kg (no anticataleptic activity) to 30 mg/kg (the most important catalepsy reversion). In FIG. 2, the compound of Example 14 (10 and 30 mg/kg) administered per os 120 minutes after Haloperidol injection clearly showed a significant anti-cataleptic effect in a dose-dependent manner.

The invention claimed is:
1. A compound selected from the group consisting of:
(a) a compound of general formula (I) as follows:

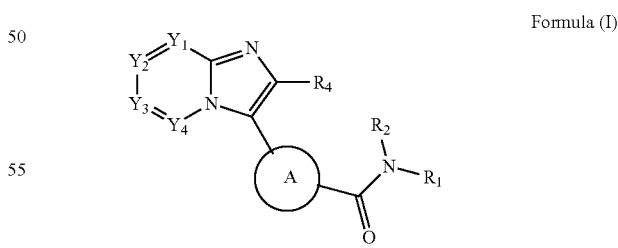

Formula (I)

wherein:
$R_1$ and $R_2$ are independently selected from alkyl, alkenyl, alkynyl, aryl, cycloalkyl, heteroaryl or heterocycloalkyl, or $R_1$ and $R_2$, together with the nitrogen atom they are attached to, form a heterocycloalkyl ring or a heteroaryl ring;
$Y_1$, $Y_2$, $Y_3$ and $Y_4$ are independently selected from CH, $CR_3$, or N;

R₃ is selected from lower alkyl, cycloalkyl, O-(lower alkyl), S-(lower alkyl), NH₂, NH-(lower alkyl), N-(lower alkyl)(lower alkyl), halogen, CF₃ or CN;

R₄ is selected from hydrogen, lower alkyl, cycloalkyl, O-(lower alkyl), S-(lower alkyl), NH₂, NH-(lower alkyl), N-(lower alkyl)(lower alkyl), halogen, CF₃ or CN;

A represents a heterocyclic group selected from:

A1
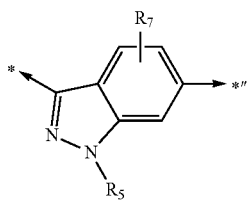

A2
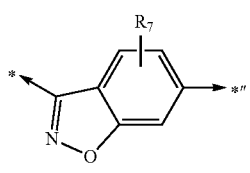

A3
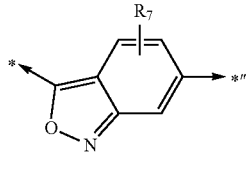

A4
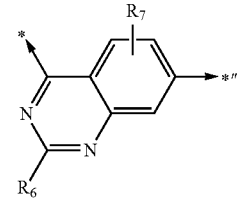

A5
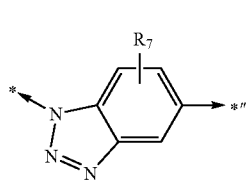

A6
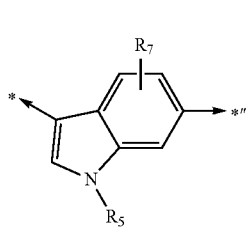

A7
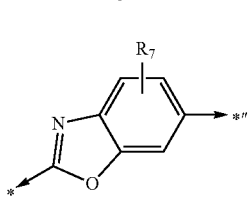

A8
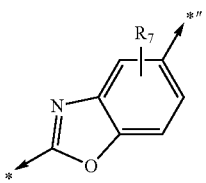

A9
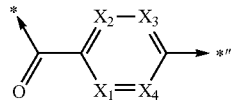

A10
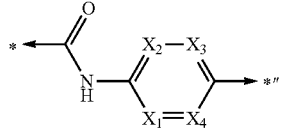

with

* being the position linked to the heterocyclic moiety comprising Y₁, Y₂, Y₃ and Y₄ in Formula (I) and *″ being the position linked to the carbonyl group in Formula (I);

R₅ being selected from hydrogen, alkyl, cycloalkyl, aryl, heteroaryl, (CH₂)₂—O—(CH₂)₂—O—CH₃, CO-alkyl, CO-aryl, CO-heterocycloalkyl, CO-cycloalkyl, CO-heteroaryl, SO₂-alkyl, SO₂-aryl, SO₂-heterocycloalkyl, SO₂-cycloalkyl or SO₂-heteroaryl;

R₆ being selected from hydrogen, lower alkyl, halogen, OH, O-(lower alkyl), NH₂, NH-(lower alkyl), N(lower alkyl)(lower alkyl) or heterocycloalkyl;

X₁, X₂, X₃ and X₄ each representing CH, CR₇ or N; and

R₇ being selected from hydrogen, lower alkyl, O-(lower alkyl), NH-(lower alkyl), N-(lower alkyl) (lower alkyl), halogen, NO₂, NH₂, NH—OH, OH, or CN;

or a pharmaceutically acceptable salt thereof; and (b) a compound of general formula (I) as follows:

Formula (I)
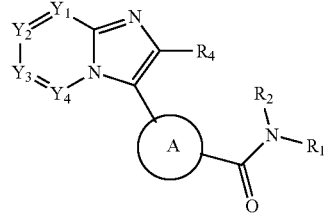

wherein:

R₁ and R₂ are independently selected from alkyl, alkenyl, alkynyl, aryl, or cycloalkyl, or R₁ and R₂, together with the nitrogen atom they are attached to, form a heterocycloalkyl ring or a heteroaryl ring;

Y₁, Y₂, Y₃ and Y₄ are independently selected from CH, CR₃, or N;

R₃ is selected from lower alkyl, cycloalkyl, O-(lower alkyl), S-(lower alkyl), NH₂, NH-(lower alkyl), N-(lower alkyl)(lower alkyl), halogen, CF₃ or CN;

R₄ is selected from hydrogen, lower alkyl, cycloalkyl, O-(lower alkyl), S-(lower alkyl), NH₂, NH-(lower alkyl), N-(lower alkyl)(lower alkyl), halogen, CF₃ or CN;

A represents a heterocyclic group A11:

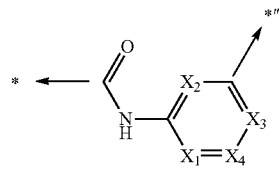

with
* being the position linked to the heterocyclic moiety comprising $Y_1$, $Y_2$, $Y_3$ and $Y_4$ in Formula (I) and *'" being the position linked to the carbonyl group in Formula (I);
$R_5$ being selected from hydrogen, alkyl, cycloalkyl, aryl, heteroaryl, $(CH_2)_2$—O—$(CH_2)_2$—O—$CH_3$, CO-alkyl, CO-aryl, CO-heterocycloalkyl, CO-cycloalkyl, CO-heteroaryl, $SO_2$-alkyl, $SO_2$-aryl, $SO_2$-heterocycloalkyl, $SO_2$-cycloalkyl or $SO_2$-heteroaryl;
$R_6$ being selected from hydrogen, lower alkyl, halogen, OH, O-(lower alkyl), $NH_2$, NH-(lower alkyl), N(lower alkyl)(lower alkyl) or heterocycloalkyl;
$X_1$, $X_2$, $X_3$ and $X_4$ each representing CH, $CR_7$ or N; and
$R_7$ being selected from hydrogen, lower alkyl, O-(lower alkyl), NH-(lower alkyl), N-(lower alkyl) (lower alkyl), halogen, $NO_2$, $NH_2$, NH—OH, OH, or CN;
or a pharmaceutically acceptable salt thereof.

2. The compound according to claim 1 or a pharmaceutically acceptable salt thereof wherein A represents a heterocyclic group selected from A1 to A8.

3. The compound according to claim 1 or a pharmaceutically acceptable salt thereof wherein A represents a heterocyclic group selected from A1 to A4.

4. The compound according to claim 1 or a pharmaceutically acceptable salt thereof wherein A represents a heterocyclic group selected from A1 or A2.

5. The compound according to claim 1 or a pharmaceutically acceptable salt thereof wherein A represents a heterocyclic group being A2.

6. The compound according to claim 1 or a pharmaceutically acceptable salt thereof, wherein not more than one of $Y_1$, $Y_2$, $Y_3$, and $Y_4$ is N and the others are independently selected from CH or $CR_3$.

7. The compound according to claim 1 or a pharmaceutically acceptable salt thereof, wherein $R_1$ and $R_2$ are independently selected from $C_{1-10}$-alkyl, $C_{6-10}$-aryl, or $C_{3-10}$-cycloalkyl, or $R_1$ and $R_2$, together with the nitrogen atom they are attached to, form a heterocycloalkyl ring having 5 to 10 ring atoms of which one, two or three are heteroatoms.

8. The compound according to claim 1 or a pharmaceutically acceptable salt thereof, wherein $R_4$ is selected from hydrogen or lower alkyl.

9. The compound of claim 1 or a pharmaceutically acceptable salt thereof, wherein $R_3$ is selected from fluorine or CN.

10. The compound according to claim 1, wherein the compound is selected from the group consisting of:
4-(8-Bromo-imidazo[1,2-a]pyridine-3-carbonyl)-N-cyclohexyl-N-ethyl-benzamide;
N-Cyclohexyl-N-ethyl-4-(7-methyl-imidazo[1,2-a]pyridine-3-carbonyl)-benzamide;
N-Cyclohexyl-N-ethyl-4-(7-ethyl-imidazo[1,2-a]pyridine-3-carbonyl)-benzamide;
4-(7-Cyano-imidazo[1,2-a]pyridine-3-carbonyl)-N-cyclohexyl-N-ethyl-benzamide;
4-(7-Chloro-imidazo[1,2-a]pyridine-3-carbonyl)-N-cyclohexyl-N-ethyl-benzamide;
4-(7-Fluoro-imidazo[1,2-a]pyridine-3-carbonyl)-N-cyclohexyl-N-ethyl-benzamide;
4-(6-Cyano-imidazo[1,2-a]pyridine-3-carbonyl)-N-cyclohexyl-N-ethyl-benzamide;
4-(6-Fluoro-imidazo[1,2-a]pyridine-3-carbonyl)-N-cyclohexyl-N-ethyl-benzamide;
4-(6-Chloro-imidazo[1,2-a]pyridine-3-carbonyl)-N-cyclohexyl-N-ethyl-benzamide;
4-(6-Bromo-imidazo[1,2-a]pyridine-3-carbonyl)-N-cyclohexyl-N-ethyl-benzamide;
N-Cyclohexyl-N-ethyl-4-(6-methyl-imidazo[1,2-a]pyridine-3-carbonyl)-benzamide;
N-Cyclohexyl-N-ethyl-4-(6-methoxy-imidazo[1,2-a]pyridine-3-carbonyl)-benzamide;
N-Cyclohexyl-N-ethyl-4-(2-methyl-imidazo[1,2-a]pyridine-3-carbonyl)-benzamide;
[4-(Azepane-1-carbonyl)-phenyl]-(6-fluoro-imidazo[1,2-a]pyridin-3-yl)-methanone;
3-[4-(Azepane-1-carbonyl)-benzoyl]-imidazo[1,2-a]pyridine-6-carbonitrile;
N-Cyclohexyl-N-ethyl-4-(imidazo[1,2-a]pyridine-3-carbonyl)-3-methyl-benzamide;
N-Cyclohexyl-N-ethyl-4-(6-fluoro-imidazo[1,2-a]pyridine-3-carbonyl)-3-methyl-benzamide;
N-Cyclohexyl-N-ethyl-4-(imidazo[1,2-a]pyridine-3-carbonyl)-3-methoxy-benzamide;
N-Cyclohexyl-N-ethyl-4-(imidazo[1,2-a]pyridine-3-carbonyl)-3-chloro-benzamide;
3-Chloro-N-cyclohexyl-N-ethyl-4-(6-fluoro-imidazo[1,2-a]pyridine-3-carbonyl)-benzamide;
N-Cyclohexyl-N-ethyl-3-fluoro-4-(6-fluoro-imidazo[1,2-a]pyridine-3-carbonyl)-benzamide;
N-Cyclohexyl-N-ethyl-4-(6-fluoro-imidazo[1,2-a]pyridine-3-carbonyl)-3-nitro-benzamide;
N-Cyclohexyl-N-ethyl-6-(imidazo[1,2-a]pyridine-3-carbonyl)-nicotinamide;
2-Chloro-N-cyclohexyl-N-ethyl-4-(6-fluoro-imidazo[1,2-a]pyridine-3-carbonyl)-benzamide;
[4-(Azepane-1-carbonyl)-phenyl]-(6-trifluoromethyl-imidazo[1,2-a]pyridin-3-yl)-methanone;
[4-(Azepane-1-carbonyl)-phenyl]-(6,8-dichloro-imidazo[1,2-a]pyridin-3-yl)-methanone;
[4-(Azepane-1-carbonyl)-2-fluoro-phenyl]-(6-fluoro-imidazo[1,2-a]pyridin-3-yl)-methanone;
[4-(Azepane-1-carbonyl)-2-nitro-phenyl]-(6-fluoro-imidazo[1,2-a]pyridin-3-yl)-methanone;
[4-(Azepane-1-carbonyl)-2-hydroxyamino-phenyl]-(6-fluoro-imidazo[1,2-a]pyridin-3-yl)-methanone;
[2-Amino-4-(azepane-1-carbonyl)-phenyl]-(6-fluoro-imidazo[1,2-a]pyridin-3-yl)-methanone;
3-Amino-N-cyclohexyl-N-ethyl-4-(6-fluoro-imidazo[1,2-a]pyridine-3-carbonyl)-benzamide;
[4-(azepan-1-ylcarbonyl)-2-fluorophenyl](6-chloroimidazo[1,2-a]pyridin-3-yl)methanone;
[4-(azepan-1-ylcarbonyl)-2-fluorophenyl](6-bromoimidazo[1,2-a]pyridin-3-yl)methanone;
[4-(azepan-1-ylcarbonyl)-2-fluorophenyl](6-methylimidazo[1,2-a]pyridin-3-yl)methanone;
[4-(azepan-1-ylcarbonyl)-2-fluorophenyl][6-(trifluoromethyl)imidazo[1,2-a]pyridin-3-yl]methanone;
[4-(azepan-1-ylcarbonyl)-2-fluorophenyl](6-ethylimidazo[1,2-a]pyridin-3-yl)methanone;
[4-(azepan-1-ylcarbonyl)-2-fluorophenyl](6-cyclopropylimidazo[1,2-a]pyridin-3-yl)methanone;

[4-(azepan-1-ylcarbonyl)-2-fluorophenyl](imidazo[1,2-a]pyridin-3-yl)methanone;
N-Cyclohexyl-4-(imidazo[1,2-a]pyridine-3-carbonyl)-N-methyl-benzamide;
N-Cyclohexyl-4-(imidazo[1,2-a]pyridine-3-carbonyl)-N-propyl-benzamide;
N-Cyclohexyl-4-(imidazo[1,2-a]pyridine-3-carbonyl)-N-isopropyl-benzamide;
N-Cyclohexyl-4-(imidazo[1,2-a]pyridine-3-carbonyl)-N-prop-2-ynyl-benzamide;
N-Cyclohexyl-N-cyclopropylmethyl-4-(imidazo[1,2-a]pyridine-3-carbonyl)-benzamide;
N-Allyl-N-cyclohexyl-4-(imidazo[1,2-a]pyridine-3-carbonyl)-benzamide;
N-Cyclohexyl-4-(imidazo[1,2-a]pyridine-3-carbonyl)-N-(2,2,2-trifluoro-ethyl)-benzamide;
N-Cyclohexyl-N-(2-dimethylamino-ethyl)-4-(imidazo[1,2-a]pyridine-3-carbonyl)-benzamide;
N-Butyl-N-cyclohexyl-4-(imidazo[1,2-a]pyridine-3-carbonyl)-benzamide;
N,N-Dicyclohexyl-4-(imidazo[1,2-a]pyridine-3-carbonyl)-benzamide;
4-(Imidazo[1,2-a]pyridine-3-carbonyl)-N-methyl-N-phenyl-benzamide;
4-(6-Fluoro-imidazo[1,2-a]pyridine-3-carbonyl)-N-methyl-N-phenyl-benzamide;
4-(6-Fluoro-imidazo[1,2-a]pyridine-3-carbonyl)-N-(4-methoxy-phenyl)-N-methyl-benzamide;
4-(6-Fluoro-imidazo[1,2-a]pyridine-3-carbonyl)-N-methyl-N-p-tolyl-benzamide;
N-(4-Chloro-phenyl)-4-(6-fluoro-imidazo[1,2-a]pyridine-3-carbonyl)-N-methyl-benzamide;
4-(6-Fluoro-imidazo[1,2-a]pyridine-3-carbonyl)-N-methyl-N-pyridin-2-yl-benzamide;
4-(6-Fluoro-imidazo[1,2-a]pyridine-3-carbonyl)-N-methyl-N-pyridin-4-yl-benzamide;
N-Ethyl-4-(imidazo[1,2-a]pyridine-3-carbonyl)-N-phenyl-benzamide;
N-Ethyl-4-(imidazo[1,2-a]pyridine-3-carbonyl)-N-pyridin-3-yl-benzamide;
N,N-Diethyl-4-(imidazo[1,2-a]pyridine-3-carbonyl)-benzamide;
N-Ethyl-4-(imidazo[1,2-a]pyridine-3-carbonyl)-N-isopropyl-benzamide;
4-(Imidazo[1,2-a]pyridine-3-carbonyl)-N,N-dimethyl-benzamide;
4-(Imidazo[1,2-a]pyridine-3-carbonyl)-N,N-dipropyl-benzamide;
Imidazo[1,2-a]pyridin-3-yl-[4-(pyrrolidine-1-carbonyl)-phenyl]-methanone;
Imidazo[1,2-a]pyridin-3-yl-[4-(piperidine-1-carbonyl)-phenyl]-methanone;
[4-(Azepane-1-carbonyl)-phenyl]-imidazo[1,2-a]pyridin-3-yl-methanone;
[4-(Azocane-1-carbonyl)-phenyl]-imidazo[1,2-a]pyridin-3-yl-methanone;
[4-(Azonane-1-carbonyl)-phenyl]-imidazo[1,2-a]pyridin-3-yl-methanone;
Imidazo[1,2-a]pyridin-3-yl-[4-(morpholine-4-carbonyl)-phenyl]-methanone;
Imidazo[1,2-a]pyridin-3-yl-[4-(4-methyl-piperazine-1-carbonyl)-phenyl]-methanone;
[4-(2,3-Dihydro-indole-1-carbonyl)-phenyl]-imidazo[1,2-a]pyridin-3-yl-methanone;
Imidazo[1,2-a]pyridin-3-yl-[4-(2-methyl-2,3-dihydro-indole-1-carbonyl)-phenyl]-methanone;
[4-(3,4-Dihydro-2H-quinoline-1-carbonyl)-phenyl]-imidazo[1,2-a]pyridin-3-yl-methanone;
Imidazo[1,2-a]pyridin-3-yl-[4-(octahydro-quinoline-1-carbonyl)-phenyl]-methanone;
3-[4-(Azepan-1-ylcarbonyl)-2-fluorobenzoyl]imidazo[1,2-a]pyridine-6-carbonitrile;
4-[(6-Fluoroimidazo[1,2-a]pyridin-3-yl)carbonyl]-N,N-diisopropylbenzamide;
N-Ethyl-3-fluoro-4-[(6-fluoroimidazo[1,2-a]pyridin-3-yl)carbonyl]-N-isopropylbenzamide;
(6-Fluoroimidazo[1,2-a]pyridin-3-yl)[2-fluoro-4-(piperidin-1-ylcarbonyl)phenyl]methanone;
(6-Bromoimidazo[1,2-a]pyridin-3-yl)[2-fluoro-4-(piperidin-1-ylcarbonyl)phenyl]methanone;
Azepan-1-yl-[3-(6-fluoro-imidazo[1,2-a]pyridin-3-yl)-1H-indazol-6-yl]-methanone;
Azepan-1-yl-[3-(6-fluoro-imidazo[1,2-a]pyridin-3-yl)-1-methyl-1H-indazol-6-yl]-methanone;
Azepan-1-yl-[3-(6-fluoro-imidazo[1,2-a]pyridin-3-yl)-1-(2-hydroxy-ethyl)-1H-indazol-6-yl]-methanone;
[6-(Azepan-1-ylcarbonyl)]-1-ethyl-3[6-fluoro-imidazo[1,2-a]pyridin-3-yl]-1H-indazole;
[6-(Azepan-1-ylcarbonyl)]-1-isopropyl-3[6-fluoro-imidazo[1,2-a]pyridin-3-yl]-1H-indazole;
[6-(Azepan-1-ylcarbonyl)]-1-isobutyl-3[6-fluoro-imidazo[1,2-a]pyridin-3-yl]-1H-indazole;
3-[6-(Azepan-1-ylcarbonyl)-1-methyl-1H-indazol-3-yl]imidazo[1,2-a]pyridine-6-carbonitrile;
[6-(Azepan-1-ylcarbonyl)]-1-methyl-3[6-(trifluoromethyl)-imidazo[1,2-a]pyridin-3-yl]-1H-indazole;
[6-(Azepan-1-ylcarbonyl)]-1-methyl-3[6-chloro-imidazo[1,2-a]pyridin-3-yl]-1H-indazole;
[6-(Azepan-1-ylcarbonyl)]-1-methyl-3[6-methyl-imidazo[1,2-a]pyridin-3-yl]-1H-indazole;
[6-(Azepan-1-ylcarbonyl)]-1-methyl-3[6-ethyl-imidazo[1,2-a]pyridin-3-yl]-1H-indazole;
[6-(Azepan-1-ylcarbonyl)]-1-methyl-3[6-cyclopropyl-imidazo[1,2-a]pyridin-3-yl]-1H-indazole;
[6-(Azepan-1-ylcarbonyl)]-1-methyl-3[6-imidazo[1,2-a]pyridin-3-yl]-1H-indazole;
[6-(Azepan-1-ylcarbonyl)]-1-methyl-3[6-bromo-imidazo[1,2-a]pyridin-3-yl]-1H-indazole;
3-(6-Fluoroimidazo[1,2-a]pyridin-3-yl)-N,1-dimethyl-N-phenyl-1H-indazole-6-carboxamide;
N-Ethyl-3-(6-fluoroimidazo[1,2-a]pyridin-3-yl)-N-isopropyl-1-methyl-1H-indazole-6-carboxamide;
[3-(6-Fluoroimidazo[1,2-a]pyridin-3-yl)-1-methyl-1H-indazol-6-yl]-(decahydroquinolin-1-yl)-methanone;
3-(6-Fluoroimidazo[1,2-a]pyridin-3-yl)-1-methyl-1H-indazol-6-carboxylic acid cyclohexyl-cyclopropyl-methyl-amide;
Azonan-1-yl-[3-(6-fluoro-imidazo[1,2-a]pyridin-3-yl)-1-methyl-1H-indazol-6-yl]-methanone;
Azocan-1-yl-[3-(6-fluoro-imidazo[1,2-a]pyridin-3-yl)-1-methyl-1H-indazol-6-yl]-methanone;
3-(6-Fluoroimidazo[1,2-a]pyridin-3-yl)-1-methyl-6-(piperidin-1-ylcarbonyl)-1H-indazole;
3-[1-Methyl-6-(piperidin-1-ylcarbonyl)-1H-indazol-3-yl]imidazo[1,2-a]pyridine-6-carbonitrile;
3-[1-Methyl-6-(pyrrolidin-1-ylcarbonyl)-1H-indazol-3-yl]imidazo[1,2-a]pyridine-6-carbonitrile;
3-(1-Methyl-6-{[(2R)-2-(methoxymethyl) pyrrolidin-1-yl]carbonyl}-1H-indazol-3-yl)imidazo[1,2-a]pyridine-6-carbonitrile;
3-(1-Methyl-6-{[(2S)-2-(methoxymethyl) pyrrolidin-1-yl]carbonyl}-1H-indazol-3-yl)imidazo[1,2-a]pyridine-6-carbonitrile;

3-[6-(8-Aza-bicyclo[3.2.1]octane-8-carbonyl)-1-methyl-1H-indazol-3-yl]-imidazo[1,2-a]pyridine-6-carbonitrile;

3-{1-Methyl-6-[(4-methylpiperazin-1-yl)carbonyl]}-1H-indazol-3-yl]imidazo[1,2-a]pyridine-6-carbonitrile;

3-(6-Cyano-imidazo[1,2-a]pyridin-3-yl)-1-methyl-1H-indazole-6-carboxylic acid diisopropylamide;

2-Methyl-3-[1-Methyl-6-(azepan-1-ylcarbonyl)-1H-indazol-3-yl]-imidazo[1,2-a]pyridine-6-carbonitrile;

Azepan-1-yl-[1-benzyl-3-(6-fluoro-imidazo[1,2-a]pyridin-3-yl)-1H-indazol-6-yl]-methanone;

Azepan-1-yl-[3-(6-fluoro-imidazo[1,2-a]pyridin-3-yl)-1-phenethyl-1H-indazol-6-yl]-methanone;

Azepan-1-yl-[3-(6-fluoro-imidazo[1,2-a]pyridin-3-yl)-1-[2-(2-methoxyethoxy)ethyl]-1H-indazol-6-yl]-methanone;

Azepan-1-yl-[3-(6-fluoro-imidazo[1,2-a]pyridin-3-yl)-1-(2-morpholin-4-yl-ethyl)-1H-indazol-6-yl]-methanone;

Azepan-1-yl-[3-(6-fluoro-imidazo[1,2-a]pyridin-3-yl)-1-[(4-methylpiperazin-1-yl)carbonyl]-1H-indazol-6-yl]-methanone;

3-(6-Fluoro-imidazo[1,2-a]pyridin-3-yl)-benzo[d]isoxazole-6-carboxylic acid cyclohexyl-ethyl-amide;

Azepan-1-yl-[3-(6-fluoro-imidazo[1,2-a]pyridin-3-yl)-benzo[d]isoxazol-6-yl]-methanone;

[4-(Azepan-1-ylcarbonyl)-2-hydroxyphenyl](6-fluoroimidazo[1,2-a]pyridin-3-yl)methanone;

N-Ethyl-3-(6-fluoroimidazo[1,2-a]pyridin-3-yl)-N-isopropyl-1,2-benzisoxazole-6-carboxamide;

3-(6-Fluoroimidazo[1,2-a]pyridin-3-yl)-6-(piperidin-1-ylcarbonyl)-1,2-benzisoxazole;

3-(6-Bromoimidazo[1,2-a]pyridin-3-yl)-6-(piperidin-1-ylcarbonyl)-1,2-benzisoxazole;

6-(Azepan-1-ylcarbonyl)-3-(6-bromoimidazo[1,2-a]pyridin-3-yl)-1,2-benzisoxazole;

(6-Bromoimidazo[1,2-a]pyridin-3-yl)[2-fluoro-4-(morpholin-4-ylcarbonyl)phenyl]methanone;

3-(6-Bromoimidazo[1,2-a]pyridin-3-yl)-6-(morpholin-4-ylcarbonyl)-1,2-benzisoxazole;

[4-(8-Azabicyclo[3.2.1]oct-8-ylcarbonyl)-2-fluorophenyl](6-bromoimidazo[1,2-a]pyridin-3-yl)methanone;

6-(8-Azabicyclo[3.2.1]oct-8-ylcarbonyl)-3-(6-bromoimidazo[1,2-a]pyridin-3-yl)-1,2-benzisoxazole;

3-[6-(Piperidin-1-ylcarbonyl)-1,2-benzisoxazol-3-yl]imidazo[1,2-a]pyridine-6-carbonitrile;

3-[6-(Azepan-1-ylcarbonyl)-1,2-benzisoxazol-3-yl]imidazo[1,2-a]pyridine-6-carbonitrile;

3-[6-(Morpholin-4-ylcarbonyl)-1,2-benzisoxazol-3-yl]imidazo[1,2-a]pyridine-6-carbonitrile;

3-[6-(8-Azabicyclo[3.2.1]oct-8-ylcarbonyl)-1,2-benzisoxazol-3-yl]imidazo[1,2-a]pyridine-6-carbonitrile;

Imidazo[1,2-a]pyridine-3-carboxylic acid [4-(cyclohexyl-ethyl-carbamoyl)-2-hydroxy-phenyl]-amide;

Imidazo[1,2-a]pyridine-3-carboxylic acid [5-(cyclohexyl-ethyl-carbamoyl)-2-hydroxy-phenyl]-amide;

2-Imidazo[1,2-a]pyridin-3-yl-benzooxazole-6-carboxylic acid cyclohexyl-ethyl-amide;

2-Imidazo[1,2-a]pyridin-3-yl-benzooxazole-5-carboxylic acid cyclohexyl-ethyl-amide;

Azepan-1-yl-[3-(6-fluoro-imidazo[1,2-a]pyridin-3-yl)-benzo[c]isoxazol-6-yl]-methanone;

5-(Azepan-1-ylcarbonyl)-1-(6-fluoroimidazo[1,2-a]pyridin-3-yl)-1H-1,2,3-benzotriazole;

Azepan-1-yl-[1-benzenesulfonyl-3-(6-fluoro-imidazo[1,2-a]pyridin-3-yl)-1H-indol-6-yl]-methanone;

3-[6-(Azepan-1-ylcarbonyl)-1H-indol-3-yl]-6-fluoroimidazo[1,2-a]pyridine;

Azepan-1-yl-[4-(6-fluoro-imidazo[1,2-a]pyridin-3-yl)-quinazolin-7-yl]-methanone;

2-Amino-7-(azepan-1-ylcarbonyl)-4-(6-fluoroimidazo[1,2-a]pyridin-3-yl)quinazoline;

2-Methyl-7-(azepan-1-ylcarbonyl)-4-(6-fluoroimidazo[1,2-a]pyridin-3-yl)quinazoline;

N-Cyclohexyl-N-ethyl-4-(imidazo[1,2-a]pyrimidin-3-ylcarbonyl)-benzamide;

N-Cyclohexyl-N-ethyl-4-(6-chloroimidazo[1,2-b]pyridazin-3-ylcarbonyl)-benzamide;

N-Cyclohexyl-N-ethyl-4-(imidazo[1,2-b]pyridazin-3-ylcarbonyl)-benzamide; and a pharmaceutically acceptable salt thereof.

11. A pharmaceutical composition comprising a compound according to claim 1 or a pharmaceutically acceptable salt thereof, in combination with a pharmaceutically acceptable excipient and/or carrier.

12. A medicament comprising the compound of formula (I) according to claim 1 or a pharmaceutically acceptable salt thereof.

13. The pharmaceutical composition according to claim 11, wherein the compound is selected from the group consisting of:

4-(8-Bromo-imidazo[1,2-a]pyridine-3-carbonyl)-N-cyclohexyl-N-ethyl-benzamide;

N-Cyclohexyl-N-ethyl-4-(7-methyl-imidazo[1,2-a]pyridine-3-carbonyl)-benzamide;

N-Cyclohexyl-N-ethyl-4-(7-ethyl-imidazo[1,2-a]pyridine-3-carbonyl)-benzamide;

4-(7-Cyano-imidazo[1,2-a]pyridine-3-carbonyl)-N-cyclohexyl-N-ethyl-benzamide;

4-(7-Chloro-imidazo[1,2-a]pyridine-3-carbonyl)-N-cyclohexyl-N-ethyl-benzamide;

4-(7-Fluoro-imidazo[1,2-a]pyridine-3-carbonyl)-N-cyclohexyl-N-ethyl-benzamide;

4-(6-Cyano-imidazo[1,2-a]pyridine-3-carbonyl)-N-cyclohexyl-N-ethyl-benzamide;

4-(6-Fluoro-imidazo[1,2-a]pyridine-3-carbonyl)-N-cyclohexyl-N-ethyl-benzamide;

4-(6-Chloro-imidazo[1,2-a]pyridine-3-carbonyl)-N-cyclohexyl-N-ethyl-benzamide;

4-(6-Bromo-imidazo[1,2-a]pyridine-3-carbonyl)-N-cyclohexyl-N-ethyl-benzamide;

N-Cyclohexyl-N-ethyl-4-(6-methyl-imidazo[1,2-a]pyridine-3-carbonyl)-benzamide;

N-Cyclohexyl-N-ethyl-4-(6-methoxy-imidazo[1,2-a]pyridine-3-carbonyl)-benzamide;

N-Cyclohexyl-N-ethyl-4-(2-methyl-imidazo[1,2-a]pyridine-3-carbonyl)-benzamide;

[4-(Azepane-1-carbonyl)-phenyl]-(6-fluoro-imidazo[1,2-a]pyridin-3-yl)-methanone;

3-[4-(Azepane-1-carbonyl)-benzoyl]-imidazo[1,2-a]pyridine-6-carbonitrile;

N-Cyclohexyl-N-ethyl-4-(imidazo[1,2-a]pyridine-3-carbonyl)-3-methyl-benzamide;

N-Cyclohexyl-N-ethyl-4-(6-fluoro-imidazo[1,2-a]pyridine-3-carbonyl)-3-methyl-benzamide;

N-Cyclohexyl-N-ethyl-4-(imidazo[1,2-a]pyridine-3-carbonyl)-3-methoxy-benzamide;

N-Cyclohexyl-N-ethyl-4-(imidazo[1,2-a]pyridine-3-carbonyl)-3-chloro-benzamide;

3-Chloro-N-cyclohexyl-N-ethyl-4-(6-fluoro-imidazo[1,2-a]pyridine-3-carbonyl)-benzamide;

N-Cyclohexyl-N-ethyl-3-fluoro-4-(6-fluoro-imidazo[1,2-a]pyridine-3-carbonyl)-benzamide;

N-Cyclohexyl-N-ethyl-4-(6-fluoro-imidazo[1,2-a]pyridine-3-carbonyl)-3-nitro-benzamide;
N-Cyclohexyl-N-ethyl-6-(imidazo[1,2-a]pyridine-3-carbonyl)-nicotinamide;
2-Chloro-N-cyclohexyl-N-ethyl-4-(6-fluoro-imidazo[1,2-a]pyridine-3-carbonyl)-benzamide;
[4-(Azepane-1-carbonyl)-phenyl]-(6-trifluoromethyl-imidazo[1,2-a]pyridin-3-yl)-methanone;
[4-(Azepane-1-carbonyl)-phenyl]-(6,8-dichloro-imidazo[1,2-a]pyridin-3-yl)-methanone;
[4-(Azepane-1-carbonyl)-2-fluoro-phenyl]-(6-fluoro-imidazo[1,2-a]pyridin-3-yl)-methanone;
[4-(Azepane-1-carbonyl)-2-nitro-phenyl]-(6-fluoro-imidazo[1,2-a]pyridin-3-yl)-methanone;
[4-(Azepane-1-carbonyl)-2-hydroxyamino-phenyl]-(6-fluoro-imidazo[1,2-a]pyridin-3-yl)-methanone;
[2-Amino-4-(azepane-1-carbonyl)-phenyl]-(6-fluoro-imidazo[1,2-a]pyridin-3-yl)-methanone;
3-Amino-N-cyclohexyl-N-ethyl-4-(6-fluoro-imidazo[1,2-a]pyridine-3-carbonyl)-benzamide;
[4-(azepan-1-ylcarbonyl)-2-fluorophenyl](6-chloroimidazo[1,2-a]pyridin-3-yl)methanone;
[4-(azepan-1-ylcarbonyl)-2-fluorophenyl](6-bromoimidazo[1,2-a]pyridin-3-yl)methanone;
[4-(azepan-1-ylcarbonyl)-2-fluorophenyl](6-methylimidazo[1,2-a]pyridin-3-yl)methanone;
[4-(azepan-1-ylcarbonyl)-2-fluorophenyl][6-(trifluoromethyl)imidazo[1,2-a]pyridin-3-yl]methanone;
[4-(azepan-1-ylcarbonyl)-2-fluorophenyl](6-ethylimidazo[1,2-a]pyridin-3-yl)methanone;
[4-(azepan-1-ylcarbonyl)-2-fluorophenyl](6-cyclopropylimidazo[1,2-a]pyridin-3-yl)methanone;
[4-(azepan-1-ylcarbonyl)-2-fluorophenyl](imidazo[1,2-a]pyridin-3-yl)methanone;
N-Cyclohexyl-4-(imidazo[1,2-a]pyridine-3-carbonyl)-N-methyl-benzamide;
N-Cyclohexyl-4-(imidazo[1,2-a]pyridine-3-carbonyl)-N-propyl-benzamide;
N-Cyclohexyl-4-(imidazo[1,2-a]pyridine-3-carbonyl)-N-isopropyl-benzamide;
N-Cyclohexyl-4-(imidazo[1,2-a]pyridine-3-carbonyl)-N-prop-2-ynyl-benzamide;
N-Cyclohexyl-N-cyclopropylmethyl-4-(imidazo[1,2-a]pyridine-3-carbonyl)-benzamide;
N-Allyl-N-cyclohexyl-4-(imidazo[1,2-a]pyridine-3-carbonyl)-benzamide;
N-Cyclohexyl-4-(imidazo[1,2-a]pyridine-3-carbonyl)-N-(2,2,2-trifluoro-ethyl)-benzamide;
N-Cyclohexyl-N-(2-dimethylamino-ethyl)-4-(imidazo[1,2-a]pyridine-3-carbonyl)-benzamide;
N-Butyl-N-cyclohexyl-4-(imidazo[1,2-a]pyridine-3-carbonyl)-benzamide;
N,N-Dicyclohexyl-4-(imidazo[1,2-a]pyridine-3-carbonyl)-benzamide;
4-(Imidazo[1,2-a]pyridine-3-carbonyl)-N-methyl-N-phenyl-benzamide;
4-(6-Fluoro-imidazo[1,2-a]pyridine-3-carbonyl)-N-methyl-N-phenyl-benzamide;
4-(6-Fluoro-imidazo[1,2-a]pyridine-3-carbonyl)-N-(4-methoxy-phenyl)-N-methyl-benzamide;
4-(6-Fluoro-imidazo[1,2-a]pyridine-3-carbonyl)-N-methyl-N-p-tolyl-benzamide;
N-(4-Chloro-phenyl)-4-(6-fluoro-imidazo[1,2-a]pyridine-3-carbonyl)-N-methyl-benzamide;
4-(6-Fluoro-imidazo[1,2-a]pyridine-3-carbonyl)-N-methyl-N-pyridin-2-yl-benzamide;
4-(6-Fluoro-imidazo[1,2-a]pyridine-3-carbonyl)-N-methyl-N-pyridin-4-yl-benzamide;
N-Ethyl-4-(imidazo[1,2-a]pyridine-3-carbonyl)-N-phenyl-benzamide;
N-Ethyl-4-(imidazo[1,2-a]pyridine-3-carbonyl)-N-pyridin-3-yl-benzamide;
N,N-Diethyl-4-(imidazo[1,2-a]pyridine-3-carbonyl)-benzamide;
N-Ethyl-4-(imidazo[1,2-a]pyridine-3-carbonyl)-N-isopropyl-benzamide;
4-(Imidazo[1,2-a]pyridine-3-carbonyl)-N,N-dimethyl-benzamide;
4-(Imidazo[1,2-a]pyridine-3-carbonyl)-N,N-dipropyl-benzamide;
Imidazo[1,2-a]pyridin-3-yl-[4-(pyrrolidine-1-carbonyl)-phenyl]-methanone;
Imidazo[1,2-a]pyridin-3-yl-[4-(piperidine-1-carbonyl)-phenyl]-methanone;
[4-(Azepane-1-carbonyl)-phenyl]-imidazo[1,2-a]pyridin-3-yl-methanone;
[4-(Azocane-1-carbonyl)-phenyl]-imidazo[1,2-a]pyridin-3-yl-methanone;
[4-(Azonane-1-carbonyl)-phenyl]-imidazo[1,2-a]pyridin-3-yl-methanone;
Imidazo[1,2-a]pyridin-3-yl-[4-(morpholine-4-carbonyl)-phenyl]-methanone;
Imidazo[1,2-a]pyridin-3-yl-[4-(4-methyl-piperazine-1-carbonyl)-phenyl]-methanone;
[4-(2,3-Dihydro-indole-1-carbonyl)-phenyl]-imidazo[1,2-a]pyridin-3-yl-methanone;
Imidazo[1,2-a]pyridin-3-yl-[4-(2-methyl-2,3-dihydro-indole-1-carbonyl)-phenyl]-methanone;
[4-(3,4-Dihydro-2H-quinoline-1-carbonyl)-phenyl]-imidazo[1,2-a]pyridin-3-yl-methanone;
Imidazo[1,2-a]pyridin-3-yl-[4-(octahydro-quinoline-1-carbonyl)-phenyl]-methanone;
3-[4-(Azepan-1-ylcarbonyl)-2-fluorobenzoyl]imidazo[1,2-a]pyridine-6-carbonitrile;
4-[(6-Fluoroimidazo[1,2-a]pyridin-3-yl)carbonyl]-N,N-diisopropylbenzamide;
N-Ethyl-3-fluoro-4-[(6-fluoroimidazo[1,2-a]pyridin-3-yl)carbonyl]-N-isopropylbenzamide;
(6-Fluoroimidazo[1,2-a]pyridin-3-yl)[2-fluoro-4-(piperidin-1-ylcarbonyl)phenyl]methanone;
(6-Bromoimidazo[1,2-a]pyridin-3-yl)[2-fluoro-4-(piperidin-1-ylcarbonyl)phenyl]methanone;
Azepan-1-yl-[3-(6-fluoro-imidazo[1,2-a]pyridin-3-yl)-1H-indazol-6-yl]-methanone;
Azepan-1-yl-[3-(6-fluoro-imidazo[1,2-a]pyridin-3-yl)-1-methyl-1H-indazol-6-yl]-methanone;
Azepan-1-yl-[3-(6-fluoro-imidazo[1,2-a]pyridin-3-yl)-1-(2-hydroxy-ethyl)-1H-indazol-6-yl]-methanone;
[6-(Azepan-1-ylcarbonyl)]-1-ethyl-3[6-fluoro-imidazo[1,2-a]pyridin-3-yl]-1H-indazole;
[6-(Azepan-1-ylcarbonyl)]-1-isopropyl-3[6-fluoro-imidazo[1,2-a]pyridin-3-yl]-1H-indazole;
[6-(Azepan-1-ylcarbonyl)]-1-isobutyl-3[6-fluoro-imidazo[1,2-a]pyridin-3-yl]-1H-indazole;
3-[6-(Azepan-1-ylcarbonyl)-1-methyl-1H-indazol-3-yl]imidazo[1,2-a]pyridine-6-carbonitrile;
[6-(Azepan-1-ylcarbonyl)]-1-methyl-3[6-(trifluoromethyl)-imidazo[1,2-a]pyridin-3-yl]-1H-indazole;
[6-(Azepan-1-ylcarbonyl)]-1-methyl-3[6-chloro-imidazo[1,2-a]pyridin-3-yl]-1H-indazole;
[6-(Azepan-1-ylcarbonyl)]-1-methyl-3[6-methyl-imidazo[1,2-a]pyridin-3-yl]-1H-indazole;

[6-(Azepan-1-ylcarbonyl)]-1-methyl-3[6-ethyl-imidazo[1,2-a]pyridin-3-yl]-1H-indazole;
[6-(Azepan-1-ylcarbonyl)]-1-methyl-3[6-cyclopropyl-imidazo[1,2-a]pyridin-3-yl]-1H-indazole;
[6-(Azepan-1-ylcarbonyl)]-1-methyl-3[6-imidazo[1,2-a]pyridin-3-yl]-1H-indazole;
[6-(Azepan-1-ylcarbonyl)]-1-methyl-3[6-bromo-imidazo[1,2-a]pyridin-3-yl]-1H-indazole;
3-(6-Fluoroimidazo[1,2-a]pyridin-3-yl)-N,1-dimethyl-N-phenyl-1H-indazole-6-carboxamide;
N-Ethyl-3-(6-fluoroimidazo[1,2-a]pyridin-3-yl)-N-isopropyl-1-methyl-1H-indazole-6-carboxamide;
[3-(6-Fluoroimidazo[1,2-a]pyridin-3-yl)-1-methyl-1H-indazol-6-yl]-(decahydroquinolin-1-yl)-methanone;
3-(6-Fluoroimidazo[1,2-a]pyridin-3-yl)-1-methyl-1H-indazol-6-carboxylic acid cyclohexyl-cyclopropyl-methyl-amide;
Azonan-1-yl-[3-(6-fluoro-imidazo[1,2-a]pyridin-3-yl)-1-methyl-1H-indazol-6-yl]-methanone;
Azocan-1-yl-[3-(6-fluoro-imidazo[1,2-a]pyridin-3-yl)-1-methyl-1H-indazol-6-yl]-methanone;
3-(6-Fluoroimidazo[1,2-a]pyridin-3-yl)-1-methyl-6-(piperidin-1-ylcarbonyl)-1H-indazole;
3-[1-Methyl-6-(piperidin-1-ylcarbonyl)-1H-indazol-3-yl]imidazo[1,2-a]pyridine-6-carbonitrile;
3-[1-Methyl-6-(pyrrolidin-1-ylcarbonyl)-1H-indazol-3-yl]imidazo[1,2-a]pyridine-6-carbonitrile;
3-(1-Methyl-6-{[(2R)-2-(methoxymethyl) pyrrolidin-1-yl]carbonyl}-1H-indazol-3-yl)imidazo[1,2-a]pyridine-6-carbonitrile;
3-(1-Methyl-6-{[(2S)-2-(methoxymethyl) pyrrolidin-1-yl]carbonyl}-1H-indazol-3-yl)imidazo[1,2-a]pyridine-6-carbonitrile;
3-[6-(8-Aza-bicyclo[3.2.1]octane-8-carbonyl)-1-methyl-1H-indazol-3-yl]-imidazo[1,2-a]pyridine-6-carbonitrile;
3-{1-Methyl-6-[(4-methylpiperazin-1-yl)carbonyl]}-1H-indazol-3-yl]imidazo[1,2-a]pyridine-6-carbonitrile;
3-(6-Cyano-imidazo[1,2-a]pyridin-3-yl)-1-methyl-1H-indazole-6-carboxylic acid diisopropylamide;
2-Methyl-3[1-Methyl-6-(azepan-1-ylcarbonyl)-1H-indazol-3-yl]-imidazo[1,2-a]pyridine-6-carbonitrile;
Azepan-1-yl-[1-benzyl-3-(6-fluoro-imidazo[1,2-a]pyridin-3-yl)-1H-indazol-6-yl]-methanone;
Azepan-1-yl-[3-(6-fluoro-imidazo[1,2-a]pyridin-3-yl)-1-phenethyl-1H-indazol-6-yl]-methanone;
Azepan-1-yl-[3-(6-fluoro-imidazo[1,2-a]pyridin-3-yl)-1-[2-(2-methoxyethoxy)ethyl]-1H-indazol-6-yl]-methanone;
Azepan-1-yl-[3-(6-fluoro-imidazo[1,2-a]pyridin-3-yl)-1-(2-morpholin-4-yl-ethyl)-1H-indazol-6-yl]-methanone;
Azepan-1-yl-[3-(6-fluoro-imidazo[1,2-a]pyridin-3-yl)-1-[(4-methylpiperazin-1-yl)carbonyl]-1H-indazol-6-yl]-methanone;
3-(6-Fluoro-imidazo[1,2-a]pyridin-3-yl)-benzo[d]isoxazole-6-carboxylic acid cyclohexyl-ethyl-amide;
Azepan-1-yl-[3-(6-fluoro-imidazo[1,2-a]pyridin-3-yl)-benzo[d]isoxazol-6-yl]-methanone;
[4-(Azepan-1-ylcarbonyl)-2-hydroxyphenyl](6-fluoroimidazo[1,2-a]pyridin-3-yl)methanone;
N-Ethyl-3-(6-fluoroimidazo[1,2-a]pyridin-3-yl)-N-isopropyl-1,2-benzisoxazole-6-carboxamide;
3-(6-Fluoroimidazo[1,2-a]pyridin-3-yl)-6-(piperidin-1-ylcarbonyl)-1,2-benzisoxazole;
3-(6-Bromoimidazo[1,2-a]pyridin-3-yl)-6-(piperidin-1-ylcarbonyl)-1,2-benzisoxazole;
6-(Azepan-1-ylcarbonyl)-3-(6-bromoimidazo[1,2-a]pyridin-3-yl)-1,2-benzisoxazole;
(6-Bromoimidazo[1,2-a]pyridin-3-yl)[2-fluoro-4-(morpholin-4-ylcarbonyl)phenyl]methanone;
3-(6-Bromoimidazo[1,2-a]pyridin-3-yl)-6-(morpholin-4-ylcarbonyl)-1,2-benzisoxazole;
[4-(8-Azabicyclo[3.2.1]oct-8-ylcarbonyl)-2-fluorophenyl](6-bromoimidazo[1,2-a]pyridin-3-yl)methanone;
6-(8-Azabicyclo[3.2.1]oct-8-ylcarbonyl)-3-(6-bromoimidazo[1,2-a]pyridin-3-yl)-1,2-benzisoxazole;
3-[6-(Piperidin-1-ylcarbonyl)-1,2-benzisoxazol-3-yl]imidazo[1,2-a]pyridine-6-carbonitrile;
3-[6-(Azepan-1-ylcarbonyl)-1,2-benzisoxazol-3-yl]imidazo[1,2-a]pyridine-6-carbonitrile;
3-[6-(Morpholin-4-ylcarbonyl)-1,2-benzisoxazol-3-yl]imidazo[1,2-a]pyridine-6-carbonitrile;
3-[6-(8-Azabicyclo[3.2.1]oct-8-ylcarbonyl)-1,2-benzisoxazol-3-yl]imidazo[1,2-a]pyridine-6-carbonitrile;
Imidazo[1,2-a]pyridine-3-carboxylic acid [4-(cyclohexyl-ethyl-carbamoyl)-2-hydroxy-phenyl]-amide;
Imidazo[1,2-a]pyridine-3-carboxylic acid [5-(cyclohexyl-ethyl-carbamoyl)-2-hydroxy-phenyl]-amide;
2-Imidazo[1,2-a]pyridin-3-yl-benzooxazole-6-carboxylic acid cyclohexyl-ethyl-amide;
2-Imidazo[1,2-a]pyridin-3-yl-benzooxazole-5-carboxylic acid cyclohexyl-ethyl-amide;
Azepan-1-yl-[3-(6-fluoro-imidazo[1,2-a]pyridin-3-yl)-benzo[c]isoxazol-6-yl]-methanone;
5-(Azepan-1-ylcarbonyl)-1-(6-fluoroimidazo[1,2-a]pyridin-3-yl)-1H-1,2,3-benzotriazole;
Azepan-1-yl-[1-benzenesulfonyl-3-(6-fluoro-imidazo[1,2-a]pyridin-3-yl)-1H-indol-6-yl]-methanone;
3-[6-(Azepan-1-ylcarbonyl)-1H-indol-3-yl]-6-fluoroimidazo[1,2-a]pyridine;
Azepan-1-yl-[4-(6-fluoro-imidazo[1,2-a]pyridin-3-yl)-quinazolin-7-yl]-methanone;
2-Amino-7-(azepan-1-ylcarbonyl)-4-(6-fluoroimidazo[1,2-a]pyridin-3-yl)quinazoline;
2-Methyl-7-(azepan-1-ylcarbonyl)-4-(6-fluoroimidazo[1,2-a]pyridin-3-yl)quinazoline;
N-Cyclohexyl-N-ethyl-4-(imidazo[1,2-a]pyrimidin-3-ylcarbonyl)-benzamide;
N-Cyclohexyl-N-ethyl-4-(6-chloroimidazo[1,2-b]pyridazin-3-ylcarbonyl)-benzamide;
N-Cyclohexyl-N-ethyl-4-(imidazo[1,2-b]pyridazin-3-ylcarbonyl)-benzamide; and
a pharmaceutically acceptable salt thereof.

14. The medicament according to claim 12, wherein the compound is selected from the group consisting of:
4-(8-Bromo-imidazo[1,2-a]pyridine-3-carbonyl)-N-cyclohexyl-N-ethyl-benzamide;
N-Cyclohexyl-N-ethyl-4-(7-methyl-imidazo[1,2-a]pyridine-3-carbonyl)-benzamide;
N-Cyclohexyl-N-ethyl-4-(7-ethyl-imidazo[1,2-a]pyridine-3-carbonyl)-benzamide;
4-(7-Cyano-imidazo[1,2-a]pyridine-3-carbonyl)-N-cyclohexyl-N-ethyl-benzamide;
4-(7-Chloro-imidazo[1,2-a]pyridine-3-carbonyl)-N-cyclohexyl-N-ethyl-benzamide;
4-(7-Fluoro-imidazo[1,2-a]pyridine-3-carbonyl)-N-cyclohexyl-N-ethyl-benzamide;
4-(6-Cyano-imidazo[1,2-a]pyridine-3-carbonyl)-N-cyclohexyl-N-ethyl-benzamide;
4-(6-Fluoro-imidazo[1,2-a]pyridine-3-carbonyl)-N-cyclohexyl-N-ethyl-benzamide;
4-(6-Chloro-imidazo[1,2-a]pyridine-3-carbonyl)-N-cyclohexyl-N-ethyl-benzamide;

4-(6-Bromo-imidazo[1,2-a]pyridine-3-carbonyl)-N-cyclohexyl-N-ethyl-benzamide;
N-Cyclohexyl-N-ethyl-4-(6-methyl-imidazo[1,2-a]pyridine-3-carbonyl)-benzamide;
N-Cyclohexyl-N-ethyl-4-(6-methoxy-imidazo[1,2-a]pyridine-3-carbonyl)-benzamide;
N-Cyclohexyl-N-ethyl-4-(2-methyl-imidazo[1,2-a]pyridine-3-carbonyl)-benzamide;
[4-(Azepane-1-carbonyl)-phenyl]-(6-fluoro-imidazo[1,2-a]pyridin-3-yl)-methanone;
3-[4-(Azepane-1-carbonyl)-benzoyl]-imidazo[1,2-a]pyridine-6-carbonitrile;
N-Cyclohexyl-N-ethyl-4-(imidazo[1,2-a]pyridine-3-carbonyl)-3-methyl-benzamide;
N-Cyclohexyl-N-ethyl-4-(6-fluoro-imidazo[1,2-a]pyridine-3-carbonyl)-3-methyl-benzamide;
N-Cyclohexyl-N-ethyl-4-(imidazo[1,2-a]pyridine-3-carbonyl)-3-methoxy-benzamide;
N-Cyclohexyl-N-ethyl-4-(imidazo[1,2-a]pyridine-3-carbonyl)-3-chloro-benzamide;
3-Chloro-N-cyclohexyl-N-ethyl-4-(6-fluoro-imidazo[1,2-a]pyridine-3-carbonyl)-benzamide;
N-Cyclohexyl-N-ethyl-3-fluoro-4-(6-fluoro-imidazo[1,2-a]pyridine-3-carbonyl)-benzamide;
N-Cyclohexyl-N-ethyl-4-(6-fluoro-imidazo[1,2-a]pyridine-3-carbonyl)-3-nitro-benzamide;
N-Cyclohexyl-N-ethyl-6-(imidazo[1,2-a]pyridine-3-carbonyl)-nicotinamide;
2-Chloro-N-cyclohexyl-N-ethyl-4-(6-fluoro-imidazo[1,2-a]pyridine-3-carbonyl)-benzamide;
[4-(Azepane-1-carbonyl)-phenyl]-(6-trifluoromethyl-imidazo[1,2-a]pyridin-3-yl)-methanone;
[4-(Azepane-1-carbonyl)-phenyl]-(6,8-dichloro-imidazo[1,2-a]pyridin-3-yl)-methanone;
[4-(Azepane-1-carbonyl)-2-fluoro-phenyl]-(6-fluoro-imidazo[1,2-a]pyridin-3-yl)-methanone;
[4-(Azepane-1-carbonyl)-2-nitro-phenyl]-(6-fluoro-imidazo[1,2-a]pyridin-3-yl)-methanone;
[4-(Azepane-1-carbonyl)-2-hydroxyamino-phenyl]-(6-fluoro-imidazo[1,2-a]pyridin-3-yl)-methanone;
[2-Amino-4-(azepane-1-carbonyl)-phenyl]-(6-fluoro-imidazo[1,2-a]pyridin-3-yl)-methanone;
3-Amino-N-cyclohexyl-N-ethyl-4-(6-fluoro-imidazo[1,2-a]pyridine-3-carbonyl)-benzamide;
[4-(azepan-1-ylcarbonyl)-2-fluorophenyl](6-chloroimidazo[1,2-a]pyridin-3-yl)methanone;
[4-(azepan-1-ylcarbonyl)-2-fluorophenyl](6-bromoimidazo[1,2-a]pyridin-3-yl)methanone;
[4-(azepan-1-ylcarbonyl)-2-fluorophenyl](6-methylimidazo[1,2-a]pyridin-3-yl)methanone;
[4-(azepan-1-ylcarbonyl)-2-fluorophenyl][6-(trifluoromethyl)imidazo[1,2-a]pyridin-3-yl]methanone;
[4-(azepan-1-ylcarbonyl)-2-fluorophenyl](6-ethylimidazo[1,2-a]pyridin-3-yl)methanone;
[4-(azepan-1-ylcarbonyl)-2-fluorophenyl](6-cyclopropylimidazo[1,2-a]pyridin-3-yl)methanone;
[4-(azepan-1-ylcarbonyl)-2-fluorophenyl](imidazo[1,2-a]pyridin-3-yl)methanone;
N-Cyclohexyl-4-(imidazo[1,2-a]pyridine-3-carbonyl)-N-methyl-benzamide;
N-Cyclohexyl-4-(imidazo[1,2-a]pyridine-3-carbonyl)-N-propyl-benzamide;
N-Cyclohexyl-4-(imidazo[1,2-a]pyridine-3-carbonyl)-N-isopropyl-benzamide;
N-Cyclohexyl-4-(imidazo[1,2-a]pyridine-3-carbonyl)-N-prop-2-ynyl-benzamide;
N-Cyclohexyl-N-cyclopropylmethyl-4-(imidazo[1,2-a]pyridine-3-carbonyl)-benzamide;
N-Allyl-N-cyclohexyl-4-(imidazo[1,2-a]pyridine-3-carbonyl)-benzamide;
N-Cyclohexyl-4-(imidazo[1,2-a]pyridine-3-carbonyl)-N-(2,2,2-trifluoro-ethyl)-benzamide;
N-Cyclohexyl-N-(2-dimethylamino-ethyl)-4-(imidazo[1,2-a]pyridine-3-carbonyl)-benzamide;
N-Butyl-N-cyclohexyl-4-(imidazo[1,2-a]pyridine-3-carbonyl)-benzamide;
N,N-Dicyclohexyl-4-(imidazo[1,2-a]pyridine-3-carbonyl)-benzamide;
4-(Imidazo[1,2-a]pyridine-3-carbonyl)-N-methyl-N-phenyl-benzamide;
4-(6-Fluoro-imidazo[1,2-a]pyridine-3-carbonyl)-N-methyl-N-phenyl-benzamide;
4-(6-Fluoro-imidazo[1,2-a]pyridine-3-carbonyl)-N-(4-methoxy-phenyl)-N-methyl-benzamide;
4-(6-Fluoro-imidazo[1,2-a]pyridine-3-carbonyl)-N-methyl-N-p-tolyl-benzamide;
N-(4-Chloro-phenyl)-4-(6-fluoro-imidazo[1,2-a]pyridine-3-carbonyl)-N-methyl-benzamide;
4-(6-Fluoro-imidazo[1,2-a]pyridine-3-carbonyl)-N-methyl-N-pyridin-2-yl-benzamide;
4-(6-Fluoro-imidazo[1,2-a]pyridine-3-carbonyl)-N-methyl-N-pyridin-4-yl-benzamide;
N-Ethyl-4-(imidazo[1,2-a]pyridine-3-carbonyl)-N-phenyl-benzamide;
N-Ethyl-4-(imidazo[1,2-a]pyridine-3-carbonyl)-N-pyridin-3-yl-benzamide;
N,N-Diethyl-4-(imidazo[1,2-a]pyridine-3-carbonyl)-benzamide;
N-Ethyl-4-(imidazo[1,2-a]pyridine-3-carbonyl)-N-isopropyl-benzamide;
4-(Imidazo[1,2-a]pyridine-3-carbonyl)-N,N-dimethyl-benzamide;
4-(Imidazo[1,2-a]pyridine-3-carbonyl)-N,N-dipropyl-benzamide;
Imidazo[1,2-a]pyridin-3-yl-[4-(pyrrolidine-1-carbonyl)-phenyl]-methanone;
Imidazo[1,2-a]pyridin-3-yl-[4-(piperidine-1-carbonyl)-phenyl]-methanone;
[4-(Azepane-1-carbonyl)-phenyl]-imidazo[1,2-a]pyridin-3-yl-methanone;
[4-(Azocane-1-carbonyl)-phenyl]-imidazo[1,2-a]pyridin-3-yl-methanone;
[4-(Azonane-1-carbonyl)-phenyl]-imidazo[1,2-a]pyridin-3-yl-methanone;
Imidazo[1,2-a]pyridin-3-yl-[4-(morpholine-4-carbonyl)-phenyl]-methanone;
Imidazo[1,2-a]pyridin-3-yl-[4-(4-methyl-piperazine-1-carbonyl)-phenyl]-methanone;
[4-(2,3-Dihydro-indole-1-carbonyl)-phenyl]-imidazo[1,2-a]pyridin-3-yl-methanone;
Imidazo[1,2-a]pyridin-3-yl-[4-(2-methyl-2,3-dihydro-indole-1-carbonyl)-phenyl]-methanone;
[4-(3,4-Dihydro-2H-quinoline-1-carbonyl)-phenyl]-imidazo[1,2-a]pyridin-3-yl-methanone;
Imidazo[1,2-a]pyridin-3-yl-[4-(octahydro-quinoline-1-carbonyl)-phenyl]-methanone;
3-[4-(Azepan-1-ylcarbonyl)-2-fluorobenzoyl]imidazo[1,2-a]pyridine-6-carbonitrile;
4-[(6-Fluoroimidazo[1,2-a]pyridin-3-yl)carbonyl]-N,N-diisopropylbenzamide;
N-Ethyl-3-fluoro-4-[(6-fluoroimidazo[1,2-a]pyridin-3-yl)carbonyl]-N-isopropylbenzamide;

(6-Fluoroimidazo[1,2-a]pyridin-3-yl)[2-fluoro-4-(piperidin-1-ylcarbonyl)phenyl]methanone;
(6-Bromoimidazo[1,2-a]pyridin-3-yl)[2-fluoro-4-(piperidin-1-ylcarbonyl)phenyl]methanone;
Azepan-1-yl-[3-(6-fluoro-imidazo[1,2-a]pyridin-3-yl)-1H-indazol-6-yl]-methanone;
Azepan-1-yl-[3-(6-fluoro-imidazo[1,2-a]pyridin-3-yl)-1-methyl-1H-indazol-6-yl]-methanone;
Azepan-1-yl-[3-(6-fluoro-imidazo[1,2-a]pyridin-3-yl)-1-(2-hydroxy-ethyl)-1H-indazol-6-yl]-methanone;
[6-(Azepan-1-ylcarbonyl)]-1-ethyl-3[6-fluoro-imidazo[1,2-a]pyridin-3-yl]-1H-indazole;
[6-(Azepan-1-ylcarbonyl)]-1-isopropyl-3[6-fluoro-imidazo[1,2-a]pyridin-3-yl]-1H-indazole;
[6-(Azepan-1-ylcarbonyl)]-1-isobutyl-3[6-fluoro-imidazo[1,2-a]pyridin-3-yl]-1H-indazole;
3-[6-(Azepan-1-ylcarbonyl)-1-methyl-1H-indazol-3-yl]imidazo[1,2-a]pyridine-6-carbonitrile;
[6-(Azepan-1-ylcarbonyl)]-1-methyl-3[6-(trifluoromethyl)-imidazo[1,2-a]pyridin-3-yl]-1H-indazole;
[6-(Azepan-1-ylcarbonyl)]-1-methyl-3[6-chloro-imidazo[1,2-a]pyridin-3-yl]-1H-indazole;
[6-(Azepan-1-ylcarbonyl)]-1-methyl-3[6-methyl-imidazo[1,2-a]pyridin-3-yl]-1H-indazole;
[6-(Azepan-1-ylcarbonyl)]-1-methyl-3[6-ethyl-imidazo[1,2-a]pyridin-3-yl]-1H-indazole;
[6-(Azepan-1-ylcarbonyl)]-1-methyl-3[6-cyclopropyl-imidazo[1,2-a]pyridin-3-yl]-1H-indazole;
[6-(Azepan-1-ylcarbonyl)]-1-methyl-3[6-imidazo[1,2-a]pyridin-3-yl]-1H-indazole;
[6-(Azepan-1-ylcarbonyl)]-1-methyl-3[6-bromo-imidazo[1,2-a]pyridin-3-yl]-1H-indazole;
3-(6-Fluoroimidazo[1,2-a]pyridin-3-yl)-N,1-dimethyl-N-phenyl-1H-indazole-6-carboxamide;
N-Ethyl-3-(6-fluoroimidazo[1,2-a]pyridin-3-yl)-N-isopropyl-1-methyl-1H-indazole-6-carboxamide;
[3-(6-Fluoroimidazo[1,2-a]pyridin-3-yl)-1-methyl-1H-indazol-6-yl]-(decahydroquinolin-1-yl)-methanone;
3-(6-Fluoroimidazo[1,2-a]pyridin-3-yl)-1-methyl-1H-indazol-6-carboxylic acid cyclohexyl-cyclopropyl-methyl-amide;
Azonan-1-yl-[3-(6-fluoro-imidazo[1,2-a]pyridin-3-yl)-1-methyl-1H-indazol-6-yl]-methanone;
Azocan-1-yl-[3-(6-fluoro-imidazo[1,2-a]pyridin-3-yl)-1-methyl-1H-indazol-6-yl]-methanone;
3-(6-Fluoroimidazo[1,2-a]pyridin-3-yl)-1-methyl-6-(piperidin-1-ylcarbonyl)-1H-indazole;
3-[1-Methyl-6-(piperidin-1-ylcarbonyl)-1H-indazol-3-yl]imidazo[1,2-a]pyridine-6-carbonitrile;
3-[1-Methyl-6-(pyrrolidin-1-ylcarbonyl)-1H-indazol-3-yl]imidazo[1,2-a]pyridine-6-carbonitrile;
3-(1-Methyl-6-{[(2R)-2-(methoxymethyl) pyrrolidin-1-yl]carbonyl}-1H-indazol-3-yl)imidazo[1,2-a]pyridine-6-carbonitrile;
3-(1-Methyl-6-{[(2S)-2-(methoxymethyl) pyrrolidin-1-yl]carbonyl}-1H-indazol-3-yl)imidazo[1,2-a]pyridine-6-carbonitrile;
3-[6-(8-Aza-bicyclo[3.2.1]octane-8-carbonyl)-1-methyl-1H-indazol-3-yl]-imidazo[1,2-a]pyridine-6-carbonitrile;
3-{1-Methyl-6-[(4-methylpiperazin-1-yl)carbonyl]}-1H-indazol-3-yl]imidazo[1,2-a]pyridine-6-carbonitrile;
3-(6-Cyano-imidazo[1,2-a]pyridin-3-yl)-1-methyl-1H-indazole-6-carboxylic acid diisopropylamide;
2-Methyl-3-[1-Methyl-6-(azepan-1-ylcarbonyl)-1H-indazol-3-yl]-imidazo[1,2-a]pyridine-6-carbonitrile;
Azepan-1-yl-[1-benzyl-3-(6-fluoro-imidazo[1,2-a]pyridin-3-yl)-1H-indazol-6-yl]-methanone;
Azepan-1-yl-[3-(6-fluoro-imidazo[1,2-a]pyridin-3-yl)-1-phenethyl-1H-indazol-6-yl]-methanone;
Azepan-1-yl-[3-(6-fluoro-imidazo[1,2-a]pyridin-3-yl)-1-[2-(2-methoxyethoxy)ethyl]-1H-indazol-6-yl]-methanone;
Azepan-1-yl-[3-(6-fluoro-imidazo[1,2-a]pyridin-3-yl)-1-(2-morpholin-4-yl-ethyl)-1H-indazol-6-yl]-methanone;
Azepan-1-yl-[3-(6-fluoro-imidazo[1,2-a]pyridin-3-yl)-1-[(4-methylpiperazin-1-yl)carbonyl]-1H-indazol-6-yl]-methanone;
3-(6-Fluoro-imidazo[1,2-a]pyridin-3-yl)-benzo[d]isoxazole-6-carboxylic acid cyclohexyl-ethyl-amide;
Azepan-1-yl-[3-(6-fluoro-imidazo[1,2-a]pyridin-3-yl)-benzo[d]isoxazol-6-yl]-methanone;
[4-(Azepan-1-ylcarbonyl)-2-hydroxyphenyl](6-fluoroimidazo[1,2-a]pyridin-3-yl)methanone;
N-Ethyl-3-(6-fluoroimidazo[1,2-a]pyridin-3-yl)-N-isopropyl-1,2-benzisoxazole-6-carboxamide;
3-(6-Fluoroimidazo[1,2-a]pyridin-3-yl)-6-(piperidin-1-ylcarbonyl)-1,2-benzisoxazole;
3-(6-Bromoimidazo[1,2-a]pyridin-3-yl)-6-(piperidin-1-ylcarbonyl)-1,2-benzisoxazole;
6-(Azepan-1-ylcarbonyl)-3-(6-bromoimidazo[1,2-a]pyridin-3-yl)-1,2-benzisoxazole;
(6-Bromoimidazo[1,2-a]pyridin-3-yl)[2-fluoro-4-(morpholin-4-ylcarbonyl)phenyl]methanone;
3-(6-Bromoimidazo[1,2-a]pyridin-3-yl)-6-(morpholin-4-ylcarbonyl)-1,2-benzisoxazole;
[4-(8-Azabicyclo[3.2.1]oct-8-ylcarbonyl)-2-fluorophenyl](6-bromoimidazo[1,2-a]pyridin-3-yl)methanone;
6-(8-Azabicyclo[3.2.1]oct-8-ylcarbonyl)-3-(6-bromoimidazo[1,2-a]pyridin-3-yl)-1,2-benzisoxazole;
3-[6-(Piperidin-1-ylcarbonyl)-1,2-benzisoxazol-3-yl]imidazo[1,2-a]pyridine-6-carbonitrile;
3-[6-(Azepan-1-ylcarbonyl)-1,2-benzisoxazol-3-yl]imidazo[1,2-a]pyridine-6-carbonitrile;
3-[6-(Morpholin-4-ylcarbonyl)-1,2-benzisoxazol-3-yl]imidazo[1,2-a]pyridine-6-carbonitrile;
3-[6-(8-Azabicyclo[3.2.1]oct-8-ylcarbonyl)-1,2-benzisoxazol-3-yl]imidazo[1,2-a]pyridine-6-carbonitrile;
Imidazo[1,2-a]pyridine-3-carboxylic acid [4-(cyclohexyl-ethyl-carbamoyl)-2-hydroxy-phenyl]-amide;
Imidazo[1,2-a]pyridine-3-carboxylic acid [5-(cyclohexyl-ethyl-carbamoyl)-2-hydroxy-phenyl]-amide;
2-Imidazo[1,2-a]pyridin-3-yl-benzooxazole-6-carboxylic acid cyclohexyl-ethyl-amide;
2-Imidazo[1,2-a]pyridin-3-yl-benzooxazole-5-carboxylic acid cyclohexyl-ethyl-amide;
Azepan-1-yl-[3-(6-fluoro-imidazo[1,2-a]pyridin-3-yl)-benzo[c]isoxazol-6-yl]-methanone;
5-(Azepan-1-ylcarbonyl)-1-(6-fluoroimidazo[1,2-a]pyridin-3-yl)-1H-1,2,3-benzotriazole;
Azepan-1-yl-[1-benzenesulfonyl-3-(6-fluoro-imidazo[1,2-a]pyridin-3-yl)-1H-indol-6-yl]-methanone;
3-[6-(Azepan-1-ylcarbonyl)-1H-indol-3-yl]-6-fluoroimidazo[1,2-a]pyridine;
Azepan-1-yl-[4-(6-fluoro-imidazo[1,2-a]pyridin-3-yl)-quinazolin-7-yl]-methanone;
2-Amino-7-(azepan-1-ylcarbonyl)-4-(6-fluoroimidazo[1,2-a]pyridin-3-yl)quinazoline;
2-Methyl-7-(azepan-1-ylcarbonyl)-4-(6-fluoroimidazo[1,2-a]pyridin-3-yl)quinazoline;
N-Cyclohexyl-N-ethyl-4-(imidazo[1,2-a]pyrimidin-3-ylcarbonyl)-benzamide;

N-Cyclohexyl-N-ethyl-4-(6-chloroimidazo[1,2-b]pyridazin-3-ylcarbonyl)-benzamide;

N-Cyclohexyl-N-ethyl-4-(imidazo[1,2-b]pyridazin-3-ylcarbonyl)-benzamide; and a pharmaceutically acceptable salt thereof.

15. A method of administering a compound of formula (I) according to claim 1, the method comprising administering the compound of formula (I) to a patient for the treatment of a disease or disorder selected from the group consisting of movement disorders, acute and chronic pain, affective disorders, central and peripheric nervous system degeneration disorders, schizophrenia and related psychosis, cognitive disorders, attention disorders, central nervous system injury, cerebral ischaemia, myocardial ischaemia, and muscle ischaemia.

16. The method according to claim 15, wherein the compound of formula (I) is administered to a patient for the treatment of a disease or disorder selected from the group consisting of Parkinson's disease, Alzheimer's disease and attention-deficit hyperactivity disorder.

17. A method of administering the compound according to claim 10, the method comprising administering the compound to a patient.

18. A method of administering the pharmaceutical composition according to claim 13, the method comprising administering the pharmaceutical composition to a patient.

19. A method of administering the medicament according to claim 14, the method comprising administering the medicament to a patient.

20. A method of administering the compound according to claim 10, the method comprising administering the compound to a patient for the treatment of a disease or disorder selected from the group consisting of movement disorders, acute and chronic pain, affective disorders, central and peripheric nervous system degeneration disorders, schizophrenia and related psychosis, cognitive disorders, attention disorders, central nervous system injury, cerebral ischaemia, myocardial ischaemia, and muscle ischaemia.

21. A method of administering the pharmaceutical composition according to claim 13, the method comprising administering the pharmaceutical composition to a patient for the treatment of a disease or disorder selected from the group consisting of movement disorders, acute and chronic pain, affective disorders, central and peripheric nervous system degeneration disorders, schizophrenia and related psychosis, cognitive disorders, attention disorders, central nervous system injury, cerebral ischaemia, myocardial ischaemia, and muscle ischaemia.

22. A method of administering the medicament according to claim 14, the method comprising administering the medicament to a patient for the treatment of a disease or disorder selected from the group consisting of movement disorders, acute and chronic pain, affective disorders, central and peripheric nervous system degeneration disorders, schizophrenia and related psychosis, cognitive disorders, attention disorders, central nervous system injury, cerebral ischaemia, myocardial ischaemia, and muscle ischaemia.

\* \* \* \* \*